US010736960B2

(12) United States Patent
Brunskill et al.

(10) Patent No.: US 10,736,960 B2
(45) Date of Patent: Aug. 11, 2020

(54) METHODS FOR INHIBITING FIBROSIS IN A SUBJECT IN NEED THEREOF

(71) Applicants: University of Leicester, Leicestershire (GB); Omeros Corporation, Seattle, WA (US)

(72) Inventors: Nigel John Brunskill, South Croxton (GB); Gregory A. Demopulos, Mercer Island, WA (US); Tom Dudler, Bellevue, WA (US); Hans-Wilhelm Schwaeble, Mountsorrel (GB)

(73) Assignees: Omeros Corporation, Seattle, WA (US); University of Leicester, Leicester (GB)

( * ) Notice: Subject to any disclaimer, the term of this patent is extended or adjusted under 35 U.S.C. 154(b) by 157 days.

(21) Appl. No.: 15/399,524

(22) Filed: Jan. 5, 2017

(65) Prior Publication Data

US 2017/0189525 A1    Jul. 6, 2017

Related U.S. Application Data

(60) Provisional application No. 62/275,025, filed on Jan. 5, 2016, provisional application No. 62/407,979, filed on Oct. 13, 2016.

(51) Int. Cl.
| | | |
|---|---|---|
| *A61K 39/395* | (2006.01) | |
| *A61P 13/12* | (2006.01) | |
| *C07K 16/40* | (2006.01) | |
| *A61K 39/00* | (2006.01) | |

(52) U.S. Cl.
CPC ........ *A61K 39/3955* (2013.01); *A61K 39/395* (2013.01); *A61P 13/12* (2018.01); *C07K 16/40* (2013.01); *A61K 2039/505* (2013.01); *A61K 2121/00* (2013.01); *C07K 2317/21* (2013.01); *C07K 2317/34* (2013.01); *C07K 2317/54* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,331,647 A | 5/1982 | Goldenberg et al. | |
| 4,816,567 A | 3/1989 | Cabilly et al. | |
| 4,946,778 A | 8/1990 | Ladner et al. | |
| 5,211,657 A | 5/1993 | Yamada et al. | |
| 5,223,409 A | 6/1993 | Ladner et al. | |
| 5,403,484 A | 4/1995 | Ladner et al. | |
| 5,552,157 A | 9/1996 | Yagi et al. | |
| 5,565,213 A | 10/1996 | Nakamori et al. | |
| 5,567,434 A | 10/1996 | Szoka | |
| 5,571,698 A | 11/1996 | Ladner et al. | |
| 5,610,288 A | 3/1997 | Rubenstein | |
| 5,693,762 A | 12/1997 | Queen et al. | |
| 5,718,709 A | 2/1998 | Considine et al. | |
| 5,738,868 A | 4/1998 | Shinkarenko | |
| 5,739,119 A | 4/1998 | Galli et al. | |
| 5,741,516 A | 4/1998 | Webb et al. | |
| 5,759,829 A | 6/1998 | Shewmaker et al. | |
| 5,789,573 A | 8/1998 | Baker et al. | |
| 5,795,587 A | 8/1998 | Gao et al. | |
| 5,801,154 A | 9/1998 | Baracchini et al. | |
| 6,649,592 B1 | 11/2003 | Larson | |
| 9,096,676 B2 | 8/2015 | Larsen et al. | |
| 2002/0019369 A1 | 2/2002 | Li et al. | |
| 2007/0172483 A1 | 7/2007 | Schwaeble et al. | |
| 2011/0311549 A1 | 12/2011 | Schwaeble et al. | |
| 2012/0282263 A1* | 11/2012 | Dudler | C07K 16/40 424/142.1 |
| 2014/0056873 A1* | 2/2014 | Schwaeble | A61K 39/3955 424/133.1 |
| 2014/0127224 A1 | 5/2014 | Neff et al. | |
| 2015/0166675 A1 | 6/2015 | Demopulos et al. | |
| 2015/0239985 A1 | 8/2015 | Demopulos et al. | |
| 2017/0189525 A1 | 7/2017 | Brunskill et al. | |

FOREIGN PATENT DOCUMENTS

| | | |
|---|---|---|
| EP | 0 321 201 B1 | 12/1994 |
| JP | 2009-532493 | 9/2009 |
| JP | 2014512363 A | 5/2014 |
| WO | WO 1988/004300 A1 | 6/1988 |

(Continued)

OTHER PUBLICATIONS

Ballardie et al. (J Am Soc Nephrol 13: 142-148, 2002). (Year: 2002).*
Yoshikawa et al. (Clin J Am Soc Nephrol 1: 511-517, 2006). (Year: 2006).*
Rosenblad et al. (Pediatr Nephrol (2014) 29:2225-2228. (Year: 2014).*
Espinosa, M., et al., "Association of C4d deposition with clinical outcomes in IgA nephropathy," *Clin J Am Soc Nephrol*, 9(5): 897-904, (2014).
Magistroni, R., et al., "New developments in the genetics, pathogenesis, and therapy of IgA nephropathy," *Kidney Int*, 88(5): 974-989, (2015).
Maillard, N., et al., "Current Understanding of the Role of Complement in IgA Nephropathy," *J Am Soc Nephrol*, 26(7): 1503-1512, (2015).

(Continued)

*Primary Examiner* — Zachary S Skelding
(74) *Attorney, Agent, or Firm* — Tineka J. Quinton

(57) ABSTRACT

In one aspect, the invention provides methods for treating, inhibiting, alleviating or preventing fibrosis in a mammalian subject suffering, or at risk of developing a disease or disorder caused or exacerbated by fibrosis and/or inflammation. In one embodiment, the invention provides methods of treating a subject suffering from renal fibrosis. In one embodiment, the invention provides methods of reducing proteinuria in a subject suffering from a renal disease or condition associated with proteinuria. The methods comprise the step of administering, to a subject in need thereof, an amount of a MASP-2 inhibitory agent effective to inhibit MASP-2-dependent complement activation.

8 Claims, 48 Drawing Sheets

Specification includes a Sequence Listing.

(56) References Cited

FOREIGN PATENT DOCUMENTS

| WO | WO 1991/011465 A1 | 8/1991 |
|---|---|---|
| WO | WO 2004/009664 A2 | 1/2004 |
| WO | WO 2004/106384 | 12/2004 |
| WO | WO2007/117996 | 10/2007 |
| WO | WO 2012/139081 A2 | 10/2012 |
| WO | WO2012/151481 | 11/2012 |
| WO | WO2014/144542 | 9/2014 |
| WO | WO 2015/058143 A1 | 4/2015 |

OTHER PUBLICATIONS

Oortwijn, B. D., et al., "Differential glycosylation of polymeric and monomeric IgA: a possible role in glomerular inflammation in IgA nephropathy," *J Am Soc Nephrol*, 17(12): 3529-3539, (2006).

Wan, J. X., et al., "Complement 3 is involved in changing the phenotype of human glomerular mesangial cells," *J Cell Physiol*, 213(2): 495-501, (2007).

Xie, J., et al., "Predicting progression of IgA nephropathy: new clinical progression risk score," *PLoS One*,7(6): e38904, (2012).

Roos, A., et al., "Human IgA activates the complement system via the mannan-binding lectin pathway," *The Journal of Immunology* 167:2861-2868 (2001).

Farrar, C.A., et al., "Collectin-11 detects stress-induced L-fucose pattern to trigger renal epithelial injury," *J Clin Invest* 126(5):1911-1925 (2016).

Mestecky, J., et al., "IgA nephropathy: Molecular mechanisms of the disease," *Annu Rev Pathol Mech Dis* 8:217-40 (2013).

Ibels, L.S., et al., "IgA nephropathy: Analysis of the natural history, important factos in the progression of renal disease, and a review of the literature," *Medicine* 73(2):79-102 (1994).

Glassock, R.J., "The pathogenesis of IgA nephropathy," *Curr Opin Nephrol Hypertens* 20:153-160 (2011).

Kiryluk, K., et al., "The genetics and immunobiology of IgA nephropathy," *J Clin Invest* 124(6):2325-2332 (2014).

Lai, K.N, et al., "Activation of podocytes by mesangial-derived TNF-$\alpha$: glomerulo-podocytic communication in IgA nephropathy," *Am J Physiol Renal Physiol* 294:F945-F955 (2008).

Suzuki, H., et al., "The pathophysiology og IgA nephropathy," *J Am Soc Nephrol* 22:1795-1803 (2011).

Kiryluk, K., et al., "Pathogenesis of immunoglobulin A nephropathy: Recent insight from genetic studies," *Annu Rev Med* 64:339-356 (2013).

Hisano, S., et al., "Mesangial IgA2 deposits and elctin-pathway-mediated complement activation in IgA glomerulonephritis," *Am J Kid Dis* 38(5):1082-1088 (2001).

Fakhouri, F., et al., "C3 glomerulopathy: a new classification," *Nat Rev Nephrol*, 6(8): 494-499, (2010).

Kopel, T., et al., C3 glomerulopathies: Dense deposit disease and C3 glomerulonephritis 2015 [updated Dec. 17, 2015]. Available from: UpToDate.com.

Horita, Y., et al., "Expression of vascular endothelial growth factor and its receptors in rats with protein-overload nephrosis," *Nephrol Dial Transplant*, 13(10): 2519-2528, (1998).

Abbate, M., et al., "Complement-mediated dysfunction of glomerular filtration barrier accelerates progressive renal injury," *J Am Soc Nephrol*, 19(6): 1158-1167, (2008).

Gorriz, J. L., et al., "Proteinuria: detection and role in native renal disease progression," *Transplant Rev (Orlando )*, 26(1): 3-13, (2012).

He, W., et al,, "Sirt1 activation protects the mouse renal medulla from oxidative injury," *J Clin Invest*, 120(4): 1056-1068, (2010).

Liu, Y., "Renal fibrosis: new insights into the pathogenesis and therapeutics," *Kidney Int*, 69(2): 213-217, (2006).

Chen, C.B., et al., "Stoichiometry of complexes between mannose-binding protein and its associated serine proteases. Defining functional units for complement activation," *J. Biol. Chem.*, 276(28):25894-25902, (2001).

Feinberg, H., et al., "Crystal structure of the CUB1-EGF-CUB2 region of mannose-binding protein associated serine protease-2," *EMBO J.* 22:2348-2359, (2003).

Lynch, N.J., et al., "L-ficolin specifically binds to lipoteichoic acid, a cell wall constituent of Gram-positive bacteria, and activates the lectin pathway of complement," *J. Immunol.* 172:1198-1202, (2004).

Stover, C.M., et al., "Two constituents of the initiation complex of the mannan-binding lectin activation pathway of complement are encoded by a single structural gene," *J. Immunol.* 162:3481-3490, (1999).

Stover, C.M., et al., "The rat and mouse homologues of MASP-2 and MAp19, components of the lectin activation pathway of complement," *J. Immunol.* 163:6848-6859, (1999).

Thiel, S., et al., "A second serine protease associated with mannan-binding lectin that activates complement," *Nature* 386:506-510, (1997).

Thiel, S., et al., "Interaction of C1q and mannan-binding lectin (MBL) with C1r, C1s, MBL-associated serine proteases 1 and 2, and the MBL-associated protein MAp19," *J. Immunol.* 165:878-887, (2000).

Vorup-Jensen, T., et al., "Distinct pathways of mannan-binding lectin (MBL)- and C1-complex autoactivation revealed by reconstitution of MBL with recombinant MBL-associated serine protease-2," *J. Immunol.* 165:2093-2100, (2000).

Thielens, N.M., et al., "Interaction properties of human mannan-binding lectin (MBL)-associated serine proteases-1 and -2, MBL-associated protein 19, and MBL," *J. Immunol.* 166:5068-5077, (2001).

Matsushita, M., et al., "Cutting edge: complement-activating complex of ficolin and mannose-binding lectin-associated serine protease," *J. Immunol.* 164:2281-2284, (2000).

Rodrigues, M.L., et al., "Engineering Fab' fragments for efficient F(ab)2 formation in *Escherichia coli* and for improved in vivo stability," *J. Immunol.* 151(12):6954-6961, (1998).

Riedermann, N.C., et al., "Complement in ischemia reperfusion injury," *Am. J. Pathol.* 162:363-367, (2003).

Matsushita, M., et al., "Activation of the lectin complement pathway by H-ficolin (Hakata antigen)," *J. Immunol.* 168(7):3502-3506, (2002).

Stengaard-Pedersen, K., et al., "Inherited deficiency of mannan-binding lectin-associated serine protease 2," *New England J. Med.* 349:554-560, (2003).

Takahashi, M., et al., "A truncated form of mannose-binding lectin-associated serine protease (MASP)-2 expressed by alternative polyadenylation is a component of the lectin complement pathway," *Int. Immunol.* 11:859-863, (1999).

Ambrus et al., "Natural substrates and inhibitors of mannan-binding lectin-associated serine protease-1 and -2: a study on recombinant catalytic fragments," *J. Immunol.* 170:1374-1382, (2003).

Moller-Kristensen, M., et al., "Levels of mannan-binding lectin-associated serine protease-2 in healthy individuals," *J. Immunol Methods* 282:159-167, (2003).

Petersen, S. V., et al., "Control of the classical and the MBL pathway of complement activation," *Mol Immunol*, 37(14): 803-811, (2000).

Dahl, M.R., et al., "MASP-3 and its association with distinct complexes of the mannan-binding lectin complement activation pathway," *Immunity* 15:127-35, (2001).

Petersen, S.V., et al., "An assay for the mannan-binding lectin pathway of complement activation," *J. Immunol. Methods* 257:107-116, (2001).

Liszewski, M.K., et al., "The Complement System," in *Fundamental Immunology*, Third Edition, Raven Press, Ltd., New York, (1993).

Collard, C.D., et al., "Complement activation after oxidative stress: role of the lectin complement pathway," *Am J. Pathol* 156(6):1549-56, (2000).

Lu, J., et al., "Collectins and ficolins: sugar pattern recognition molecules of the mammalian innate immune system," *Biochim Biophys Acta* 1572:387-400, (2002).

Jordan et al., "Inhibition of mannose-binding lectin reduces postischemic myocardial reperfusion injury," *Circulation* 104(12):1413-1418, (2001).

(56) References Cited

OTHER PUBLICATIONS

Maynard, Y., et al., "Characterization of a mannose and N-acetylglucosamine-specific lectin present in rat hepatocytes," *J. Biol. Chem.* 257:3788-3794, (1982).
Lee, R.T., et al., "Multivalent ligand binding by serum mannose-binding protein," *Archiv. Biochem. Biophys.* 299:129-136, (1992).
Collard et al., "Endothelial oxidative stress activates the lectin complement pathway: role of cytokeratin 1," *Am. J. Pathol.* 159(3):1045-1054, (2001).
Ji, Y.H., et al., "Activation of the C4 and C2 components of complement by a proteinase in serum bactericidal factor, Ra reactive factor," *J. Immunol.* 150:571-578, (1993).
Kilpatrick, D.C., et al., "Mannan-binding lectin: clinical significance and applications," *Biochim Biophys Acta* 1572:401-413, (2002).
Weis, W.I., et al., "Structure of a C-type mannose-binding protein complexed with an oligosaccharide," *Nature* 360:127-134, (1992).
Kalli, K.R., et al., "Therapeutic uses of recombinant complement protein inhibitors," *Springer Semin. Immunopathol.* 15:417-431, (1994).
Wallis, R., et al., "Localization of the serine protease-binding sites in the collagen-like domain of mannose-binding protein: indirect effects of naturally occurring mutations on protease binding and activation," *J. Biol. Chem.* 279:14065-73, (2004).
Wallis, R., et al., "Interaction of mannose-binding protein with associated serine proteases: effects of naturally occurring mutations," *J. Biol. Chem.* 275:30962-30969, (2000).
Sim, R.B., et al., "Innate Immunity," *Biochem. Soc. Trans.* 28:545-550, (2000).
Petersen, S. V., et al., "Generation of antibodies Towards MASP-1 and MASP-2 Using Bacterial Expression Systems," *Molecular Immunology*, 35(6-7): 409, (1998).
Cech, T.R., et al., "Biological catalysis by RNA," *Ann. Rev. Biochem.* 55:599-629, (1986).
Clackson, T., et al., "Making antibody fragments using phage display libraries," *Nature* 352:624-628, (1991).
Chen, P.F., et al., "Development of the non-palindromic adaptor polymerase chain reaction (NPA-PCR) for the amplification of alpha- and beta-chain T-cell receptor cDNAs," *Scand. J. Immunol.* 35:539-549, (1992).
Bird, et al., "Single-chain antigen-binding proteins," *Science* 242(4877):423-426, (1988).
Climie, S., et al., "Chemical synthesis of the thymidylate synthase gene," *Proc. Nat'l Acad. Sci. USA* 87(2):633, (1990).
Carter, P., et al., "Humanization of an anti-p185HER2 antibody for human cancer therapy," *Proc. Nat'l. Acad. Sci. USA* 89(10):4285-4289, (1992).
Altschul, S.F., et al., "Gapped BLAST and PSI-BLAST: a new generation of protein database search programs," *Nucl. Acids Res.* 25:3389-3402, (1997).
Makino, K., "A Microcapsule Self-Regulating Delivery System for Insulin," *J. Controlled Release* 12:235-239, (1990).
Lee, V.H.L., "Protease Inhibitors and Penetration Enhancers as Approaches to Modify Peptide Absorption," *J. Controlled Release* 13:213, (1990).
Jolliffe, L.K., et al., "Humanized antibodies: enhancing therapeutic utility through antibody engineering," *Int'l Rev. Immunol.* 10:241-250, (1993).
Jackson, D.Y., et al., "Potent alpha 4 beta 1 peptide antagonists as potential anti-inflammatory agents," *J. Med. Chem.* 40:3359-68, (1997).
Hori, R., et al., "Enhanced bioavailability of subcutaneously injected insulin coadministered with collagen in rats and humans," *Pharm. Res.* 6:813, (1989).
Satomura, A., et al., "Significant elevations in serum mannose-binding lectin levels in patients with chronic renal failure," *Nephron*, 92(3): 702-704, (2002).
Daha, M.R., et al., "C3 nephritic factor (C3NeF): stabilization of fluid phase and cell-bound alternative pathway convertase," *J. Immunol.* 116(1):1-7, (1976).
Greenspan, N.S., et al., "Idiotypes: structure and immunogenicity," *FASEB J.* 7(5):437-444, (1993).
DeBoer, A.G., et al., "Rectal Absorption Enhancement of Peptide Drugs," *J. Controlled Release* 13:241, (1990).
Fuertges, F., et al., "The Clinical Efficacy of Poly(ethylene Glycol)-modified Proteins," *J. Controlled Release* 11:139, (1990).
Singer, I.I., et al., "Optimal humanization of 1B4, an anti-CD18 murine monoclonal antibody, is achieved by correct choice of human V-region framework sequences," *J. Immun.* 150:2844, (1993).
Siegert, C.E., et al., "The relationship between serum titers of autoantibodies to C1q and age in the general population and in patients with systemic lupus erythematosus," *Clin. Immunol. Immunopathol.* 67:204-9, (1993).
Schwaeble, W., et al., "The mannan-binding lectin-associated serine proteases (MASPs) and MAp19: four components of the lectin pathway activation complex encoded by two genes," *Immunobiology* 205:455-466, (2002).
Sandhu, J.S., "Protein engineering of antibodies," *Crit. Rev. Biotech.* 12:437-462, (1992).
Ravetch, J.V., et al., "Fc receptors," *Annu. Rev. Immunol.* 9:457-492, (1991).
Rosenblatt, J., et al., "The Effect of Collagen Fiber Size Distribution on the Release Rate of Proteins from Collagen Matrices by Diffusion," *J. Controlled Release* 9:195, (1989).
Porter, R.R., "The hydrolysis of rabbit y-globulin and antibodies with crystalline papain," *Biochem. J.* 73:119, (1959).
Merrifield, R.B., "Solid Phase Peptide Synthesis. I. The Synthesis of a Tetrapeptide," in *J. Amer. Chem. Soc.* 85:2149-2154, (1963).
Presta, L.G., "Antibody engineering," *Curr. Op. Struct. Biol.* 2:593-596, (1992).
Lee, V.H.L., "Enzymatic Barriers to Peptide and Protein Absorption," *Crit. Rev. Ther. Drug Carrier Sys.* 5(2):69-97, (1988).
Yamakawa, I., et al., "Sustained release of insulin by double-layered implant using poly(D,L-lactic acid)," *J. Pharm. Sci.* 79:505, (1990).
Ohman, E.M., et al., "Early clinical experience with integrelin, an inhibitor of the platelet glycoprotein IIb/IIIa integrin receptor," *European Heart J.* 16:50-55, (1995).
Pack, P., et al., "Improved bivalent miniantibodies, with identical avidity as whole antibodies, produced by high cell density fermentation of *Escherichia coli*," *Bio/Technology* 11:1271, (1993).
Zhang, L., et al., "A discrete site modulates activation of I domains. Application to integrin alphaMbeta2," *J. Biol. Chem.* 271(47):29953-57, (1996).
Taylor, L.D., et al., "Human immunoglobulin transgenes undergo rearrangement, somatic mutation and class switching in mice that lack endogenous IgM," *Int. Immun.* 6:579, (1994).
Takakura, Y., et al., "Control of pharmaceutical properties of soybean trypsin inhibitor by conjugation with dextran. I: Synthesis and characterization," *J. Pharm. Sci.* 78:117, (1989).
Van de Winkel, J.G., et al., "Human IgG Fc receptor heterogeneity: molecular aspects and clinical implications," *Immunol. Today* 14:215-221, (1993).
Vaughan, T.J., et al., "Human antibodies by design," *Nature Biotechnical* 16:535-539, (1998).
Scatchard, G., "The Attraction of Proteins for Small Molecules and Ions," *NY Acad. Sci.* 51:660-672, (1949).
Green, L.L., et al., "Antigen-specific human monoclonal antibodies from mice engineered with human Ig heavy and light chain YACs," *Nature Genet.* 7:13-21, (1994).
Glover, G.I., et al., "Synthetic peptide inhibitors of complement serine proteases--I. Identification of functionally equivalent protease inhibitor sequences in serpins and inhibition of C1s and D," *Mol. Immunol.* 25:1261, (1988).
Fedor, M.J., et al., "Substrate sequence effects on 'hammerhead' RNA catalytic efficiency," *Proc. Natl. Acad. Sci. USA* 87:1668-1672, (1990).
Duncan, A.R., et al., "The binding site for C1q on IgG," *Nature* 332:738-740, (1988).
Dodds, A.W., "Small-scale preparation of complement components C3 and C4," *Methods Enzymol.* 223:46, (1993).
Haseloff, J., et al., "Simple RNA enzymes with new and highly specific endoribonuclease activities," *Nature* 334:585-591, (1988).

(56) References Cited

OTHER PUBLICATIONS

Matsushita, M., et al., "Activation of the classical complement pathway by mannose-binding protein in association with a novel C1s-like serine protease," *J. Exp. Med.* 176(6):1497-2284, (2000).
Morgan, B.P., "Clinical complementology: recent progress and future trends," *Eur. J. Clinical Investig.* 24(4):219-228, (1994).
Itakura, K., et al., "Synthesis and use of synthetic oligonucleotides," *Annu. Rev. Biochem.* 53:323, (1984).
Kuntz, I.D., et al., "Structure-based strategies for drug design and discovery," *Science* 257:1078, (1992).
Holmskov, U., et al., "Collections and ficolins: humoral lectins of the innate immune defense," *Annu. Rev. Immunol.* 21:547-578, (2003).
Ikeda, K., et al., "Serum lectin with known structure activates complement through the classical pathway," *J. Biol. Chem.* 262:7451-7454, (1987).
Jensen, J., et al., "Taming of transposable elements by homology-dependent gene silencing," *Nat. Genet.* 21(2):209-12, (1999).
Lloyd, B.H., et al., "Determination of optimal sites of antisense oligonucleotide cleavage within TNFalpha mRNA," *Nucleic Acids Res.* 29:3665-3673, (2001).
DesJarlais, R.L., et al., "Structure-based design of nonpeptide inhibitors specific for the human immunodeficiency virus 1 protease," *PNAS* 87:6644-6648, (1990).
Bae, Y.H., et al., "Insulin Permeation Through Thermo-Sensitive Hydrogels," *J. Controlled Release* 9:271, (1989).
Asano, M., et al., "In Vivo Characteristics of Low Molecular Weight Copoly(L-Lactice Acid/Glycolic Acid) Formulations with Controlled Release of Luteinizing Hormone-Releasing Hormone Agonist," *J. Controlled Release* 9:111-112, (1989).
Kohler, G., et al., "Continuous cultures of fused cells secreting antibody of predefined specificity," *Nature* 256:495, (1975).
Kuntz, I.D., et al., "A geometric approach to macromolecule-ligand interactions," *J. Mol. Biol.* 161:269-288, (1982).
Kuhlman, et al., "The human mannose-binding protein functions as an opsonin," *J. Exp. Med.* 169:1733, (1989).
Losman, M.J., et al., "Baboon anti-idiotype antibodies mimic a carcinoembryonic antigen epitope," *Int. J. Cancer* 46:310, (1990).
Lonberg, N., et al., "Antigen-specific human antibodies from mice comprising four distinct genetic modifications," *Nature* 368:856, (1994).
Marks, J.D., et al., "By-passing immunization. Human antibodies from V-gene libraries displayed on phage," *J. Mol. Biol.* 222:581-597, (1991).
Matsushita et al., "A novel human serum lectin with collagen- and fibrinogen-like domains that functions as an opsonin," *J. Biol. Chem.* 271(5):2448-54, (1996).
Mariani, M., et al., "A new enzymatic method to obtain high-yield F(ab)2 suitable for clinical use from mouse IgG1," *Mol. Immunol.* 28:69-71, (1991).
Morrison, S.L., et al., "Chimeric human antibody molecules: mouse antigen-binding domains with human constant region domains," *Proc. Nat'l Acad. Sci. USA* 81:6851-6855, (1984).
Murayama, O., et al., "Novel peptide ligands for integrin alpha 6 beta 1 selected from a phage display library," *J. Biochem.* 120:445-51, (1996).
Nisonoff, A., et al., "Separation of univalent fragments from the bivalent rabbit antibody molecule by reduction of disulfide bonds," *Arch. Biochem. Biophys.* 89:230-244, (1960).
Scherr, M., et al., "Rapid determination and quantitation of the accessibility to native RNAs by antisense oligodeoxynucleotides in murine cell extracts," *Nucleic Acids Res.* 26:5079-5085, (1998).
Isaacs, J.D., et al., "Therapy with monoclonal antibodies. An in vivo model for the assessment of therapeutic potential," *J. Immunol.* 148(10):3062-3071, (1992).
Whitlow, M., et al., "Single-chain Fv Proteins and Their Fusion Proteins," *Methods: A Companion to Methods in Enzymology* 2:97-105, (1991).
Larrick, J.W., et al., "PCR Amplification of Antibody Genes," *Methods: A Companion to Methods in Enzymology* 2:106-110, (1991).
Jones, P.T., et al., "Replacing the complementarity-determining regions in a human antibody with those from a mouse," *Nature* 321:522-525, (1986).
Ward et al., "Genetic Manipulation and Expression of Antibodies," in *Monoclonal Antibodies: Principles and Applications*, Birch et al., (eds.) p. 137, Wiley-Liss, Inc., (1995).
Courtenay-Luck, N.S., "Genetic Manipulation of Monoclonal Antibodies," in *Monoclonal Antibodies: Production, Engineering and Clinical Application*, Ritter et al., (eds.) p. 166, Cambridge University Press, (1995).
Kelley, R.F., "Engineering Therapeutic Antibodies," in *Protein Engineering: Principles and Practice*, Cleland et al., (eds.) John Wiley & Sons, Inc., pp. 399-434, (1996).
Baines et al., "Purification of Immunoglobulin G, (IgG)," in *Methods in Molecular Biology vol. 10: Immunochemical Protocols*, Chapter 8, pp. 79-105, (1992).
Matsushita, M., et al., "The role of ficolins in innate immunity," *Immunobiology*, 205(4-5):490-497, (2002).
Hovind, P., et al., "Mannose-binding lectin as a predictor of microalbuminuria in type 1 diabetes: an inception cohort study," *Diabetes*, 54(5): 1523-1527, (2005).
Tezel, G., et al., "Oxidative stress and the regulation of complement activation in human glaucoma" *Invest Ophthalmol Vis Sci* 51:5071-5082, (2010).
Harlow, E., et al., *Antibodies: A Laboratory Manual*, Cold Spring Harbor Laboratory, New York, (1988).
Olesen, H. V., et al., "The mannan-binding lectin pathway and lung disease in cystic fibrosis—dysfunction of mannan-binding lectin-associated serine protease 2 (MASP-2) may be a major modifier," *Clin Immunol*, 121(3): 324-331, (2006).
Endo, M., et al., "Glomerular deposition of mannose-binding lectin (MBL) indicates a novel mechanism of complement activation in IgA nephropathy," *Nephrol Dial Transplant*, 13(8): 1984-1990, (1998).
Hisano, S., et al., "Activation of the lectin complement pathway in Henoch-Schonlein purpura nephritis," *Am J Kidney Dis*, 45(2): 295-302, (2005).
Sato, N., et al., "Significance of glomerular activation of the alternative pathway and lectin pathway in lupus nephritis," *Lupus*, 20(13): 1378-1386, (2011).
Roos, A., et al., "Glomerular activation of the lectin pathway of complement in IgA nephropathy is associated with more severe renal disease," *J Am Soc Nephrol*, 17(6): 1724-1734, (2006).
Lhotta, K., et al., "Glomerular deposition of mannose-binding lectin in human glomerulonephritis," *Nephrol Dial Transplant*, 14(4): 881-886, (1999).
Heja, D., et al., "Monospecific Inhibitors Show That Both Mannan-binding Lectin-associated Serine Protease-1 (MASP-1) and -2 Are Essential for Lectin Pathway Activation and Reveal Structural Plasticity of MASP-2," *J Biol Chem*, 287(24): 20290-20300, (2012).
Risitano, A.M., et al., "Complement fraction 3 binding on erythrocytes as additional mechanism of disease in paroxysmal nocturnal hemoglobinuria patients treated by eculizumab," *Blood* 113(17):4094-100, (2009).
Teh, C., et al., "M-ficolin is expressed on monocytes and is a lectin binding to N-acetyl-D-glucosamine and mediates monocyte adhesion and phagocytosis of *Escherichia coli*," *Immunology* 101:225-232, (2000).
Hansen, et al, "Collectin 11 (CL-11, CL-K1) is a MASP-1/3-associated plasma collectin with microbial-binding activity," *J. Immunol* 185(10):6096-6104, (2010).
Jack, D.L., et al., "Mannose-binding lectin enhances phagocytosis and killing of Neisseria meningitidis by human macrophages" *J Leukoc Biol.*, 77(3):328-36, (2005).
Aoyagi et al., "Role of L-ficolin/mannose-binding lectin-associated serine protease complexes in the opsonophagocytosis of type III group B streptococci," *J Immunol*, 174(1):418-25(2005).
Degn, S.E., et al., "MAp19, the alternative splice product of the MASP2 gene," *J Immunol. Methods*, 373(1-2):89-101, (2011).

(56) References Cited

OTHER PUBLICATIONS

Noris M et al. "Atypical Hemolytic-Uremic Syndrome," Nov. 16, 2007 [Updated, Mar. 10, 2011]. In: Pagon RA, Bird TD, Dolan CR, et al., editors. GeneReviews™, Seattle, (WA): University of Washington, Seattle.
Guessous, F., et al., "Shiga toxin 2 and lipopolysaccharide induce human microvascular endothelial cells to release chemokines and factors that stimulate platelet function," *Infect. Immun.*, 73(12): 8306-8316, (2005).
Kaufman, R.J., et al., "Improved vectors for stable expression of foreign genes in mammalian cells by use of the untranslated leader sequence from EMC virus," *Nucleic Acids Research* 19:4485-90, (1991).
Kaufman, R.J., "Selection and coamplification of heterologous genes in mammalian cells," *Methods in Enzymology*, 185:537-66, (1990).
Maniatis, A., et al., "Intermediate-dose melphalan for refractory myeloma," *Blood* 74(3):1177, (1989).
Shea, K.J., "Molecular Imprinting of Synthetic Network Polymers: The De Novo synthesis of Macromolecular Binding and Catalytic Sties," *TRIP* 2(5):166-173, (1994).
Colligan, "Production of Monoclonal Antibosies," *Current Protocols in Immunology*, vol. 1., John Wiley & Sons, pp. 2.5.1-2.6.7, (1991).
Gal et al., "A true autoactivating enzyme. Structural insight into mannose-binding lectin-associated serine protease-2 activations," *J. Biol. Chem.* 280(39):33435-44, (2005).
Megyeri, M., et al., "Quantitative characterization of the activation steps of mannan-binding lectin (MBL)-associated serine proteases (MASPs) points to the central role of MASP-1 in the initiation of the complement lectin pathway," *J Biol Chem*, 288(13): 8922-8934, (2013).
Hej a, D., et al., "Revised mechanism of complement lectin-pathway activation revealing the role of serine protease MASP-1 as the exclusive activator of MASP-2," *Proc Natl Acad Sci USA*, 109(26): 10498-10503, (2012).
Reichmann, L., et al., "Reshaping human antibodies for therapy," *Nature* 332:323-329, (1988).
Lee, W.A., "Permeation enhancers for the nasal delivery of protein and peptide therapeutics," *Biopharm.* 3:22-25, (1990).
Gunn, B. M., et al., "Mannose binding lectin is required for alphavirus-induced arthritis/myositis," *PLoS Pathog*, 8(3): e1002586, (2012).
Berger, S. P., et al., "Association between mannose-binding lectin levels and graft survival in kidney transplantation," *Am J Transplant*, 5(6): 1361-1366, (2005).
Yoshihiro, I., et al., "An Insulin-Releasing System that is Responsive to Glucose," *J. Controlled Release* 10:195-203, (1989).
Green, J.A., et al., "Production of polyclonal antisera," In: Immunochemical protocols. Methods in molecular biology, vol. 10. Humana Press, Totowa, N.J., p. 1, (1992).
King, L.A., et al., "Propagation, titration and purification of AcMNPV in cell culture," *The Baculovirus Expression System: A Laboratory Guide*, Chapman and Hall Ltd., London, pp. 106-126, (1992).
Asgari, E., et al., "Mannan-binding lectin-associated serine protease 2 is critical for the development of renal ischemia reperfusion injury and mediates tissue injury in the absence of complement C4," *FASEB J*, 28(9): 3996-4003, (2014).
Tampe, D., et al., "Potential approaches to reverse or repair renal fibrosis," *Nat Rev Nephrol*, 10(4): 226-237, (2014).
Fearn, A., et al., "The influence of complement activation on chronic renal inflammation and fibrosis," *Molecular Immunology*, 48(14): 1721, (2011).
Gastoldi, S., et al., "C5a/C5aR interaction mediates complement activation and thrombosis on endothelial cells in atypical hemolytic uremic syndrome (aHUS)," *Immunobiology* 217(11):1145-1146, (2012).
Pippin, J. W., et al., "Inducible rodent models of acquired podocyte diseases," *Am J Physiol Renal Physiol*, 296(2): F213-F229, (2009).

Pickering, M. C., et al., "C3 glomerulopathy: consensus report," *Kidney Int*, 84(6): 1079-1089, (2013).
Remuzzi, G., et al., "Pathophysiology of progressive nephropathies," *N Engl J Med*, 339(20): 1448-1456, (1998).
Ruggenenti, P., et al., "Mechanisms and treatment of CKD," *J Am Soc Nephrol*, 23(12): 1917-1928, (2012).
Eddy, A. A., "Interstitial nephritis induced by protein-overload proteinuria," *Am J Pathol*, 135(4): 719-733, (1989).
Sheerin, N. S., et al., "Synthesis of complement protein C3 in the kidney is an important mediator of local tissue injury," *FASEB J*, 22(4): 1065-1072, (2008).
Chevalier, R. L., et al., "Ureteral obstruction as a model of renal interstitial fibrosis and obstructive nephropathy," *Kidney Int*, 75(11): 1145-1152, (2009).
Wynn, T. A., "Fibrotic disease and the T(H)1/T(H)2 paradigm," *Nat Rev Immunol*, 4(8): 583-594, (2004).
Boor, P., et al., "Complement C5 mediates experimental tubulointerstitial fibrosis," *J Am Soc Nephrol*, 18(5): 1508-1515, (2007).
Nishikawa, T., et al., "Programmed cell death in the myocardium of arrhythmogenic right ventricular cardiomyopathy in children and adults," *Cardiovasc Pathol*, 8(4): 185-189, (1999).
Khan, R., et al., "Fibrosis in heart disease: understanding the role of transforming growth factor-beta in cardiomyopathy, valvular disease and arrhythmia," *Immunology*, 118(1): 10-24, (2006).
Burke, A. P., et al., "Arrhythmogenic right ventricular cardiomyopathy and fatty replacement of the right ventricular myocardium: are they different diseases?," *Circulation*, 97(16): 1571-1580, (1998).
Abbate, M., et al., "How does proteinuria cause progressive renal damage?," *J Am Soc Nephrol*, 17(11): 2974-2984, (2006).
Mathern, D. R., et al., "Molecules Great and Small: The Complement System," *Clin J Am Soc Nephrol*, 10(9): 1636-1650, (2015).
Liu et al., "Glomerular mannose-binding lectin deposition is a useful prognostic predictor in immunoglobulin a nephropathy," *Clin Exp Immunol* 174(1):152-60 (2013).
Rensen et al., "Activation of the Complement System in Human Nonalcoholic Fatty Liver Disease," *Hepatology* 50(6): 1809-17 (2009).
Quigg R.J, "Complement and the Kidney," *J Immunol* 171:3319-3324, (2003).
Naik A., et al., "Complement regulation in renal disease models," *Semin Nephrol* 33:575-585, (2013).
Bao, L., et al., "Unrestricted C3 activation occurs in Crry-deficient kidneys and rapidly leads to chronic renal failure," *J Am Soc Nephrol*, 18(3): 811-822, (2007).
Tang, Z., et al., "C3a mediates epithelial-to-mesenchymal transition in proteinuric nephropathy," *J Am Soc Nephrol*, 20(3): 593-603, (2009).
Bao, L., et al., "Distinct roles for C3a and C5a in complement-induced tubulointerstitial injury," *Kidney Int*, 80(5): 524-534, (2011).
Whitworth, J. A., "Progression of renal failure—the role of hypertension," *Ann Acad Med Singapore*, 34(1): 8-15, (2005).
Gharaee-Kermani, M., et al., "Animal Models of Pulmonary Fibrosis," *Methods Mol. Med.* 117:251-259, (2005).
Brown, K. S., et al., "Severe fibrosis in hepatitis C virus-infected patients is associated with increased activity of the mannan-binding lectin (MBL)/MBL-associated serine protease 1 (MASP-1) complex," *Clin Exp Immunol.* 147(1):90-8, (2007).
El Saadany, S. A., et al., "Fibrosis severity and mannan-binding lectin (MBL)/MBL-associated serine protease 1 (MASP-1) complex in HCV-infected patients," *Arab J Gastroenterol*, 12(2): 68-73, (2011).
Saeed, A., et al., "Mannan binding lectin-associated serine protease 1 is induced by hepatitis C virus infection and activates human hepatic stellate cells," *Clin Exp Immunol*, 174(2): 265-273, (2013).
Risdon, R. A., et al., "Relationship between renal function and histological changes found in renal-biopsy specimens from patients with persistent glomerular nephritis," *Lancet*, 2(7564): 363-366, (1968).
Schainuck, L. I., et al., "Structural-functional correlations in renal disease. II. The correlations," *Hum Pathol*, 1(4): 631-641, (1970).
Nath K.A., "Tubulointerstitial changes as a major determinant in the progression of renal damage," *Am J Kid Dis* 20:1-17, (1992).

(56) References Cited

OTHER PUBLICATIONS

Liu, Y., "Cellular and molecular mechanisms of renal fibrosis," *Nat Rev Nephrol*, 7(12): 684-696, (2011).
Duffield, J. S., "Cellular and molecular mechanisms in kidney fibrosis," *J Clin Invest*, 124(6): 2299-2306, (2014).
Whittaker, P., et al., "Quantitative assessment of myocardial collagen with picrosirius red staining and circularly polarized light," *Basic Res Cardiol*, 89(5): 397-410, (1994).
Furness, P. N., et al., "Semiautomatic quantitation of macrophages in human renal biopsy specimens in proteinuric states," *J Clin Pathol*, 50(2): 118-122, (1997).
Yang, H. C., et al., "Models of chronic kidney disease," *Drug Discov Today Dis Models*, 7(1-2): 13-19, (2010).
Brunskill, N. J., "Albumin signals the coming of age of proteinuric nephropathy," *J Am Soc Nephrol*, 15(2): 504-505, (2004).
Tryggvason, K., et al., "Causes and consequences of proteinuria: the kidney filtration barrier and progressive renal failure," *J Intern Med*, 254(3): 216-224, (2003).
Williams, M. E., "Diabetic nephropathy: the proteinuria hypothesis," *Am J Nephrol*, 25(2): 77-94, (2005).
Baines, R. J., et al., "Tubular toxicity of proteinuria," *Nat Rev Nephrol*, 7(3): 177-180, (2011).
Lozano, R., et al., "Global and regional mortality from 235 causes of death for 20 age groups in 1990 and 2010: a systematic analysis for the Global Burden of Disease Study 2010," *Lancet*, 380(9859): 2095-2128, (2012).
Clark, W. F., et al., "Excessive fluid intake as a novel cause of proteinuria," *CMAJ*, 178(2): 173-175, (2008).
Ishola, D. A., Jr., et al., "In mice, proteinuria and renal inflammatory responses to albumin overload are strain-dependent," *Nephrol Dial Transplant*, 21(3): 591-597, (2006).
David, S., et al., "Alternative pathway complement activation induces proinflammatory activity in human proximal tubular epithelial cells," *Nephrol Dial Transplant*, 12(1): 51-56, (1997).
Lee, V. W., et al., "Adriamycin nephropathy: a model of focal segmental glomerulosclerosis," *Nephrology (Carlton)*, 16(1): 30-38, (2011).
Drawz, P., et al., "Chronic kidney disease," *Ann Intern Med*, 162(11): ITC1-16, (2015).
Wyatt, R. J., et al., "IgA nephropathy," *N Engl J Med*, 368(25): 2402-2414, (2013).
Goto, M., et al., "A scoring system to predict renal outcome in IgA nephropathy: a nationwide 10-year prospective cohort study," *Nephrol Dial Transplant*, 24(10): 3068-3074, (2009).
Berthoux, F., et al., "Predicting the risk for dialysis or death in IgA nephropathy," *J Am Soc Nephrol*, 22(4): 752-761, (2011).
Coppo, R., et al., "Factors predicting progression of IgA nephropathies," *J Nephrol*, 18(5): 503-512, (2005).
Reich, H. N., et al., "Remission of proteinuria improves prognosis in IgA nephropathy," *J Am Soc Nephrol*, 18(12): 3177-3183, (2007).
D'Amico, G., "Natural history of idiopathic IgA nephropathy: role of clinical and histological prognostic factors," *Am J Kidney Dis*, 36(2): 227-237, (2000).
Matsuda, M., et al., "Deposition of mannan binding protein and mannan binding protein-mediated complement activation in the glomeruli of patients with IgA nephropathy," *Nephron*, 80(4): 408-413, (1998).
Liu, L. L., et al., "Urinary mannose-binding lectin is a biomarker for predicting the progression of immunoglobulin (Ig)A nephropathy," *Clin Exp Immunol*, 169(2): 148-155, (2012).
KDIGO, "KDIGO Clinical Practice Guideline for Glomerulonephritis," *Int. Soc of Nephrol* 2(2):139-274, (2012).
Heurich, M., et al, "Common polymorphisms in C3, factor B, and factor H collaborate to determine systemic complement activity and disease risk." *Proc. Natl. Acad. Sci. U S. A* 108(21): 8761-8766, (2011).
Harboe, M., et al., "Design of a complement mannose-binding lectin pathway-specific activation system applicable at low serum dilutions." *Clin. Exp. Immunol* 144(3): 512-520, (2006).

Faria, B., et al., "Combined C4d and CD3 immunostaining predicts immunoglobulin (Ig)A nephropathy progression." *Clin Exp Immunol* 179(2): 354-361, (2015).
Oortwijn, B. D., et al., "Demonstration of secretory IgA in kidneys of patients with IgA nephropathy." *Nephrol Dial Transplant* 22(11): 3191-3195, (2007).
Daha, M. R., et al., "Role of complement in IgA nephropathy," *J Nephrol* 29(1): 1-4, (2016).
Nasri, H., et al. (2015). "Association of glomerular C4d deposition with various demographic data in IgA nephropathy patients; a preliminary study." J Nephropathol 4(1): 19-23.
Glassock, R. J., "IgA nephropathy: challenges and opportunities." *Cleve Clin J Med* 75(8): 569-576, (2008).
Ohsawa, I., et al., "Cryoprecipitate of patients with cryoglobulinemic glomerulonephritis contains molecules of the lectin complement pathway," *Clin Immunol* 101(1):59-66 (2001).
Endo, M., et al., "Regulation of in situ complement activation via the lectin pathway in patients with IgA nephropathy," *Clin Nephrol* 55(3):185-191 (2001).
Endo, M., et al., "Complement activation through the lectin pathway in patients with Henoch-Schonlein purpura nephritis," *Am J Kidney Dis* 35(3):401-407 (2000).
Donadio, J.V., et al., "IgA nephrology," *N Eng J Med* 347(10):738-748 (2002).
Geddes, C.C., et al., "A tricomtonental view of IgA nephropathy," *Nephrol Dial Transplant* 18:1541-1548 (2003).
Inker, L.A., et al., "GFR decline as an alternative end point to kidney failure in clinical trials: A meta-analysis of treatment effects from 37 randomized trials," *Am J Kidney Dis* 64(6):848-859 (2014).
Inker, L.A., et al., "Early change in urine proein as a surrogate end point in studies of IgA nephropathy: An individual-patient meta-analysis," *Am J Kidney Dis* 68(3):392-401 (2016).
Levey, A.S., et al., "GFR decline as an end point for clinical trials in CKD: A scientific workshop sponsored by the national kidney foundation and the US food and drug administration," *Am J Kid Dis* 64(6):821-835 (2014).
Ohsawa, I., et al., "Pathological scenario with the mannose-binding lectin in patients with IgA nephropathy," *J Biomed Biotechnol* 2012:476739 (2012). Epub Apr. 10, 2012.
Pettersson, E., "IgA nephropathy: 30 years on," *J Int Med* 242:349-353 (1997).
Reich, H.N., et al., "Remission of proteinuria improves prognosis in IgA nephropathy," *J Am Soc Nephrol* 18:3177-3183 (2007).
Schena, F.P., "A retrospective analysis of the natural history of primary IgA nephropathy worldwide" *Am J Med* 89:209-215 (1990).
Tang, S.C.W., et al., "Long-term study of mycophenolate mofetil treatment in IgA nephropathy," *Kidney Int* 77:543-549 (2010).
Kamei, K., et al., "Risk factors for persistent proteinuria after a 2-year combination therapy for severe childhood IgA nephropathy," *Pediatr Nephrol* 30:961-967 (2015).
Ong, A.C.M., et al., "Loss of glomerular function and tubulointerstitial fibrosis: Cause or effect?" *Kidney Internationl* 45:345-351 (1994).
Tang, S., et al., "Mycophenylate mofetil alleviates persistent proteinuria in IgA nephropathy," *Kidney International* 68:802-812 (2005).
Ricklin, D., et al., "Complement in immune and inflammatory disorders: Therapeutic interventions," *J Immunol* 190:3839-3847 (2013).
Omeros Corporation; "Omeros Announces Additional Positive Data in OMS721 Phase 2 Clinical Trial—Company Plans for Phase 3 Program Based on Consistent Response in TMA Patients" Press Release; Aug. 18, 2015; [Available from: https://investor.omeros.com/news-releases/news-release-details/omeros-announces-additional-positive-data-oms721-phase-2]; (2015).
Nangaku, M., et al., "Mechanisms of immune-deposit formation and the mediation of immune renal injury," *Clin Exp Nephrol* 9(3):183-191 (2005).
Ma, H.; et al., "The role of complement in membranous nephropathy," *Semin Nephrol* 33(6):531-542 (2013).
Lv, J., et al., "Corticosteroid therapy in IgA nephropathy," *J Am Soc Nephrol* 23(6):1108-1116 (2012).
Howman, A., et al., "Immunosuppression for progressive membranous nephropathy: a UK randomised controlled trial," *Lancet* 381(9868):744-751 (2013).

(56) References Cited

OTHER PUBLICATIONS

Nowicki, M., et al., "Dose-Finding Clinical Trial of OMS721 for the Treatment of Atypical Hemolytic Uremic Syndrome (aHUS)—Stage 1 Results;" Poster No. SAT-218; International Society of Nephrology's World Congress of Nephrology; Mexico City, MX; Apr. 22, 2017; [Abstract of Poster Published on the International Society of Nephrology website at: https://www.theisn.org/], (2017).

Omeros Corporation; "Omeros to Present Results from Dose-Ranging Stage of OMS721 Clinical Trial in Atypical Hemolytic Uremic Syndrome at World Congress of Nephrology;" Press Release; Mar. 27, 2017; [Available from: https://investor.omeros.com/news-releases/news-release-details/omerospresent-results-dose-ranging-stage-oms721-clinical-trial#]; (2017).

Block, G., et al., "The Effect of Oms721 on Proteinuria in Patients with Iga Nephropathy," *Nephrol Dial Transpl* 32:iii143 (2017).

El Karoui, K., et al., "A clinicopathologic study of thrombotic microangiopathy in IgA nephropathy," *J Am Soc Nephrol* 23(1):137-148 (2012).

Khaled, S. K., et al., "Early Results of Phase II Study Using OMS721 in Patients with Hematopoietic Stem Cell Transplant-Associated Thrombotic Microangiopathy (HCT-TMA)," *Biol Blood Marrow Transplant* 23(3):S282-S283 (2017).

Wallim, L. R., et al., "Mannose binding lectin deposition in skin of lupus erythematosus patients: a case series," *Hum Immunol* 75(7):629-632 (2014).

Nisihara, R. M., et al., "Deposition of the lectin pathway of complement in renal biopsies of lupus nephritis patients," *Hum Immunol* 74(8):907-910 (2013).

Panda, A. K., et al., "Mannose binding lectin: a biomarker of systemic lupus erythematosus disease activity," *Arthritis Res Ther* 14(5):R218 (2012).

John Hopkins, Immunosuppresive Medications 2014 [Available from: https://web.archive.org/web20141215155451/https://www.hopkinslupus.org/lupus-medfications/immunosuppressive-medications/].

Mok, C. C., et al., "Tacrolimus for induction therapy of diffuse proliferative lupus nephritis: an open-labeled pilot study," *Kidney Int* 68(2):813-817 (2005).

* cited by examiner

**p=0.0035

*p=0.0109

* p=0.0182

*p=0.0477

**p=0.0002
***p=0.0052

*p = 0.0324
**p = 0.0349

*p=0.011
**p=0.0285 though with low affinity, with multiple MBL carbohydrate recognition domains. MBL recognizes the carbohydrate patterns that decorate a large number of microorganisms including bacteria, yeast, parasites and certain viruses. In contrast, MBL does not recognize D-galactose and sialic acid, the penultimate and ultimate sugars that usually "decorate" complex glycoconjugates present on mammalian plasma membranes and serum glycoproteins. This binding specificity is thought to help protect from self-activation. However, MBL does bind with high affinity to clusters of high-mannose "precursor" glycans on N-linked glycoproteins sequestered in the endoplasmic reticulum and Golgi of mammalian cells (Maynard and Baenziger, J. Biol. Chem. 257:3788-3794, (1982); Mizuno et al., J. Biol. Chem. 256:4247-4252 (1981)). In addition, MBL binds to cytokeratin on aberrant glycoproteins found on the surface of necrotic and apoptotic cells (Collard et al., Am. J. Pathol. 156:1549-1556, (2000); Nauta et al., Eur. J. Immunol. 33:2853-2863, (2003)).

SEQUENCE LISTING

```
<160> NUMBER OF SEQ ID NOS: 85

<210> SEQ ID NO 1
<211> LENGTH: 725
<212> TYPE: DNA
<213> ORGANISM: Homo sapiens
<220> FEATURE:
<221> NAME/KEY: CDS
<222> LOCATION: (27)..(584)

<400> SEQUENCE: 1
ggccaggcca gctggacggg cacacc atg agg ctg ctg acc ctc ctg ggc ctt      53
                              Met Arg Leu Leu Thr Leu Leu Gly Leu
                                1               5 ctg tgt ggc tcg gtg gcc acc ccc ttg ggc ccg aag tgg cct gaa cct     101
Leu Cys Gly Ser Val Ala Thr Pro Leu Gly Pro Lys Trp Pro Glu Pro
 10                  15                  20                  25 gtg ttc ggg cgc ctg gca tcc ccc ggc ttt cca ggg gag tat gcc aat     149
Val Phe Gly Arg Leu Ala Ser Pro Gly Phe Pro Gly Glu Tyr Ala Asn
                 30                  35                  40 gac cag gag cgg cgc tgg acc ctg act gca ccc ccc ggc tac cgc ctg     197
Asp Gln Glu Arg Arg Trp Thr Leu Thr Ala Pro Pro Gly Tyr Arg Leu
             45                  50                  55 cgc ctc tac ttc acc cac ttc gac ctg gag ctc tcc cac ctc tgc gag     245
Arg Leu Tyr Phe Thr His Phe Asp Leu Glu Leu Ser His Leu Cys Glu
         60                  65                  70 tac gac ttc gtc aag ctg agc tcg ggg gcc aag gtg ctg gcc acg ctg     293
Tyr Asp Phe Val Lys Leu Ser Ser Gly Ala Lys Val Leu Ala Thr Leu
     75                  80                  85 tgc ggg cag gag agc aca gac acg gag cgg gcc cct ggc aag gac act     341
Cys Gly Gln Glu Ser Thr Asp Thr Glu Arg Ala Pro Gly Lys Asp Thr
 90                  95                 100                 105 ttc tac tcg ctg ggc tcc agc ctg gac att acc ttc cgc tcc gac tac     389
Phe Tyr Ser Leu Gly Ser Ser Leu Asp Ile Thr Phe Arg Ser Asp Tyr
                110                 115                 120 tcc aac gag aag ccg ttc acg ggg ttc gag gcc ttc tat gca gcc gag     437
Ser Asn Glu Lys Pro Phe Thr Gly Phe Glu Ala Phe Tyr Ala Ala Glu
```

-continued

```
                    125                 130                 135
gac att gac gag tgc cag gtg gcc ccg gga gag gcg ccc acc tgc gac       485
Asp Ile Asp Glu Cys Gln Val Ala Pro Gly Glu Ala Pro Thr Cys Asp
        140                 145                 150 cac cac tgc cac aac cac ctg ggc ggt ttc tac tgc tcc tgc cgc gca       533
His His Cys His Asn His Leu Gly Gly Phe Tyr Cys Ser Cys Arg Ala
    155                 160                 165 ggc tac gtc ctg cac cgt aac aag cgc acc tgc tca gag cag agc ctc       581
Gly Tyr Val Leu His Arg Asn Lys Arg Thr Cys Ser Glu Gln Ser Leu
170                 175                 180                 185 tag cctcccctgg agctccggcc tgcccagcag gtcagaagcc agagccagcc            634
tgctggcctc agctccgggt tgggctgaga tggctgtgcc ccaactccca ttcacccacc     694
atggacccaa taataaacct ggccccaccc c                                    725
```

<210> SEQ ID NO 2
<211> LENGTH: 185
<212> TYPE: PRT
<213> ORGANISM: Homo sapiens

<400> SEQUENCE: 2

```
Met Arg Leu Leu Thr Leu Leu Gly Leu Leu Cys Gly Ser Val Ala Thr
1               5                   10                  15

Pro Leu Gly Pro Lys Trp Pro Glu Pro Val Phe Gly Arg Leu Ala Ser
            20                  25                  30

Pro Gly Phe Pro Gly Glu Tyr Ala Asn Asp Gln Glu Arg Arg Trp Thr
        35                  40                  45

Leu Thr Ala Pro Pro Gly Tyr Arg Leu Arg Leu Tyr Phe Thr His Phe
    50                  55                  60

Asp Leu Glu Leu Ser His Leu Cys Glu Tyr Asp Phe Val Lys Leu Ser
65                  70                  75                  80

Ser Gly Ala Lys Val Leu Ala Thr Leu Cys Gly Gln Glu Ser Thr Asp
                85                  90                  95

Thr Glu Arg Ala Pro Gly Lys Asp Thr Phe Tyr Ser Leu Gly Ser Ser
            100                 105                 110

Leu Asp Ile Thr Phe Arg Ser Asp Tyr Ser Asn Glu Lys Pro Phe Thr
        115                 120                 125

Gly Phe Glu Ala Phe Tyr Ala Ala Glu Asp Ile Asp Glu Cys Gln Val
    130                 135                 140

Ala Pro Gly Glu Ala Pro Thr Cys Asp His His Cys His Asn His Leu
145                 150                 155                 160

Gly Gly Phe Tyr Cys Ser Cys Arg Ala Gly Tyr Val Leu His Arg Asn
                165                 170                 175

Lys Arg Thr Cys Ser Glu Gln Ser Leu
            180                 185
```

<210> SEQ ID NO 3
<211> LENGTH: 170
<212> TYPE: PRT
<213> ORGANISM: Homo sapiens

<400> SEQUENCE: 3

```
Thr Pro Leu Gly Pro Lys Trp Pro Glu Pro Val Phe Gly Arg Leu Ala
1               5                   10                  15

Ser Pro Gly Phe Pro Gly Glu Tyr Ala Asn Asp Gln Glu Arg Arg Trp
            20                  25                  30

Thr Leu Thr Ala Pro Pro Gly Tyr Arg Leu Arg Leu Tyr Phe Thr His
```

```
                35                  40                  45
Phe Asp Leu Glu Leu Ser His Leu Cys Glu Tyr Asp Phe Val Lys Leu
 50                  55                  60
Ser Ser Gly Ala Lys Val Leu Ala Thr Leu Cys Gly Gln Glu Ser Thr
65                  70                  75                  80
Asp Thr Glu Arg Ala Pro Gly Lys Asp Thr Phe Tyr Ser Leu Gly Ser
                85                  90                  95
Ser Leu Asp Ile Thr Phe Arg Ser Asp Tyr Ser Asn Glu Lys Pro Phe
            100                 105                 110
Thr Gly Phe Glu Ala Phe Tyr Ala Ala Glu Asp Ile Asp Glu Cys Gln
        115                 120                 125
Val Ala Pro Gly Glu Ala Pro Thr Cys Asp His His Cys His Asn His
    130                 135                 140
Leu Gly Gly Phe Tyr Cys Ser Cys Arg Ala Gly Tyr Val Leu His Arg
145                 150                 155                 160
Asn Lys Arg Thr Cys Ser Glu Gln Ser Leu
                165                 170

<210> SEQ ID NO 4
<211> LENGTH: 2460
<212> TYPE: DNA
<213> ORGANISM: Homo sapiens
<220> FEATURE:
<221> NAME/KEY: CDS
<222> LOCATION: (22)..(2082)

<400> SEQUENCE: 4
```

| | | | | | | | | | | | | |
|---|---|---|---|---|---|---|---|---|---|---|---|---|
| ggccagctgg acgggcacac c | atg | agg | ctg | ctg | acc | ctc | ctg | ggc | ctt | ctg | | 51 |
| | Met | Arg | Leu | Leu | Thr | Leu | Leu | Gly | Leu | Leu | | |
| | 1 | | | | 5 | | | | | 10 | | |
| tgt | ggc | tcg | gtg | gcc | acc | ccc | ttg | ggc | ccg | aag | tgg cct gaa cct gtg | 99 |
| Cys | Gly | Ser | Val | Ala | Thr | Pro | Leu | Gly | Pro | Lys | Trp Pro Glu Pro Val | |
| | | | | 15 | | | | | 20 | | 25 | |
| ttc | ggg | cgc | ctg | gca | tcc | ccc | ggc | ttt | cca | ggg | gag tat gcc aat gac | 147 |
| Phe | Gly | Arg | Leu | Ala | Ser | Pro | Gly | Phe | Pro | Gly | Glu Tyr Ala Asn Asp | |
| | | | 30 | | | | | 35 | | | 40 | |
| cag | gag | cgg | cgc | tgg | acc | ctg | act | gca | ccc | ccc | ggc tac cgc ctg cgc | 195 |
| Gln | Glu | Arg | Arg | Trp | Thr | Leu | Thr | Ala | Pro | Pro | Gly Tyr Arg Leu Arg | |
| | | 45 | | | | | 50 | | | | 55 | |
| ctc | tac | ttc | acc | cac | ttc | gac | ctg | gag | ctc | tcc | cac ctc tgc gag tac | 243 |
| Leu | Tyr | Phe | Thr | His | Phe | Asp | Leu | Glu | Leu | Ser | His Leu Cys Glu Tyr | |
| | 60 | | | | | 65 | | | | | 70 | |
| gac | ttc | gtc | aag | ctg | agc | tcg | ggg | gcc | aag | gtg | ctg gcc acg ctg tgc | 291 |
| Asp | Phe | Val | Lys | Leu | Ser | Ser | Gly | Ala | Lys | Val | Leu Ala Thr Leu Cys | |
| 75 | | | | | 80 | | | | | 85 | | 90 |
| ggg | cag | gag | agc | aca | gac | acg | gag | cgg | gcc | cct | ggc aag gac act ttc | 339 |
| Gly | Gln | Glu | Ser | Thr | Asp | Thr | Glu | Arg | Ala | Pro | Gly Lys Asp Thr Phe | |
| | | | | 95 | | | | | 100 | | | 105 |
| tac | tcg | ctg | ggc | tcc | agc | ctg | gac | att | acc | ttc | cgc tcc gac tac tcc | 387 |
| Tyr | Ser | Leu | Gly | Ser | Ser | Leu | Asp | Ile | Thr | Phe | Arg Ser Asp Tyr Ser | |
| | | | 110 | | | | | 115 | | | | 120 |
| aac | gag | aag | ccg | ttc | acg | ggg | ttc | gag | gcc | ttc | tat gca gcc gag gac | 435 |
| Asn | Glu | Lys | Pro | Phe | Thr | Gly | Phe | Glu | Ala | Phe | Tyr Ala Ala Glu Asp | |
| | | 125 | | | | | 130 | | | | | 135 |
| att | gac | gag | tgc | cag | gtg | gcc | ccg | gga | gag | gcg | ccc acc tgc gac cac | 483 |
| Ile | Asp | Glu | Cys | Gln | Val | Ala | Pro | Gly | Glu | Ala | Pro Thr Cys Asp His | |
| | 140 | | | | | 145 | | | | | 150 | |
| cac | tgc | cac | aac | cac | ctg | ggc | ggt | ttc | tac | tgc | tcc tgc cgc gca ggc | 531 |
| His | Cys | His | Asn | His | Leu | Gly | Gly | Phe | Tyr | Cys | Ser Cys Arg Ala Gly | |

```
                                                          -continued
       155                 160                 165                 170
tac gtc ctg cac cgt aac aag cgc acc tgc tca gcc ctg tgc tcc ggc          579
Tyr Val Leu His Arg Asn Lys Arg Thr Cys Ser Ala Leu Cys Ser Gly
                    175                 180                 185 cag gtc ttc acc cag agg tct ggg gag ctc agc agc cct gaa tac cca          627
Gln Val Phe Thr Gln Arg Ser Gly Glu Leu Ser Ser Pro Glu Tyr Pro
                190                 195                 200 cgg ccg tat ccc aaa ctc tcc agt tgc act tac agc atc agc ctg gag          675
Arg Pro Tyr Pro Lys Leu Ser Ser Cys Thr Tyr Ser Ile Ser Leu Glu
            205                 210                 215 gag ggg ttc agt gtc att ctg gac ttt gtg gag tcc ttc gat gtg gag          723
Glu Gly Phe Ser Val Ile Leu Asp Phe Val Glu Ser Phe Asp Val Glu
        220                 225                 230 aca cac cct gaa acc ctg tgt ccc tac gac ttt ctc aag att caa aca          771
Thr His Pro Glu Thr Leu Cys Pro Tyr Asp Phe Leu Lys Ile Gln Thr
235                 240                 245                 250 gac aga gaa gaa cat ggc cca ttc tgt ggg aag aca ttg ccc cac agg          819
Asp Arg Glu Glu His Gly Pro Phe Cys Gly Lys Thr Leu Pro His Arg
                    255                 260                 265 att gaa aca aaa agc aac acg gtg acc atc acc ttt gtc aca gat gaa          867
Ile Glu Thr Lys Ser Asn Thr Val Thr Ile Thr Phe Val Thr Asp Glu
                270                 275                 280 tca gga gac cac aca ggc tgg aag atc cac tac acg agc aca gcg cag          915
Ser Gly Asp His Thr Gly Trp Lys Ile His Tyr Thr Ser Thr Ala Gln
            285                 290                 295 cct tgc cct tat ccg atg gcg cca cct aat ggc cac gtt tca cct gtg          963
Pro Cys Pro Tyr Pro Met Ala Pro Pro Asn Gly His Val Ser Pro Val
        300                 305                 310 caa gcc aaa tac atc ctg aaa gac agc ttc tcc atc ttt tgc gag act         1011
Gln Ala Lys Tyr Ile Leu Lys Asp Ser Phe Ser Ile Phe Cys Glu Thr
315                 320                 325                 330 ggc tat gag ctt ctg caa ggt cac ttg ccc ctg aaa tcc ttt act gca         1059
Gly Tyr Glu Leu Leu Gln Gly His Leu Pro Leu Lys Ser Phe Thr Ala
                    335                 340                 345 gtt tgt cag aaa gat gga tct tgg gac cgg cca atg ccc gcg tgc agc         1107
Val Cys Gln Lys Asp Gly Ser Trp Asp Arg Pro Met Pro Ala Cys Ser
                350                 355                 360 att gtt gac tgt ggc cct cct gat gat cta ccc agt ggc cga gtg gag         1155
Ile Val Asp Cys Gly Pro Pro Asp Asp Leu Pro Ser Gly Arg Val Glu
            365                 370                 375 tac atc aca ggt cct gga gtg acc acc tac aaa gct gtg att cag tac         1203
Tyr Ile Thr Gly Pro Gly Val Thr Thr Tyr Lys Ala Val Ile Gln Tyr
        380                 385                 390 agc tgt gaa gag acc ttc tac aca atg aaa gtg aat gat ggt aaa tat         1251
Ser Cys Glu Glu Thr Phe Tyr Thr Met Lys Val Asn Asp Gly Lys Tyr
395                 400                 405                 410 gtg tgt gag gct gat gga ttc tgg acg agc tcc aaa gga gaa aaa tca         1299
Val Cys Glu Ala Asp Gly Phe Trp Thr Ser Ser Lys Gly Glu Lys Ser
                    415                 420                 425 ctc cca gtc tgt gag cct gtt tgt gga cta tca gcc cgc aca aca gga         1347
Leu Pro Val Cys Glu Pro Val Cys Gly Leu Ser Ala Arg Thr Thr Gly
                430                 435                 440 ggg cgt ata tat gga ggg caa aag gca aaa cct ggt gat ttt cct tgg         1395
Gly Arg Ile Tyr Gly Gly Gln Lys Ala Lys Pro Gly Asp Phe Pro Trp
            445                 450                 455 caa gtc ctg ata tta ggt gga acc aca gca gca ggt gca ctt tat tat         1443
Gln Val Leu Ile Leu Gly Gly Thr Thr Ala Ala Gly Ala Leu Leu Tyr
        460                 465                 470 gac aac tgg gtc cta aca gct gct cat gcc gtc tat gag caa aaa cat         1491
```

```
Asp Asn Trp Val Leu Thr Ala Ala His Ala Val Tyr Glu Gln Lys His
475                 480                 485                 490 gat gca tcc gcc ctg gac att cga atg ggc acc ctg aaa aga cta tca      1539
Asp Ala Ser Ala Leu Asp Ile Arg Met Gly Thr Leu Lys Arg Leu Ser
                495                 500                 505 cct cat tat aca caa gcc tgg tct gaa gct gtt ttt ata cat gaa ggt      1587
Pro His Tyr Thr Gln Ala Trp Ser Glu Ala Val Phe Ile His Glu Gly
                510                 515                 520 tat act cat gat gct ggc ttt gac aat gac ata gca ctg att aaa ttg      1635
Tyr Thr His Asp Ala Gly Phe Asp Asn Asp Ile Ala Leu Ile Lys Leu
            525                 530                 535 aat aac aaa gtt gta atc aat agc aac atc acg cct att tgt ctg cca      1683
Asn Asn Lys Val Val Ile Asn Ser Asn Ile Thr Pro Ile Cys Leu Pro
        540                 545                 550 aga aaa gaa gct gaa tcc ttt atg agg aca gat gac att gga act gca      1731
Arg Lys Glu Ala Glu Ser Phe Met Arg Thr Asp Asp Ile Gly Thr Ala
555                 560                 565                 570 tct gga tgg gga tta acc caa agg ggt ttt ctt gct aga aat cta atg      1779
Ser Gly Trp Gly Leu Thr Gln Arg Gly Phe Leu Ala Arg Asn Leu Met
                575                 580                 585 tat gtc gac ata ccg att gtt gac cat caa aaa tgt act gct gca tat      1827
Tyr Val Asp Ile Pro Ile Val Asp His Gln Lys Cys Thr Ala Ala Tyr
                590                 595                 600 gaa aag cca ccc tat cca agg gga agt gta act gct aac atg ctt tgt      1875
Glu Lys Pro Pro Tyr Pro Arg Gly Ser Val Thr Ala Asn Met Leu Cys
            605                 610                 615 gct ggc tta gaa agt ggg ggc aag gac agc tgc aga ggt gac agc gga      1923
Ala Gly Leu Glu Ser Gly Gly Lys Asp Ser Cys Arg Gly Asp Ser Gly
620                 625                 630 ggg gca ctg gtg ttt cta gat agt gaa aca gag agg tgg ttt gtg gga      1971
Gly Ala Leu Val Phe Leu Asp Ser Glu Thr Glu Arg Trp Phe Val Gly
635                 640                 645                 650 gga ata gtg tcc tgg ggt tcc atg aat tgt ggg gaa gca ggt cag tat      2019
Gly Ile Val Ser Trp Gly Ser Met Asn Cys Gly Glu Ala Gly Gln Tyr
                655                 660                 665 gga gtc tac aca aaa gtt att aac tat att ccc tgg atc gag aac ata      2067
Gly Val Tyr Thr Lys Val Ile Asn Tyr Ile Pro Trp Ile Glu Asn Ile
                670                 675                 680 att agt gat ttt taa cttgcgtgtc tgcagtcaag gattcttcat ttttagaaat      2122
Ile Ser Asp Phe
            685 gcctgtgaag accttggcag cgacgtggct cgagaagcat tcatcattac tgtggacatg    2182 gcagttgttg ctcccaccca aaaaacagac tccaggtgag ctgctgtca tttctccact     2242 tgccagttta attccagcct tacccattga ctcaagggga cataaaccac gagagtgaca    2302 gtcatctttg cccacccagt gtaatgtcac tgctcaaatt acatttcatt accttaaaaa    2362 gccagtctct tttcatactg gctgttggca tttctgtaaa ctgcctgtcc atgctctttg    2422 tttttaaact tgttcttatt gaaaaaaaaa aaaaaaa                             2460

<210> SEQ ID NO 5
<211> LENGTH: 686
<212> TYPE: PRT
<213> ORGANISM: Homo sapiens

<400> SEQUENCE: 5

Met Arg Leu Leu Thr Leu Leu Gly Leu Leu Cys Gly Ser Val Ala Thr
1               5                   10                  15

Pro Leu Gly Pro Lys Trp Pro Glu Pro Val Phe Gly Arg Leu Ala Ser
```

```
            20                  25                  30
Pro Gly Phe Pro Gly Glu Tyr Ala Asn Asp Gln Glu Arg Arg Trp Thr
            35                  40                  45
Leu Thr Ala Pro Pro Gly Tyr Arg Leu Arg Leu Tyr Phe Thr His Phe
50                      55                  60
Asp Leu Glu Leu Ser His Leu Cys Glu Tyr Asp Phe Val Lys Leu Ser
65                  70                  75                  80
Ser Gly Ala Lys Val Leu Ala Thr Leu Cys Gly Gln Glu Ser Thr Asp
                85                  90                  95
Thr Glu Arg Ala Pro Gly Lys Asp Thr Phe Tyr Ser Leu Gly Ser Ser
                100                 105                 110
Leu Asp Ile Thr Phe Arg Ser Asp Tyr Ser Asn Glu Lys Pro Phe Thr
                115                 120                 125
Gly Phe Glu Ala Phe Tyr Ala Ala Glu Asp Ile Asp Glu Cys Gln Val
                130                 135                 140
Ala Pro Gly Glu Ala Pro Thr Cys Asp His His Cys His Asn His Leu
145                 150                 155                 160
Gly Gly Phe Tyr Cys Ser Cys Arg Ala Gly Tyr Val Leu His Arg Asn
                165                 170                 175
Lys Arg Thr Cys Ser Ala Leu Cys Ser Gly Gln Val Phe Thr Gln Arg
                180                 185                 190
Ser Gly Glu Leu Ser Ser Pro Glu Tyr Pro Arg Pro Tyr Pro Lys Leu
                195                 200                 205
Ser Ser Cys Thr Tyr Ser Ile Ser Leu Glu Glu Gly Phe Ser Val Ile
                210                 215                 220
Leu Asp Phe Val Glu Ser Phe Asp Val Glu Thr His Pro Glu Thr Leu
225                 230                 235                 240
Cys Pro Tyr Asp Phe Leu Lys Ile Gln Thr Asp Arg Glu Glu His Gly
                245                 250                 255
Pro Phe Cys Gly Lys Thr Leu Pro His Arg Ile Glu Thr Lys Ser Asn
                260                 265                 270
Thr Val Thr Ile Thr Phe Val Thr Asp Glu Ser Gly Asp His Thr Gly
                275                 280                 285
Trp Lys Ile His Tyr Thr Ser Thr Ala Gln Pro Cys Pro Tyr Pro Met
                290                 295                 300
Ala Pro Pro Asn Gly His Val Ser Pro Val Gln Ala Lys Tyr Ile Leu
305                 310                 315                 320
Lys Asp Ser Phe Ser Ile Phe Cys Glu Thr Gly Tyr Glu Leu Leu Gln
                325                 330                 335
Gly His Leu Pro Leu Lys Ser Phe Thr Ala Val Cys Gln Lys Asp Gly
                340                 345                 350
Ser Trp Asp Arg Pro Met Pro Ala Cys Ser Ile Val Asp Cys Gly Pro
                355                 360                 365
Pro Asp Asp Leu Pro Ser Gly Arg Val Glu Tyr Ile Thr Gly Pro Gly
                370                 375                 380
Val Thr Thr Tyr Lys Ala Val Ile Gln Tyr Ser Cys Glu Glu Thr Phe
385                 390                 395                 400
Tyr Thr Met Lys Val Asn Asp Gly Lys Tyr Val Cys Glu Ala Asp Gly
                405                 410                 415
Phe Trp Thr Ser Ser Lys Gly Glu Lys Ser Leu Pro Val Cys Glu Pro
                420                 425                 430
Val Cys Gly Leu Ser Ala Arg Thr Thr Gly Gly Arg Ile Tyr Gly Gly
                435                 440                 445
```

```
Gln Lys Ala Lys Pro Gly Asp Phe Pro Trp Gln Val Leu Ile Leu Gly
    450                 455                 460
Gly Thr Thr Ala Ala Gly Ala Leu Leu Tyr Asp Asn Trp Val Leu Thr
465                 470                 475                 480
Ala Ala His Ala Val Tyr Glu Gln Lys His Asp Ala Ser Ala Leu Asp
                485                 490                 495
Ile Arg Met Gly Thr Leu Lys Arg Leu Ser Pro His Tyr Thr Gln Ala
            500                 505                 510
Trp Ser Glu Ala Val Phe Ile His Glu Gly Tyr Thr His Asp Ala Gly
        515                 520                 525
Phe Asp Asn Asp Ile Ala Leu Ile Lys Leu Asn Asn Lys Val Val Ile
    530                 535                 540
Asn Ser Asn Ile Thr Pro Ile Cys Leu Pro Arg Lys Glu Ala Glu Ser
545                 550                 555                 560
Phe Met Arg Thr Asp Asp Ile Gly Thr Ala Ser Gly Trp Gly Leu Thr
                565                 570                 575
Gln Arg Gly Phe Leu Ala Arg Asn Leu Met Tyr Val Asp Ile Pro Ile
            580                 585                 590
Val Asp His Gln Lys Cys Thr Ala Ala Tyr Glu Lys Pro Pro Tyr Pro
        595                 600                 605
Arg Gly Ser Val Thr Ala Asn Met Leu Cys Ala Gly Leu Glu Ser Gly
    610                 615                 620
Gly Lys Asp Ser Cys Arg Gly Asp Ser Gly Gly Ala Leu Val Phe Leu
625                 630                 635                 640
Asp Ser Glu Thr Glu Arg Trp Phe Val Gly Gly Ile Val Ser Trp Gly
                645                 650                 655
Ser Met Asn Cys Gly Glu Ala Gly Gln Tyr Gly Val Tyr Thr Lys Val
            660                 665                 670
Ile Asn Tyr Ile Pro Trp Ile Glu Asn Ile Ile Ser Asp Phe
        675                 680                 685

<210> SEQ ID NO 6
<211> LENGTH: 671
<212> TYPE: PRT
<213> ORGANISM: Homo sapiens

<400> SEQUENCE: 6

Thr Pro Leu Gly Pro Lys Trp Pro Glu Pro Val Phe Gly Arg Leu Ala
1               5                   10                  15
Ser Pro Gly Phe Pro Gly Glu Tyr Ala Asn Asp Gln Glu Arg Arg Trp
            20                  25                  30
Thr Leu Thr Ala Pro Pro Gly Tyr Arg Leu Arg Leu Tyr Phe Thr His
        35                  40                  45
Phe Asp Leu Glu Leu Ser His Leu Cys Glu Tyr Asp Phe Val Lys Leu
    50                  55                  60
Ser Ser Gly Ala Lys Val Leu Ala Thr Leu Cys Gly Gln Glu Ser Thr
65                  70                  75                  80
Asp Thr Glu Arg Ala Pro Gly Lys Asp Thr Phe Tyr Ser Leu Gly Ser
                85                  90                  95
Ser Leu Asp Ile Thr Phe Arg Ser Asp Tyr Ser Asn Glu Lys Pro Phe
            100                 105                 110
Thr Gly Phe Glu Ala Phe Tyr Ala Ala Glu Asp Ile Asp Glu Cys Gln
        115                 120                 125
Val Ala Pro Gly Glu Ala Pro Thr Cys Asp His His Cys His Asn His
```

-continued

```
            130                 135                 140
Leu Gly Gly Phe Tyr Cys Ser Cys Arg Ala Gly Tyr Val Leu His Arg
145                 150                 155                 160

Asn Lys Arg Thr Cys Ser Ala Leu Cys Ser Gly Gln Val Phe Thr Gln
                165                 170                 175

Arg Ser Gly Glu Leu Ser Ser Pro Glu Tyr Pro Arg Pro Tyr Pro Lys
            180                 185                 190

Leu Ser Ser Cys Thr Tyr Ser Ile Ser Leu Glu Glu Gly Phe Ser Val
                195                 200                 205

Ile Leu Asp Phe Val Glu Ser Phe Asp Val Glu Thr His Pro Glu Thr
            210                 215                 220

Leu Cys Pro Tyr Asp Phe Leu Lys Ile Gln Thr Asp Arg Glu Glu His
225                 230                 235                 240

Gly Pro Phe Cys Gly Lys Thr Leu Pro His Arg Ile Glu Thr Lys Ser
                245                 250                 255

Asn Thr Val Thr Ile Thr Phe Val Thr Asp Glu Ser Gly Asp His Thr
                260                 265                 270

Gly Trp Lys Ile His Tyr Thr Ser Thr Ala Gln Pro Cys Pro Tyr Pro
            275                 280                 285

Met Ala Pro Pro Asn Gly His Val Ser Pro Val Gln Ala Lys Tyr Ile
290                 295                 300

Leu Lys Asp Ser Phe Ser Ile Phe Cys Glu Thr Gly Tyr Glu Leu Leu
305                 310                 315                 320

Gln Gly His Leu Pro Leu Lys Ser Phe Thr Ala Val Cys Gln Lys Asp
                325                 330                 335

Gly Ser Trp Asp Arg Pro Met Pro Ala Cys Ser Ile Val Asp Cys Gly
            340                 345                 350

Pro Pro Asp Asp Leu Pro Ser Gly Arg Val Glu Tyr Ile Thr Gly Pro
            355                 360                 365

Gly Val Thr Thr Tyr Lys Ala Val Ile Gln Tyr Ser Cys Glu Glu Thr
            370                 375                 380

Phe Tyr Thr Met Lys Val Asn Asp Gly Lys Tyr Val Cys Glu Ala Asp
385                 390                 395                 400

Gly Phe Trp Thr Ser Ser Lys Gly Glu Lys Ser Leu Pro Val Cys Glu
                405                 410                 415

Pro Val Cys Gly Leu Ser Ala Arg Thr Thr Gly Gly Arg Ile Tyr Gly
            420                 425                 430

Gly Gln Lys Ala Lys Pro Gly Asp Phe Pro Trp Gln Val Leu Ile Leu
            435                 440                 445

Gly Gly Thr Thr Ala Ala Gly Ala Leu Leu Tyr Asp Asn Trp Val Leu
            450                 455                 460

Thr Ala Ala His Ala Val Tyr Glu Gln Lys His Asp Ala Ser Ala Leu
465                 470                 475                 480

Asp Ile Arg Met Gly Thr Leu Lys Arg Leu Ser Pro His Tyr Thr Gln
                485                 490                 495

Ala Trp Ser Glu Ala Val Phe Ile His Glu Gly Tyr Thr His Asp Ala
                500                 505                 510

Gly Phe Asp Asn Asp Ile Ala Leu Ile Lys Leu Asn Asn Lys Val Val
            515                 520                 525

Ile Asn Ser Asn Ile Thr Pro Ile Cys Leu Pro Arg Lys Glu Ala Glu
            530                 535                 540

Ser Phe Met Arg Thr Asp Asp Ile Gly Thr Ala Ser Gly Trp Gly Leu
545                 550                 555                 560
```

```
Thr Gln Arg Gly Phe Leu Ala Arg Asn Leu Met Tyr Val Asp Ile Pro
            565                 570                 575
Ile Val Asp His Gln Lys Cys Thr Ala Ala Tyr Glu Lys Pro Pro Tyr
        580                 585                 590
Pro Arg Gly Ser Val Thr Ala Asn Met Leu Cys Ala Gly Leu Glu Ser
    595                 600                 605
Gly Gly Lys Asp Ser Cys Arg Gly Asp Ser Gly Gly Ala Leu Val Phe
610                 615                 620
Leu Asp Ser Glu Thr Glu Arg Trp Phe Val Gly Ile Val Ser Trp
625                 630                 635                 640
Gly Ser Met Asn Cys Gly Glu Ala Gly Gln Tyr Gly Val Tyr Thr Lys
                645                 650                 655
Val Ile Asn Tyr Ile Pro Trp Ile Glu Asn Ile Ile Ser Asp Phe
            660                 665                 670

<210> SEQ ID NO 7
<211> LENGTH: 4900
<212> TYPE: DNA
<213> ORGANISM: Homo sapiens

<400> SEQUENCE: 7
```

| | | | | | |
|---|---|---|---|---|---|
| cctgtcctgc | ctgcctggaa | ctctgagcag | gctggagtca | tggagtcgat | tcccagaatc | 60 |
| ccagagtcag | ggaggctggg | ggcaggggca | ggtcactgga | caaacagatc | aaaggtgaga | 120 |
| ccagcgtagg | actgcagacc | aggccaggcc | agctggacgg | gcacaccatg | aggtaggtgg | 180 |
| gcgccacagc | ctccctgcag | ggtgtggggt | gggagcacag | gcctgggcct | caccgcccct | 240 |
| gccctgccca | taggctgctg | accctcctgg | gccttctgtg | tggctcggtg | gccacccct | 300 |
| taggcccgaa | gtggcctgaa | cctgtgttcg | ggcgcctggc | atccccggc | tttccagggg | 360 |
| agtatgccaa | tgaccaggag | cggcgctgga | ccctgactgc | acccccggc | taccgcctgc | 420 |
| gcctctactt | cacccacttc | gacctggagc | tctcccacct | ctgcgagtac | gacttcgtca | 480 |
| aggtgccgtc | agacgggagg | gctggggttt | ctcagggtcg | gggggtcccc | aaggagtagc | 540 |
| cagggttcag | ggacacctgg | gagcagggggc | caggcttggc | caggagggag | atcaggcctg | 600 |
| ggtcttgcct | tcactccctg | tgacacctga | ccccacagct | gagctcgggg | gccaaggtgc | 660 |
| tggccacgct | gtgcgggcag | gagagcacag | acacggagcg | ggcccctggc | aaggacactt | 720 |
| tctactcgct | gggctccagc | ctggacatta | ccttccgctc | cgactactcc | aacgagaagc | 780 |
| cgttcacggg | gttcgaggcc | ttctatgcag | ccgagggtga | gccaagaggg | gtcctgcaac | 840 |
| atctcagtct | gcgcagctgg | ctgtgggggt | aactctgtct | taggccaggc | agccctgcct | 900 |
| tcagtttccc | cacctttccc | agggcagggg | agaggcctct | ggcctgacat | catccacaat | 960 |
| gcaaagacca | aaacagccgt | gacctccatt | cacatgggct | gagtgccaac | tctgagccag | 1020 |
| ggatctgagg | acagcatcgc | ctcaagtgac | gcagggactg | gccgggcgcg | gcagctcacg | 1080 |
| cctgtaattc | cagcactttg | ggaggccgag | gctggcttga | taatttgagg | gtcaggagtt | 1140 |
| caaggccagc | cagggcaaca | cggtgaaact | ctatctccac | taaaactaca | aaaattagct | 1200 |
| gggcgtggtg | gtgcgcacct | ggaatcccag | ctactaggga | ggctgaggca | ggagaattgc | 1260 |
| ttgaacctgc | gaggtggagg | ctgcagtgaa | cagagattgc | accactacac | tccacctggg | 1320 |
| cgacagacta | gactccgtct | caaaaaacaa | aaacaaaaa | ccacgcaggg | ccgagggccc | 1380 |
| atttacaagc | tgacaaagtg | ggccctgcca | gcggagcgc | tgcaggatgt | ttgattttca | 1440 |
| gatcccagtc | cctgcagaga | ccaactgtgt | gacctctggc | aagtggctca | atttctctgc | 1500 |

```
tccttagaag ctgctgcaag ggttcagcgc tgtagcccg ccccctgggt ttgattgact    1560
cccctcatta gctgggtgac ctcggccgga cactgaaact cccactggtt taacagaggt    1620
gatgtttgca tctttctccc agcgctgctg ggagcttgca gcgacccctag gcctgtaagg   1680
tgattggccc ggcaccagtc ccgcaccccta gacaggacct aggcctcctc tgaggtccac    1740
tctgaggtca tggatctcct gggaggagtc caggctggat ccgcctcttt tccctcctga    1800
cggcctgcct ggccctgcct ctcccccaga cattgacgag tgccaggtgg ccccgggaga    1860
ggcgcccacc tgcgaccacc actgccacaa ccacctgggc ggtttctact gctcctgccg    1920
cgcaggctac gtcctgcacc gtaacaagcg cacctgctca ggtgagggag gctgcctggg    1980
ccccaacgca ccctctcctg ggatacccgg ggctcctcag ggccattgct gctctgccca    2040
ggggtgcgga gggcctgggc ctggacactg ggtgcttcta ggccctgctg cctccagctc    2100
cccttctcag ccctgcttcc cctctcagca gccaggctca tcagtgccac cctgccctag    2160
cactgagact aattctaaca tcccactgtg tacctggttc cacctgggct ctgggaaccc    2220
ctcatgtagc cacgggagag tcggggtatc taccctcgtt ccttggactg ggttcctgtt    2280
ccctgcactg ggggacgggc cagtgctctg gggcgtgggc agcccaccc tgtgcgctg    2340
accctgctcc cccgactcgg tttctcctct cggggtctct ccttgcctct ctgatctctc    2400
ttccagagca gagcctctag cctccctgg agctccggct gcccagcagg tcagaagcca    2460
gagccaggct gctggcctca gctccgggtt gggctgagat gctgtgcccc aactcccatt    2520
cacccaccat ggacccaata ataaacctgg ccccacccca cctgctgccg cgtgtctctg    2580
gggtgggagg gtcgggaggc ggtggggcgc gctcctctct gcctaccctc ctcacagcct    2640
catgaacccc aggtctgtgg gagcctcctc catggggcca cacggtcctt ggcctcaccc    2700
cctgttttga agatggggca ctgaggccgg agaggggtaa ggcctcgctc gagtccaggt    2760
ccccagaggc tgagcccaga gtaatcttga accaccccca ttcagggtct ggcctggagg    2820
agcctgaccc acagaggaga caccctggga gatattcatt gaggggtaat ctggtccccc    2880
gcaaatccag gggtgattcc cactgcccca taggcacagc cacgtggaag aaggcaggca    2940
atgttgggggc tcctcacttc ctagaggcct cacaactcaa atgcccccca ctgcagctgg    3000
gggtggggtg gtggtatggg atggggacca agccttcctt gaaggataga gcccagccca    3060
acaccccgcc ccgtggcagc agcatcacgt gttccagcga ggaaggagag caccagactc    3120
agtcatgatc actgttgcct tgaacttcca agaacagccc cagggcaagg gtcaaaacag    3180
gggaaagggg gtgatgagag atccttcttc cggatgttcc tccaggaacc aggggctgg    3240
ctggtcttgg ctgggttcgg gtaggagacc catgatgaat aaacttggga atcactgggg    3300
tggctgtaag ggaatttagg ggagctccga agggccctt aggctcgagg agatgctcct    3360
ctcttttccc gaattcccag ggacccagga gagtgtccct tcttcctctt cctgtgtgtc    3420
catccacccc cgcccccgc cctggcagag ctggtggaac tcagtgctct agcccctacc    3480
ctggggttgc gactctggct caggacacca ccacgctccc tgggggtgtg agtgagggcc    3540
tgtgcgctcc atcccgagtg ctgcctgttt cagctaaagc ctcaaagcaa gagaaacccc    3600
ctctctaagc ggcccctcag ccatcgggtg ggtcgtttgg tttctgggta ggcctcaggg    3660
gctggccacc tgcagggccc agcccaaccc agggatgcag atgtcccagc cacatccctg    3720
tcccagtttc ctgctcccca aggcatccac cctgctgttg gtgcgagggc tgatagaggg    3780
cacgccaagt cactcccctg cccttccctc cttccagccc tgtgctccgg ccaggtcttc    3840
```

```
acccagaggt ctggggagct cagcagccct gaatacccac ggccgtatcc caaactctcc   3900
agttgcactt acagcatcag cctggaggag gggttcagtg tcattctgga ctttgtggag   3960
tccttcgatg tggagacaca ccctgaaacc ctgtgtccct acgactttct caaggtctgg   4020
ctcctgggcc cctcatcttg tcccagatcc tccccttca gcccagctgc acccctact    4080
tcctgcagca tggcccccac cacgttccg tcaccctcgg tgaccccacc tcttcaggtg    4140
ctctatggag gtcaaggctg gggcttcgag tacaagtgtg ggaggcagag tggggagggg   4200
caccccaatc catggcctgg gttggcctca ttggctgtcc ctgaaatgct gaggaggtgg   4260
gttacttccc tccgcccagg ccagaccag gcagctgctc cccagctttc atgagcttct    4320
ttctcagatt caaacagaca gagaagaaca tggcccattc tgtgggaaga cattgcccca   4380
caggattgaa acaaaaagca acacggtgac catcaccttt gtcacagatg aatcaggaga   4440
ccacacaggc tggaagatcc actacacgag cacagtgagc aagtgggctc agatccttgg   4500
tggaagcgca gagctgcctc tctctggagt gcaaggagct gtagagtgta gggctcttct   4560
gggcaggact aggaagggac accaggttta gtggtgctga ggtctgaggc agcagcttct   4620
aaggggaagc acccgtgccc tcctcagcag cacccagcat cttcaccact cattcttcaa   4680
ccacccattc acccatcact catcttttac ccacccaccc tttgccactc atccttctgt   4740
ccctcatcct tccaaccatt catcaatcac ccacccatcc atcctttgcc acacaaccat   4800
ccacccattc ttctacctac ccatcctatc catccatcct tctatcagca tccttctacc   4860
acccatcctt cgttcggtca tccatcatca tccatccatc                        4900
```

<210> SEQ ID NO 8
<211> LENGTH: 136
<212> TYPE: PRT
<213> ORGANISM: Homo sapiens
<400> SEQUENCE: 8

```
Met Arg Leu Leu Thr Leu Leu Gly Leu Leu Cys Gly Ser Val Ala Thr
1               5                   10                  15

Pro Leu Gly Pro Lys Trp Pro Glu Pro Val Phe Gly Arg Leu Ala Ser
            20                  25                  30

Pro Gly Phe Pro Gly Glu Tyr Ala Asn Asp Gln Glu Arg Arg Trp Thr
        35                  40                  45

Leu Thr Ala Pro Pro Gly Tyr Arg Leu Arg Leu Tyr Phe Thr His Phe
    50                  55                  60

Asp Leu Glu Leu Ser His Leu Cys Glu Tyr Asp Phe Val Lys Leu Ser
65                  70                  75                  80

Ser Gly Ala Lys Val Leu Ala Thr Leu Cys Gly Gln Glu Ser Thr Asp
                85                  90                  95

Thr Glu Arg Ala Pro Gly Lys Asp Thr Phe Tyr Ser Leu Gly Ser Ser
            100                 105                 110

Leu Asp Ile Thr Phe Arg Ser Asp Tyr Ser Asn Glu Lys Pro Phe Thr
        115                 120                 125

Gly Phe Glu Ala Phe Tyr Ala Ala
    130                 135
```

<210> SEQ ID NO 9
<211> LENGTH: 181
<212> TYPE: PRT
<213> ORGANISM: Homo sapiens
<400> SEQUENCE: 9

```
Met Arg Leu Leu Thr Leu Leu Gly Leu Leu Cys Gly Ser Val Ala Thr
1               5                   10                  15

Pro Leu Gly Pro Lys Trp Pro Glu Pro Val Phe Gly Arg Leu Ala Ser
            20                  25                  30

Pro Gly Phe Pro Gly Glu Tyr Ala Asn Asp Gln Glu Arg Arg Trp Thr
            35                  40                  45

Leu Thr Ala Pro Pro Gly Tyr Arg Leu Arg Leu Tyr Phe Thr His Phe
    50                  55                  60

Asp Leu Glu Leu Ser His Leu Cys Glu Tyr Asp Phe Val Lys Leu Ser
65                  70                  75                  80

Ser Gly Ala Lys Val Leu Ala Thr Leu Cys Gly Gln Glu Ser Thr Asp
                85                  90                  95

Thr Glu Arg Ala Pro Gly Lys Asp Thr Phe Tyr Ser Leu Gly Ser Ser
            100                 105                 110

Leu Asp Ile Thr Phe Arg Ser Asp Tyr Ser Asn Glu Lys Pro Phe Thr
            115                 120                 125

Gly Phe Glu Ala Phe Tyr Ala Ala Glu Asp Ile Asp Glu Cys Gln Val
    130                 135                 140

Ala Pro Gly Glu Ala Pro Thr Cys Asp His His Cys His Asn His Leu
145                 150                 155                 160

Gly Gly Phe Tyr Cys Ser Cys Arg Ala Gly Tyr Val Leu His Arg Asn
                165                 170                 175

Lys Arg Thr Cys Ser
            180

<210> SEQ ID NO 10
<211> LENGTH: 293
<212> TYPE: PRT
<213> ORGANISM: Homo sapiens

<400> SEQUENCE: 10

Met Arg Leu Leu Thr Leu Leu Gly Leu Leu Cys Gly Ser Val Ala Thr
1               5                   10                  15

Pro Leu Gly Pro Lys Trp Pro Glu Pro Val Phe Gly Arg Leu Ala Ser
            20                  25                  30

Pro Gly Phe Pro Gly Glu Tyr Ala Asn Asp Gln Glu Arg Arg Trp Thr
            35                  40                  45

Leu Thr Ala Pro Pro Gly Tyr Arg Leu Arg Leu Tyr Phe Thr His Phe
    50                  55                  60

Asp Leu Glu Leu Ser His Leu Cys Glu Tyr Asp Phe Val Lys Leu Ser
65                  70                  75                  80

Ser Gly Ala Lys Val Leu Ala Thr Leu Cys Gly Gln Glu Ser Thr Asp
                85                  90                  95

Thr Glu Arg Ala Pro Gly Lys Asp Thr Phe Tyr Ser Leu Gly Ser Ser
            100                 105                 110

Leu Asp Ile Thr Phe Arg Ser Asp Tyr Ser Asn Glu Lys Pro Phe Thr
            115                 120                 125

Gly Phe Glu Ala Phe Tyr Ala Ala Glu Asp Ile Asp Glu Cys Gln Val
    130                 135                 140

Ala Pro Gly Glu Ala Pro Thr Cys Asp His His Cys His Asn His Leu
145                 150                 155                 160

Gly Gly Phe Tyr Cys Ser Cys Arg Ala Gly Tyr Val Leu His Arg Asn
                165                 170                 175

Lys Arg Thr Cys Ser Ala Leu Cys Ser Gly Gln Val Phe Thr Gln Arg
            180                 185                 190
```

```
Ser Gly Glu Leu Ser Ser Pro Glu Tyr Pro Arg Pro Tyr Pro Lys Leu
            195                 200                 205

Ser Ser Cys Thr Tyr Ser Ile Ser Leu Glu Glu Gly Phe Ser Val Ile
    210                 215                 220

Leu Asp Phe Val Glu Ser Phe Asp Val Glu Thr His Pro Glu Thr Leu
225                 230                 235                 240

Cys Pro Tyr Asp Phe Leu Lys Ile Gln Thr Asp Arg Glu Glu His Gly
                245                 250                 255

Pro Phe Cys Gly Lys Thr Leu Pro His Arg Ile Glu Thr Lys Ser Asn
                260                 265                 270

Thr Val Thr Ile Thr Phe Val Thr Asp Glu Ser Gly Asp His Thr Gly
                275                 280                 285

Trp Lys Ile His Tyr
        290

<210> SEQ ID NO 11
<211> LENGTH: 41
<212> TYPE: PRT
<213> ORGANISM: Homo sapiens

<400> SEQUENCE: 11

Glu Asp Ile Asp Glu Cys Gln Val Ala Pro Gly Glu Ala Pro Thr Cys
1               5                   10                  15

Asp His His Cys His Asn Leu Gly Gly Phe Tyr Cys Ser Cys Arg
            20                  25                  30

Ala Gly Tyr Val Leu His Arg Asn Lys
        35                  40

<210> SEQ ID NO 12
<211> LENGTH: 242
<212> TYPE: PRT
<213> ORGANISM: Homo sapiens

<400> SEQUENCE: 12

Ile Tyr Gly Gly Gln Lys Ala Lys Pro Gly Asp Phe Pro Trp Gln Val
1               5                   10                  15

Leu Ile Leu Gly Gly Thr Thr Ala Ala Gly Ala Leu Leu Tyr Asp Asn
            20                  25                  30

Trp Val Leu Thr Ala Ala His Ala Val Tyr Glu Gln Lys His Asp Ala
        35                  40                  45

Ser Ala Leu Asp Ile Arg Met Gly Thr Leu Lys Arg Leu Ser Pro His
    50                  55                  60

Tyr Thr Gln Ala Trp Ser Glu Ala Val Phe Ile His Glu Gly Tyr Thr
65                  70                  75                  80

His Asp Ala Gly Phe Asp Asn Asp Ile Ala Leu Ile Lys Leu Asn Asn
                85                  90                  95

Lys Val Val Ile Asn Ser Asn Ile Thr Pro Ile Cys Leu Pro Arg Lys
            100                 105                 110

Glu Ala Glu Ser Phe Met Arg Thr Asp Asp Ile Gly Thr Ala Ser Gly
        115                 120                 125

Trp Gly Leu Thr Gln Arg Gly Phe Leu Ala Arg Asn Leu Met Tyr Val
    130                 135                 140

Asp Ile Pro Ile Val Asp His Gln Lys Cys Thr Ala Ala Tyr Glu Lys
145                 150                 155                 160

Pro Pro Tyr Pro Arg Gly Ser Val Thr Ala Asn Met Leu Cys Ala Gly
                165                 170                 175
```

Leu Glu Ser Gly Gly Lys Asp Ser Cys Arg Gly Asp Ser Gly Gly Ala
            180                 185                 190

Leu Val Phe Leu Asp Ser Glu Thr Glu Arg Trp Phe Val Gly Gly Ile
        195                 200                 205

Val Ser Trp Gly Ser Met Asn Cys Gly Glu Ala Gly Gln Tyr Gly Val
    210                 215                 220

Tyr Thr Lys Val Ile Asn Tyr Ile Pro Trp Ile Glu Asn Ile Ile Ser
225                 230                 235                 240

Asp Phe

<210> SEQ ID NO 13
<211> LENGTH: 16
<212> TYPE: PRT
<213> ORGANISM: Artificial Sequence
<220> FEATURE:
<223> OTHER INFORMATION: Synthetic

<400> SEQUENCE: 13

Gly Lys Asp Ser Cys Arg Gly Asp Ala Gly Gly Ala Leu Val Phe Leu
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Synthetic

<400> SEQUENCE: 14

Thr Pro Leu Gly Pro Lys Trp Pro Glu Pro Val Phe Gly Arg Leu
1               5                   10                  15

<210> SEQ ID NO 15
<211> LENGTH: 43
<212> TYPE: PRT
<213> ORGANISM: Artificial Sequence
<220> FEATURE:
<223> OTHER INFORMATION: Synthetic

<400> SEQUENCE: 15

Thr Ala Pro Pro Gly Tyr Arg Leu Arg Leu Tyr Phe Thr His Phe Asp
1               5                   10                  15

Leu Glu Leu Ser His Leu Cys Glu Tyr Asp Phe Val Lys Leu Ser Ser
            20                  25                  30

Gly Ala Lys Val Leu Ala Thr Leu Cys Gly Gln
        35                  40

<210> SEQ ID NO 16
<211> LENGTH: 8
<212> TYPE: PRT
<213> ORGANISM: Artificial Sequence
<220> FEATURE:
<223> OTHER INFORMATION: Synthetic

<400> SEQUENCE: 16

Thr Phe Arg Ser Asp Tyr Ser Asn
1               5

<210> SEQ ID NO 17
<211> LENGTH: 25
<212> TYPE: PRT
<213> ORGANISM: Artificial Sequence
<220> FEATURE:

<223> OTHER INFORMATION: Synthetic

<400> SEQUENCE: 17

Phe Tyr Ser Leu Gly Ser Ser Leu Asp Ile Thr Phe Arg Ser Asp Tyr
1               5                   10                  15
Ser Asn Glu Lys Pro Phe Thr Gly Phe
            20                  25

<210> SEQ ID NO 18
<211> LENGTH: 9
<212> TYPE: PRT
<213> ORGANISM: Artificial Sequence
<220> FEATURE:
<223> OTHER INFORMATION: Synthetic

<400> SEQUENCE: 18

Ile Asp Glu Cys Gln Val Ala Pro Gly
1               5

<210> SEQ ID NO 19
<211> LENGTH: 25
<212> TYPE: PRT
<213> ORGANISM: Artificial Sequence
<220> FEATURE:
<223> OTHER INFORMATION: Synthetic

<400> SEQUENCE: 19

Ala Asn Met Leu Cys Ala Gly Leu Glu Ser Gly Gly Lys Asp Ser Cys
1               5                   10                  15
Arg Gly Asp Ser Gly Gly Ala Leu Val
            20                  25

<210> SEQ ID NO 20
<211> LENGTH: 960
<212> TYPE: DNA
<213> ORGANISM: Homo sapiens
<220> FEATURE:
<221> NAME/KEY: CDS
<222> LOCATION: (51)..(797)

<400> SEQUENCE: 20

```
attaactgag attaaccttc cctgagtttt ctcacaccaa ggtgaggacc atg tcc         56
                                                      Met Ser
                                                        1 ctg ttt cca tca ctc cct ctc ctt ctc ctg agt atg gtg gca gcg tct      104
Leu Phe Pro Ser Leu Pro Leu Leu Leu Leu Ser Met Val Ala Ala Ser
        5                  10                  15 tac tca gaa act gtg acc tgt gag gat gcc caa aag acc tgc cct gca      152
Tyr Ser Glu Thr Val Thr Cys Glu Asp Ala Gln Lys Thr Cys Pro Ala
    20                  25                  30 gtg att gcc tgt agc tct cca ggc atc aac ggc ttc cca ggc aaa gat      200
Val Ile Ala Cys Ser Ser Pro Gly Ile Asn Gly Phe Pro Gly Lys Asp
35                  40                  45                  50 ggg cgt gat ggc acc aag gga gaa aag ggg gaa cca ggc caa ggg ctc      248
Gly Arg Asp Gly Thr Lys Gly Glu Lys Gly Glu Pro Gly Gln Gly Leu
                55                  60                  65 aga ggc tta cag ggc ccc cct gga aag ttg ggg cct cca gga aat cca      296
Arg Gly Leu Gln Gly Pro Pro Gly Lys Leu Gly Pro Pro Gly Asn Pro
            70                  75                  80 ggg cct tct ggg tca cca gga cca aag ggc caa aaa gga gac cct gga      344
Gly Pro Ser Gly Ser Pro Gly Pro Lys Gly Gln Lys Gly Asp Pro Gly
        85                  90                  95 aaa agt ccg gat ggt gat agt agc ctg gct gcc tca gaa aga aaa gct      392
```

```
              Lys Ser Pro Asp Gly Asp Ser Ser Leu Ala Ala Ser Glu Arg Lys Ala
                  100                 105                 110 ctg caa aca gaa atg gca cgt atc aaa aag tgg ctc acc ttc tct ctg       440
Leu Gln Thr Glu Met Ala Arg Ile Lys Lys Trp Leu Thr Phe Ser Leu
115                 120                 125                 130 ggc aaa caa gtt ggg aac aag ttc ttc ctg acc aat ggt gaa ata atg       488
Gly Lys Gln Val Gly Asn Lys Phe Phe Leu Thr Asn Gly Glu Ile Met
                135                 140                 145 acc ttt gaa aaa gtg aag gcc ttg tgt gtc aag ttc cag gcc tct gtg       536
Thr Phe Glu Lys Val Lys Ala Leu Cys Val Lys Phe Gln Ala Ser Val
            150                 155                 160 gcc acc ccc agg aat gct gca gag aat gga gcc att cag aat ctc atc       584
Ala Thr Pro Arg Asn Ala Ala Glu Asn Gly Ala Ile Gln Asn Leu Ile
        165                 170                 175 aag gag gaa gcc ttc ctg ggc atc act gat gag aag aca gaa ggg cag       632
Lys Glu Glu Ala Phe Leu Gly Ile Thr Asp Glu Lys Thr Glu Gly Gln
    180                 185                 190 ttt gtg gat ctg aca gga aat aga ctg acc tac aca aac tgg aac gag       680
Phe Val Asp Leu Thr Gly Asn Arg Leu Thr Tyr Thr Asn Trp Asn Glu
195                 200                 205                 210 ggt gaa ccc aac aat gct ggt tct gat gaa gat tgt gta ttg cta ctg       728
Gly Glu Pro Asn Asn Ala Gly Ser Asp Glu Asp Cys Val Leu Leu Leu
                215                 220                 225 aaa aat ggc cag tgg aat gac gtc ccc tgc tcc acc tcc cat ctg gcc       776
Lys Asn Gly Gln Trp Asn Asp Val Pro Cys Ser Thr Ser His Leu Ala
            230                 235                 240 gtc tgt gag ttc cct atc tga aggtcatat cactcaggcc ctccttgtct           827
Val Cys Glu Phe Pro Ile
            245 ttttactgca acccacaggc ccacagtatg cttgaaaaga taaattatat caatttcctc     887 atatccagta ttgttccttt tgtgggcaat cactaaaaat gatcactaac agcaccaaca     947 aagcaataat agt                                                        960

<210> SEQ ID NO 21
<211> LENGTH: 248
<212> TYPE: PRT
<213> ORGANISM: Homo sapiens

<400> SEQUENCE: 21

Met Ser Leu Phe Pro Ser Leu Pro Leu Leu Leu Leu Ser Met Val Ala
1               5                   10                  15

Ala Ser Tyr Ser Glu Thr Val Thr Cys Glu Asp Ala Gln Lys Thr Cys
            20                  25                  30

Pro Ala Val Ile Ala Cys Ser Ser Pro Gly Ile Asn Gly Phe Pro Gly
        35                  40                  45

Lys Asp Gly Arg Asp Gly Thr Lys Gly Glu Lys Gly Glu Pro Gly Gln
    50                  55                  60

Gly Leu Arg Gly Leu Gln Gly Pro Pro Gly Lys Leu Gly Pro Pro Gly
65                  70                  75                  80

Asn Pro Gly Pro Ser Gly Ser Pro Gly Pro Lys Gly Gln Lys Gly Asp
                85                  90                  95

Pro Gly Lys Ser Pro Asp Gly Asp Ser Ser Leu Ala Ala Ser Glu Arg
            100                 105                 110

Lys Ala Leu Gln Thr Glu Met Ala Arg Ile Lys Lys Trp Leu Thr Phe
        115                 120                 125

Ser Leu Gly Lys Gln Val Gly Asn Lys Phe Phe Leu Thr Asn Gly Glu
    130                 135                 140
```

```
Ile Met Thr Phe Glu Lys Val Lys Ala Leu Cys Val Lys Phe Gln Ala
145                 150                 155                 160

Ser Val Ala Thr Pro Arg Asn Ala Ala Glu Asn Gly Ala Ile Gln Asn
                165                 170                 175

Leu Ile Lys Glu Glu Ala Phe Leu Gly Ile Thr Asp Glu Lys Thr Glu
            180                 185                 190

Gly Gln Phe Val Asp Leu Thr Gly Asn Arg Leu Thr Tyr Thr Asn Trp
        195                 200                 205

Asn Glu Gly Glu Pro Asn Asn Ala Gly Ser Asp Glu Asp Cys Val Leu
    210                 215                 220

Leu Leu Lys Asn Gly Gln Trp Asn Asp Val Pro Cys Ser Thr Ser His
225                 230                 235                 240

Leu Ala Val Cys Glu Phe Pro Ile
                245
```

<210> SEQ ID NO 22
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Wherein X at position 1 represents
      hydroxyproline
<220> FEATURE:
<221> NAME/KEY: MISC_FEATURE
<222> LOCATION: (4)..(4)
<223> OTHER INFORMATION: Wherein X at position 4 represents hydrophobic
      residue

<400> SEQUENCE: 22

```
Xaa Gly Lys Xaa Gly Pro
1               5
```

<210> SEQ ID NO 23
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Wherein X represents hydroxyproline

<400> SEQUENCE: 23

```
Xaa Gly Lys Leu Gly
1               5
```

<210> SEQ ID NO 24
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (9)..(15)
<223> OTHER INFORMATION: Wherein X at positions 9 and 15 represents
      hydroxyproline

<400> SEQUENCE: 24

```
Gly Leu Arg Gly Leu Gln Gly Pro Xaa Gly Lys Leu Gly Pro Xaa Gly
1               5                   10                  15
```

```
<210> SEQ ID NO 25
<211> LENGTH: 27
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(27)
<223> OTHER INFORMATION: Wherein X at positions 3, 6, 15, 21, 24, 27
      represents hydroxyproline

<400> SEQUENCE: 25

Gly Pro Xaa Gly Pro Xaa Gly Leu Arg Gly Leu Gln Gly Pro Xaa Gly
1               5                   10                  15

Lys Leu Gly Pro Xaa Gly Pro Xaa Gly Pro Xaa
            20                  25

<210> SEQ ID NO 26
<211> LENGTH: 53
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (41)..(41)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any naturally occurring amino acid

<400> SEQUENCE: 26

Gly Lys Asp Gly Arg Asp Gly Thr Lys Gly Glu Lys Gly Glu Pro Gly
1               5                   10                  15

Gln Gly Leu Arg Gly Leu Gln Gly Pro Xaa Gly Lys Leu Gly Pro Xaa
            20                  25                  30

Gly Asn Xaa Gly Pro Ser Gly Ser Xaa Gly Pro Lys Gly Gln Lys Gly
        35                  40                  45

Asp Xaa Gly Lys Ser
    50

<210> SEQ ID NO 27
<211> LENGTH: 33
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(33)
<223> OTHER INFORMATION: Wherein X at positions 3, 6, 12, 18, 21, 30, 33
      represents hydroxyproline

<400> SEQUENCE: 27
```

```
Gly Ala Xaa Gly Ser Xaa Gly Glu Lys Gly Ala Xaa Gly Pro Gln Gly
1               5                   10                  15

Pro Xaa Gly Pro Xaa Gly Lys Met Gly Pro Lys Gly Glu Xaa Gly Asp
            20                  25                  30

Xaa

<210> SEQ ID NO 28
<211> LENGTH: 45
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(45)
<223> OTHER INFORMATION: Wherein X at positions 3, 6, 9, 27, 30, 36, 42,
      45 represents hydroxyproline

<400> SEQUENCE: 28

Gly Cys Xaa Gly Leu Xaa Gly Ala Xaa Gly Asp Lys Gly Glu Ala Gly
1               5                   10                  15

Thr Asn Gly Lys Arg Gly Glu Arg Gly Pro Xaa Gly Pro Xaa Gly Lys
            20                  25                  30

Ala Gly Pro Xaa Gly Pro Asn Gly Ala Xaa Gly Glu Xaa
            35                  40              45

<210> SEQ ID NO 29
<211> LENGTH: 24
<212> TYPE: PRT
<213> ORGANISM: Artificial Sequence
<220> FEATURE:
<223> OTHER INFORMATION: Synthetic

<400> SEQUENCE: 29

Leu Gln Arg Ala Leu Glu Ile Leu Pro Asn Arg Val Thr Ile Lys Ala
1               5                   10                  15

Asn Arg Pro Phe Leu Val Phe Ile
            20

<210> SEQ ID NO 30
<211> LENGTH: 559
<212> TYPE: DNA
<213> ORGANISM: Homo sapiens

<400> SEQUENCE: 30
atgaggctgc tgaccctcct gggccttctg tgtggctcgg tgccacccc cttgggcccg      60 aagtggcctg aacctgtgtt cgggcgcctg catccccg gctttccagg ggagtatgcc     120
aatgaccagg agcggcgctg gaccctgact gcacccccg gctaccgcct gcgcctctac     180
ttcacccact cgacctgga gctctcccac ctctgcgagt acgacttcgt caagctgagc     240
tcggggccca ggtgctggc cacgctgtgc gggcaggaga gcacagacac ggagcgggcc     300
cctggcaagg acactttcta ctcgctgggc tccagcctgg acattacctt ccgctccgac     360
tactccaacg agaagccgtt cacggggttc gaggccttct atgcagccga ggacattgac     420
gagtgccagg tgcccccggg agaggcgccc acctgcgacc accactgcca caaccacctg     480
ggcggtttct actgctcctg ccgcgcaggc tacgtcctgc accgtaacaa gcgcacctgc     540
tcagccctgt gctccggcc                                                   559

<210> SEQ ID NO 31
<211> LENGTH: 34
```

```
<212> TYPE: DNA
<213> ORGANISM: Artificial Sequence
<220> FEATURE:
<223> OTHER INFORMATION: Synthetic

<400> SEQUENCE: 31
cgggcacacc atgaggctgc tgaccctcct gggc                              34

<210> SEQ ID NO 32
<211> LENGTH: 33
<212> TYPE: DNA
<213> ORGANISM: Artificial Sequence
<220> FEATURE:
<223> OTHER INFORMATION: Synthetic

<400> SEQUENCE: 32
gacattacct tccgctccga ctccaacgag aag                               33

<210> SEQ ID NO 33
<211> LENGTH: 33
<212> TYPE: DNA
<213> ORGANISM: Artificial Sequence
<220> FEATURE:
<223> OTHER INFORMATION: Synthetic

<400> SEQUENCE: 33
agcagccctg aatacccacg gccgtatccc aaa                               33

<210> SEQ ID NO 34
<211> LENGTH: 26
<212> TYPE: DNA
<213> ORGANISM: Artificial Sequence
<220> FEATURE:
<223> OTHER INFORMATION: Synthetic

<400> SEQUENCE: 34
cgggatccat gaggctgctg accctc                                       26

<210> SEQ ID NO 35
<211> LENGTH: 19
<212> TYPE: DNA
<213> ORGANISM: Artificial Sequence
<220> FEATURE:
<223> OTHER INFORMATION: Synthetic

<400> SEQUENCE: 35
ggaattccta ggctgcata                                               19

<210> SEQ ID NO 36
<211> LENGTH: 19
<212> TYPE: DNA
<213> ORGANISM: Artificial Sequence
<220> FEATURE:
<223> OTHER INFORMATION: Synthetic

<400> SEQUENCE: 36
ggaattccta cagggcgct                                               19

<210> SEQ ID NO 37
<211> LENGTH: 19
<212> TYPE: DNA
<213> ORGANISM: Artificial Sequence
<220> FEATURE:
<223> OTHER INFORMATION: Synthetic

<400> SEQUENCE: 37
```

```
ggaattccta gtagtggat                                              19

<210> SEQ ID NO 38
<211> LENGTH: 25
<212> TYPE: DNA
<213> ORGANISM: Artificial Sequence
<220> FEATURE:
<223> OTHER INFORMATION: Synthetic

<400> SEQUENCE: 38
tgcggccgct gtaggtgctg tcttt                                       25

<210> SEQ ID NO 39
<211> LENGTH: 23
<212> TYPE: DNA
<213> ORGANISM: Artificial Sequence
<220> FEATURE:
<223> OTHER INFORMATION: Synthetic

<400> SEQUENCE: 39
ggaattcact cgttattctc gga                                         23

<210> SEQ ID NO 40
<211> LENGTH: 17
<212> TYPE: DNA
<213> ORGANISM: Artificial Sequence
<220> FEATURE:
<223> OTHER INFORMATION: Synthetic

<400> SEQUENCE: 40
tccgagaata acgagtg                                                17

<210> SEQ ID NO 41
<211> LENGTH: 29
<212> TYPE: DNA
<213> ORGANISM: Artificial Sequence
<220> FEATURE:
<223> OTHER INFORMATION: Synthetic

<400> SEQUENCE: 41
cattgaaagc tttggggtag aagttgttc                                   29

<210> SEQ ID NO 42
<211> LENGTH: 27
<212> TYPE: DNA
<213> ORGANISM: Artificial Sequence
<220> FEATURE:
<223> OTHER INFORMATION: Synthetic

<400> SEQUENCE: 42
cgcggccgca gctgctcaga gtgtaga                                     27

<210> SEQ ID NO 43
<211> LENGTH: 28
<212> TYPE: DNA
<213> ORGANISM: Artificial Sequence
<220> FEATURE:
<223> OTHER INFORMATION: Synthetic

<400> SEQUENCE: 43
cggtaagctt cactggctca gggaaata                                    28

<210> SEQ ID NO 44
<211> LENGTH: 37
<212> TYPE: DNA
<213> ORGANISM: Artificial Sequence
```

```
<220> FEATURE:
<223> OTHER INFORMATION: Synthetic

<400> SEQUENCE: 44
aagaagcttg ccgccaccat ggattggctg tggaact                                37

<210> SEQ ID NO 45
<211> LENGTH: 31
<212> TYPE: DNA
<213> ORGANISM: Artificial Sequence
<220> FEATURE:
<223> OTHER INFORMATION: Synthetic

<400> SEQUENCE: 45
cgggatcctc aaactttctt gtccaccttg g                                      31

<210> SEQ ID NO 46
<211> LENGTH: 36
<212> TYPE: DNA
<213> ORGANISM: Artificial Sequence
<220> FEATURE:
<223> OTHER INFORMATION: Synthetic

<400> SEQUENCE: 46
aagaaagctt gccgccacca tgttctcact agctct                                 36

<210> SEQ ID NO 47
<211> LENGTH: 26
<212> TYPE: DNA
<213> ORGANISM: Artificial Sequence
<220> FEATURE:
<223> OTHER INFORMATION: Synthetic

<400> SEQUENCE: 47
cgggatcctt ctccctctaa cactct                                            26

<210> SEQ ID NO 48
<211> LENGTH: 9
<212> TYPE: PRT
<213> ORGANISM: Artificial Sequence
<220> FEATURE:
<223> OTHER INFORMATION: Synthetic

<400> SEQUENCE: 48

Glu Pro Lys Ser Cys Asp Lys Thr His
1               5

<210> SEQ ID NO 49
<211> LENGTH: 4960
<212> TYPE: DNA
<213> ORGANISM: Homo Sapiens

<400> SEQUENCE: 49
ccggacgtgg tggcgcatgc ctgtaatccc agctactcgg gaggctgagg caggagaatt       60
gctcgaaccc cggaggcaga ggtttggtgg ctcacacctg taatcccagc actttgcgag      120
gctgaggcag gtgcatcgct ttggctcagg agttcaagac cagcctgggc aacacaggga      180
gacccccatc tctacaaaaa acaaaaacaa atataaaggg gataaaaaaa aaaaaaagac      240
aagacatgaa tccatgagga cagagtgtgg aagaggaagc agcagcctca agttctgga       300 agctggaaga acagataaac aggtgtgaaa taactgcctg gaaagcaact tctttttttt      360
tttttttttt tttgaggtgg agtctcactc tgtcgtccag gctggagtgc agtggtgcga      420
tctcggatca ctgcaacctc cgcctcccag gctcaagcaa ttctcctgcc tcagcctccc      480
```

```
gagtagctgg gattataagt gcgcgctgcc acacctggat gattttttgta tttttagtag    540
agatgggatt tcaccatgtt ggtcaggctg gtctcaaact cccaacctcg tgatccaccc    600
accttggcct cccaaagtgc tgggattaca ggtataagcc accgagccca gccaaaagcg    660
acttctaagc ctgcaaggga atcgggaatt ggtggcacca ggtccttctg acagggttta    720
agaaattagc cagcctgagg ctgggcacgg tggctcacac ctgtaatccc agcactttgg    780
gaggctaagg caggtggatc acctgagggc aggagttcaa gaccagcctg accaacatgg    840
agaaacccca tccctaccaa aaataaaaaa ttagccaggt gtggtggtgc tcgcctgtaa    900
tcccagctac ttgggaggct gaggtgggag gattgcttga acacaggaag tagaggctgc    960
agtgagctat gattgcagca ctgcactgaa gccgggcaa cagaacaaga tccaaaaaaa   1020
agggaggggt gaggggcaga gccaggattt gtttccaggc tgttgttacc taggtccgac   1080
tcctggctcc cagagcagcc tgtcctgcct gcctggaact ctgagcaggc tggagtcatg   1140
gagtcgattc ccagaatccc agagtcaggg aggctggggg caggggcagg tcactggaca   1200
aacagatcaa aggtgagacc agcgtagggc tgcagaccag gccaggccag ctggacgggc   1260
acaccatgag gtaggtgggc gcccacagcc tccctgcagg gtgtggggtg ggagcacagg   1320
cctgggccct caccgcccct gccctgccca taggctgctg accctcctgg gccttctgtg   1380
tggctcggtg gccaccccct gggcccgaa gtggcctgaa cctgtgttcg ggcgcctggc   1440
atccccggc tttccagggg agtatgccaa tgaccaggag cggcgctgga ccctgactgc   1500
acccccggc taccgcctgc gcctctactt cacccacttc gacctggagc tctcccacct   1560
ctgcgagtac gacttcgtca aggtgccgtc aggacgggag ggctggggtt tctcagggtc   1620
gggggtccc caaggagtag ccagggttca gggacacctg ggagcagggg ccaggcttgg   1680
ccaggaggga gatcaggcct gggtcttgcc ttcactccct gtgacacctg accccacagc   1740
tgagctcggg ggccaaggtg ctggccacgc tgtgcgggca ggagagcaca gacacggagc   1800
gggcccctgg caaggacact ttctactcgc tgggctccag cctggacatt accttccgct   1860
ccgactactc caacgagaag ccgttcacgg ggttcgaggc cttctatgca gccgagggtg   1920
agccaagagg ggtcctgcaa catctcagtc tgcgcagctg gctgtggggg taactctgtc   1980
ttaggccagg cagccctgcc ttcagttttcc ccacctttcc cagggcaggg gagaggcctc   2040
tggcctgaca tcatccacaa tgcaaagacc aaaacagccg tgacctccat tcacatgggc   2100
tgagtgccaa ctctgagcca gggatctgag gacagcatcg cctcaagtga cgcagggact   2160
ggccgggcgc agcagctcac gcctgtaatt ccagcacttt gggaggccga ggctggctga   2220
tcatttgagg tcaggagttc aaggccagcc agggcaacac ggtgaaactc tatctccact   2280
aaaactacaa aaattagctg gcgtggtgg tgcgcacctg gaatcccagc tactagggag   2340
gctgaggcag gagaattgct tgaacctgcg aggtggaggc tgcagtgaac agagattgca   2400
ccactacact ccagcctggg cgacagagct agactccgtc tcaaaaaaca aaaaacaaaa   2460
acgacgcagg ggccgagggc cccatttaca gctgacaaag tggggccctg ccagcgggag   2520
cgctgccagt atgtttgatt tcagatccca gtccctgcag agaccaactg tgtgacctct   2580
ggcaagtggc tcaatttctc tgctccttag gaagctgctg caagggttca gcgctgtagc   2640
cccgccccct gggtttgatt gactcccctc attagctggg tgacctcggg ccggacactg   2700
aaactcccac tggtttaaca gaggtgatgt ttgcatcttt ctcccagcgc tgctgggagc   2760
ttgcagcgac cctaggcctg taaggtgatt ggcccggcac cagtcccgca ccctagacag   2820
```

```
gacgaggcct cctctgaggt ccactctgag gtcatggatc tcctgggagg agtccaggct    2880
ggatcccgcc tctttccctc ctgacggcct gcctggccct gcctctcccc cagacattga    2940
cgagtgccag gtggccccgg gagaggcgcc cacctgcgac caccactgcc acaaccacct    3000
gggcggtttc tactgctcct gccgcgcagg ctacgtcctg caccgtaaca agcgcacctg    3060
ctcagccctg tgctccggcc aggtcttcac ccagaggtct ggggagctca gcagccctga    3120
atacccacgg ccgtatccca aactctccag ttgcacttac agcatcagcc tggaggaggg    3180
gttcagtgtc attctggact tgtggagtc cttcgatgtg agacacacc ctgaaaccct    3240 gtgtccctac gactttctca agattcaaac agacagagaa gaacatggcc cattctgtgg    3300
gaagacattg ccccacagga ttgaaacaaa aagcaacacg gtgaccatca cctttgtcac    3360
agatgaatca ggagaccaca caggctggaa gatccactac acgagcacag cgcacgcttg    3420
cccttatccg atggcgccac ctaatggcca cgtttcacct gtgcaagcca aatacatcct    3480
gaaagacagc ttctccatct tttgcgagac tggctatgag cttctgcaag gtcacttgcc    3540
cctgaaatcc tttactgcag tttgtcagaa agatggatct tgggaccggc caatgcccgc    3600
gtgcagcatt gttgactgtg gccctcctga tgatctaccc agtggccgag tggagtacat    3660
cacaggtcct ggagtgacca cctacaaagc tgtgattcag tacagctgtg aagagacctt    3720
ctacacaatg aaagtgaatg atggtaaata tgtgtgtgag gctgatggat tctggacgag    3780
ctccaaagga gaaaaatcac tcccagtctg tgagcctgtt tgtggactat cagcccgcac    3840
aacaggaggg cgtatatatg gagggcaaaa ggcaaaacct ggtgattttc cttggcaagt    3900
cctgatatta ggtggaacca cagcagcagg tgcactttta tatgacaact gggtcctaac    3960
agctgctcat gccgtctatg agcaaaaaca tgatgcatcc gccctggaca ttcgaatggg    4020
caccctgaaa agactatcac ctcattatac acaagcctgg tctgaagctg tttttataca    4080
tgaaggttat actcatgatg ctggctttga caatgacata gcactgatta aattgaataa    4140
caaagttgta atcaatagca acatcacgcc tatttgtctg ccaagaaaag aagctgaatc    4200
ctttatgagg acagatgaca ttggaactgc atctggatgg ggattaaccc aaagggggttt    4260 tcttgctaga aatctaatgt atgtcgacat accgattgtt gaccatcaaa aatgtactgc    4320
tgcatatgaa aagccaccct atccaagggg aagtgtaact gctaacatgc tttgtgctgg    4380
cttagaaagt gggggcaagg acagctgcag aggtgacagc ggaggggcac tggtgtttct    4440
agatagtgaa acagagaggt ggtttgtggg aggaatagtg tcctggggtt ccatgaattg    4500 tgggggaagca ggtcagtatg gagtctacac aaaaagttatt aactatattc cctggatcga    4560
gaacataatt agtgattttt aacttgcgtg tctgcagtca aggattcttc atttttagaa    4620
atgcctgtga agaccttggc agcgacgtgg ctcgagaagc attcatcatt actgtggaca    4680
tggcagttgt tgctccaccc aaaaaaacag actccaggtg aggctgctgt catttctcca    4740
cttgccagtt taattccagc cttacccatt gactcaaggg gacataaacc acgagagtga    4800
cagtcatctt tgcccaccca gtgtaatgtc actgctcaaa ttacatttca ttaccttaaa    4860
aagccagtct cttttcatac tggctgttgg catttctgta aactgcctgt ccatgctctt    4920
tgtttttaaa cttgttctta ttgaaaaaaa aaaaaaaaa                           4960
```

<210> SEQ ID NO 50
<211> LENGTH: 2090
<212> TYPE: DNA
<213> ORGANISM: Murine
<220> FEATURE:
<221> NAME/KEY: CDS

<222> LOCATION: (33)..(2090)

<400> SEQUENCE: 50

| | | |
|---|---|---|
| ggcgctggac tgcagagcta tgtggcaca cc atg agg cta ctc atc ttc ctg<br>　　　　　　　　　　　　　　　　　Met Arg Leu Leu Ile Phe Leu<br>　　　　　　　　　　　　　　　　　1　　　　　5 | 53 |
| ggt ctg ctg tgg agt ttg gtg gcc aca ctt ctg ggt tca aag tgg cct<br>Gly Leu Leu Trp Ser Leu Val Ala Thr Leu Leu Gly Ser Lys Trp Pro<br>　　　10　　　　　　　　15　　　　　　　　20 | 101 |
| gaa cct gta ttc ggg cgc ctg gtg tcc cct ggc ttc cca gag aag tat<br>Glu Pro Val Phe Gly Arg Leu Val Ser Pro Gly Phe Pro Glu Lys Tyr<br>25　　　　　　　　30　　　　　　　　35 | 149 |
| gct gac cat caa gat cga tcc tgg aca ctg act gca ccc cct ggc tac<br>Ala Asp His Gln Asp Arg Ser Trp Thr Leu Thr Ala Pro Pro Gly Tyr<br>40　　　　　　　　45　　　　　　　　50　　　　　　　　55 | 197 |
| cgc ctg cgc ctc tac ttc acc cac ttt gac ctg gaa ctc tct tac cgc<br>Arg Leu Arg Leu Tyr Phe Thr His Phe Asp Leu Glu Leu Ser Tyr Arg<br>　　　　60　　　　　　　　65　　　　　　　　70 | 245 |
| tgc gag tat gac ttt gtc aag ttg agc tca ggg acc aag gtg ctg gcc<br>Cys Glu Tyr Asp Phe Val Lys Leu Ser Ser Gly Thr Lys Val Leu Ala<br>75　　　　　　　　80　　　　　　　　85 | 293 |
| aca ctg tgt ggg cag gag agt aca gac act gag cag gca cct ggc aat<br>Thr Leu Cys Gly Gln Glu Ser Thr Asp Thr Glu Gln Ala Pro Gly Asn<br>　　　90　　　　　　　　95　　　　　　　　100 | 341 |
| gac acc ttc tac tca ctg ggt ccc agc cta aag gtc acc ttc cac tcc<br>Asp Thr Phe Tyr Ser Leu Gly Pro Ser Leu Lys Val Thr Phe His Ser<br>105　　　　　　　　110　　　　　　　　115 | 389 |
| gac tac tcc aat gag aag ccg ttc aca ggg ttt gag gcc ttc tat gca<br>Asp Tyr Ser Asn Glu Lys Pro Phe Thr Gly Phe Glu Ala Phe Tyr Ala<br>120　　　　　　　　125　　　　　　　　130　　　　　　　　135 | 437 |
| gcg gag gat gtg gat gaa tgc aga gtg tct ctg gga gac tca gtc cct<br>Ala Glu Asp Val Asp Glu Cys Arg Val Ser Leu Gly Asp Ser Val Pro<br>　　　　140　　　　　　　　145　　　　　　　　150 | 485 |
| tgt gac cat tat tgc cac aac tac ttg ggc ggc tac tat tgc tcc tgc<br>Cys Asp His Tyr Cys His Asn Tyr Leu Gly Gly Tyr Tyr Cys Ser Cys<br>　　　　155　　　　　　　　160　　　　　　　　165 | 533 |
| aga gcg ggc tac att ctc cac cag aac aag cac acg tgc tca gcc ctt<br>Arg Ala Gly Tyr Ile Leu His Gln Asn Lys His Thr Cys Ser Ala Leu<br>170　　　　　　　　175　　　　　　　　180 | 581 |
| tgt tca ggc cag gtg ttc aca gga aga tct ggg tat ctc agt agc cct<br>Cys Ser Gly Gln Val Phe Thr Gly Arg Ser Gly Tyr Leu Ser Ser Pro<br>185　　　　　　　　190　　　　　　　　195 | 629 |
| gag tac ccg cag cca tac ccc aag ctc tcc agc tgc acc tac agc atc<br>Glu Tyr Pro Gln Pro Tyr Pro Lys Leu Ser Ser Cys Thr Tyr Ser Ile<br>200　　　　　　　　205　　　　　　　　210　　　　　　　　215 | 677 |
| cgc ctg gag gac ggc ttc agt gtc atc ctg gac ttc gtg gag tcc ttc<br>Arg Leu Glu Asp Gly Phe Ser Val Ile Leu Asp Phe Val Glu Ser Phe<br>　　　　220　　　　　　　　225　　　　　　　　230 | 725 |
| gat gtg gag acg cac cct gaa gcc cag tgc ccc tat gac tcc ctc aag<br>Asp Val Glu Thr His Pro Glu Ala Gln Cys Pro Tyr Asp Ser Leu Lys<br>　　　　235　　　　　　　　240　　　　　　　　245 | 773 |
| att caa aca gac aag ggg gaa cac ggc cca ttt tgt ggg aag acg ctg<br>Ile Gln Thr Asp Lys Gly Glu His Gly Pro Phe Cys Gly Lys Thr Leu<br>250　　　　　　　　255　　　　　　　　260 | 821 |
| cct ccc agg att gaa act gac agc cac aag gtg acc atc acc ttt gcc<br>Pro Pro Arg Ile Glu Thr Asp Ser His Lys Val Thr Ile Thr Phe Ala<br>265　　　　　　　　270　　　　　　　　275 | 869 |
| act gac gag tcg ggg aac cac aca ggc tgg aag ata cac tac aca agc<br>Thr Asp Glu Ser Gly Asn His Thr Gly Trp Lys Ile His Tyr Thr Ser<br>280　　　　　　　　285　　　　　　　　290　　　　　　　　295 | 917 |

```
aca gca cgg ccc tgc cct gat cca acg gcg cca cct aat ggc agc att      965
Thr Ala Arg Pro Cys Pro Asp Pro Thr Ala Pro Pro Asn Gly Ser Ile
            300             305             310 tca cct gtg caa gcc acg tat gtc ctg aag gac agg ttt tct gtc ttc     1013
Ser Pro Val Gln Ala Thr Tyr Val Leu Lys Asp Arg Phe Ser Val Phe
            315             320             325 tgc aag aca ggc ttc gag ctt ctg caa ggt tct gtc ccc ctg aaa tca     1061
Cys Lys Thr Gly Phe Glu Leu Leu Gln Gly Ser Val Pro Leu Lys Ser
            330             335             340 ttc act gct gtc tgt cag aaa gat gga tct tgg gac cgg ccg atg cca     1109
Phe Thr Ala Val Cys Gln Lys Asp Gly Ser Trp Asp Arg Pro Met Pro
        345             350             355 gag tgc agc att att gat tgt ggc cct ccc gat gac cta ccc aat ggc     1157
Glu Cys Ser Ile Ile Asp Cys Gly Pro Pro Asp Asp Leu Pro Asn Gly
360             365             370             375 cat gtg gac tat atc aca ggc cct caa gtg act acc tac aaa gct gtg     1205
His Val Asp Tyr Ile Thr Gly Pro Gln Val Thr Thr Tyr Lys Ala Val
                380             385             390 att cag tac agc tgt gaa gag act ttc tac aca atg agc agc aat ggt     1253
Ile Gln Tyr Ser Cys Glu Glu Thr Phe Tyr Thr Met Ser Ser Asn Gly
                395             400             405 aaa tat gtg tgt gag gct gat gga ttc tgg acg agc tcc aaa gga gaa     1301
Lys Tyr Val Cys Glu Ala Asp Gly Phe Trp Thr Ser Ser Lys Gly Glu
            410             415             420 aaa ctc ccc ccg gtt tgt gag cct gtt tgt ggg ctg tcc aca cac act     1349
Lys Leu Pro Pro Val Cys Glu Pro Val Cys Gly Leu Ser Thr His Thr
            425             430             435 ata gga gga cgc ata gtt gga ggg cag cct gca aag cct ggt gac ttt     1397
Ile Gly Gly Arg Ile Val Gly Gly Gln Pro Ala Lys Pro Gly Asp Phe
440             445             450             455 cct tgg caa gtc ttg ttg ctg ggt caa act aca gca gca ggt gca         1445
Pro Trp Gln Val Leu Leu Leu Gly Gln Thr Thr Ala Ala Gly Ala
            460             465             470 ctt ata cat gac aat tgg gtc cta aca gcc gct cat gct gta tat gag     1493
Leu Ile His Asp Asn Trp Val Leu Thr Ala Ala His Ala Val Tyr Glu
                475             480             485 aaa aga atg gca gcg tcc tcc ctg aac atc cga atg ggc atc ctc aaa     1541
Lys Arg Met Ala Ala Ser Ser Leu Asn Ile Arg Met Gly Ile Leu Lys
            490             495             500 agg ctc tca cct cat tac act caa gcc tgg ccc gag gaa atc ttt ata     1589
Arg Leu Ser Pro His Tyr Thr Gln Ala Trp Pro Glu Glu Ile Phe Ile
            505             510             515 cat gaa ggc tac act cac ggt gct ggt ttt gac aat gat ata gca ttg     1637
His Glu Gly Tyr Thr His Gly Ala Gly Phe Asp Asn Asp Ile Ala Leu
520             525             530             535 att aaa ctc aag aac aaa gtc aca atc aac gga agc atc atg cct gtt     1685
Ile Lys Leu Lys Asn Lys Val Thr Ile Asn Gly Ser Ile Met Pro Val
            540             545             550 tgc cta ccg cga aaa gaa gct gca tcc tta atg aga aca gac ttc act     1733
Cys Leu Pro Arg Lys Glu Ala Ala Ser Leu Met Arg Thr Asp Phe Thr
            555             560             565 gga act gtg gct ggc tgg ggg tta acc cag aag ggg ctt ctt gct aga     1781
Gly Thr Val Ala Gly Trp Gly Leu Thr Gln Lys Gly Leu Leu Ala Arg
            570             575             580 aac cta atg ttt gtg gac ata cca att gct gac cac caa aaa tgt acc     1829
Asn Leu Met Phe Val Asp Ile Pro Ile Ala Asp His Gln Lys Cys Thr
            585             590             595 acc gtg tat gaa aag ctc tat cca gga gta aga gta agc gct aac atg    1877
Thr Val Tyr Glu Lys Leu Tyr Pro Gly Val Arg Val Ser Ala Asn Met
```

|  |  |  |  |
|---|---|---|---|
| ctc tgt gct ggc tta gag act ggt ggc aag gac agc tgc aga ggt gac | | | 1925 |
| Leu Cys Ala Gly Leu Glu Thr Gly Gly Lys Asp Ser Cys Arg Gly Asp | | | |
| 620 625 630 | | | |
| | | | |
| agt ggg ggg gca tta gtg ttt cta gat aat gag aca cag cga tgg ttt | | | 1973 |
| Ser Gly Gly Ala Leu Val Phe Leu Asp Asn Glu Thr Gln Arg Trp Phe | | | |
| 635 640 645 | | | |
| | | | |
| gtg gga gga ata gtt tcc tgg ggt tcc att aat tgt ggg gcg gca ggc | | | 2021 |
| Val Gly Gly Ile Val Ser Trp Gly Ser Ile Asn Cys Gly Ala Ala Gly | | | |
| 650 655 660 | | | |
| | | | |
| cag tat ggg gtc tac aca aaa gtc atc aac tat att ccc tgg aat gag | | | 2069 |
| Gln Tyr Gly Val Tyr Thr Lys Val Ile Asn Tyr Ile Pro Trp Asn Glu | | | |
| 665 670 675 | | | |
| | | | |
| aac ata ata agt aat ttc taa | | | 2090 |
| Asn Ile Ile Ser Asn Phe | | | |
| 680 685 | | | |

<210> SEQ ID NO 51
<211> LENGTH: 685
<212> TYPE: PRT
<213> ORGANISM: Murine

<400> SEQUENCE: 51

Met Arg Leu Leu Ile Phe Leu Gly Leu Leu Trp Ser Leu Val Ala Thr
1               5                   10                  15

Leu Leu Gly Ser Lys Trp Pro Glu Pro Val Phe Gly Arg Leu Val Ser
                20                  25                  30

Pro Gly Phe Pro Glu Lys Tyr Ala Asp His Gln Asp Arg Ser Trp Thr
            35                  40                  45

Leu Thr Ala Pro Pro Gly Tyr Arg Leu Arg Leu Tyr Phe Thr His Phe
        50                  55                  60

Asp Leu Glu Leu Ser Tyr Arg Cys Glu Tyr Asp Phe Val Lys Leu Ser
65                  70                  75                  80

Ser Gly Thr Lys Val Leu Ala Thr Leu Cys Gly Gln Glu Ser Thr Asp
                85                  90                  95

Thr Glu Gln Ala Pro Gly Asn Asp Thr Phe Tyr Ser Leu Gly Pro Ser
            100                 105                 110

Leu Lys Val Thr Phe His Ser Asp Tyr Ser Asn Glu Lys Pro Phe Thr
        115                 120                 125

Gly Phe Glu Ala Phe Tyr Ala Ala Glu Asp Val Asp Glu Cys Arg Val
    130                 135                 140

Ser Leu Gly Asp Ser Val Pro Cys Asp His Tyr Cys His Asn Tyr Leu
145                 150                 155                 160

Gly Gly Tyr Tyr Cys Ser Cys Arg Ala Gly Tyr Ile Leu His Gln Asn
                165                 170                 175

Lys His Thr Cys Ser Ala Leu Cys Ser Gly Gln Val Phe Thr Gly Arg
            180                 185                 190

Ser Gly Tyr Leu Ser Ser Pro Glu Tyr Pro Gln Pro Tyr Pro Lys Leu
        195                 200                 205

Ser Ser Cys Thr Tyr Ser Ile Arg Leu Glu Asp Gly Phe Ser Val Ile
    210                 215                 220

Leu Asp Phe Val Glu Ser Phe Asp Val Glu Thr His Pro Glu Ala Gln
225                 230                 235                 240

Cys Pro Tyr Asp Ser Leu Lys Ile Gln Thr Asp Lys Gly Glu His Gly
                245                 250                 255

Pro Phe Cys Gly Lys Thr Leu Pro Pro Arg Ile Glu Thr Asp Ser His

```
            260                 265                 270
Lys Val Thr Ile Thr Phe Ala Thr Asp Glu Ser Gly Asn His Thr Gly
            275                 280                 285

Trp Lys Ile His Tyr Thr Ser Thr Ala Arg Pro Cys Pro Asp Pro Thr
            290                 295                 300

Ala Pro Pro Asn Gly Ser Ile Ser Pro Val Gln Ala Thr Tyr Val Leu
305                 310                 315                 320

Lys Asp Arg Phe Ser Val Phe Cys Lys Thr Gly Phe Glu Leu Leu Gln
            325                 330                 335

Gly Ser Val Pro Leu Lys Ser Phe Thr Ala Val Cys Gln Lys Asp Gly
            340                 345                 350

Ser Trp Asp Arg Pro Met Pro Glu Cys Ser Ile Ile Asp Cys Gly Pro
            355                 360                 365

Pro Asp Asp Leu Pro Asn Gly His Val Asp Tyr Ile Thr Gly Pro Gln
            370                 375                 380

Val Thr Thr Tyr Lys Ala Val Ile Gln Tyr Ser Cys Glu Glu Thr Phe
385                 390                 395                 400

Tyr Thr Met Ser Ser Asn Gly Lys Tyr Val Cys Glu Ala Asp Gly Phe
                    405                 410                 415

Trp Thr Ser Ser Lys Gly Glu Lys Leu Pro Pro Val Cys Glu Pro Val
                    420                 425                 430

Cys Gly Leu Ser Thr His Thr Ile Gly Gly Arg Ile Val Gly Gly Gln
                435                 440                 445

Pro Ala Lys Pro Gly Asp Phe Pro Trp Gln Val Leu Leu Leu Gly Gln
    450                 455                 460

Thr Thr Ala Ala Ala Gly Ala Leu Ile His Asp Asn Trp Val Leu Thr
465                 470                 475                 480

Ala Ala His Ala Val Tyr Glu Lys Arg Met Ala Ala Ser Ser Leu Asn
                485                 490                 495

Ile Arg Met Gly Ile Leu Lys Arg Leu Ser Pro His Tyr Thr Gln Ala
                500                 505                 510

Trp Pro Glu Glu Ile Phe Ile His Glu Gly Tyr Thr His Gly Ala Gly
                515                 520                 525

Phe Asp Asn Asp Ile Ala Leu Ile Lys Leu Lys Asn Lys Val Thr Ile
530                 535                 540

Asn Gly Ser Ile Met Pro Val Cys Leu Pro Arg Lys Glu Ala Ala Ser
545                 550                 555                 560

Leu Met Arg Thr Asp Phe Thr Gly Thr Val Ala Gly Trp Gly Leu Thr
                565                 570                 575

Gln Lys Gly Leu Leu Ala Arg Asn Leu Met Phe Val Asp Ile Pro Ile
            580                 585                 590

Ala Asp His Gln Lys Cys Thr Thr Val Tyr Glu Lys Leu Tyr Pro Gly
            595                 600                 605

Val Arg Val Ser Ala Asn Met Leu Cys Ala Gly Leu Glu Thr Gly Gly
            610                 615                 620

Lys Asp Ser Cys Arg Gly Asp Ser Gly Gly Ala Leu Val Phe Leu Asp
625                 630                 635                 640

Asn Glu Thr Gln Arg Trp Phe Val Gly Gly Ile Val Ser Trp Gly Ser
                645                 650                 655

Ile Asn Cys Gly Ala Ala Gly Gln Tyr Gly Val Tyr Thr Lys Val Ile
                660                 665                 670

Asn Tyr Ile Pro Trp Asn Glu Asn Ile Ile Ser Asn Phe
            675                 680                 685
```

<210> SEQ ID NO 52
<211> LENGTH: 670
<212> TYPE: PRT
<213> ORGANISM: Murine

<400> SEQUENCE: 52

```
Thr Leu Leu Gly Ser Lys Trp Pro Glu Pro Val Phe Gly Arg Leu Val
1               5                   10                  15

Ser Pro Gly Phe Pro Glu Lys Tyr Ala Asp His Gln Asp Arg Ser Trp
            20                  25                  30

Thr Leu Thr Ala Pro Pro Gly Tyr Arg Leu Arg Leu Tyr Phe Thr His
        35                  40                  45

Phe Asp Leu Glu Leu Ser Tyr Arg Cys Glu Tyr Asp Phe Val Lys Leu
    50                  55                  60

Ser Ser Gly Thr Lys Val Leu Ala Thr Leu Cys Gly Gln Glu Ser Thr
65                  70                  75                  80

Asp Thr Glu Gln Ala Pro Gly Asn Asp Thr Phe Tyr Ser Leu Gly Pro
                85                  90                  95

Ser Leu Lys Val Thr Phe His Ser Asp Tyr Ser Asn Glu Lys Pro Phe
            100                 105                 110

Thr Gly Phe Glu Ala Phe Tyr Ala Ala Glu Asp Val Asp Glu Cys Arg
        115                 120                 125

Val Ser Leu Gly Asp Ser Val Pro Cys Asp His Tyr Cys His Asn Tyr
    130                 135                 140

Leu Gly Gly Tyr Tyr Cys Ser Cys Arg Ala Gly Tyr Ile Leu His Gln
145                 150                 155                 160

Asn Lys His Thr Cys Ser Ala Leu Cys Ser Gly Gln Val Phe Thr Gly
                165                 170                 175

Arg Ser Gly Tyr Leu Ser Ser Pro Glu Tyr Pro Gln Pro Tyr Pro Lys
            180                 185                 190

Leu Ser Ser Cys Thr Tyr Ser Ile Arg Leu Glu Asp Gly Phe Ser Val
        195                 200                 205

Ile Leu Asp Phe Val Glu Ser Phe Asp Val Glu Thr His Pro Glu Ala
    210                 215                 220

Gln Cys Pro Tyr Asp Ser Leu Lys Ile Gln Thr Asp Lys Gly Glu His
225                 230                 235                 240

Gly Pro Phe Cys Gly Lys Thr Leu Pro Pro Arg Ile Glu Thr Asp Ser
                245                 250                 255

His Lys Val Thr Ile Thr Phe Ala Thr Asp Glu Ser Gly Asn His Thr
            260                 265                 270

Gly Trp Lys Ile His Tyr Thr Ser Thr Ala Arg Pro Cys Pro Asp Pro
        275                 280                 285

Thr Ala Pro Pro Asn Gly Ser Ile Ser Pro Val Gln Ala Thr Tyr Val
    290                 295                 300

Leu Lys Asp Arg Phe Ser Val Phe Cys Lys Thr Gly Phe Glu Leu Leu
305                 310                 315                 320

Gln Gly Ser Val Pro Leu Lys Ser Phe Thr Ala Val Cys Gln Lys Asp
                325                 330                 335

Gly Ser Trp Asp Arg Pro Met Pro Glu Cys Ser Ile Ile Asp Cys Gly
            340                 345                 350

Pro Pro Asp Asp Leu Pro Asn Gly His Val Asp Tyr Ile Thr Gly Pro
        355                 360                 365

Gln Val Thr Thr Tyr Lys Ala Val Ile Gln Tyr Ser Cys Glu Glu Thr
```

```
              370                 375                 380
Phe Tyr Thr Met Ser Ser Asn Gly Lys Tyr Val Cys Glu Ala Asp Gly
385                 390                 395                 400

Phe Trp Thr Ser Ser Lys Gly Glu Lys Leu Pro Pro Val Cys Glu Pro
                405                 410                 415

Val Cys Gly Leu Ser Thr His Thr Ile Gly Gly Arg Ile Val Gly Gly
            420                 425                 430

Gln Pro Ala Lys Pro Gly Asp Phe Pro Trp Gln Val Leu Leu Leu Gly
        435                 440                 445

Gln Thr Thr Ala Ala Ala Gly Ala Leu Ile His Asp Asn Trp Val Leu
    450                 455                 460

Thr Ala Ala His Ala Val Tyr Glu Lys Arg Met Ala Ala Ser Ser Leu
465                 470                 475                 480

Asn Ile Arg Met Gly Ile Leu Lys Arg Leu Ser Pro Tyr Thr Gln
                485                 490                 495

Ala Trp Pro Glu Glu Ile Phe Ile His Glu Gly Tyr Thr His Gly Ala
                500                 505                 510

Gly Phe Asp Asn Asp Ile Ala Leu Ile Lys Leu Lys Asn Lys Val Thr
            515                 520                 525

Ile Asn Gly Ser Ile Met Pro Val Cys Leu Pro Arg Lys Glu Ala Ala
530                 535                 540

Ser Leu Met Arg Thr Asp Phe Thr Gly Thr Val Ala Gly Trp Gly Leu
545                 550                 555                 560

Thr Gln Lys Gly Leu Leu Ala Arg Asn Leu Met Phe Val Asp Ile Pro
                565                 570                 575

Ile Ala Asp His Gln Lys Cys Thr Thr Val Tyr Glu Lys Leu Tyr Pro
                580                 585                 590

Gly Val Arg Val Ser Ala Asn Met Leu Cys Ala Gly Leu Glu Thr Gly
            595                 600                 605

Gly Lys Asp Ser Cys Arg Gly Asp Ser Gly Gly Ala Leu Val Phe Leu
        610                 615                 620

Asp Asn Glu Thr Gln Arg Trp Phe Val Gly Gly Ile Val Ser Trp Gly
625                 630                 635                 640

Ser Ile Asn Cys Gly Ala Ala Gly Gln Tyr Gly Val Tyr Thr Lys Val
                645                 650                 655

Ile Asn Tyr Ile Pro Trp Asn Glu Asn Ile Ile Ser Asn Phe
                660                 665                 670

<210> SEQ ID NO 53
<211> LENGTH: 2091
<212> TYPE: DNA
<213> ORGANISM: Rat
<220> FEATURE:
<221> NAME/KEY: CDS
<222> LOCATION: (10)..(2067)

<400> SEQUENCE: 53 tggcacaca atg agg cta ctg atc gtc ctg ggt ctg ctt tgg agt ttg gtg      51
          Met Arg Leu Leu Ile Val Leu Gly Leu Leu Trp Ser Leu Val
          1               5                   10 gcc aca ctt ttg ggc tcc aag tgg cct gag cct gta ttc ggg cgc ctg        99
Ala Thr Leu Leu Gly Ser Lys Trp Pro Glu Pro Val Phe Gly Arg Leu
15                  20                  25                  30 gtg tcc ctg gcc ttc cca gag aag tat ggc aac cat cag gat cga tcc       147
Val Ser Leu Ala Phe Pro Glu Lys Tyr Gly Asn His Gln Asp Arg Ser
                35                  40                  45
```

-continued

| | |
|---|---|
| tgg acg ctg act gca ccc cct ggc ttc cgc ctg cgc ctc tac ttc acc<br>Trp Thr Leu Thr Ala Pro Pro Gly Phe Arg Leu Arg Leu Tyr Phe Thr<br>              50                          55                          60 | 195 |
| cac ttc aac ctg gaa ctc tct tac cgc tgc gag tat gac ttt gtc aag<br>His Phe Asn Leu Glu Leu Ser Tyr Arg Cys Glu Tyr Asp Phe Val Lys<br>        65                          70                          75 | 243 |
| ttg acc tca ggg acc aag gtg cta gcc acg ctg tgt ggg cag gag agt<br>Leu Thr Ser Gly Thr Lys Val Leu Ala Thr Leu Cys Gly Gln Glu Ser<br>  80                          85                          90 | 291 |
| aca gat act gag cgg gca cct ggc aat gac acc ttc tac tca ctg ggt<br>Thr Asp Thr Glu Arg Ala Pro Gly Asn Asp Thr Phe Tyr Ser Leu Gly<br>95                        100                      105            110 | 339 |
| ccc agc cta aag gtc acc ttc cac tcc gac tac tcc aat gag aag cca<br>Pro Ser Leu Lys Val Thr Phe His Ser Asp Tyr Ser Asn Glu Lys Pro<br>              115                      120                      125 | 387 |
| ttc aca gga ttt gag gcc ttc tat gca gcg gag gat gtg gat gaa tgc<br>Phe Thr Gly Phe Glu Ala Phe Tyr Ala Ala Glu Asp Val Asp Glu Cys<br>            130                      135                      140 | 435 |
| aga aca tcc ctg gga gac tca gtc cct tgt gac cat tat tgc cac aac<br>Arg Thr Ser Leu Gly Asp Ser Val Pro Cys Asp His Tyr Cys His Asn<br>              145                      150                      155 | 483 |
| tac ctg ggc ggc tac tac tgc tcc tgc cga gtg ggc tac att ctg cac<br>Tyr Leu Gly Gly Tyr Tyr Cys Ser Cys Arg Val Gly Tyr Ile Leu His<br>    160                          165                      170 | 531 |
| cag aac aag cat acc tgc tca gcc ctt tgt tca ggc cag gtg ttc act<br>Gln Asn Lys His Thr Cys Ser Ala Leu Cys Ser Gly Gln Val Phe Thr<br>175                        180                      185                      190 | 579 |
| ggg agg tct ggc ttt ctc agt agc cct gag tac cca cag cca tac ccc<br>Gly Arg Ser Gly Phe Leu Ser Ser Pro Glu Tyr Pro Gln Pro Tyr Pro<br>              195                      200                      205 | 627 |
| aaa ctc tcc agc tgc gcc tac aac atc cgc ctg gag gaa ggc ttc agt<br>Lys Leu Ser Ser Cys Ala Tyr Asn Ile Arg Leu Glu Glu Gly Phe Ser<br>            210                      215                      220 | 675 |
| atc acc ctg gac ttc gtg gag tcc ttt gat gtg gag atg cac cct gaa<br>Ile Thr Leu Asp Phe Val Glu Ser Phe Asp Val Glu Met His Pro Glu<br>              225                      230                      235 | 723 |
| gcc cag tgc ccc tac gac tcc ctc aag att caa aca gac aag agg gaa<br>Ala Gln Cys Pro Tyr Asp Ser Leu Lys Ile Gln Thr Asp Lys Arg Glu<br>    240                          245                      250 | 771 |
| tac ggc ccg ttt tgt ggg aag acg ctg ccc ccc agg att gaa act gac<br>Tyr Gly Pro Phe Cys Gly Lys Thr Leu Pro Pro Arg Ile Glu Thr Asp<br>255                        260                      265                      270 | 819 |
| agc aac aag gtg acc att acc ttt acc acc gac gag tca ggg aac cac<br>Ser Asn Lys Val Thr Ile Thr Phe Thr Thr Asp Glu Ser Gly Asn His<br>            275                      280                      285 | 867 |
| aca ggc tgg aag ata cac tac aca agc aca gca cag ccc tgc cct gat<br>Thr Gly Trp Lys Ile His Tyr Thr Ser Thr Ala Gln Pro Cys Pro Asp<br>              290                      295                      300 | 915 |
| cca acg gcg cca cct aat ggt cac att tca cct gtg caa gcc acg tat<br>Pro Thr Ala Pro Pro Asn Gly His Ile Ser Pro Val Gln Ala Thr Tyr<br>    305                          310                      315 | 963 |
| gtc ctg aag gac agc ttt tct gtc ttc tgc aag act ggc ttc gag ctt<br>Val Leu Lys Asp Ser Phe Ser Val Phe Cys Lys Thr Gly Phe Glu Leu<br>320                        325                      330 | 1011 |
| ctg caa ggt tct gtc ccc ctg aag tca ttc act gct gtc tgt cag aaa<br>Leu Gln Gly Ser Val Pro Leu Lys Ser Phe Thr Ala Val Cys Gln Lys<br>335                        340                      345                      350 | 1059 |
| gat gga tct tgg gac cgg ccg ata cca gag tgc agc att att gac tgt<br>Asp Gly Ser Trp Asp Arg Pro Ile Pro Glu Cys Ser Ile Ile Asp Cys<br>            355                      360                      365 | 1107 |

```
ggc cct ccc gat gac cta ccc aat ggc cac gtg gac tat atc aca ggc    1155
Gly Pro Pro Asp Asp Leu Pro Asn Gly His Val Asp Tyr Ile Thr Gly
        370                 375                 380 cct gaa gtg acc acc tac aaa gct gtg att cag tac agc tgt gaa gag    1203
Pro Glu Val Thr Thr Tyr Lys Ala Val Ile Gln Tyr Ser Cys Glu Glu
    385                 390                 395 act ttc tac aca atg agc agc aat ggt aaa tat gtg tgt gag gct gat    1251
Thr Phe Tyr Thr Met Ser Ser Asn Gly Lys Tyr Val Cys Glu Ala Asp
400                 405                 410 gga ttc tgg acg agc tcc aaa gga gaa aaa tcc ctc ccg gtt tgc aag    1299
Gly Phe Trp Thr Ser Ser Lys Gly Glu Lys Ser Leu Pro Val Cys Lys
415                 420                 425                 430 cct gtc tgt gga ctg tcc aca cac act tca gga ggc cgt ata att gga    1347
Pro Val Cys Gly Leu Ser Thr His Thr Ser Gly Gly Arg Ile Ile Gly
                435                 440                 445 gga cag cct gca aag cct ggt gac ttt cct tgg caa gtc ttg tta ctg    1395
Gly Gln Pro Ala Lys Pro Gly Asp Phe Pro Trp Gln Val Leu Leu Leu
            450                 455                 460 ggt gaa act aca gca gca ggt gct ctt ata cat gac gac tgg gtc cta    1443
Gly Glu Thr Thr Ala Ala Gly Ala Leu Ile His Asp Asp Trp Val Leu
        465                 470                 475 aca gcg gct cat gct gta tat ggg aaa aca gag gcg atg tcc tcc ctg    1491
Thr Ala Ala His Ala Val Tyr Gly Lys Thr Glu Ala Met Ser Ser Leu
    480                 485                 490 gac atc cgc atg ggc atc ctc aaa agg ctc tcc ctc att tac act caa    1539
Asp Ile Arg Met Gly Ile Leu Lys Arg Leu Ser Leu Ile Tyr Thr Gln
495                 500                 505                 510 gcc tgg cca gag gct gtc ttt atc cat gaa ggc tac act cac gga gct    1587
Ala Trp Pro Glu Ala Val Phe Ile His Glu Gly Tyr Thr His Gly Ala
                515                 520                 525 ggt ttt gac aat gat ata gca ctg att aaa ctc aag aac aaa gtc aca    1635
Gly Phe Asp Asn Asp Ile Ala Leu Ile Lys Leu Lys Asn Lys Val Thr
            530                 535                 540 atc aac aga aac atc atg ccg att tgt cta cca aga aaa gaa gct gca    1683
Ile Asn Arg Asn Ile Met Pro Ile Cys Leu Pro Arg Lys Glu Ala Ala
        545                 550                 555 tcc tta atg aaa aca gac ttc gtt gga act gtg gct ggc tgg ggg tta    1731
Ser Leu Met Lys Thr Asp Phe Val Gly Thr Val Ala Gly Trp Gly Leu
    560                 565                 570 acc cag aag ggg ttt ctt gct aga aac cta atg ttt gtg gac ata cca    1779
Thr Gln Lys Gly Phe Leu Ala Arg Asn Leu Met Phe Val Asp Ile Pro
575                 580                 585                 590 att gtt gac cac caa aaa tgt gct act gcg tat aca aag cag ccc tac    1827
Ile Val Asp His Gln Lys Cys Ala Thr Ala Tyr Thr Lys Gln Pro Tyr
                595                 600                 605 cca gga gca aaa gtg act gtt aac atg ctc tgt gct ggc cta gac cgc    1875
Pro Gly Ala Lys Val Thr Val Asn Met Leu Cys Ala Gly Leu Asp Arg
            610                 615                 620 ggt ggc aag gac agc tgc aga ggt gac agc gga ggg gca tta gtg ttt    1923
Gly Gly Lys Asp Ser Cys Arg Gly Asp Ser Gly Gly Ala Leu Val Phe
        625                 630                 635 cta gac aat gaa aca cag aga tgg ttt gtg gga gga ata gtt tcc tgg    1971
Leu Asp Asn Glu Thr Gln Arg Trp Phe Val Gly Gly Ile Val Ser Trp
    640                 645                 650 ggt tct att aac tgt ggg ggg tca gaa cag tat ggg gtc tac acg aaa    2019
Gly Ser Ile Asn Cys Gly Gly Ser Glu Gln Tyr Gly Val Tyr Thr Lys
655                 660                 665                 670 gtc acg aac tat att ccc tgg att gag aac ata ata aat aat ttc taa    2067
Val Thr Asn Tyr Ile Pro Trp Ile Glu Asn Ile Ile Asn Asn Phe
```
tttgcaaaaa aaaaaaaaaa aaaa                                                 2091

<210> SEQ ID NO 54
<211> LENGTH: 685
<212> TYPE: PRT
<213> ORGANISM: Rat

<400> SEQUENCE: 54

Met Arg Leu Leu Ile Val Leu Gly Leu Leu Trp Ser Leu Val Ala Thr
1               5                   10                  15

Leu Leu Gly Ser Lys Trp Pro Glu Pro Val Phe Gly Arg Leu Val Ser
            20                  25                  30

Leu Ala Phe Pro Glu Lys Tyr Gly Asn His Gln Asp Arg Ser Trp Thr
        35                  40                  45

Leu Thr Ala Pro Pro Gly Phe Arg Leu Arg Leu Tyr Phe Thr His Phe
    50                  55                  60

Asn Leu Glu Leu Ser Tyr Arg Cys Glu Tyr Asp Phe Val Lys Leu Thr
65                  70                  75                  80

Ser Gly Thr Lys Val Leu Ala Thr Leu Cys Gly Gln Glu Ser Thr Asp
                85                  90                  95

Thr Glu Arg Ala Pro Gly Asn Asp Thr Phe Tyr Ser Leu Gly Pro Ser
            100                 105                 110

Leu Lys Val Thr Phe His Ser Asp Tyr Ser Asn Glu Lys Pro Phe Thr
        115                 120                 125

Gly Phe Glu Ala Phe Tyr Ala Ala Glu Asp Val Asp Glu Cys Arg Thr
    130                 135                 140

Ser Leu Gly Asp Ser Val Pro Cys Asp His Tyr Cys His Asn Tyr Leu
145                 150                 155                 160

Gly Gly Tyr Tyr Cys Ser Cys Arg Val Gly Tyr Ile Leu His Gln Asn
                165                 170                 175

Lys His Thr Cys Ser Ala Leu Cys Ser Gly Gln Val Phe Thr Gly Arg
            180                 185                 190

Ser Gly Phe Leu Ser Ser Pro Glu Tyr Pro Gln Pro Tyr Pro Lys Leu
        195                 200                 205

Ser Ser Cys Ala Tyr Asn Ile Arg Leu Glu Glu Gly Phe Ser Ile Thr
    210                 215                 220

Leu Asp Phe Val Glu Ser Phe Asp Val Glu Met His Pro Glu Ala Gln
225                 230                 235                 240

Cys Pro Tyr Asp Ser Leu Lys Ile Gln Thr Asp Lys Arg Glu Tyr Gly
                245                 250                 255

Pro Phe Cys Gly Lys Thr Leu Pro Pro Arg Ile Glu Thr Asp Ser Asn
            260                 265                 270

Lys Val Thr Ile Thr Phe Thr Thr Asp Glu Ser Gly Asn His Thr Gly
        275                 280                 285

Trp Lys Ile His Tyr Thr Ser Thr Ala Gln Pro Cys Pro Asp Pro Thr
    290                 295                 300

Ala Pro Pro Asn Gly His Ile Ser Pro Val Gln Ala Thr Tyr Val Leu
305                 310                 315                 320

Lys Asp Ser Phe Ser Val Phe Cys Lys Thr Gly Phe Glu Leu Leu Gln
                325                 330                 335

Gly Ser Val Pro Leu Lys Ser Phe Thr Ala Val Cys Gln Lys Asp Gly
            340                 345                 350

Ser Trp Asp Arg Pro Ile Pro Glu Cys Ser Ile Ile Asp Cys Gly Pro

```
                355                 360                 365
Pro Asp Asp Leu Pro Asn Gly His Val Asp Tyr Ile Thr Gly Pro Glu
        370                 375                 380

Val Thr Thr Tyr Lys Ala Val Ile Gln Tyr Ser Cys Glu Glu Thr Phe
385                 390                 395                 400

Tyr Thr Met Ser Ser Asn Gly Lys Tyr Val Cys Glu Ala Asp Gly Phe
                405                 410                 415

Trp Thr Ser Ser Lys Gly Glu Lys Ser Leu Pro Val Cys Lys Pro Val
        420                 425                 430

Cys Gly Leu Ser Thr His Thr Ser Gly Gly Arg Ile Ile Gly Gly Gln
            435                 440                 445

Pro Ala Lys Pro Gly Asp Phe Pro Trp Gln Val Leu Leu Leu Gly Glu
        450                 455                 460

Thr Thr Ala Ala Gly Ala Leu Ile His Asp Asp Trp Val Leu Thr Ala
465                 470                 475                 480

Ala His Ala Val Tyr Gly Lys Thr Glu Ala Met Ser Ser Leu Asp Ile
                485                 490                 495

Arg Met Gly Ile Leu Lys Arg Leu Ser Leu Ile Tyr Thr Gln Ala Trp
            500                 505                 510

Pro Glu Ala Val Phe Ile His Glu Gly Tyr Thr His Gly Ala Gly Phe
        515                 520                 525

Asp Asn Asp Ile Ala Leu Ile Lys Leu Lys Asn Lys Val Thr Ile Asn
530                 535                 540

Arg Asn Ile Met Pro Ile Cys Leu Pro Arg Lys Glu Ala Ala Ser Leu
545                 550                 555                 560

Met Lys Thr Asp Phe Val Gly Thr Val Ala Gly Trp Gly Leu Thr Gln
                565                 570                 575

Lys Gly Phe Leu Ala Arg Asn Leu Met Phe Val Asp Ile Pro Ile Val
            580                 585                 590

Asp His Gln Lys Cys Ala Thr Ala Tyr Thr Lys Gln Pro Tyr Pro Gly
        595                 600                 605

Ala Lys Val Thr Val Asn Met Leu Cys Ala Gly Leu Asp Arg Gly Gly
        610                 615                 620

Lys Asp Ser Cys Arg Gly Asp Ser Gly Gly Ala Leu Val Phe Leu Asp
625                 630                 635                 640

Asn Glu Thr Gln Arg Trp Phe Val Gly Gly Ile Val Ser Trp Gly Ser
                645                 650                 655

Ile Asn Cys Gly Gly Ser Glu Gln Tyr Gly Val Tyr Thr Lys Val Thr
            660                 665                 670

Asn Tyr Ile Pro Trp Ile Glu Asn Ile Ile Asn Asn Phe
        675                 680                 685

<210> SEQ ID NO 55
<211> LENGTH: 670
<212> TYPE: PRT
<213> ORGANISM: Rat

<400> SEQUENCE: 55

Thr Leu Leu Gly Ser Lys Trp Pro Glu Pro Val Phe Gly Arg Leu Val
1               5                   10                  15

Ser Leu Ala Phe Pro Glu Lys Tyr Gly Asn His Gln Asp Arg Ser Trp
                20                  25                  30

Thr Leu Thr Ala Pro Pro Gly Phe Arg Leu Arg Leu Tyr Phe Thr His
            35                  40                  45
```

-continued

```
Phe Asn Leu Glu Leu Ser Tyr Arg Cys Glu Tyr Asp Phe Val Lys Leu
 50                  55                  60

Thr Ser Gly Thr Lys Val Leu Ala Thr Leu Cys Gly Gln Glu Ser Thr
 65                  70                  75                  80

Asp Thr Glu Arg Ala Pro Gly Asn Asp Thr Phe Tyr Ser Leu Gly Pro
                 85                  90                  95

Ser Leu Lys Val Thr Phe His Ser Asp Tyr Ser Asn Glu Lys Pro Phe
            100                 105                 110

Thr Gly Phe Glu Ala Phe Tyr Ala Ala Glu Asp Val Asp Glu Cys Arg
        115                 120                 125

Thr Ser Leu Gly Asp Ser Val Pro Cys Asp His Tyr Cys His Asn Tyr
130                 135                 140

Leu Gly Gly Tyr Tyr Cys Ser Cys Arg Val Gly Tyr Ile Leu His Gln
145                 150                 155                 160

Asn Lys His Thr Cys Ser Ala Leu Cys Ser Gly Gln Val Phe Thr Gly
                165                 170                 175

Arg Ser Gly Phe Leu Ser Ser Pro Glu Tyr Pro Gln Pro Tyr Pro Lys
            180                 185                 190

Leu Ser Ser Cys Ala Tyr Asn Ile Arg Leu Glu Glu Gly Phe Ser Ile
        195                 200                 205

Thr Leu Asp Phe Val Glu Ser Phe Asp Val Glu Met His Pro Glu Ala
210                 215                 220

Gln Cys Pro Tyr Asp Ser Leu Lys Ile Gln Thr Asp Lys Arg Glu Tyr
225                 230                 235                 240

Gly Pro Phe Cys Gly Lys Thr Leu Pro Pro Arg Ile Glu Thr Asp Ser
                245                 250                 255

Asn Lys Val Thr Ile Thr Phe Thr Thr Asp Glu Ser Gly Asn His Thr
            260                 265                 270

Gly Trp Lys Ile His Tyr Thr Ser Thr Ala Gln Pro Cys Pro Asp Pro
        275                 280                 285

Thr Ala Pro Pro Asn Gly His Ile Ser Pro Val Gln Ala Thr Tyr Val
290                 295                 300

Leu Lys Asp Ser Phe Ser Val Phe Cys Lys Thr Gly Phe Glu Leu Leu
305                 310                 315                 320

Gln Gly Ser Val Pro Leu Lys Ser Phe Thr Ala Val Cys Gln Lys Asp
                325                 330                 335

Gly Ser Trp Asp Arg Pro Ile Pro Glu Cys Ser Ile Ile Asp Cys Gly
            340                 345                 350

Pro Pro Asp Asp Leu Pro Asn Gly His Val Asp Tyr Ile Thr Gly Pro
        355                 360                 365

Glu Val Thr Thr Tyr Lys Ala Val Ile Gln Tyr Ser Cys Glu Glu Thr
370                 375                 380

Phe Tyr Thr Met Ser Ser Asn Gly Lys Tyr Val Cys Glu Ala Asp Gly
385                 390                 395                 400

Phe Trp Thr Ser Ser Lys Gly Glu Lys Ser Leu Pro Val Cys Lys Pro
                405                 410                 415

Val Cys Gly Leu Ser Thr His Thr Ser Gly Arg Ile Ile Gly Gly
            420                 425                 430

Gln Pro Ala Lys Pro Gly Asp Phe Pro Trp Gln Val Leu Leu Leu Gly
        435                 440                 445

Glu Thr Thr Ala Ala Gly Ala Leu Ile His Asp Asp Trp Val Leu Thr
450                 455                 460

Ala Ala His Ala Val Tyr Gly Lys Thr Glu Ala Met Ser Ser Leu Asp
```

```
                465                 470                 475                 480
    Ile Arg Met Gly Ile Leu Lys Arg Leu Ser Leu Ile Tyr Thr Gln Ala
                        485                 490                 495

Trp Pro Glu Ala Val Phe Ile His Glu Gly Tyr Thr His Gly Ala Gly
                        500                 505                 510

Phe Asp Asn Asp Ile Ala Leu Ile Lys Leu Lys Asn Lys Val Thr Ile
                        515                 520                 525

Asn Arg Asn Ile Met Pro Ile Cys Leu Pro Arg Lys Glu Ala Ala Ser
                        530                 535                 540

Leu Met Lys Thr Asp Phe Val Gly Thr Val Ala Gly Trp Gly Leu Thr
    545                 550                 555                 560

Gln Lys Gly Phe Leu Ala Arg Asn Leu Met Phe Val Asp Ile Pro Ile
                        565                 570                 575

Val Asp His Gln Lys Cys Ala Thr Ala Tyr Thr Lys Gln Pro Tyr Pro
                        580                 585                 590

Gly Ala Lys Val Thr Val Asn Met Leu Cys Ala Gly Leu Asp Arg Gly
                        595                 600                 605

Gly Lys Asp Ser Cys Arg Gly Asp Ser Gly Gly Ala Leu Val Phe Leu
                        610                 615                 620

Asp Asn Glu Thr Gln Arg Trp Phe Val Gly Gly Ile Val Ser Trp Gly
    625                 630                 635                 640

Ser Ile Asn Cys Gly Gly Ser Glu Gln Tyr Gly Val Tyr Thr Lys Val
                        645                 650                 655

Thr Asn Tyr Ile Pro Trp Ile Glu Asn Ile Ile Asn Asn Phe
                        660                 665                 670

<210> SEQ ID NO 56
<211> LENGTH: 28
<212> TYPE: DNA
<213> ORGANISM: Artificial Sequence
<220> FEATURE:
<223> OTHER INFORMATION: Homo Sapiens

<400> SEQUENCE: 56
atgaggctgc tgaccctcct gggccttc                                          28

<210> SEQ ID NO 57
<211> LENGTH: 23
<212> TYPE: DNA
<213> ORGANISM: Artificial Sequence
<220> FEATURE:
<223> OTHER INFORMATION: Homo Sapiens

<400> SEQUENCE: 57
gtgcccctcc tgcgtcacct ctg                                               23

<210> SEQ ID NO 58
<211> LENGTH: 23
<212> TYPE: DNA
<213> ORGANISM: Artificial Sequence
<220> FEATURE:
<223> OTHER INFORMATION: Homo Sapiens

<400> SEQUENCE: 58
cagaggtgac gcaggagggg cac                                               23

<210> SEQ ID NO 59
<211> LENGTH: 27
<212> TYPE: DNA
<213> ORGANISM: Artificial Sequence
```

```
<220> FEATURE:
<223> OTHER INFORMATION: Homo Sapiens

<400> SEQUENCE: 59
ttaaaatcac taattatgtt ctcgatc                                        27

<210> SEQ ID NO 60
<211> LENGTH: 22
<212> TYPE: DNA
<213> ORGANISM: Artificial Sequence
<220> FEATURE:
<223> OTHER INFORMATION: Murine

<400> SEQUENCE: 60
atgaggctac tcatcttcct gg                                             22

<210> SEQ ID NO 61
<211> LENGTH: 23
<212> TYPE: DNA
<213> ORGANISM: Artificial Sequence
<220> FEATURE:
<223> OTHER INFORMATION: Murine

<400> SEQUENCE: 61
ctgcagaggt gacgcagggg ggg                                            23

<210> SEQ ID NO 62
<211> LENGTH: 23
<212> TYPE: DNA
<213> ORGANISM: Artificial Sequence
<220> FEATURE:
<223> OTHER INFORMATION: Murine

<400> SEQUENCE: 62 cccccctgc gtcacctctg cag                                             23

<210> SEQ ID NO 63
<211> LENGTH: 29
<212> TYPE: DNA
<213> ORGANISM: Artificial Sequence
<220> FEATURE:
<223> OTHER INFORMATION: Murine

<400> SEQUENCE: 63
ttagaaatta cttattatgt tctcaatcc                                      29

<210> SEQ ID NO 64
<211> LENGTH: 29
<212> TYPE: DNA
<213> ORGANISM: Artificial Sequence
<220> FEATURE:
<223> OTHER INFORMATION: Rat

<400> SEQUENCE: 64
gaggtgacgc aggaggggca ttagtgttt                                      29

<210> SEQ ID NO 65
<211> LENGTH: 37
<212> TYPE: DNA
<213> ORGANISM: Artificial Sequence
<220> FEATURE:
<223> OTHER INFORMATION: Rat

<400> SEQUENCE: 65
ctagaaacac taatgcccct cctgcgtcac ctctgca                             37
```

<210> SEQ ID NO 66
<211> LENGTH: 354
<212> TYPE: DNA
<213> ORGANISM: Artificial Sequence
<220> FEATURE:
<223> OTHER INFORMATION: Synthetic

<400> SEQUENCE: 66

```
caggtcacct tgaaggagtc tggtcctgtg ctggtgaaac ccacagagac cctcacgctg      60
acctgcaccg tctctgggtt ctcactcagc aggggtaaaa tgggtgtgag ctggatccgt     120
cagcccccag ggaaggccct ggagtggctt gcacacattt tttcgagtga cgaaaaatcc     180
tacaggacat cgctgaagag caggctcacc atctccaagg acacctccaa aaaccaggtg     240
gtccttacaa tgaccaacat ggaccctgtg gacacagcca cgtattactg tgcacggata     300
cgacgtggag gaattgacta ctggggccag ggaaccctgg tcactgtctc ctca           354
```

<210> SEQ ID NO 67
<211> LENGTH: 118
<212> TYPE: PRT
<213> ORGANISM: Artificial Sequence
<220> FEATURE:
<223> OTHER INFORMATION: Synthetic

<400> SEQUENCE: 67

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Arg Gly
            20                  25                  30

Lys Met Gly Val Ser Trp Ile Arg Gln Pro Pro Gly Lys Ala Leu Glu
        35                  40                  45

Trp Leu Ala His Ile Phe Ser Ser Asp Glu Lys Ser Tyr Arg Thr Ser
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile Arg Arg Gly Gly Ile Asp Tyr Trp Gly Gln Gly Thr
            100                 105                 110

Leu Val Thr Val Ser Ser
        115

<210> SEQ ID NO 68
<211> LENGTH: 121
<212> TYPE: PRT
<213> ORGANISM: Artificial Sequence
<220> FEATURE:
<223> OTHER INFORMATION: Synthetic

<400> SEQUENCE: 68

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Thr
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn

```
                    65                  70                  75                  80
Gln Phe Ser Leu Gln Leu Asn Ser Val Thr Pro Glu Asp Thr Ala Val
                    85                  90                  95

Tyr Tyr Cys Ala Arg Asp Pro Phe Gly Val Pro Phe Asp Ile Trp Gly
            100                 105                 110

Gln Gly Thr Met Val Thr Val Ser Ser
            115                 120

<210> SEQ ID NO 69
<211> LENGTH: 106
<212> TYPE: PRT
<213> ORGANISM: Artificial Sequence
<220> FEATURE:
<223> OTHER INFORMATION: Synthetic

<400> SEQUENCE: 69

Gln Pro Val Leu Thr Gln Pro Ser Leu Ser Val Ser Pro Gly Gln
1               5                   10                  15

Thr Ala Ser Ile Thr Cys Ser Gly Glu Lys Leu Gly Asp Lys Tyr Ala
            20                  25                  30

Tyr Trp Tyr Gln Gln Lys Pro Gly Gln Ser Pro Val Leu Val Met Tyr
        35                  40                  45

Gln Asp Lys Gln Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Ala Val
                85                  90                  95

Phe Gly Gly Gly Thr Lys Leu Thr Val Leu
            100                 105

<210> SEQ ID NO 70
<211> LENGTH: 324
<212> TYPE: DNA
<213> ORGANISM: Artificial Sequence
<220> FEATURE:
<223> OTHER INFORMATION: Synthetic

<400> SEQUENCE: 70
tcctatgagc tgatacagcc accctcggtg tcagtggccc caggacagac ggccaccatt      60
acctgtgcgg gagacaacct tgggaagaaa cgtgtgcact ggtaccagca gaggccaggc     120
caggcccctg tgttggtcat ctatgatgat agcgaccggc cctcagggat ccctgaccga     180
ttctctgcct ccaactctgg gaacacggcc accctgacca tcactagggg cgaagccggg     240
gatgaggccg actattattg tcaggtgtgg gacattgcta ctgatcatgt ggtcttcggc     300
ggagggacca agctcaccgt ccta                                            324

<210> SEQ ID NO 71
<211> LENGTH: 120
<212> TYPE: PRT
<213> ORGANISM: Artificial Sequence
<220> FEATURE:
<223> OTHER INFORMATION: Synthetic

<400> SEQUENCE: 71

Ser Tyr Glu Leu Ile Gln Pro Pro Ser Val Ser Val Ala Pro Gly Gln
1               5                   10                  15

Thr Ala Thr Ile Thr Cys Ala Gly Asp Asn Leu Gly Lys Lys Arg Val
            20                  25                  30
```

```
His Trp Tyr Gln Gln Arg Pro Gly Gln Ala Pro Val Leu Val Ile Tyr
        35                  40                  45

Asp Asp Ser Asp Arg Pro Ser Gly Ile Pro Asp Arg Phe Ser Ala Ser
    50                  55                  60

Asn Ser Gly Asn Thr Ala Thr Leu Thr Ile Thr Arg Gly Glu Ala Gly
65                  70                  75                  80

Asp Glu Ala Asp Tyr Tyr Cys Gln Val Trp Asp Ile Ala Thr Asp His
                85                  90                  95

Val Val Phe Gly Gly Gly Thr Lys Leu Thr Val Leu Ala Ala Ala Gly
            100                 105                 110

Ser Glu Gln Lys Leu Ile Ser Glu
        115                 120

<210> SEQ ID NO 72
<211> LENGTH: 36
<212> TYPE: PRT
<213> ORGANISM: Artificial Sequence
<220> FEATURE:
<223> OTHER INFORMATION: Synthetic

<400> SEQUENCE: 72

Leu Glu Val Thr Cys Glu Pro Gly Thr Thr Phe Lys Asp Lys Cys Asn
1               5                   10                  15

Thr Cys Arg Cys Gly Ser Asp Gly Lys Ser Ala Val Cys Thr Lys Leu
            20                  25                  30

Trp Cys Asn Gln
        35

<210> SEQ ID NO 73
<211> LENGTH: 33
<212> TYPE: PRT
<213> ORGANISM: Artificial Sequence
<220> FEATURE:
<223> OTHER INFORMATION: Synthetic

<400> SEQUENCE: 73

Thr Cys Glu Pro Gly Thr Thr Phe Lys Asp Lys Cys Asn Thr Cys Arg
1               5                   10                  15

Cys Gly Ser Asp Gly Lys Ser Ala Val Cys Thr Lys Leu Trp Cys Asn
            20                  25                  30

Gln

<210> SEQ ID NO 74
<211> LENGTH: 20
<212> TYPE: PRT
<213> ORGANISM: Artificial Sequence
<220> FEATURE:
<223> OTHER INFORMATION: Synthetic

<400> SEQUENCE: 74

Thr Cys Arg Cys Gly Ser Asp Gly Lys Ser Ala Val Cys Thr Lys Leu
1               5                   10                  15

Trp Cys Asn Gln
            20

<210> SEQ ID NO 75
<211> LENGTH: 491
<212> TYPE: PRT
<213> ORGANISM: Artificial Sequence
<220> FEATURE:
<223> OTHER INFORMATION: Synthetic
```

<400> SEQUENCE: 75

Leu Glu Val Thr Cys Glu Pro Gly Thr Thr Phe Lys Asp Lys Cys Asn
1               5                   10                  15

Thr Cys Arg Cys Gly Ser Asp Gly Lys Ser Ala Val Cys Thr Lys Leu
            20                  25                  30

Trp Cys Asn Gln Gly Thr Gly Gly Ser Gly Ser Ser Ser Gln Val
        35                  40                  45

Thr Leu Lys Glu Ser Gly Pro Val Leu Val Lys Pro Thr Glu Thr Leu
    50                  55                  60

Thr Leu Thr Cys Thr Val Ser Gly Phe Ser Leu Ser Arg Gly Lys Met
65                  70                  75                  80

Gly Val Ser Trp Ile Arg Gln Pro Pro Gly Lys Ala Leu Glu Trp Leu
                85                  90                  95

Ala His Ile Phe Ser Ser Asp Glu Lys Ser Tyr Arg Thr Ser Leu Lys
            100                 105                 110

Ser Arg Leu Thr Ile Ser Lys Asp Thr Ser Lys Asn Gln Val Val Leu
            115                 120                 125

Thr Met Thr Asn Met Asp Pro Val Asp Thr Ala Thr Tyr Tyr Cys Ala
130                 135                 140

Arg Ile Arg Arg Gly Gly Ile Asp Tyr Trp Gly Gln Gly Thr Leu Val
145                 150                 155                 160

Thr Val Ser Ser Ala Ser Thr Lys Gly Pro Ser Val Phe Pro Leu Ala
                165                 170                 175

Pro Cys Ser Arg Ser Thr Ser Glu Ser Thr Ala Ala Leu Gly Cys Leu
            180                 185                 190

Val Lys Asp Tyr Phe Pro Glu Pro Val Thr Val Ser Trp Asn Ser Gly
            195                 200                 205

Ala Leu Thr Ser Gly Val His Thr Phe Pro Ala Val Leu Gln Ser Ser
210                 215                 220

Gly Leu Tyr Ser Leu Ser Ser Val Val Thr Val Pro Ser Ser Ser Leu
225                 230                 235                 240

Gly Thr Lys Thr Tyr Thr Cys Asn Val Asp His Lys Pro Ser Asn Thr
                245                 250                 255

Lys Val Asp Lys Arg Val Glu Ser Lys Tyr Gly Pro Pro Cys Pro Pro
            260                 265                 270

Cys Pro Ala Pro Glu Phe Leu Gly Gly Pro Ser Val Phe Leu Phe Pro
        275                 280                 285

Pro Lys Pro Lys Asp Thr Leu Met Ile Ser Arg Thr Pro Glu Val Thr
    290                 295                 300

Cys Val Val Val Asp Val Ser Gln Glu Asp Pro Glu Val Gln Phe Asn
305                 310                 315                 320

Trp Tyr Val Asp Gly Val Glu Val His Asn Ala Lys Thr Lys Pro Arg
                325                 330                 335

Glu Glu Gln Phe Asn Ser Thr Tyr Arg Val Val Ser Val Leu Thr Val
            340                 345                 350

Leu His Gln Asp Trp Leu Asn Gly Lys Glu Tyr Lys Cys Lys Val Ser
        355                 360                 365

Asn Lys Gly Leu Pro Ser Ser Ile Glu Lys Thr Ile Ser Lys Ala Lys
    370                 375                 380

Gly Gln Pro Arg Glu Pro Gln Val Tyr Thr Leu Pro Pro Ser Gln Glu
385                 390                 395                 400

Glu Met Thr Lys Asn Gln Val Ser Leu Thr Cys Leu Val Lys Gly Phe

```
                405                 410                 415
Tyr Pro Ser Asp Ile Ala Val Glu Trp Glu Ser Asn Gly Gln Pro Glu
            420                 425                 430

Asn Asn Tyr Lys Thr Thr Pro Pro Val Leu Asp Ser Asp Gly Ser Phe
            435                 440                 445

Phe Leu Tyr Ser Arg Leu Thr Val Asp Lys Ser Arg Trp Gln Glu Gly
            450                 455                 460

Asn Val Phe Ser Cys Ser Val Met His Glu Ala Leu His Asn His Tyr
465                 470                 475                 480

Thr Gln Lys Ser Leu Ser Leu Ser Leu Gly Lys
                485                 490

<210> SEQ ID NO 76
<211> LENGTH: 491
<212> TYPE: PRT
<213> ORGANISM: Artificial Sequence
<220> FEATURE:
<223> OTHER INFORMATION: Synthetic

<400> SEQUENCE: 76

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Arg Gly
            20                  25                  30

Lys Met Gly Val Ser Trp Ile Arg Gln Pro Pro Gly Lys Ala Leu Glu
        35                  40                  45

Trp Leu Ala His Ile Phe Ser Ser Asp Glu Lys Ser Tyr Arg Thr Ser
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile Arg Arg Gly Gly Ile Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
```

```
            275                 280                 285
Pro Arg Glu Glu Gln Phe Asn Ser Thr Tyr Arg Val Ser Val Leu
        290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys Ala Ala Gly
                435                 440                 445

Gly Ser Gly Leu Glu Val Thr Cys Glu Pro Gly Thr Thr Phe Lys Asp
        450                 455                 460

Lys Cys Asn Thr Cys Arg Cys Gly Ser Asp Gly Lys Ser Ala Val Cys
465                 470                 475                 480

Thr Lys Leu Trp Cys Asn Gln Gly Ser Gly Ala
                485                 490

<210> SEQ ID NO 77
<211> LENGTH: 258
<212> TYPE: PRT
<213> ORGANISM: Artificial Sequence
<220> FEATURE:
<223> OTHER INFORMATION: Synthetic

<400> SEQUENCE: 77

Leu Glu Val Thr Cys Glu Pro Gly Thr Thr Phe Lys Asp Lys Cys Asn
1               5                   10                  15

Thr Cys Arg Cys Gly Ser Asp Gly Lys Ser Ala Val Cys Thr Lys Leu
                20                  25                  30

Trp Cys Asn Gln Gly Thr Gly Gly Ser Gly Ser Ser Gln Pro
                35                  40                  45

Val Leu Thr Gln Pro Pro Ser Leu Ser Val Ser Pro Gly Gln Thr Ala
        50                  55                  60

Ser Ile Thr Cys Ser Gly Glu Lys Leu Gly Asp Lys Tyr Ala Tyr Trp
65                  70                  75                  80

Tyr Gln Gln Lys Pro Gly Gln Ser Pro Val Leu Val Met Tyr Gln Asp
                85                  90                  95

Lys Gln Arg Pro Ser Gly Ile Pro Glu Arg Phe Ser Gly Ser Asn Ser
            100                 105                 110

Gly Asn Thr Ala Thr Leu Thr Ile Ser Gly Thr Gln Ala Met Asp Glu
                115                 120                 125

Ala Asp Tyr Tyr Cys Gln Ala Trp Asp Ser Ser Thr Ala Val Phe Gly
            130                 135                 140

Gly Gly Thr Lys Leu Thr Val Leu Gly Gln Pro Lys Ala Ala Pro Ser
```

```
            145                 150                 155                 160
Val Thr Leu Phe Pro Ser Ser Glu Glu Leu Gln Ala Asn Lys Ala
                165                 170                 175

Thr Leu Val Cys Leu Ile Ser Asp Phe Tyr Pro Gly Ala Val Thr Val
            180                 185                 190

Ala Trp Lys Ala Asp Ser Ser Pro Val Lys Ala Gly Val Glu Thr Thr
            195                 200                 205

Thr Pro Ser Lys Gln Ser Asn Asn Lys Tyr Ala Ala Ser Ser Tyr Leu
        210                 215                 220

Ser Leu Thr Pro Glu Gln Trp Lys Ser His Arg Ser Tyr Ser Cys Gln
225                 230                 235                 240

Val Thr His Glu Gly Ser Thr Val Glu Lys Thr Val Ala Pro Thr Glu
                245                 250                 255

Cys Ser

<210> SEQ ID NO 78
<211> LENGTH: 258
<212> TYPE: PRT
<213> ORGANISM: Artificial Sequence
<220> FEATURE:
<223> OTHER INFORMATION: Synthetic

<400> SEQUENCE: 78

Gln Pro Val Leu Thr Gln Pro Pro Ser Leu Ser Val Ser Pro Gly Gln
1               5                   10                  15

Thr Ala Ser Ile Thr Cys Ser Gly Glu Lys Leu Gly Asp Lys Tyr Ala
            20                  25                  30

Tyr Trp Tyr Gln Gln Lys Pro Gly Gln Ser Pro Val Leu Val Met Tyr
        35                  40                  45

Gln Asp Lys Gln Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Ala Val
                85                  90                  95

Phe Gly Gly Gly Thr Lys Leu Thr Val Leu Gly Gln Pro Lys Ala Ala
            100                 105                 110

Pro Ser Val Thr Leu Phe Pro Pro Ser Ser Glu Glu Leu Gln Ala Asn
        115                 120                 125

Lys Ala Thr Leu Val Cys Leu Ile Ser Asp Phe Tyr Pro Gly Ala Val
130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
        195                 200                 205

Thr Glu Cys Ser Ala Ala Gly Gly Ser Gly Leu Glu Val Thr Cys Glu
    210                 215                 220

Pro Gly Thr Thr Phe Lys Asp Lys Cys Asn Thr Cys Arg Cys Gly Ser
225                 230                 235                 240

Asp Gly Lys Ser Ala Val Cys Thr Lys Leu Trp Cys Asn Gln Gly Ser
                245                 250                 255
```

Gly Ala

<210> SEQ ID NO 79
<211> LENGTH: 10
<212> TYPE: PRT
<213> ORGANISM: Artificial Sequence
<220> FEATURE:
<223> OTHER INFORMATION: Synthetic

<400> SEQUENCE: 79

Gly Thr Gly Gly Gly Ser Gly Ser Ser Ser
1               5                   10

<210> SEQ ID NO 80
<211> LENGTH: 6
<212> TYPE: PRT
<213> ORGANISM: Artificial Sequence
<220> FEATURE:
<223> OTHER INFORMATION: Synthetic

<400> SEQUENCE: 80

Ala Ala Gly Gly Ser Gly
1               5

<210> SEQ ID NO 81
<211> LENGTH: 4
<212> TYPE: PRT
<213> ORGANISM: Artificial Sequence
<220> FEATURE:
<223> OTHER INFORMATION: Synthetic

<400> SEQUENCE: 81

Gly Ser Gly Ala
1

<210> SEQ ID NO 82
<211> LENGTH: 1533
<212> TYPE: DNA
<213> ORGANISM: Artificial Sequence
<220> FEATURE:
<223> OTHER INFORMATION: Synthetic

<400> SEQUENCE: 82

```
atgatgtcct ttgtctctct gctcctggtt ggcatcctat tccatgccac ccaggccttg      60
gaagtgacgt gtgagcccgg aacgacattc aaagacaagt gcaatacttg tcggtgcggt     120
tcagatggga atcggcggt ctgcacaaag ctctggtgta accagggcac cggtggaggg     180
tcgggatcca gctcacaggt caccttgaag gagtctggtc ctgtgctggt gaaacccaca     240
gagacccctca cgctgacctg caccgtctct gggttctcac tcagcagggg taaaatgggt     300
gtgagctgga tccgtcagcc cccagggaag gccctggagt ggcttgcaca cattttttcg     360
agtgacgaaa aatcctacag gacatcgctg aagagcaggc tcaccatctc aaggacacc     420
tccaaaaacc aggtggtcct acaatgacc aacatggacc ctgtggacac agccacgtat     480
tactgtgcac ggatacgacg tggaggaatt gactactggg gccagggaac cctggtcact     540
gtctcctcag cctccaccaa gggcccatcg gtcttccccc tggcgccctg ctccaggagc     600
acctccgaga gcacagccgc cctgggctgc ctggtcaagg actacttccc cgaaccggtg     660
acggtgtcgt ggaactcagg cgccctgacc agcggcgtgc acaccttccc ggctgtccta     720
cagtcctcag gactctactc cctcagcagc gtggtgaccg tgccctccag cagcttgggc     780
acgaagacct acacctgcaa cgtagatcac aagcccagca acaccaaggt ggacaagaga     840
```

| | |
|---|---|
| gttgagtcca aatatggtcc cccatgccca ccatgcccag cacctgagtt cctgggggga | 900 |
| ccatcagtct tcctgttccc cccaaaaccc aaggacactc tcatgatctc ccggacccct | 960 |
| gaggtcacgt gcgtggtggt ggacgtgagc caggaagacc ccgaggtcca gttcaactgg | 1020 |
| tacgtggatg gcgtggaggt gcataatgcc aagacaaagc cgcgggagga gcagttcaac | 1080 |
| agcacgtacc gtgtggtcag cgtcctcacc gtcctgcacc aggactggct gaacggcaag | 1140 |
| gagtacaagt gcaaggtctc caacaaaggc ctcccgtcct ccatcgagaa aaccatctcc | 1200 |
| aaagccaaag gcagccccg agagccacag gtgtacaccc tgcccccatc ccaggaggag | 1260 |
| atgaccaaga accaggtcag cctgacctgc ctggtcaaag cttctaccc cagcgacatc | 1320 |
| gccgtggagt gggagagcaa tgggcagccg gagaacaact acaagaccac gcctcccgtg | 1380 |
| ctggactccg acggctcctt cttcctctac agcaggctaa ccgtggacaa gagcaggtgg | 1440 |
| caggagggga atgtcttctc atgctccgtg atgcatgagg ctctgcacaa ccactacaca | 1500 |
| cagaagagcc tctccctgtc tctcgggaaa tga | 1533 |

<210> SEQ ID NO 83
<211> LENGTH: 1533
<212> TYPE: DNA
<213> ORGANISM: Artificial Sequence
<220> FEATURE:
<223> OTHER INFORMATION: Synthetic

<400> SEQUENCE: 83

| | |
|---|---|
| atgatgtcct ttgtctctct gctcctggtt ggcatcctat tccatgccac ccaggcccag | 60 |
| gtcaccttga aggagtctgg tcctgtgctg gtgaaaccca cagagaccct cacgctgacc | 120 |
| tgcaccgtct ctgggttctc actcagcagg ggtaaaatgg gtgtgagctg gatccgtcag | 180 |
| cccccaggga aggccctgga gtggcttgca cacatttttt cgagtgacga aaaatcctac | 240 |
| aggacatcgc tgaagagcag gctcaccatc tccaaggaca cctccaaaaa ccaggtggtc | 300 |
| cttacaatga ccaacatgga ccctgtggac acagccacgt attactgtgc acggatacga | 360 |
| cgtggaggaa ttgactactg gggccaggga accctggtca ctgtctcctc agcctccacc | 420 |
| aagggcccat ccgtcttccc cctggcgccc tgctccagga gcacctccga gagcacagcc | 480 |
| gccctgggct gcctggtcaa ggactacttc cccgaaccgg tgacggtgtc gtggaactca | 540 |
| ggcgccctga ccagcggcgt gcacaccttc ccggctgtcc tacagtcctc aggactctac | 600 |
| tccctcagca gcgtggtgac cgtgccctcc agcagcttgg gcacgaagac ctacacctgc | 660 |
| aacgtagatc acaagcccag caacaccaag gtggacaaga gagttgagtc caaatatggt | 720 |
| ccccccatgcc caccatgccc agcacctgag ttcctggggg gaccatcagt cttcctgttc | 780 |
| cccccaaaac ccaaggacac tctcatgatc tcccggaccc ctgaggtcac gtgcgtggtg | 840 |
| gtggacgtga gccaggaaga ccccgaggtc cagttcaact ggtacgtgga tggcgtggag | 900 |
| gtgcataatg ccaagacaaa gccgcgggag gagcagttca acagcacgta ccgtgtggtc | 960 |
| agcgtcctca ccgtcctgca ccaggactgg ctgaacggca aggagtacaa gtgcaaggtc | 1020 |
| tccaacaaag gcctcccgtc ctccatcgag aaaaccatct ccaaagccaa agggcagccc | 1080 |
| cgagagccac aggtgtacac cctgccccca tccaggagg atgaccaa gaaccaggtc | 1140 |
| agcctgacct gcctggtcaa aggcttctac cccagcgaca tcgccgtgga gtgggagagc | 1200 |
| aatgggcagc cggagaacaa ctacaagacc acgcctcccg tgctggactc cgacggctcc | 1260 |
| ttcttcctct acagcaggct aaccgtggac aagagcaggt ggcaggaggg gaatgtcttc | 1320 |

| | |
|---|---|
| tcatgctccg tgatgcatga ggctctgcac aaccactaca cacagaagag cctctccctg | 1380 |
| tctctcggga aagccgctgg tggtagtggt ttggaagtga cgtgtgagcc cggaacgaca | 1440 |
| ttcaaagaca agtgcaatac ttgtcggtgc ggttcagatg ggaaatcggc ggtctgcaca | 1500 |
| aagctctggt gtaaccaggg tagtggtgct tga | 1533 |

<210> SEQ ID NO 84
<211> LENGTH: 834
<212> TYPE: DNA
<213> ORGANISM: Artificial Sequence
<220> FEATURE:
<223> OTHER INFORMATION: Synthetic

<400> SEQUENCE: 84

| | |
|---|---|
| atgatgtcct ttgtctctct gctcctggtt ggcatcctat tccatgccac ccaggccttg | 60 |
| gaagtgacgt gtgagcccgg aacgacattc aaagacaagt gcaatacttg tcggtgcggt | 120 |
| tcagatggga atcggcggt ctgcacaaag ctctggtgta accagggcac cggtggaggg | 180 |
| tcgggatcca gctcacagcc agtgctgact cagccccct cactgtccgt gtccccagga | 240 |
| cagacagcca gcatcacctg ctctggagag aaattggggg ataaatatgc ttactggtat | 300 |
| cagcagaagc caggccagtc ccctgtgttg gtcatgtatc aagataaaca gcggccctca | 360 |
| gggatccctg agcgattctc tggctccaac tctgggaaca gccactct gaccatcagc | 420 |
| gggacccagg ctatggatga ggctgactat tactgtcagg cgtgggacag cagcactgcg | 480 |
| gtattcggcg agggaccaa gctgaccgtc ctaggccagc ctaaggcggc ccctcggtc | 540 |
| accctgttcc cgcccctc tgaggagctt caagccaaca ggccacact ggtgtgtctc | 600 |
| ataagtgact ctacccggg agccgtgaca gtggcctgga aggcagatag cagccccgtc | 660 |
| aaggcgggag tggagaccac cacaccctcc aaacaaagca caacaagta cgcggccagc | 720 |
| agctatctga gcctgacgcc tgagcagtgg aagtcccaca aagctacag ctgccaggtc | 780 |
| acgcatgaag ggagcaccgt ggagaagaca gtggccccta cagaatgttc atag | 834 |

<210> SEQ ID NO 85
<211> LENGTH: 834
<212> TYPE: DNA
<213> ORGANISM: Artificial Sequence
<220> FEATURE:
<223> OTHER INFORMATION: Synthetic

<400> SEQUENCE: 85

| | |
|---|---|
| atgatgtcct ttgtctctct gctcctggtt ggcatcctat tccatgccac ccaggcccag | 60 |
| ccagtgctga ctcagccccc ctcactgtcc gtgtcccag acagacagc cagcatcacc | 120 |
| tgctctggag agaaattggg ggataaatat gcttactggt atcagcagaa gccaggccag | 180 |
| tcccctgtgt tggtcatgta tcaagataaa cagcggccct cagggatccc tgagcgattc | 240 |
| tctggctcca actctgggaa cacagccact ctgaccatca gcgggaccca ggctatggat | 300 |
| gaggctgact attactgtca ggcgtgggac agcagcactg cggtattcgg cggagggacc | 360 |
| aagctgaccg tcctaggcca gcctaaggcg gcgccctcgg tcaccctgtt cccgccctcc | 420 |
| tctgaggagc ttcaagccaa caaggccaca ctggtgtgtc tcataagtga cttctacccg | 480 |
| ggagccgtga cagtggcctg gaaggcagat agcagccccg tcaaggcggg agtggagacc | 540 |
| accacaccct ccaaacaaag caacaacaag tacgcggcca gcagctatct gagcctgacg | 600 |
| cctgagcagt ggaagtccca cagaagctac agctgccagg tcacgcatga agggagcacc | 660 |
| gtggagaaga cagtggcccc tacagaatgt tcagccgctg gtggtagtgg tttggaagtg | 720 |

```
acgtgtgagc ccggaacgac attcaaagac aagtgcaata cttgtcggtg cggttcagat    780
gggaaatcgg cggtctgcac aaagctctgg tgtaaccagg gtagtggtgc ttag          834
```

METHODS FOR INHIBITING FIBROSIS IN A SUBJECT IN NEED THEREOF

CROSS-REFERENCES TO RELATED APPLICATIONS

This application claims the benefit of Provisional Application No. 62/275,025, filed Jan. 5, 2016, and Provisional Application No. 62/407,979, filed Oct. 13, 2016, both of which are incorporated herein by reference in their entirety.

STATEMENT REGARDING SEQUENCE LISTING

The sequence listing associated with this application is provided in text format in lieu of a paper copy and is hereby incorporated by reference into the specification. The name of the text file containing the sequence listing is MP_1_0250_US_Sequence_Listing_20170104_ST25. The text file is 136 KB; was created on Jan. 4, 2017; and is being submitted via EFS-Web with the filing of the specification.

BACKGROUND

The complement system provides an early acting mechanism to initiate, amplify and orchestrate the immune response to microbial infection and other acute insults (M. K. Liszewski and J. P. Atkinson, 1993, in *Fundamental Immunology*, Third Edition, edited by W. E. Paul, Raven Press, Ltd., New York), in humans and other vertebrates. While complement activation provides a valuable first-line defense against potential pathogens, the activities of complement that promote a protective immune response can also represent a potential threat to the host (K. R. Kalli, et al., *Springer Semin. Immunopathol.* 15:417-431, 1994; B. P. Morgan, *Eur. J. Clinical Investig.* 24:219-228, 1994). For example, C3 and C5 proteolytic products recruit and activate neutrophils. While indispensable for host defense, activated neutrophils are indiscriminate in their release of destructive enzymes and may cause organ damage. In addition, complement activation may cause the deposition of lytic complement components on nearby host cells as well as on microbial targets, resulting in host cell lysis.

The complement system has also been implicated in the pathogenesis of numerous acute and chronic disease states, including: myocardial infarction, stroke, ARDS, reperfusion injury, septic shock, capillary leakage following thermal burns, postcardiopulmonary bypass inflammation, transplant rejection, rheumatoid arthritis, multiple sclerosis, myasthenia gravis, and Alzheimer's disease. In almost all of these conditions, complement is not the cause but is one of several factors involved in pathogenesis. Nevertheless, complement activation may be a major pathological mechanism and represents an effective point for clinical control in many of these disease states. The growing recognition of the importance of complement-mediated tissue injury in a variety of disease states underscores the need for effective complement inhibitory drugs. To date, Eculizumab (Solaris®), an antibody against C5, is the only complement-targeting drug that has been approved for human use. Yet, C5 is one of several effector molecules located "downstream" in the complement system, and blockade of C5 does not inhibit activation of the complement system. Therefore, an inhibitor of the initiation steps of complement activation would have significant advantages over a "downstream" complement inhibitor.

Currently, it is widely accepted that the complement system can be activated through three distinct pathways: the classical pathway, the lectin pathway, and the alternative pathway. The classical pathway is usually triggered by a complex composed of host antibodies bound to a foreign particle (i.e., an antigen) and thus requires prior exposure to an antigen for the generation of a specific antibody response. Since activation of the classical pathway depends on a prior adaptive immune response by the host, the classical pathway is part of the acquired immune system. In contrast, both the lectin and alternative pathways are independent of adaptive immunity and are part of the innate immune system.

The activation of the complement system results in the sequential activation of serine protease zymogens. The first step in activation of the classical pathway is the binding of a specific recognition molecule, C1q, to antigen-bound IgG and IgM molecules. C1q is associated with the C1r and C1s serine protease proenzymes as a complex called C1. Upon binding of C1q to an immune complex, autoproteolytic cleavage of the Arg-Ile site of C1r is followed by C1r-mediated cleavage and activation of C1s, which thereby acquires the ability to cleave C4 and C2. C4 is cleaved into two fragments, designated C4a and C4b, and, similarly, C2 is cleaved into C2a and C2b. C4b fragments are able to form covalent bonds with adjacent hydroxyl or amino groups and generate the C3 convertase (C4b2a) through noncovalent interaction with the C2a fragment of activated C2. C3 convertase (C4b2a) activates C3 by proteolytic cleavage into C3a and C3b subcomponents leading to generation of the C5 convertase (C4b2a3b), which, by cleaving C5 leads to the formation of the membrane attack complex (C5b combined with C6, C7, C8 and C-9, also referred to as "MAC") that can disrupt cellular membranes leading to cell lysis. The activated forms of C3 and C4 (C3b and C4b) are covalently deposited on the foreign target surfaces, which are recognized by complement receptors on multiple phagocytes.

Independently, the first step in activation of the complement system through the 10 lectin pathway is also the binding of specific recognition molecules, which is followed by the activation of associated serine protease proenzymes. However, rather than the binding of immune complexes by C1q, the recognition molecules in the lectin pathway comprise a group of carbohydrate-binding proteins (mannan-binding lectin (MBL), H-ficolin, M-ficolin, L-ficolin and C-type lectin CL-1), collectively referred to as lectins. See J. Lu et al., *Biochim. Biophys. Acta* 1572:387-400, (2002); Holmskov et al., *Annm. Rev. Immunol.* 21:547-578 (2003); Teh et al., *Immunology* 101:225-232 (2000)). See also J. Luet et al., *Biochim Biophys Acta* 1572:387-400 (2002); Holmskov et al, *Annu Rev Immunol* 21:547-578 (2003); Teh et al., *Immunology* 101:225-232 (2000); Hansen et al, *J. Immunol* 185(10):6096-6104 (2010).

Ikeda et al. first demonstrated that, like C1q, MBL could activate the complement system upon binding to yeast mannan-coated erythrocytes in a C4-dependent manner (Ikeda et al., *J. Biol. Chem.* 262:7451-7454, (1987)). MBL, a member of the collectin protein family, is a calcium-dependent lectin that binds carbohydrates with 3- and 4-hydroxy groups oriented in the equatorial plane of the pyranose ring. Prominent ligands for MBL are thus D-mannose and N-acetyl-D-glucosamine, while carbohydrates not fitting this steric requirement have undetectable affinity for MBL (Weis et al., *Nature* 360:127-134, (1992)). The interaction between MBL and monovalent sugars is extremely weak, with dissociation constants typically in the single-digit millimolar range. MBL achieves tight, specific binding to glycan ligands by avidity, i.e., by interacting simultaneously with multiple monosaccharide residues located in close proximity to each other (Lee et al., *Archiv. Biochem. Biophys.* 299:129-136, (1992)). MBL recognizes the carbohydrate patterns that commonly decorate microorganisms such as bacteria, yeast, parasites and certain viruses. In contrast, MBL does not recognize D-galactose and sialic acid, the penultimate and ultimate sugars that usually decorate "mature" complex glycoconjugates present on mammalian plasma and cell surface glycoproteins. This binding specificity is thought to promote recognition of "foreign" surfaces and help protect from "self-activation." However, MBL does bind with high affinity to clusters of high-mannose "precursor" glycans on N-linked glycoproteins and glycolipids sequestered in the endoplasmic reticulum and Golgi of mammalian cells (Maynard et al., *J. Biol. Chem.* 257:3788-3794, (1982)). Therefore, damaged cells are potential targets for lectin pathway activation via MBL binding.

The ficolins possess a different type of lectin domain than MBL, called the fibrinogen-like domain. Ficolins bind sugar residues in a $Ca^{++}$-independent manner. In humans, three kinds of ficolins (L-ficolin, M-ficolin and H-ficolin) have been identified. The two serum ficolins, L-ficolin and H-ficolin, have in common a specificity for N-acetyl-D-glucosamine; however, H-ficolin also binds N-acetyl-D-galactosamine. The difference in sugar specificity of L-ficolin, H-ficolin, CL-11, and MBL means that the different lectins may be complementary and target different, though overlapping, glycoconjugates. This concept is supported by the recent report that, of the known lectins in the lectin pathway, only L-ficolin binds specifically to lipoteichoic acid, a cell wall glycoconjugate found on all Gram-positive bacteria (Lynch et al., *J. Immunol.* 172:1198-1202, (2004)). The collectins (i.e., MBL) and the ficolins bear no significant similarity in amino acid sequence. However, the two groups of proteins have similar domain organizations and, like C1q, assemble into oligomeric structures, which maximize the possibility of multisite binding.

The serum concentrations of MBL are highly variable in healthy populations and this is genetically controlled by polymorphisms/mutations in both the promoter and coding regions of the MBL gene. As an acute phase protein, the expression of MBL is further upregulated during inflammation. L-ficolin is present in serum at concentrations similar to those of MBL. Therefore, the L-ficolin branch of the lectin pathway is potentially comparable to the MBL arm in strength. MBL and ficolins can also function as opsonins, which allow phagocytes to target MBL- and ficolin-decorated surfaces (see Jack et al., *J Leukoc Biol.,* 77(3):328-36 (2004), Matsushita and Fujita, *Immunobiology,* 205(4-5): 490-7 (2002), Aoyagi et al., *J Immunol.* 174(1):418-25 (2005). This opsonization requires the interaction of these proteins with phagocyte receptors (Kuhlman et al., *J. Exp. Med.* 169:1733, (1989); Matsushita et al., *J. Biol. Chem.* 271:2448-54, (1996)), the identity of which has not been established.

Human MBL forms a specific and high-affinity interaction through its collagen-like domain with unique C1r/C1s-like serine proteases, termed MBL-associated serine proteases (MASPs). To date, three MASPs have been described. First, a single enzyme "MASP" was identified and characterized as the enzyme responsible for the initiation of the complement cascade (i.e., cleaving C2 and C4) (Matsushita et al., *J Exp Med* 176(6):1497-1502 (1992); Ji et al., *J. Immunol.* 150:571-578, (1993)). It was subsequently determined that the MASP activity was, in fact, a mixture of two proteases: MASP-1 and MASP-2 (Thiel et al., *Nature* 386:506-510, (1997)). However, it was demonstrated that the MBL-MASP-2 complex alone is sufficient for complement activation (Vorup-Jensen et al., *J. Immunol.* 165:2093-2100, (2000)). Furthermore, only MASP-2 cleaved C2 and C4 at high rates (Ambrus et al., *J. Immunol.* 170:1374-1382, (2003)). Therefore, MASP-2 is the protease responsible for activating C4 and C2 to generate the C3 convertase, C4b2a. This is a significant difference from the C1 complex of the classical pathway, where the coordinated action of two specific serine proteases (C1r and C1s) leads to the activation of the complement system. In addition, a third novel protease, MASP-3, has been isolated (Dahl, M. R., et al., *Immunity* 15:127-35, 2001). MASP-1 and MASP-3 are alternatively spliced products of the same gene.

MASPs share identical domain organizations with those of C1r and C1s, the enzymatic components of the C1 complex (Sim et al., *Biochem. Soc. Trans.* 28:545, (2000)). These domains include an N-terminal C1r/C1s/sea urchin VEGF/bone morphogenic protein (CUB) domain, an epidermal growth factor-like domain, a second CUB domain, a tandem of complement control protein domains, and a serine protease domain. As in the C1 proteases, activation of MASP-2 occurs through cleavage of an Arg-Ile bond adjacent to the serine protease domain, which splits the enzyme into disulfide-linked A and B chains, the latter consisting of the serine protease domain.

MBL can also associate with an alternatively sliced form of MASP-2, known as MBL-associated protein of 19 kDa (MAp19) or small MBL-associated protein (sMAP), which lacks the catalytic activity of MASP-2. (Stover, *J. Immunol.* 162:3481-90, (1999); Takahashi et al., *Int. Immunol.* 11:859-863, (1999)). MAp19 comprises the first two domains of MASP-2, followed by an extra sequence of four unique amino acids. The function of MAp19 is unclear (Degn et al., *J Immunol. Methods,* 2011). The MASP-1 and MASP-2 genes are located on human chromosomes 3 and 1, respectively (Schwaeble et al., *Immunobiology* 205:455-466, (2002)).

Several lines of evidence suggest that there are different MBL-MASP complexes and a large fraction of the MASPs in serum is not complexed with MBL (Thiel, et al., *J. Immunol.* 165:878-887, (2000)). Both H- and L-ficolin bind to all MASPs and activate the 10 lectin complement pathway, as does MBL (Dahl et al., *Immunity* 15:127-35, (2001); Matsushita et al., *J. Immunol.* 168:3502-3506, (2002)). Both the lectin and classical pathways form a common C3 convertase (C4b2a) and the two pathways converge at this step.

The lectin pathway is widely thought to have a major role in host defense against infection in the naïve host. Strong evidence for the involvement of MBL in host defense comes from analysis of patients with decreased serum levels of functional MBL (Kilpatrick, *Biochim. Biophys. Acta* 1572: 401-413, (2002)). Such patients display susceptibility to recurrent bacterial and fungal infections. These symptoms are usually evident early in life, during an apparent window of vulnerability as maternally derived antibody titer wanes, but before a full repertoire of antibody responses develops. This syndrome often results from mutations at several sites in the collagenous portion of MBL, which interfere with proper formation of MBL oligomers. However, since MBL can function as an opsonin independent of complement, it is not known to what extent the increased susceptibility to infection is due to impaired complement activation.

All three pathways (i.e., the classical, lectin and alternative) have been thought to converge at C5, which is cleaved to form products with multiple proinflammatory effects. The converged pathway has been referred to as the terminal complement pathway. C5a is the most potent anaphylatoxin, inducing alterations in smooth muscle and vascular tone, as well as vascular permeability. It is also a powerful chemotaxin and activator of both neutrophils and monocytes. C5a-mediated cellular activation can significantly amplify inflammatory responses by inducing the release of multiple additional inflammatory mediators, including cytokines, hydrolytic enzymes, arachidonic acid metabolites, and reactive oxygen species. C5 cleavage leads to the formation of C5b-9, also known as the membrane attack complex (MAC). There is now strong evidence that sublytic MAC deposition may play an important role in inflammation in addition to its role as a lytic pore-forming complex.

In addition to its essential role in immune defense, the complement system contributes to tissue damage in many clinical conditions. Although there is extensive evidence implicating both the classical and alternative complement pathways in the pathogenesis of non-infectious human diseases, the role of the lectin pathway is just beginning to be evaluated. Recent studies provide evidence that activation of the lectin pathway can be responsible for complement activation and related inflammation in ischemia/reperfusion injury. Collard et al. (2000) reported that cultured endothelial cells subjected to oxidative stress bind MBL and show deposition of C3 upon exposure to human serum (Collard et al., *Am. J. Pathol.* 156:1549-1556, (2000)). In addition, treatment of human sera with blocking anti-MBL monoclonal antibodies inhibited MBL binding and complement activation. These findings were extended to a rat model of myocardial ischemia-reperfusion in which rats treated with a blocking antibody directed against rat MBL showed significantly less myocardial damage upon occlusion of a coronary artery than rats treated with a control antibody (Jordan et al., *Circulation* 104:1413-1418, (2001)). The molecular mechanism of MBL binding to the vascular endothelium after oxidative stress is unclear; a recent study suggests that activation of the lectin pathway after oxidative stress may be mediated by MBL binding to vascular endothelial cytokeratins, and not to glycoconjugates (Collard et al., *Am. J. Pathol.* 159:1045-1054, (2001)). Other studies have implicated the classical and alternative pathways in the pathogenesis of ischemia/reperfusion injury and the role of the lectin pathway in this disease remains controversial (Riedermann, N.C., et al., *Am. J. Pathol.* 162:363-367, 2003).

Fibrosis is the formation of excessive connective tissue in an organ or tissue, commonly in response to damage or injury. A hallmark of fibrosis is the production of excessive extracellular matrix following local trauma. The normal physiological response to injury results in the deposition of connective tissue, but this initially beneficial reparative process may persist and become pathological, altering the architecture and function of the tissue. At the cellular level, epithelial cells and fibroblasts proliferate and differentiate into myofibroblasts, resulting in matrix contraction, increased rigidity, microvascular compression, and hypoxia. An influx of inflammatory cells, including macrophages and lymphocytes, results in cytokine release and amplifies the deposition of collagen, fibronectin and other molecular markers of fibrosis. Conventional therapeutic approaches have largely been targeted towards the inflammatory process of fibrosis, using corticosteroids and immunosuppressive drugs. Unfortunately, these anti-inflammatory agents have had little to no clinical effect. Currently there are no effective treatments or therapeutics for fibrosis, but both animal studies and anecdotal human reports suggest that fibrotic tissue damage may be reversed (Tampe and Zeisberg, *Nat Rev Nephrol*, Vol 10:226-237, 2014).

The kidney has a limited capacity to recover from injury. Various renal pathologies result in local inflammation that causes scarring and fibrosis of renal tissue. The perpetuation of inflammatory stimuli drives tubulointerstitial inflammation and fibrosis and progressive renal functional impairment in chronic kidney disease. Its progression to end-stage renal failure is associated with significant morbidity and mortality. Since tubulointerstitial fibrosis is the common end point of multiple renal pathologies, it represents a key target for therapies aimed at preventing renal failure. Risk factors (e.g., proteinuria) independent of the primary renal disease contribute to the development of renal fibrosis and loss of renal excretory function by driving local inflammation, which in turn enhances disease progression.

In view of the role of fibrosis in many diseases and disorders, such as, for example, tubulointerstitial fibrosis leading to chronic kidney disease, there is a pressing need to develop therapeutically effective agents for treating diseases and conditions caused or exacerbated by fibrosis. In further view of the paucity of new and existing treatments targeting inflammatory pro-fibrotic pathways in renal disease, there is a need to develop therapeutically effective agents to treat, inhibit, prevent and/or reverse renal fibrosis and thereby prevent progressive chronic kidney disease.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, the invention provides a method for treating, inhibiting, alleviating or preventing fibrosis in a mammalian subject suffering, or at risk of developing a disease or disorder caused or exacerbated by fibrosis and/or inflammation, comprising administering to the subject an amount of a MASP-2 inhibitory agent effective to inhibit fibrosis. In one embodiment, the MASP-2 inhibitory agent is a MASP-2 antibody or fragment thereof. In one embodiment, the MASP-2 inhibitory agent is a MASP-2 monoclonal antibody, or fragment thereof that specifically binds to a portion of SEQ ID NO:6. In one embodiment, the MASP-2 inhibitory agent selectively inhibits lectin pathway complement activation without substantially inhibiting C1q-dependent complement activation. In one embodiment, the subject is suffering from a disease or disorder caused by or exacerbated by at least one of (i) fibrosis and/or inflammation associated with an ischemia reperfusion injury, (ii) renal fibrosis and/or renal inflammation (e.g., tubulointerstitial fibrosis, chronic kidney disease, chronic renal failure, glomerular disease (e.g., focal segmental glomerulosclerosis), an immune complex disorder (e.g., IgA nephropathy, membraneous nephropathy), lupus nephritis, nephrotic syndrome, diabetic nephropathy, tubulointerstitial damage and glomerulonepthritis (e.g., C3 glomerulopathy), (iii) pulmonary fibrosis and/or inflammation (e.g., chronic obstructive pulmonary disease, cystic fibrosis, pulmonary fibrosis associated with scleroderma, bronchiectasis and pulmonary hypertension), (iv) hepatic fibrosis and/or inflammation (e.g., cirrhosis, nonalcoholic fatty liver disease (steatohepatitis)), liver fibrosis secondary to alcohol abuse, liver fibrosis secondary to acute or chronic hepatitis, biliary disease and toxic liver injury (e.g., hepatotoxicity due to drug-induced liver damage induced by acetaminophen or other drug), (v) cardiac fibrosis and/or inflammation (e.g., cardiac fibrosis, myocardial infarction, valvular fibrosis, atrial fibrosis, endomyocardial fibrosis arrhythmogenic right ventricular cardiomyopathy (ARVC), (vi) vascular fibrosis (e.g., vascular disease, an atherosclerotic vascular disease, vascular stenosis, restenosis, vasculitis, phlebitis, deep vein thrombosis and abdominal aortic aneurysm), (vii) fibrosis of the skin (e.g., excessive wound healing, scleroderma, systemic sclerosis, keloids, connective tissue diseases, scarring, and hypertrophic scars), (viii) fibrosis of the joints (e.g., arthrofibrosis), (ix) fibrosis of the central nervous system (e.g., stroke, traumatic brain injury and spinal cord injury), (x) fibrosis of the digestive system (e.g., Crohn's disease, pancreatic fibrosis and ulcerative colitis), (xi) ocular fibrosis (e.g., anterior subcapsular cataract, posterior capsule opacification, macular degeneration, and retinal and vitreal retinopathy), (xii) fibrosis of musculoskeletal soft-tissue structures (e.g., adhesive capsulitis, Dupuytren's contracture and myelofibrosis), (xiii) fibrosis of the reproductive organs (e.g., endometriosis and Peyronie's disease), (xiv) a chronic infectious disease that causes fibrosis and/or inflammation (e.g., alpha virus, Hepatitis A, Hepatitis B, Hepatitis C, tuberculosis, HIV and influenza), (xv) an autoimmune disease that causes fibrosis and/or inflammation (e.g., scleroderma and systemic lupus erythematosus (SLE), (xvi) scarring associated with trauma (e.g., wherein the scarring associated with trauma is selected from the group consisting of surgical complications (e.g., surgical adhesions wherein scar tissue can form between internal organs causing contracture, pain and can cause infertility), chemotherapeutic drug-induced fibrosis, radiation-induced fibrosis and scarring associated with burns), or (xvii) organ transplant, breast fibrosis, muscle fibrosis, retroperitoneal fibrosis, thyroid fibrosis, lymph node fibrosis, bladder fibrosis and pleural fibrosis.

In another aspect, the present invention provides a method for treating, inhibiting, alleviating or preventing renal fibrosis in a mammalian subject suffering, or at risk of developing a disease or disorder caused or exacerbated by renal fibrosis and/or inflammation, comprising administering to the subject an amount of a MASP-2 inhibitory agent effective to inhibit renal fibrosis. In one embodiment, the MASP-2 inhibitory agent is a MASP-2 antibody or fragment thereof. In one embodiment, the MASP-2 inhibitory agent is a MASP-2 monoclonal antibody, or fragment thereof that specifically binds to a portion of SEQ ID NO:6. In one embodiment, the MASP-2 antibody or fragment thereof specifically binds to a polypeptide comprising SEQ ID NO:6 with an affinity of at least 10 times greater than it binds to a different antigen in the complement system. In one embodiment, the antibody or fragment thereof is selected from the group consisting of a recombinant antibody, an antibody having reduced effector function, a chimeric antibody, a humanized antibody and a human antibody. In one embodiment, the MASP-2 inhibitory agent selectively inhibits lectin pathway complement activation without substantially inhibiting C1q-dependent complement activation. In one embodiment, the MASP-2 inhibitory agent is administered subcutaneously, intraperitoneally, intra-muscularly, intra-arterially, intravenously, or as an inhalant. In one embodiment, the MASP-2 inhibitory agent is administered in an amount effective to inhibit tubulointerstitial fibrosis. In one embodiment, the MASP-2 inhibitory agent is administered in an amount effective to reduce, delay or eliminate the need for dialysis in the subject. In one embodiment, the subject is suffering from a renal disease or disorder selected from the group consisting of chronic kidney disease, chronic renal failure, glomerular disease (e.g., focal segmental glomerulosclerosis), an immune complex disorder (e.g., IgA nephropathy, membraneous nephropathy), lupus nephritis, nephrotic syndrome, diabetic nephropathy, tubulointerstitial damage and glomerulonephritis (e.g., C3 glomerulopathy). In one embodiment, the subject is suffering from proteinuria and the MASP-2 inhibitory agent is administered in an amount effective to reduce proteinuria in the subject. In one embodiment, the MASP-2 inhibitory agent is administered in an amount and for a time effective to achieve at least a 20 percent reduction (e.g., at least a 30 percent reduction, or at least a 40 percent reduction, or at least a 50 percent reduction) in 24-hour urine protein excretion as compared to baseline 24-hour urine protein excretion in the subject prior to treatment. In one embodiment, the subject is suffering from a renal disease or disorder associated with proteinuria selected from the group consisting of nephrotic syndrome, pre-eclampsia, eclampsia, toxic lesions of kidneys, amyloidosis, collagen vascular diseases (e.g., systemic lupus erythematosus), dehydration, glomerular diseases (e.g. membranous glomerulonephritis, focal segmental glomerulonephritis, C3 glomerulopathy, minimal change disease, lipoid nephrosis), strenuous exercise, stress, benign orthostatis (postural) proteinuria, focal segmental glomerulosclerosis, IgA nephropathy (i.e., Berger's disease), IgM nephropathy, membranoproliferative glomerulonephritis, membranous nephropathy, minimal change disease, sarcoidosis, Alport's syndrome, diabetes mellitus (diabetic nephropathy), drug-induced toxicity (e.g., NSAIDS, nicotine, penicillamine, lithium carbonate, gold and other heavy metals, ACE inhibitors, antibiotics (e.g., adriamycin) or opiates (e.g. heroin) or other nephrotoxins); Fabry's disease, infections (e.g., HIV, syphilis, hepatitis A, B or C, poststreptococcal infection, urinary schistosomiasis); aminoaciduria, Fanconi syndrome, hypertensive nephrosclerosis, interstitial nephritis, sickle cell disease, hemoglobinuria, multiple myeloma, myoglobinuria, organ rejection (e.g., kidney transplant rejection), ebola hemorrhagic fever, Nail patella syndrome, familial mediterranean fever, HELLP syndrome, systemic lupus erythematosus, Wegener's granulomatosis, Rheumatoid arthritis, Glycogen storage disease type 1, Goodpasture's syndrome, Henoch-Schonlein purpura, urinary tract infection which has spread to the kidneys, Sjögren's syndrome and post-infections glomerulonepthritis. In one embodiment, the subject is suffering from IgA nephropathy. In one embodiment, the subject is suffering from membranous nephropathy.

In another aspect, the present invention provides a method of preventing or reducing renal damage in a subject suffering from a disease or condition associated with proteinuria comprising administering an amount of a MASP-2 inhibitory agent effective to reduce or prevent proteinurea in the subject. In one embodiment, the MASP-2 inhibitory agent is a MASP-2 antibody or fragment thereof. In one embodiment, the MASP-2 inhibitory agent is a MASP-2 monoclonal antibody or fragment thereof that specifically binds to a portion of SEQ ID NO:6. In one embodiment, the MASP-2 inhibitory agent selectively inhibits lectin pathway complement activation without substantially inhibiting C1q-dependent complement activation. In one embodiment, the disease or condition associated with proteinuria is selected from the group consisting of nephrotic syndrome, pre-eclampsia, eclampsia, toxic lesions of kidneys, amyloidosis, collagen vascular diseases (e.g., systemic lupus erythematosus), dehydration, glomerular diseases (e.g. membranous glomerulonephritis, focal segmental glomerulonephritis, C3 glomerulopathy, minimal change disease, lipoid nephrosis), strenuous exercise, stress, benign orthostatis (postural) proteinuria, focal segmental glomerulosclerosis, IgA nephropathy (i.e., Berger's disease), IgM nephropathy, membranoproliferative glomerulonephritis, membranous nephropathy, minimal change disease, sarcoidosis, Alport's syndrome, diabetes mellitus (diabetic nephropathy), drug-induced toxicity (e.g., NSAIDS, nicotine, penicillamine, lithium carbonate, gold and other heavy metals, ACE inhibitors, antibiotics (e.g., adriamycin) or opiates (e.g. heroin)); Fabry's disease, infections (e.g., HIV, syphilis, hepatitis A, B or C, poststreptococcal infection, urinary schistosomiasis); aminoaciduria, Fanconi syndrome, hypertensive nephrosclerosis, interstitial nephritis, sickle cell disease, hemoglobinuria, multiple myeloma, myoglobinuria, organ rejection (e.g., kidney transplant rejection), ebola hemorrhagic fever, Nail patella syndrome, familial mediterranean fever, HELLP syndrome, systemic lupus erythematosus, Wegener's granulomatosis, Rheumatoid arthritis, Glycogen storage disease type 1, Goodpasture's syndrome, Henoch-Schonlein purpura, urinary tract infection which has spread to the kidneys, Sjögren's syndrome and post-infections glomerulonepthritis. In one embodiment, the MASP-2 inhibitory agent is administered in an amount and for a time effective to achieve at least a 20 percent reduction (e.g., at least a 30 percent reduction, or at least a 40 percent reduction, or at least a 50 percent reduction) in 24-hour urine protein excretion as compared to baseline 24-hour urine protein excretion in the subject prior to treatment.

In another aspect, the present invention provides a method of inhibiting the progression of chronic kidney disease, comprising administering an amount of a MASP-2 inhibitory agent effective to reduce or prevent renal fibrosis, e.g., tubulointerstitial fibrosis, in a subject in need thereof. In one embodiment, the MASP-2 inhibitory agent is a MASP-2 antibody or fragment thereof. In one embodiment, the MASP-2 inhibitory agent is a MASP-2 monoclonal antibody, or fragment thereof that specifically binds to a portion of SEQ ID NO:6. In one embodiment, the MASP-2 inhibitory agent selectively inhibits lectin pathway complement activation without substantially inhibiting C1q-dependent complement activation. In one embodiment, the subject in need thereof exhibits proteinuria prior to administration of the MASP-2 inhibitory agent and administration of the MASP-2 inhibitory agent decreases proteinuria in the subject. In one embodiment, the MASP-2 inhibitory agent is administered in an amount and for a time effective to achieve at least a 20 percent reduction (e.g., at least a 30 percent reduction, or at least a 40 percent reduction, or at least a 50 percent reduction) in 24-hour urine protein excretion as compared to baseline 24-hour urine protein excretion in the subject prior to treatment. In one embodiment, the MASP-2 inhibitory agent is administered in an amount effective to reduce, delay or eliminate the need for dialysis in the subject.

In another aspect, the invention provides a method of protecting a kidney from renal injury in a subject that has undergone, is undergoing, or will undergo treatment with one or more nephrotoxic agents, comprising administering an amount of a MASP-2 inhibitory agent effective to prevent or ameliorate drug-induced nephropathy. In one embodiment, the MASP-2 inhibitory agent is a MASP-2 antibody or fragment thereof. In one embodiment, the MASP-2 inhibitory agent is a MASP-2 monoclonal antibody or fragment thereof that specifically binds to a portion of SEQ ID NO:6. In one embodiment, the MASP-2 inhibitory agent selectively inhibits lectin pathway complement activation without substantially inhibiting C1q-dependent complement activation.

In another aspect, the invention provides a method of treating a human subject suffering from Immunoglobulin A Nephropathy (IgAN) comprising administering to the subject a composition comprising an amount of a MASP-2 inhibitory antibody, or antigen-binding fragment thereof, effective to inhibit MASP-2-dependent complement activation. In one embodiment, the subject is suffering from steroid-dependent IgAN. In one embodiment, the MASP-2 inhibitory antibody is a monoclonal antibody, or fragment thereof that specifically binds to human MASP-2. In one embodiment, the antibody or fragment thereof is selected from the group consisting of a recombinant antibody, an antibody having reduced effector function, a chimeric antibody, a humanized antibody, and a human antibody. In one embodiment, the MASP-2 inhibitory antibody does not substantially inhibit the classical pathway. In one embodiment, the MASP-2 inhibitory antibody inhibits C3b deposition in 90% human serum with an $IC_{50}$ of 30 nM or less. In one embodiment, the method further comprises identifying a human subject having steroid-dependent IgAN prior to the step of administering to the subject a composition comprising an amount of a MASP-2 inhibitory antibody, or antigen-binding fragment thereof, effective to improve renal function. In one embodiment, the MASP-2 inhibitory antibody or antigen-binding fragment thereof is administered in an amount effective to improve renal function. In one embodiment, the MASP-2 inhibitory antibody or antigen-binding fragment thereof is administered in an amount effective and for a time sufficient to achieve at least a 20 percent reduction in 24-hour urine protein excretion as compared to baseline 24-hour urine protein excretion in the subject prior to treatment. In one embodiment, the composition is administered in an amount sufficient to improve renal function and decrease the corticosteroid dosage in said subject. In one embodiment, the MASP-2 inhibitory antibody or antigen-binding fragment thereof comprises a heavy chain variable region comprising CDR-H1, CDR-H2 and CDR-H3 of the amino acid sequence set forth as SEQ ID NO:67 and a light chain variable region comprising CDR-L1, CDR-L2 and CDR-L3 of the amino acid sequence set forth as SEQ ID NO:70.

In another aspect, the invention provides a method of treating a human subject suffering from membranous nephropathy (MN) comprising administering to the subject a composition comprising an amount of a MASP-2 inhibitory antibody, or antigen-binding fragment thereof, effective to inhibit MASP-2-dependent complement activation. In one embodiment, the subject is suffering from steroid-dependent MN. In one embodiment, the MASP-2 inhibitory antibody is a monoclonal antibody, or fragment thereof that specifically binds to human MASP-2. In one embodiment, the MASP-2 inhibitory antibody or antigen-binding fragment thereof is administered in an amount effective to improve renal function. In one embodiment, the MASP-2 inhibitory antibody or antigen-binding fragment thereof is administered in an amount effective and for a time sufficient to achieve at least a 20 percent reduction in 24-hour urine protein excretion as compared to baseline 24-hour urine protein excretion in the subject prior to treatment. In one embodiment, the composition is administered in an amount sufficient to improve renal function and decrease the corticosteroid dosage in said subject. In one embodiment, the MASP-2 inhibitory antibody or antigen-binding fragment thereof comprises a heavy chain variable region comprising CDR-H1, CDR-H2 and CDR-H3 of the amino acid sequence set forth as SEQ ID NO:67 and a light chain variable region comprising CDR-L1, CDR-L2 and CDR-L3 of the amino acid sequence set forth as SEQ ID NO:70.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DESCRIPTION OF THE SEQUENCE LISTING

Figure 1:
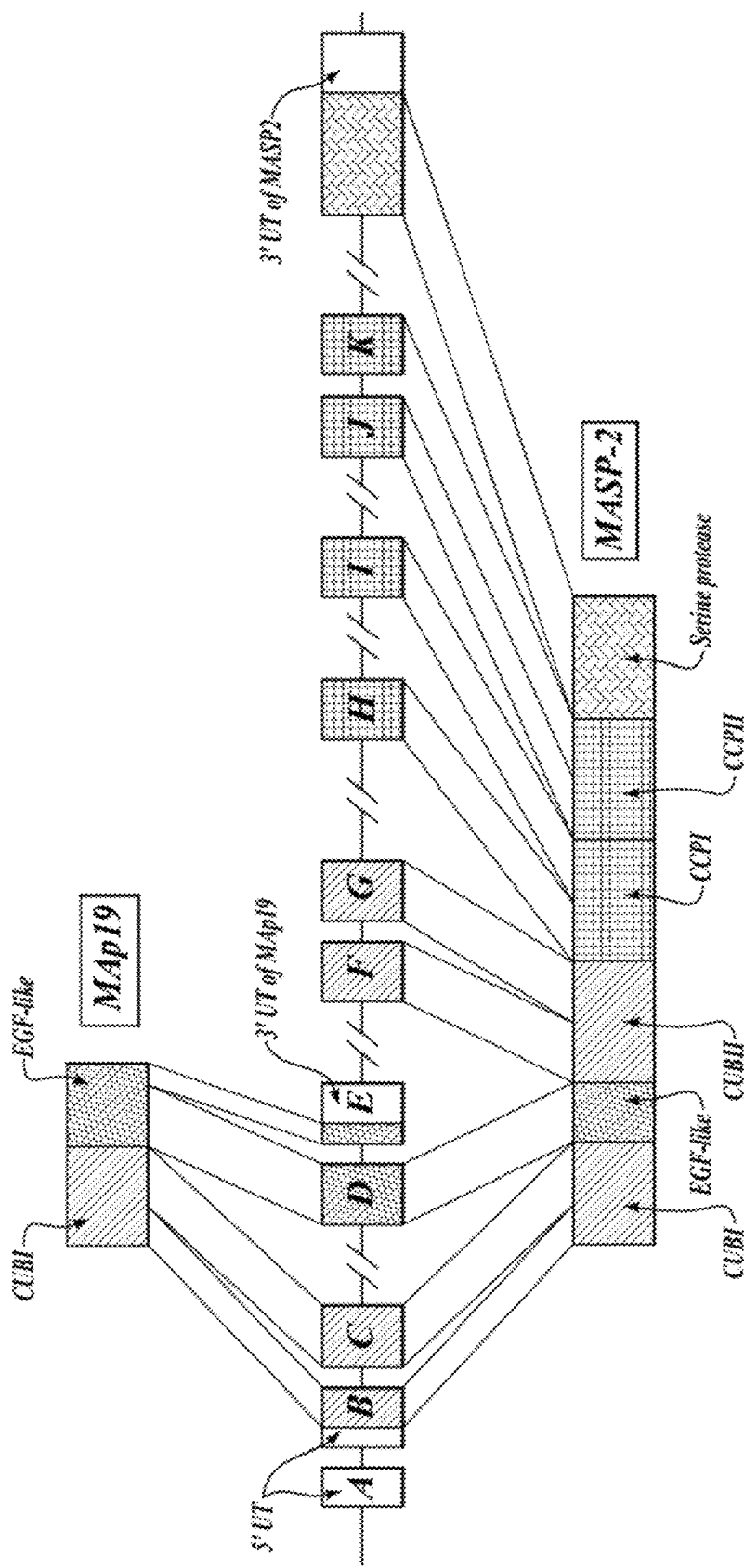
FIG. 1 is a diagram illustrating the genomic structure of human MASP-2.

SEQ ID NO:1 human MAp19 cDNA
SEQ ID NO:2 human MAp19 protein (with leader)
SEQ ID NO:3 human MAp19 protein (mature)
SEQ ID NO:4 human MASP-2 cDNA
SEQ ID NO:5 human MASP-2 protein (with leader)
SEQ ID NO:6 human MASP-2 protein (mature)
SEQ ID NO:7 human MASP-2 gDNA (exons 1-6)
Antigens: (in Reference to the MASP-2 Mature Protein)
SEQ ID NO:8 CUBI sequence (aa 1-121)
SEQ ID NO:9 CUBEGF sequence (aa 1-166)
SEQ ID NO:10 CUBEGFCUBII (aa 1-293)
SEQ ID NO:11 EGF region (aa 122-166)
SEQ ID NO:12 serine protease domain (aa 429-671)
SEQ ID NO:13 serine protease domain inactive (aa 610-625 with Ser618 to Ala mutation)
SEQ ID NO:14 TPLGPKWPEPVFGRL (CUBI peptide)
SEQ ID NO: 15 TAPPGYRLRLYFTHFDLELSHLCEY-DFVKLSSGAKVLATLCGQ (CUBI peptide)
SEQ ID NO: 16 TFRSDYSN (MBL binding region core)
SEQ ID NO: 17 FYSLGSSLDITFRSDYSNEKPFTGF (MBL binding region)
SEQ ID NO:18 IDECQVAPG (EGF PEPTIDE)
SEQ ID NO:19 ANMLCAGLESGGKD-SCRGDSGGALV (serine protease binding core)
Detailed Description
Peptide Inhibitors:
SEQ ID NO:20 MBL full length cDNA
SEQ ID NO:21 MBL full length protein
SEQ ID NO:22 OGK-X-GP (consensus binding)
SEQ ID NO:23 OGKLG
SEQ ID NO:24 GLR GLQ GPO GKL GPO G
SEQ ID NO:25 GPO GPO GLR GLQ GPO GKL GPO GPO GPO
SEQ ID NO:26 GKDGRDGTKGEKGEPGQGLR-GLQGPOGKLGPOG
SEQ ID NO:27 GAOGSOGEKGAOGPQGPOGPOGK-MGPKGEOGDO (human h-ficolin)
SEQ ID NO:28 GCOGLOGAOGDKGEAGTNGKRG-ERGPOGPOGKAGPOGPNGA OGEO (human ficolin p35)
SEQ ID NO:29 LQRALEILPNRVTIKANRPFLVFI (C4 cleavage site)
Expression Inhibitors:
SEQ ID NO:30 cDNA of CUBI-EGF domain (nucleotides 22-680 of SEQ ID NO:4)
SEQ ID NO:31 5' CGGGCACACCATGAGGCTGCT-GACCCTCCTGGGC 3' Nucleotides 12-45 of SEQ ID NO:4 including the MASP-2 translation start site (sense)
SEQ ID NO:32 5'GACATTACCTTCCGCTCCGACTC-CAACGAGAAG3' Nucleotides 361-396 of SEQ ID NO:4 encoding a region comprising the MASP-2 MBL binding site (sense)
SEQ ID NO:33 5'AGCAGCCCTGAATACCCACGGC-CGTATCCCAAA3' Nucleotides 610-642 of SEQ ID NO:4 encoding a region comprising the CUBII domain
Cloning Primers:
SEQ ID NO:34 CGGGATCCATGAGGCTGCTGAC-CCTC (5' PCR for CUB)
SEQ ID NO:35 GGAATTCCTAGGCTGCATA (3' PCR FOR CUB)
SEQ ID NO:36 GGAATTCCTACAGGGCGCT (3' PCR FOR CUBIEGF)
SEQ ID NO:37 GGAATTCCTAGTAGTGGAT (3' PCR FOR CUBIEGFCUBII)
SEQ ID NOS:38-47 are cloning primers for humanized antibody
SEQ ID NO:48 is 9 aa peptide bond
Expression Vector:
SEQ ID NO:49 is the MASP-2 minigene insert
SEQ ID NO: 50 is the murine MASP-2 cDNA
SEQ ID NO: 51 is the murine MASP-2 protein (w/leader)
SEQ ID NO: 52 is the mature murine MASP-2 protein
SEQ ID NO: 53 the rat MASP-2 cDNA
SEQ ID NO: 54 is the rat MASP-2 protein (w/leader)
SEQ ID NO: 55 is the mature rat MASP-2 protein
SEQ ID NO: 56-59 are the oligonucleotides for site-directed mutagenesis of human MASP-2 used to generate human MASP-2A
SEQ ID NO: 60-63 are the oligonucleotides for site-directed mutagenesis of murine MASP-2 used to generate murine MASP-2A
SEQ ID NO: 64-65 are the oligonucleotides for site-directed mutagenesis of rat MASP-2 used to generate rat MASP-2A
SEQ ID NO: 66 DNA encoding 17D20_dc35VH21N11VL (OMS646) heavy chain variable region (VH) (without signal peptide)
SEQ ID NO: 67 17D20_dc35VH21N11VL (OMS646) heavy chain variable region (VH) polypeptide
SEQ ID NO: 68 17N16 mc heavy chain variable region (VH) polypeptide
SEQ ID NO:70 DNA encoding 17D20_dc35VH21N11VL (OMS646) light chain variable region (VL)
SEQ ID NO:69 17D20_dc35VH21N11VL (OMS646) light chain variable region (VL) polypeptide
SEQ ID NO: 71 17N16_dc17N9 light chain variable region (VL) polypeptide
SEQ ID NO:72: SGMI-2L (full-length)
SEQ ID NO: 73: SGMI-2M (medium truncated version)
SEQ ID NO:74: SGMI-2S (short truncated version)
SEQ ID NO:75: mature polypeptide comprising the VH-M2ab6-SGMI-2-N and the human IgG4 constant region with hinge mutation
SEQ ID NO:76: mature polypeptide comprising the VH-M2ab6-SGMI-2-C and the human IgG4 constant region with hinge mutation
SEQ ID NO:77: mature polypeptide comprising the VL-M2ab6-SGMI-2-N and the human Ig lambda constant region
SEQ ID NO:78: mature polypeptide comprising the VL-M2ab6-SGMI-2-C and the human Ig lambda constant region
SEQ ID NO:79: peptide linker (10aa)
SEQ ID NO:80: peptide linker (6aa)
SEQ ID NO:81: peptide linker (4aa)
SEQ ID NO:82: polynucleotide encoding the polypeptide comprising the VH-M2ab6-SGMI-2-N and the human IgG4 constant region with hinge mutation SEQ ID NO:83: polynucleotide encoding the polypeptide comprising the VH-M2ab6-SGMI-2-C and the human IgG4 constant region with hinge mutation SEQ ID NO:84: polynucleotide encoding the polypeptide comprising the VL-M2ab6-SGMI-2-N and the human Ig lambda constant region SEQ ID NO:85: polynucleotide encoding the polypeptide comprising the VL-M2ab6-SGMI-2-C and the human Ig lambda constant region DETAILED DESCRIPTION The present invention is based upon the surprising discovery by the present inventors that inhibition of mannan-binding lectin-associated serine protease-2 (MASP-2), the key regulator of the lectin pathway of the complement system, significantly reduces inflammation and fibrosis in various animal models of fibrotic disease including the unilateral ureteral obstruction (UUO) model, the protein overload model and the adriamycin-induced nephrology model of renal fibrosis. Therefore, the inventors have demonstrated that inhibition of MASP-2-mediated lectin pathway activation provides an effective therapeutic approach to ameliorate, treat or prevent renal fibrosis, e.g., tubulointerstitial inflammation and fibrosis, regardless of the underlying cause. As further described herein, the use of a MASP-2 inhibitory antibody (OMS646) is effective to improve renal function and decrease corticosteroid needs in human subjects suffering from Immunoglobulin A Nephropathy (IgAN) and membranous nephropathy (MN).

I. Definitions

Unless specifically defined herein, all terms used herein have the same meaning as would be understood by those of ordinary skill in the art of the present invention. The following definitions are provided in order to provide clarity with respect to the terms as they are used in the specification and claims to describe the present invention.

As used herein, the term "MASP-2-dependent complement activation" comprises MASP-2-dependent activation of the lectin pathway, which occurs under physiological conditions (i.e., in the presence of $Ca^{++}$) leading to the formation of the lectin pathway C3 convertase C4b2a and upon accumulation of the C3 cleavage product C3b subsequently to the C5 convertase C4b2a(C3b)n, which has been determined to primarily cause opsonization.

As used herein, the term "alternative pathway" refers to complement activation that is triggered, for example, by zymosan from fungal and yeast cell walls, lipopolysaccharide (LPS) from Gram negative outer membranes, and rabbit erythrocytes, as well as from many pure polysaccharides, rabbit erythrocytes, viruses, bacteria, animal tumor cells, parasites and damaged cells, and which has traditionally been thought to arise from spontaneous proteolytic generation of C3b from complement factor C3.

As used herein, the term "lectin pathway" refers to complement activation that occurs via the specific binding of serum and non-serum carbohydrate-binding proteins including mannan-binding lectin (MBL), CL-11 and the ficolins (H-ficolin, M-ficolin, or L-ficolin).

As used herein, the term "classical pathway" refers to complement activation that is triggered by antibody bound to a foreign particle and requires binding of the recognition molecule C1q.

As used herein, the term "MASP-2 inhibitory agent" refers to any agent that binds to or directly interacts with MASP-2 and effectively inhibits MASP-2-dependent complement activation, including anti-MASP-2 antibodies and MASP-2 binding fragments thereof, natural and synthetic peptides, small molecules, soluble MASP-2 receptors, expression inhibitors and isolated natural inhibitors, and also encompasses peptides that compete with MASP-2 for binding to another recognition molecule (e.g., MBL, H-ficolin, M-ficolin, or L-ficolin) in the lectin pathway, but does not encompass antibodies that bind to such other recognition molecules. MASP-2 inhibitory agents useful in the method of the invention may reduce MASP-2-dependent complement activation by greater than 20%, such as greater than 50%, such as greater than 90%. In one embodiment, the MASP-2 inhibitory agent reduces MASP-2-dependent complement activation by greater than 90% (i.e., resulting in MASP-2 complement activation of only 10% or less).

As used herein, the term "fibrosis" refers to the formation or presence of excessive connective tissue in an organ or tissue. Fibrosis may occur as a repair or replacement response to a stimulus such as tissue injury or inflammation. A hallmark of fibrosis is the production of excessive extracellular matrix. The normal physiological response to injury results in the deposition of connective tissue as part of the healing process, but this connective tissue deposition may persist and become pathological, altering the architecture and function of the tissue. At the cellular level, epithelial cells and fibroblasts proliferate and differentiate into myofibroblasts, resulting in matrix contraction, increased rigidity, microvascular compression, and hypoxia.

As used herein, the term "treating fibrosis in a mammalian subject suffering from or at risk of developing a disease or disorder caused or exacerbated by fibrosis and/or inflammation" refers to reversing, alleviating, ameliorating, or inhibiting fibrosis in said mammalian subject.

As used herein, the term "proteinuria" refers to the presence of urinary protein in an abnormal amount, such as in amounts exceeding 0.3 g protein in a 24-hour urine collection from a human subject, or in concentrations of more than Ig per liter in a human subject.

As used herein, the term "improving proteinuria" or "reducing proteinuria" refers to reducing the 24-hour urine protein excretion in a subject suffering from proteinuria by at least 20%, such as at least 30%, such as at least 40%, such at least 50% or more in comparison to baseline 24-hour urine protein excretion in the subject prior to treatment with a MASP-2 inhibitory agent. In one embodiment, treatment with a MASP-2 inhibitory agent in accordance with the methods of the invention is effective to reduce proteinuria in a human subject such as to achieve greater than 20 percent reduction in 24-hour urine protein excretion, or such as greater than 30 percent reduction in 24-hour urine protein excretion, or such as greater than 40 percent reduction in 24-hour urine protein excretion, or such as greater than 50 percent reduction in 24-hour urine protein excretion).

As used herein, the term "antibody" encompasses antibodies and antibody fragments thereof, derived from any antibody-producing mammal (e.g., mouse, rat, rabbit, and primate including human), or from a hybridoma, phage selection, recombinant expression or transgenic animals (or other methods of producing antibodies or antibody fragments"), that specifically bind to a target polypeptide, such as, for example, MASP-2, polypeptides or portions thereof. It is not intended that the term "antibody" limited as regards to the source of the antibody or the manner in which it is made (e.g., by hybridoma, phage selection, recombinant expression, transgenic animal, peptide synthesis, etc). Exemplary antibodies include polyclonal, monoclonal and recombinant antibodies; pan-specific, multispecific antibodies (e.g., bispecific antibodies, trispecific antibodies);

humanized antibodies; murine antibodies; chimeric, mouse-human, mouse-primate, primate-human monoclonal antibodies; and anti-idiotype antibodies, and may be any intact antibody or fragment thereof. As used herein, the term "antibody" encompasses not only intact polyclonal or monoclonal antibodies, but also fragments thereof (such as dAb, Fab, Fab', F(ab')$_2$, Fv), single chain (ScFv), synthetic variants thereof, naturally occurring variants, fusion proteins comprising an antibody portion with an antigen-binding fragment of the required specificity, humanized antibodies, chimeric antibodies, and any other modified configuration of the immunoglobulin molecule that comprises an antigen-binding site or fragment (epitope recognition site) of the required specificity.

A "monoclonal antibody" refers to a homogeneous antibody population wherein the monoclonal antibody is comprised of amino acids (naturally occurring and non-naturally occurring) that are involved in the selective binding of an epitope. Monoclonal antibodies are highly specific for the target antigen. The term "monoclonal antibody" encompasses not only intact monoclonal antibodies and full-length monoclonal antibodies, but also fragments thereof (such as Fab, Fab', F(ab')$_2$, Fv), single chain (ScFv), variants thereof, fusion proteins comprising an antigen-binding portion, humanized monoclonal antibodies, chimeric monoclonal antibodies, and any other modified configuration of the immunoglobulin molecule that comprises an antigen-binding fragment (epitope recognition site) of the required specificity and the ability to bind to an epitope. It is not intended to be limited as regards the source of the antibody or the manner in which it is made (e.g., by hybridoma, phage selection, recombinant expression, transgenic animals, etc.). The term includes whole immunoglobulins as well as the fragments etc. described above under the definition of "antibody".

As used herein, the term "antibody fragment" refers to a portion derived from or related to a full-length antibody, such as, for example, an anti-MASP-2 antibody, generally including the antigen binding or variable region thereof. Illustrative examples of antibody fragments include Fab, Fab', F(ab)$_2$, F(ab')$_2$ and Fv fragments, scFv fragments, diabodies, linear antibodies, single-chain antibody molecules and multispecific antibodies formed from antibody fragments.

As used herein, a "single-chain Fv" or "scFv" antibody fragment comprises the $V_H$ and $V_L$ domains of an antibody, wherein these domains are present in a single polypeptide chain. Generally, the Fv polypeptide further comprises a polypeptide linker between the $V_H$ and $V_L$ domains, which enables the scFv to form the desired structure for antigen binding.

As used herein, a "chimeric antibody" is a recombinant protein that contains the variable domains and complementarity-determining regions derived from a non-human species (e.g., rodent) antibody, while the remainder of the antibody molecule is derived from a human antibody.

As used herein, a "humanized antibody" is a chimeric antibody that comprises a minimal sequence that conforms to specific complementarity-determining regions derived from non-human immunoglobulin that is transplanted into a human antibody framework.

Humanized antibodies are typically recombinant proteins in which only the antibody complementarity-determining regions are of non-human origin.

As used herein, the term "mannan-binding lectin" ("MBL") is equivalent to mannan-binding protein ("MBP").

As used herein, the "membrane attack complex" ("MAC") refers to a complex of the terminal five complement components (C5b combined with C6, C7, C8 and C-9) that inserts into and disrupts membranes (also referred to as C5b-9).

As used herein, "a subject" includes all mammals, including without limitation humans, non-human primates, dogs, cats, horses, sheep, goats, cows, rabbits, pigs and rodents.

As used herein, the amino acid residues are abbreviated as follows: alanine (Ala;A), asparagine (Asn;N), aspartic acid (Asp;D), arginine (Arg;R), cysteine (Cys;C), glutamic acid (Glu;E), glutamine (Gln;Q), glycine (Gly;G), histidine (His;H), isoleucine (Ile;I), leucine (Leu;L), lysine (Lys;K), methionine (Met;M), phenylalanine (Phe;F), proline (Pro;P), serine (Ser,S), threonine (Thr;T), tryptophan (Trp;W), tyrosine (Tyr;Y), and valine (Val;V).

In the broadest sense, the naturally occurring amino acids can be divided into groups based upon the chemical characteristic of the side chain of the respective amino acids. By "hydrophobic" amino acid is meant either Ile, Leu, Met, Phe, Trp, Tyr, Val, Ala, Cys or Pro. By "hydrophilic" amino acid is meant either Gly, Asn, Gin, Ser, Thr, Asp, Glu, Lys, Arg or His. This grouping of amino acids can be further subclassed as follows. By "uncharged hydrophilic" amino acid is meant either Ser, Thr, Asn or Gin. By "acidic" amino acid is meant either Glu or Asp. By "basic" amino acid is meant either Lys, Arg or His.

As used herein the term "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine.

The term "oligonucleotide" as used herein refers to an oligomer or polymer of ribonucleic acid (RNA) or deoxyribonucleic acid (DNA) or mimetics thereof. This term also covers those oligonucleobases composed of naturally-occurring nucleotides, sugars and covalent internucleoside (backbone) linkages as well as oligonucleotides having non-naturally-occurring modifications.

As used herein, an "epitope" refers to the site on a protein (e.g., a human MASP-2 protein) that is bound by an antibody. "Overlapping epitopes" include at least one (e.g., two, three, four, five, or six) common amino acid residue(s), including linear and non-linear epitopes.

As used herein, the terms "polypeptide," "peptide," and "protein" are used interchangeably and mean any peptide-linked chain of amino acids, regardless of length or post-translational modification. The MASP-2 protein described herein can contain or be wild-type proteins or can be variants that have not more than 50 (e.g., not more than one, two, three, four, five, six, seven, eight, nine, ten, 12, 15, 20, 25, 30, 35, 40, or 50) conservative amino acid substitutions. Conservative substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine.

In some embodiments, the human MASP-2 protein can have an amino acid sequence that is, or is greater than, 70 (e.g., 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100) % identical to the human MASP-2 protein having the amino acid sequence set forth in SEQ ID NO: 5.

In some embodiments, peptide fragments can be at least 6 (e.g., at least 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, 500, or 600 or more) amino acid residues in length (e.g., at least 6 contiguous amino acid residues of SEQ ID NO: 5). In some embodiments, an antigenic peptide fragment of a human MASP-2 protein is fewer than 500 (e.g., fewer than 450, 400, 350, 325, 300, 275, 250, 225, 200, 190, 180, 170, 160, 150, 140, 130, 120, 110, 100, 95, 90, 85, 80, 75, 70, 65, 60, 55, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, or 6) amino acid residues in length (e.g., fewer than 500 contiguous amino acid residues in any one of SEQ ID NOS: 5).

Percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

II. Overview of the Invention

As described herein, the inventors have identified the central role of the lectin pathway in the initiation and disease progression of tubular renal pathology, thereby implicating a key role of the lectin pathway activation in the pathophysiology of a diverse range of renal diseases including IgA nephropathy, C3 glomerulopathy and other glomerulonephritides. As further described herein, the inventors discovered that inhibition of mannan-binding lectin-associated serine protease-2 (MASP-2), the key regulator of the lectin pathway of the complement system, significantly reduces inflammation and fibrosis in various animal models of fibrotic disease including the unilateral ureteral obstruction (UUO) model, the protein overload model and the adriamycin-induced nephrology model of renal fibrosis. Therefore, the inventors have demonstrated that inhibition of MASP-2-mediated lectin pathway activation provides an effective therapeutic approach to ameliorate, treat or prevent renal fibrosis, e.g., tubulointerstitial fibrosis, regardless of the underlying cause.

Lectins (MBL, M-ficolin, H-ficolin, L-ficolin and CL-11) are the specific recognition molecules that trigger the innate complement system and the system includes the lectin initiation pathway and the associated terminal pathway amplification loop that amplifies lectin-initiated activation of terminal complement effector molecules. C1q is the specific recognition molecule that triggers the acquired complement system and the system includes the classical initiation pathway and associated terminal pathway amplification loop that amplifies C1q-initiated activation of terminal complement effector molecules. We refer to these two major complement activation systems as the lectin-dependent complement system and the C1q-dependent complement system, respectively.

In addition to its essential role in immune defense, the complement system contributes to tissue damage in many clinical conditions. Thus, there is a pressing need to develop therapeutically effective complement inhibitors to prevent these adverse effects. With the recognition that it is possible to inhibit the lectin mediated MASP-2 pathway while leaving the classical pathway intact comes the realization that it would be highly desirable to specifically inhibit only the complement activation system causing a particular pathology without completely shutting down the immune defense capabilities of complement. For example, in disease states in which complement activation is mediated predominantly by the lectin-dependent complement system, it would be advantageous to specifically inhibit only this system. This would leave the C1q-dependent complement activation system intact to handle immune complex processing and to aid in host defense against infection.

The preferred protein component to target in the development of therapeutic agents to specifically inhibit the lectin-dependent complement system is MASP-2. Of all the known protein components of the lectin-dependent complement system (MBL, H-ficolin, M-ficolin, L-ficolin, MASP-2, C2-C9, Factor B, Factor D, and properdin), only MASP-2 is both unique to the lectin-dependent complement system and required for the system to function. The lectins (MBL, H-ficolin, M-ficolin, L-ficolin and CL-11) are also unique components in the lectin-dependent complement system. However, loss of any one of the lectin components would not necessarily inhibit activation of the system due to lectin redundancy. It would be necessary to inhibit all five lectins in order to guarantee inhibition of the lectin-dependent complement activation system. Furthermore, since MBL and the ficolins are also known to have opsonic activity independent of complement, inhibition of lectin function would result 15 in the loss of this beneficial host defense mechanism against infection. In contrast, this complement-independent lectin opsonic activity would remain intact if MASP-2 was the inhibitory target. An added benefit of MASP-2 as the therapeutic target to inhibit the lectin-dependent complement activation system is that the plasma concentration of MASP-2 is among the lowest of any complement protein (~500 ng/ml); therefore, correspondingly low concentrations of high-affinity inhibitors of MASP-2 may be sufficient to obtain full inhibition (Moller-Kristensen, M., et al., *J. Immunol Methods* 282:159-167, 2003).

As described herein in Example 14, it was determined in an animal model of fibrotic kidney disease (unilateral ureteral obstruction UUO) that mice without the MASP-2 gene (MASP-2−/−) exhibited significantly less kidney disease compared to wild-type control animals, as shown by inflammatory cell infiltrates (75% reduction) and histological markers of fibrosis such as collagen deposition (one third reduction). As further shown in Example 15, wild-type mice systemically treated with an anti-MASP-2 monoclonal antibody that selectively blocks the lectin pathway while leaving the classical pathway intact, were protected from renal fibrosis, as compared to wild-type mice treated with an isotype control antibody. These results demonstrate that the lectin pathway is a key contributor to kidney disease and further demonstrate that a MASP-2 inhibitor that blocks the lectin pathway, such as a MASP-2 antibody, is effective as an antifibrotic agent. As further shown in Example 16, in the protein overload model, wild-type mice treated with bovine-serum albumin (BSA) developed proteinuric nephropathy, whereas MASP-2−/− mice treated with the same level of BSA had reduced renal injury. As shown in Example 17, wild-type mice systemically treated with an anti-MASP-2 monoclonal antibody that selectively blocks the lectin pathway while leaving the classical pathway intact, were protected from renal injury in the protein overload model. As described in Example 18, MASP-2−/− mice exhibited less renal inflammation and tubulointerstitial injury in an Adriamycin-induced nephrology model of renal fibrosis as compared to wild-type mice. As described in Example 19, in an ongoing Phase 2 open-label renal trial, patients with IgA nephropathy that were treated with an anti-MASP-2 antibody demonstrated a clinically meaningful and statistically significant decrease in urine albumin-to-creatinine ratios (uACRs) throughout the trial and reduction in 24-hour urine protein levels from baseline to the end of treatment. As further described in Example 19, in the same Phase 2 renal trial, patients with membranous nephropathy that were treated with an anti-MASP-2 antibody also demonstrated reductions in uACR during treatment.

In accordance with the foregoing, the present invention relates to the use of MASP-2 inhibitory agents, such as MASP-2 inhibitory antibodies, as antifibrotic agents, the use of MASP-2 inhibitory agents for the manufacture of a medicament for the treatment of a fibrotic condition, and methods of preventing, treating, alleviating or reversing a fibrotic condition in a human subject in need thereof, said method comprising administering to said patient an efficient amount of a MASP-2 inhibitory agent (e.g., an anti-MASP-2 antibody).

The methods of the invention can be used to prevent, treat, alleviate or reverse a fibrotic condition in a human subject suffering from any disease or disorder caused or exacerbated by fibrosis and/or inflammation, including diseases of the kidney (e.g., chronic kidney disease, IgA nephropathy, C3 glomerulopathy and other glomerulonephritides), lung (e.g., idiopathic pulmonary fibrosis, cystic fibrosis, bronchiectasis), liver (e.g., cirrhosis, nonalcoholic fatty liver disease), heart (e.g., myocardial infarction, atrial fibrosis, valvular fibrosis, endomyocardial fibrosis), brain (e.g., stroke), skin (e.g., excessive wound healing, scleroderma, systemic sclerosis, keloids), vasculature (e.g., atherosclerotic vascular disease), intestine (e.g., Crohn's disease), eye (e.g., anterior subcapsular cataract, posterior capsule opacification), musculoskeletal soft-tissue structures (e.g., adhesive capsulitis, Dupuytren's contracture, myelofibrosis), reproductive organs (e.g., endometriosis, Peyronie's disease), and some infectious diseases (e.g., alpha virus, Hepatitis C, and Hepatitis B).

III. The Role of MASP-2 in Diseases and Conditions Caused or Exacerbated by Fibrosis Fibrosis is the formation or presence of excessive connective tissue in an organ or tissue, commonly in response to damage or injury. A hallmark of fibrosis is the production of excessive extracellular matrix following an injury. In the kidney, fibrosis is characterized as a progressive detrimental connective tissue deposition on the kidney parenchyma which inevitably leads to a decline in renal function independently of the primary renal disease which causes the original kidney injury. So called epithelial to mesenchymal transition (EMT), a change in cellular characteristics in which tubular epithelial cells are transformed to mesenchymal fibroblasts, constitutes the principal mechanism of renal fibrosis. Fibrosis affects nearly all tissues and organ systems and may occur as a repair or replacement response to a stimulus such as tissue injury or inflammation. The normal physiological response to injury results in the deposition of connective tissue but, if this process becomes pathological, the replacement of highly differentiated cells by scarring connective tissue alters the architecture and function of the tissue. At the cellular level, epithelial cells and fibroblasts proliferate and differentiate into myofibroblasts, resulting in matrix contraction, increased rigidity, microvascular compression, and hypoxia. Currently there are no effective treatments or therapeutics for fibrosis, but both animal studies and anecdotal human reports suggest that fibrotic tissue damage may be reversed (Tampe and Zeisberg, *Nat Rev Nephrol*, vol 10:226-237, 2014).

Many diseases result in fibrosis that causes progressive organ failure, including diseases of the kidney (e.g., chronic kidney disease, IgA nephropathy, C3 glomerulopathy and other glomerulonephritides), lung (e.g., idiopathic pulmonary fibrosis, cystic fibrosis, bronchiectasis), liver (e.g., cirrhosis, nonalcoholic fatty liver disease), heart (e.g., myocardial infarction, atrial fibrosis, valvular fibrosis, endomyocardial fibrosis), brain (e.g., stroke), skin (e.g., excessive wound healing, scleroderma, systemic sclerosis, keloids), vasculature (e.g., atherosclerotic vascular disease), intestine (e.g., Crohn's disease), eye (e.g., anterior subcapsular cataract, posterior capsule opacification), musculoskeletal soft-tissue structures (e.g., adhesive capsulitis, Dupuytren's contracture, myelofibrosis), reproductive organs (e.g., endometriosis, Peyronie's disease), and some infectious diseases (e.g., alpha virus, Hepatitis C, Hepatitis B, etc.).

While fibrosis occurs in many tissues and diseases, there are common molecular and cellular mechanisms to its pathology. The deposition of extracellular matrix by fibroblasts is accompanied by immune cell infiltrates, predominately mononuclear cells (see Wynn T., *Natl Rev Immunol* 4(8):583-594, 2004, hereby incorporated herein by reference). A robust inflammatory response results in the expression of growth factors (TGF-beta, VEGF, Hepatocyte Growth Factor, connective tissue growth factor), cytokines and hormones (endothelin, IL-4, IL-6, IL-13, chemokines), degradative enzymes (elastase, matrix metaloproteinases, cathepsins), and extracellular matrix proteins (collagens, fibronectin, integrins).

In addition, the complement system becomes activated in numerous fibrotic diseases. Complement components, including the membrane attack complex, have been identified in numerous fibrotic tissue specimens. For example, components of the lectin pathway have been found in fibrotic lesions of kidney disease (Satomura et al., *Nephron.* 92(3):702-4 (2002); Sato et al., *Lupus* 20(13):1378-86 (2011); Liu et al., *Clin Exp Immunol,* 174(1):152-60 (2013)); liver disease (Rensen et al., *Hepatology* 50(6): 1809-17 (2009)); and lung disease (Olesen et al., *Clin Immunol* 121(3):324-31 (2006)).

Overshooting complement activation has been established as a key contributor to immune complex-mediated as well as antibody independent glomerulonephritides. There is, however, a strong line of evidence demonstrating that uncontrolled activation of complement in situ is intrinsically involved in the pathophysiological progression of TI fibrosis in non-glomerular disease (Quigg R. J, *J Immunol* 171:3319-3324, 2003, Naik A. et al., *Semin Nephrol* 33:575-585, 2013, Mathern D. R. et al., *Clin J Am Soc Nephrol* 10:P1636-1650, 2015). The strong proinflammatory signals that are triggered by local complement activation may be initiated by complement components filtered into the proximal tubule and subsequently entering the interstitial space, or abnormal synthesis of complement components by tubular or other resident and infiltrating cells, or by altered expression of complement regulatory proteins on kidney cells, or absence or loss or gain for function mutations in complement regulatory components (Mathern D. R. et al., *Clin. J Am Soc Nephrol* 10:P1636-1650, 2015, Sheerin N. S., et al., *FASEB*

J 22: 1065-1072, 2008). In mice for example, deficiency of the complement regulatory protein CR1-related gene/protein y (Crry), results in tubulointerstitial (TI) complement activation with consequent inflammation and fibrosis typical of the injury seen in human TI diseases (Naik A. et al., *Semin Nephrol* 33:575-585, 2013, Bao L. et al., *J Am Soc Nephrol* 18:811-822, 2007). Exposure of tubular epithelial cells to the anaphylatoxin C3a results in epithelial to mesenchymal transition (Tsang Z. et al., *J Am Soc Nephrol* 20:593-603, 2009). Blocking C3a signaling via the C3a receptor alone has recently been shown to lessen renal TI fibrosis in proteinuric and non-proteinuric animals (Tsang Z. et al., *J Am Soc Nephrol* 20:593-603, 2009, Bao L. et al., *Kidney Int.* 80: 524-534, 2011).

As described herein, the inventors have identified the central role of the lectin pathway in the initiation and disease progression of tubular renal pathology, thereby implicating a key role of the lectin pathway activation in the pathophysiology of a diverse range of renal diseases including IgA nephropathy, C3 glomerulopathy and other glomerulonephritides (Endo M. et al., *Nephrol Dialysis Transplant* 13: 1984-1990, 1998; Hisano S. et al., *Am J Kidney Dis* 45:295-302, 2005; Roos A. et al., *J Am Soc Nephrol* 17: 1724-1734, 2006; Liu L. L. et al., *Clin Exp. Immunol* 174:152-160, 2013; Lhotta K. et al., *Nephrol Dialysis Transplant* 14:881-886, 1999; Pickering et al., *Kidney International* 84:1079-1089, 2013), diabetic nephropathy (Hovind P. et al., *Diabetes* 54:1523-1527, 2005), ischaemic reperfusion injury (Asgari E. et al., *FASEB J* 28:3996-4003, 2014) and transplant rejection (Berger S. P. et al., *Am J Transplant* 5:1361-1366, 2005).

As further described herein, the inventors have demonstrated that MASP-2 inhibition reduces inflammation and fibrosis in mouse models of tubulointerstitial disease. Therefore, MASP-2 inhibitory agents are expected to be useful in the treatment of renal fibrosis, including tubulointerstitial inflammation and fibrosis, proteinuria, IgA nephropathy, C3 glomerulopathy and other glomerulonephritides and renal ischaemia reperfusion injury.

Kidney Diseases and Disorders

According to the National Kidney Foundation, 26 million American adults suffer from Chronic Kidney Disease (CKD). Most patients have progressive disease leading to kidney failure, requiring treatment with erythropoiesis stimulating drugs, dialysis or a kidney transplant for survival. There are several drugs that can treat the main symptom of CKD, hypertension, but currently there are no drugs that address its root cause.

Studies have shown that progressive renal injury is caused by capillary hypertension in substructures of the kidney known as nephrons (Whitworth J. A., *Annals Acad of Med*, vol 34(1):2005). As nephrons (the filtration units of the kidney) are injured or destroyed in this process, inflammation and tissue scarring occur, replacing nephrons with non-functional scar tissue. As a result, the ability of the kidney to filter blood declines over time. This is referred to as renal fibrosis, which is the common pathway of progressive renal disease. Irrespective of the nature of the initial insult, renal fibrosis is considered to be the common final pathway by which kidney disease progresses to end-stage renal failure. Amelioration of renal fibrosis may be determined by one or more of the following: assessment of interstitial volume, collagen IV deposition, and/or connective tissue growth mRNA levels. The compounds and methods described herein are useful in the treatment of renal fibrosis.

Renal fibrosis and inflammation are prominent features of late-stage kidney disease of virtually any etiology (see Boor et al., Boor P. et al., *J of Am Soc of Nephrology* 18:1508-1515, 2007 and Chevalier et al., *Kidney International* 75:1145-1152, 2009). Kidney failure can be caused by a heterogeneous group of disorders. Progressive kidney dysfunction leads to proteinuria and renal insufficiency. As patient health deteriorates, dialysis may be necessary simply to forestall the damage to the kidney and to prevent multisystem failure. Over time, kidney failure and renal insufficiency can progress to end-stage renal disease (ESRD), which is total, or nearly total, permanent loss of kidney function. Depending on the form of kidney disease, renal function may be lost in a matter of days or weeks or may deteriorate slowly and gradually over the course of decades. Once a patient has progressed to ESRD, dialysis (hemidialysis or peritoneal dialysis) is required to prevent death. Patients must remain on some form of dialysis regimen or must obtain a kidney transplant.

Components of the lectin pathway have been found in fibrotic lesions of kidney disease (Satomura et al., *Nephron.* 92(3):702-4 (2002); Sato et al., *Lupus* 20(13):1378-86 (2011); Liu et al., *Clin Exp Immunol*, 174(1):152-60 (2013)). In IgA nephropathy, patients with glomerular MBL deposition had more severe proteinuria, decreased renal function, lower levels of serum albumin, more severe histology, and greater hypertension than patients without MBL deposition (Liu et al., *Clin Erp Immunol.* 2013 October; 174(1):152-60). Patients with lupus nephritis (Sato et al., *Lupus,* 20(13): 1378-86, 2011) and chronic renal failure (Satomura et al., *Nephron* 92(3):702-4, 2002) also have increased levels of MBL and lectin pathway activity.

It has also been demonstrated that C5 deficiency led to a significant amelioration of major components of renal fibrosis in a nonproteinuric model of primary tubulointerstitial damage, namely unilateral ureteral obstruction (UUO) (Boor P. et al., *J of Am Soc of Nephrology* 18:1508-1515, 2007). It has also been reported that C3 gene expression was increased in wild-type mice following UUO, and that collagen deposition was significantly reduced in C3−/− mice following UUO as compared to wild-type mice, suggesting a role of complement activation in renal fibrosis (Fearn et al., *Mol Immunol* 48:1666-1733, 2011: Abstract). However, prior to the discovery described herein by the present inventors, the complement components involved in renal fibrosis were not well defined. As described herein in Examples 14-17, the present inventors have unexpectedly determined that a deficiency of MASP-2 or blockade of MASP-2 with an inhibitory antibody that selectively blocks the lectin pathway, while leaving intact the classical pathway, clearly protects mice from renal fibrosis in various animal models of kidney disease.

Accordingly, in certain embodiments, the disclosure provides a method of inhibiting renal fibrosis in a subject suffering from a kidney disease or disorder caused or exacerbated by fibrosis and/or inflammation comprising administering a MASP-2 inhibitory agent, such as an anti-MASP-2 antibody, to a subject in need thereof. This method includes administering a composition comprising an amount of a MASP-2 inhibitor effective to inhibit renal fibrosis to a subject suffering from a kidney disease or disorder caused or exacerbated by fibrosis and/or inflammation.

The MASP-2 inhibitory composition may be administered locally to the region of fibrosis, such as by local application of the composition during surgery or local injection, either directly or remotely, for example, by catheter. Alternately, the MASP-2 inhibitory agent may be administered to the subject systemically, such as by intra-arterial, intravenous, intramuscular, inhalational, nasal, subcutaneous or other parenteral administration, or potentially by oral administration for non-peptidergic agents. Administration may be repeated as determined by a physician until the condition has been resolved or is controlled.

In certain embodiments, the MASP-2 inhibitory agents (e.g., anti-MASP-2 antibodies) are administered in combination with one or more agents or treatment modalities appropriate for the underlying kidney disease or condition. In certain embodiments, the MASP-2 inhibitory agents (e.g., anti-MASP-2 antibodies) are administered in combination with a dialysis or plasmapheresis regimen. In certain embodiments, the MASP-2 inhibitory agents (e.g., anti-MASP-2 antibodies) are used to decrease the frequency with which dialysis or plasmapheresis is required. In certain other embodiments, the MASP-2 inhibitory agents (e.g., anti-MASP-2 antibodies) are used in combination with kidney transplantation. In certain other embodiments, the MASP-2 inhibitory agents (e.g., anti-MASP-2 antibodies) are used to control renal insufficiency and prevent the further decline in renal function in patients awaiting kidney transplantation.

By way of example, in certain embodiments, anti-MASP-2 antibodies are used to inhibit renal fibrosis and thereby treat or ameliorate (including treating or ameliorating the symptoms of a disease) glomerular diseases such as focal segmental glomerulosclerosis and nephrotic syndrome. Exemplary symptoms that can be treated include, but are not limited to, hypertension, proteinuria, hyperlipidemia, hematuria, and hypercholestermia. In some embodiments, the MASP-2 inhibitory agent inhibits tubulointerstitial fibrosis. In certain embodiments, treating comprises improving renal function, decreasing proteinuria, improving hypertension, and/or decreasing renal fibrosis. In certain embodiments, treating comprises (i) delaying or preventing progression to renal insufficiency, renal failure, or ESRD; (ii) delaying, reducing, or preventing need for dialysis; or (iii) delaying or preventing need for kidney transplantation.

Certain specific kidney diseases and disorders caused or exacerbated by fibrosis and/or inflammation are described below.

In certain embodiments, the kidney disease caused or exacerbated by fibrosis and/or inflammation is a glomerular disease such as focal segmental glomerulosclerosis (FSGS). Glomerular diseases damage the glomeruli, letting protein and sometimes red blood cells leak into the urine. Sometimes a glomerular disease also interferes with the clearance of waste products by the kidney, so they begin to build up in the blood. Symptoms of glomerular disease include proteinuria, hematuria, reduced glomerular filtration rate, hypoproteinemia, and edema. A number of different diseases can result in glomerular disease. It may be the direct result of an infection or a drug toxic to the kidneys, or it may result from a disease that affects the entire body, such as hypertension, diabetes or lupus. FSGS is one particular glomerular disease, but even this particular condition characterized by scarring in the kidney can have numerous causes. Patients with FSGS typically progress to end stage renal disease within 5-20 years, although patients with aggressive forms of the disease progress to ESRD in 2 to 3 years.

In certain embodiments, the kidney disease caused or exacerbated by fibrosis and/or inflammation is diabetic nephropathy (DN), which is an area of substantial unmet medical need. Diabetic nephropathy is kidney disease or damage that results as a complication of diabetes. The condition is exacerbated by high blood pressure, high blood sugar levels, and high cholesterol and lipid levels. The exact cause of diabetic nephropathy is unknown. However, without being bound by theory, it is believed that uncontrolled high blood sugar leads to the development of kidney damage, such as fibrosis and scarring of tissue. In humans, DN manifests as a clinical syndrome that is composed of albuminuria, progressively declining glomerular filtration rate (GFR) and increased risk for cardiovascular disease. Diabetic albuminuria is associated with the development of characteristic histo-pathologic features, including ticking of the glomerular basement membrane (GBM) and mesangial expansion. As albuminuria progress and renal insufficiency ensues, glomerulosclerosis, arteriolar hyalinosis and tubulointerstitial fibrosis develop.

Accordingly, in one embodiment, the present disclosure provides methods for treating diabetic nephropathy comprising administering an effective amount of a MASP-2 inhibitory agent (e.g., a MASP-2 inhibitory antibody) to a subject in need thereof. In certain embodiments, treating comprises reducing one or more symptoms of diabetic nephropathy. In certain embodiments, treating comprises reducing, delaying or eliminating the need for dialysis. In certain embodiments, treating comprises reducing, delaying, or eliminating the need for kidney transplantation. In certain embodiments, treating comprises delaying, preventing or reversing the progression of diabetic nephropathy to renal failure or end stage renal disease.

In certain embodiments, the kidney disease caused or exacerbated by fibrosis and/or inflammation is lupus nephritis. As described in more detail below, lupus nephritis, which is a severe complication of systemic lupus erythematosus (SLE), is another example of renal fibrosis that can be treated with MASP-2 inhibitory agents (e.g., anti-MASP-2 antibodies).

Accordingly, in one embodiment, the present disclosure provides methods for inhibiting renal fibrosis in a subject suffering from a kidney disease or disorder caused or exacerbated by fibrosis and/or inflammation comprising administering an effective amount of a MASP-2 inhibitory agent (e.g., a MASP-2 inhibitory antibody). In some embodiments, the kidney disease or disorder exacerbated by fibrosis and/or inflammation is selected from the group consisting of chronic kidney disease, chronic renal failure, glomerular disease (e.g., focal segmental glomerulosclerosis), an immune complex disorder (e.g., IgA nephropathy, membranous nephropathy), lupus nephritis, nephrotic syndrome, diabetic nephropathy, tubulointerstitial damage and C3 glomerulopathy or other types of glomerulonepthritis.

Methods of Preventing or Treating Renal Injury Caused by Drug-Induced Toxicity

Another cause of renal injury includes drug-induced toxicity. For example, nephrotoxins can cause direct toxicity on tubular epithelial cells. As described herein, the inventors have demonstrated that MASP-2 deficient mice are protected from Adriamycin-induced nephropathy.

Nephrotoxins include, but are not limited to, therapeutic drugs, (e.g., cisplatin, gentamicin, cephaloridine, cyclosporin, amphotericin, Adriamycin), radiocontrast dye, pesticides (e.g., paraquat), and environmental contaminants (e.g., trichloriethylene and dichloroacetylene). Other examples include puromycin aminonucleoside (PAN); aminoglycosides, such as gentamicin; cephalosporins, such as cephaloridine; calcineurin inhibitors, such as tacrolimus or sirolimus. Drug-induced nephrotoxicity may also be caused by non-steroidal anti-inflammatories, anti-retrovirals, anti-cytokines, immunosuppressants, oncological drugs or ACE inhibitors. The drug-induced nephrotoxicity may further be caused by nalgesic abuse, ciprofloxacin, clopidogrel, cocaine, cox-2 inhibitors, diuretics, foscarnet, gold, ifosfamide, immunoglobin, Chinese herbs, interferon, lithium, mannitol, mesalamine, mitomycin, nitrosoureas, penicillamine, penicillins, pentamidine, quinine, rifampin, streptozocin, sulfonamides, ticlopidine, triamterene, valproic acid, doxorubicin, glycerol, cidofovir, tobramycin, neomycin sulfate, colistimethate, vancomycin, amikacin, cefotaxime, cisplatin, acyclovir, lithium, interleukin-2, cyclosporin or indinavir.

Accordingly, in one embodiment, a subject at risk for developing or suffering from renal injury may be receiving one or more therapeutic drugs that have a nephrotoxic effect. These subjects may be administered the MASP-2 inhibitors of the invention prior to or simultaneously with such therapeutic agents. Likewise, MASP-2 inhibitors may be administered after the therapeutic agent to treat or reduce the likelihood of developing nephrotoxicity.

Diseases and Conditions Associated with Proteinuria

It has been established that impaired glomerular filtration of protein results in proteinuria and accelerates the progressive loss of nephrons that occurs in all chronic renal diseases (Remuzzi and Bertani, *New Eng. J Med* vol 339 (20):1448-1456, 1998). For example, in a study described in Eddy et al., *Am J Pathol* 135:719-33, 1989, glomerular filtration of albumin was consistently followed by the development of interstitial lesions and scarring. As further described in Eddy et al., 1989, deposition of complement C3 on the luminal surface of proximal tubules was observed in the rats with nephropathy induced by protein-overload, indicating that components of the complement system that are filtered by glomeruli can cause interstitial injury. It has been demonstrated that complement depletion or the lack of C6 ameliorated tubulointerstitial injury in proteinuric animal models such as mesangioproliferative glomerulonephritis, Adriamycin nephropathy, five-sixths nephrectomy and puromycin aminonucleoside nephrosis (Boor et al., et al., *J of Am Soc of Nephrology:* JASN 18:1508-1515, 2007). Human studies have shown that proteinuria is an independent predictor of progression of chronic kidney disease and that reduction in proteinuria is renal-protective (Ruggenenti P. et al., *J Am Soc Nephrol* 23:1917-1928, 2012).

Accordingly, in one embodiment, the present disclosure provides methods for preventing or reducing proteinurea and/or preventing or reducing renal damage in a subject suffering from a disease or condition associated with proteinuria comprising administering an amount of a MASP-2 inhibitory agent (e.g., a MASP-2 inhibitory antibody) effective to reduce or prevent proteinurea in the subject. In some embodiments, the disease or condition associated with proteinuria is selected from the group consisting of nephrotic syndromes, pre-eclampsia, eclampsia, toxic lesions of kidneys, amyloidosis, collagen vascular diseases (e.g., systemic lupus erythematosus), dehydration, glomerular diseases (e.g. membranous glomerulonephritis, focal segmental glomerulonephritis, minimal change disease, lipoid nephrosis), strenuous exercise, stress, benign orthostatis (postural) proteinuria, focal segmental glomerulosclerosis, IgA nephropathy (i.e., Berger's disease), IgM nephropathy, membranoproliferative glomerulonephritis, membranous nephropathy, minimal change disease, sarcoidosis, Alport's syndrome, diabetes mellitus (diabetic nephropathy), drug-induced toxicity (e.g., NSAIDS, nicotine, penicillamine, lithium carbonate, gold and other heavy metals, ACE inhibitors, antibiotics or opiates (e.g. heroin)); Fabry's disease, infections (e.g., HIV, syphilis, hepatitis A, B or C, poststreptococcal infection, urinary schistosomiasis); aminoaciduria, Fanconi syndrome, hypertensive nephrosclerosis, interstitial nephritis, sickle cell disease, hemoglobinuria, multiple myeloma, myoglobinuria, organ rejection (e.g., kidney transplant rejection), ebola hemorrhagic fever, Nail patella syndrome, familial mediterranean fever, HELLP syndrome, systemic lupus erythematosus, Wegener's granulomatosis, Rheumatoid arthritis, Glycogen storage disease type 1, Goodpasture's syndrome, Henoch-Schonlein purpura, urinary tract infection which has spread to the kidneys, Sjögren's syndrome and post-infections glomerulonepthritis.

Liver Disease

Liver fibrosis, also called hepatic fibrosis, is caused by the accumulation of scar tissue in the liver and is a characteristic of most types of liver disease. The replacement of healthy liver tissue with scar tissue impairs the ability of the liver to function properly. If the condition causing the scarring is not treated, liver fibrosis may progress to liver cirrhosis and complete liver failure, a life-threatening condition. The major causes of liver fibrosis are alcohol abuse, chronic hepatitis C virus infection, nonalcoholic steatohepatitis and hepatotoxicity (e.g., drug-induced liver damage induced by acetaminophen or other drug).

Components of the lectin pathway have been found in fibrotic lesions of liver disease (Rensen et al., *Hepatology* 50(6): 1809-17 (2009)). For example, in nonalcoholic steatohepatitis (also known as fatty liver disease), there is widespread activation of complement system proteins, and their expression is associated with disease severity (Rensen et al., *Hepatology* 50(6): 1809-17 (2009), where in addition to C3 and C9 deposition, MBL accumulation was found, confirming activation of the lectin pathway.

Accordingly, in certain embodiments, the disclosure provides a method of inhibiting hepatic fibrosis in a subject suffering from a liver disease or disorder caused or exacerbated by fibrosis and/or inflammation comprising administering a MASP-2 inhibitory agent, such as a MASP-2 inhibitory antibody, to a subject in need thereof. This method includes administering a composition comprising an amount of a MASP-2 inhibitor effective to inhibit hepatic fibrosis to a subject suffering from a liver disease or disorder caused or exacerbated by fibrosis and/or inflammation.

The MASP-2 inhibitory composition may be administered locally to the region of fibrosis, such as by local application of the composition during surgery or local injection, either directly or remotely, for example, by catheter. Alternately, the MASP-2 inhibitory agent may be administered to the subject systemically, such as by intra-arterial, intravenous, intramuscular, inhalational, nasal, subcutaneous or other parenteral administration, or potentially by oral administration for non-peptidergic agents. Administration may be repeated as determined by a physician until the condition has been resolved or is controlled.

In certain embodiments, the MASP-2 inhibitory agents (e.g., MASP-2 inhibitory antibodies) are administered in combination with one or more agents or treatment modalities appropriate for the underlying liver disease or condition.

In some embodiments, the liver disease or disorder caused or exacerbated by fibrosis and/or inflammation is selected from the group consisting of: cirrhosis, nonalcoholic fatty liver disease (steatohepatitis), liver fibrosis secondary to alcohol abuse, liver fibrosis secondary to acute or chronic hepatitis, biliary disease and toxic liver injury (e.g., hepatotoxicity due to drug-induced liver damage induced by acetaminophen or other drug).

Lung Disease

Pulmonary fibrosis is the formation or development of excess fibrous connective tissue in the lungs, wherein normal lung tissue is replaced with fibrotic tissue. This scarring leads to stiffness of the lungs and impaired lung structure and function. In humans, pulmonary fibrosis is thought to result from repeated injury to the tissue within and between the tiny air sacs (alveoli) in the lungs. In an experimental setting, a variety of animal models have replicated aspects of the human disease. For example, a foreign agent such as bleomycin, fluorescein isothiocyanate, silica, or asbestos may be instilled into the trachea of an animal (Gharaee-Kermani et al., *Animal Models of Pulmonary Fibrosis. Methods Mol. Med.,* 2005, 117:251-259).

Accordingly, in certain embodiments, the disclosure provides a method of inhibiting pulmonary fibrosis in a subject suffering from a lung disease or disorder caused or exacerbated by fibrosis and/or inflammation comprising administering a MASP-2 inhibitory agent, such as a MASP-2 inhibitory antibody, to a subject in need thereof. This method includes administering a composition comprising an amount of a MASP-2 inhibitor effective to inhibit pulmonary fibrosis, decrease lung fibrosis, and/or improve lung function. Improvements in symptoms of lung function include improvement of lung function and/or capacity, decreased fatigue, and improvement in oxygen saturation.

In some embodiments, the disclosure provides a method of treating, inhibiting, preventing or ameliorating pulmonary fibrosis in a subject suffering from cystic fibrosis comprising administering a MASP-2 inhibitory agent, such as a MASP-2 inhibitory antibody to a subject in need thereof.

The MASP-2 inhibitory composition may be administered locally to the region of fibrosis, such as by local application of the composition during surgery or local injection, either directly or remotely, for example, by catheter. Alternately, the MASP-2 inhibitory agent may be administered to the subject systemically, such as by intra-arterial, intravenous, intramuscular, inhalational, nasal, subcutaneous or other parenteral administration, or potentially by oral administration for non-peptidergic agents. Administration may be repeated as determined by a physician until the condition has been resolved or is controlled.

In certain embodiments, the MASP-2 inhibitory agents (e.g., MASP-2 inhibitory antibodies) are administered in combination with one or more agents or treatment modalities appropriate for the underlying lung disease or condition.

Certain specific lung diseases and disorders caused or exacerbated by fibrosis and/or inflammation are described below.

In certain embodiments, the lung disease caused or exacerbated by fibrosis and/or inflammation is chronic obstructive pulmonary disease (COPD). COPD is a disease in which airway walls are fibrotic with the accumulation of myofibroblasts and collagen, is a major cause of disability, and it's the fourth leading cause of death in the United States. COPD blocks airflow and makes it increasingly difficult for a sufferer to breathe. COPD is caused by damage to the airways that eventually interferes with the exchange of oxygen and carbon dioxide in the lungs. COPD includes chronic obstructive bronchitis and emphysema and often both. COPD patients, whose lungs are already damaged and whose lung function is already compromised, are at increased risk of complications associated with bacterial and viral infections.

Accordingly, in one embodiment, the present disclosure provides methods for treating chronic obstructive pulmonary disease (COPD) comprising administering an effective amount of a MASP-2 inhibitory agent (e.g., an anti-MASP-2 antibody) to inhibit and/or decrease lung fibrosis in a subject in need thereof. In certain embodiments, treating comprises reducing one or more symptoms of COPD. Symptoms of COPD and/or lung fibrosis include, but are not limited to, cough with mucus, shortness of breath (dyspnea) that may get worse with mild activity, fatigue, frequent respiratory infections, wheezing, chest tightness, irregular heartbeats (arrhythmias), need for breathing machine and oxygen therapy, right-sided heart failure or cor pulmonale (heart swelling and heart failure due to chronic lung disease), pneumonia, pneumothorax, severe weight loss and malnutrition. Symptoms also include decrease in lung function, as evaluated using one or more standard tests of lung function.

In certain embodiments, the lung disease caused or exacerbated by fibrosis and/or inflammation is pulmonary fibrosis associated with scleroderma. As described in more detail below, pulmonary fibrosis associated with scleroderma is another example of pulmonary fibrosis that can be treated with MASP-2 inhibitory agents (e.g., MASP-2 inhibitory antibodies).

In some embodiments, the lung disease or disorder caused or exacerbated by fibrosis and/or inflammation is selected from the group consisting of: chronic obstructive pulmonary disease, cystic fibrosis, pulmonary fibrosis associated with scleroderma, bronchiectasis and pulmonary hypertension.

Heart and Vascular Diseases

A number of different cardiac and vascular pathologies are caused by a common fibrotic process. Excessive deposition of fibrotic tissue in the heart results in cardiac pathology, in which the excess production of extracellular matrix proteins alter the structure, architecture, shape and affect the contractile function of the heart (Khan and Sheppard, *Immunology* 118: 10-24, 2006).

Studies indicate that fibrosis may contribute significantly to cardiac dysfunction in ischaemic, dilated and hypertrophic cardiomyopathy. For example, it has been demonstrated that patients with chronic atrial fibrillation were found to have higher levels of myocardial interstitial fibrosis as compared to controls (Khan and Sheppard, Immunology 118: 10-24, 2006). As another example, it has been determined that most cases of arrhythmogenic right ventricular cardiomyopathy (ARVC) in the US exhibit fat infiltration and scarring (fibrofatty ARVC) (Burke et al., *Circulation* 97:1571-1580, 1998). In a study that examined the histopathologic characteristics of the ventricular myocardium in human subjects with ARVC it was determined that extensive fibrosis was present in biopsy specimens from pediatric patients with ARVC (Nishikawa T. et al., *Cardiovascular Pathology vol* 8 (4):185-189, 1999).

Accordingly, in certain embodiments, the disclosure provides a method of preventing, treating, reverting, inhibiting and/or reducing fibrosis and/or inflammation in a subject suffering from a cardiac or vascular disease or disorder caused or exacerbated by fibrosis and/or inflammation comprising administering a MASP-2 inhibitory agent, such as a MASP-2 inhibitory antibody, to a subject in need thereof. This method includes administering a composition comprising an amount of a MASP-2 inhibitor effective to inhibit cardiac and/or vascular fibrosis, and/or improve cardiac and/or vascular function.

In some embodiments, the disclosure provides a method of treating, inhibiting, preventing or ameliorating fibrosis in a subject suffering from valvular fibrosis comprising administering a MASP-2 inhibitory agent, such as a MASP-2 inhibitory antibody to a subject in need thereof.

The MASP-2 inhibitory composition may be administered locally to the region of fibrosis, such as by local application of the composition during surgery or local injection, either directly or remotely, for example, by catheter. Alternately, the MASP-2 inhibitory agent may be administered to the subject systemically, such as by intra-arterial, intravenous, intramuscular, inhalational, nasal, subcutaneous or other parenteral administration, or potentially by oral administration for non-peptidergic agents. Administration may be repeated as determined by a physician until the condition has been resolved or is controlled.

In certain embodiments, the MASP-2 inhibitory agents (e.g., MASP-2 inhibitory antibodies) are administered in combination with one or more agents or treatment modalities appropriate for the underlying heart disease, or vascular disease or condition.

In some embodiments, the cardiac or vascular disease or disorder caused or exacerbated by fibrosis and/or inflammation is selected from the group consisting of: cardiac fibrosis, myocardial infarction, atrial fibrosis, endomyocardial fibrosis arrhythmogenic right ventricular cardiomyopathy (ARVC), vascular disease, atherosclerotic vascular disease, vascular stenosis, restenosis, vasculitis, phlebitis, deep vein thrombosis and abdominal aortic aneurysm.

Chronic Infectious Diseases

Chronic infectious diseases such as Hepatitis C and Hepatitis B cause tissue inflammation and fibrosis, and high lectin pathway activity may be detrimental. In such diseases, inhibitors of MASP-2 may be beneficial. For example, MBL and MASP-1 levels are found to be a significant predictor of the severity of liver fibrosis in hepatitis C virus (HCV) infection (Brown et al., *Clin Exp Immunol.* 147(1):90-8, 2007; Saadanay et al., *Arab J Gastroenterol.* 12(2):68-73, 2011; Saeed et al., *Clin Fxp Immunol.* 174(2):265-73, 2013). MASP-1 has previously been shown to be a potent activator of MASP-2 and the lectin pathway (Megyeri et al., *J Biol Chem.* 29: 288(13):8922-34, 2013). Alphaviruses such as chikungunya virus and Ross River virus induce a strong host inflammatory response resulting in arthritis and myositis, and this pathology is mediated by MBL and the lectin pathway (Gunn et al., *PLoS Pathog.* 8(3):e1002586, 2012).

Accordingly, in certain embodiments, the disclosure provides a method of preventing, treating, reverting, inhibiting and/or reducing fibrosis and/or inflammation in a subject suffering from, or having previously suffered from, a chronic infectious disease that causes inflammation and/or fibrosis, comprising administering a MASP-2 inhibitory agent, such as a MASP-2 inhibitory antibody, to a subject in need thereof.

The MASP-2 inhibitory composition may be administered locally to the region of fibrosis, such as by local application of the composition during surgery or local injection, either directly or remotely, for example, by catheter. Alternately, the MASP-2 inhibitory agent may be administered to the subject systemically, such as by intra-arterial, intravenous, intramuscular, inhalational, nasal, subcutaneous or other parenteral administration, or potentially by oral administration for non-peptidergic agents. Administration may be repeated as determined by a physician until the condition has been resolved or is controlled.

In certain embodiments, the MASP-2 inhibitory agents (e.g., MASP-2 inhibitory antibodies) are administered in combination with one or more agents or treatment modalities appropriate for the underlying chronic infectious disease.

In some embodiments, the chronic infectious disease that causes inflammation and/or fibrosis is selected from the group consisting of: alpha virus, Hepatitis A, Hepatitis B, Hepatitis C, tuberculosis, HIV and influenza.

Autoimmune Diseases:

Scleroderma is a chronic autoimmune disease characterized by fibrosis, vascular alterations, and autoantibodies. There are two major forms: limited systemic scleroderma and diffuse systemic scleroderma. The cutaneous symptoms of limited systemic scleroderma affect the hands, arms and face. Patients with this form of scleroderma frequently have one or more of the following complications: calcinosis, Raynaud's phenomenon, esophageal dysfunction, sclerodactyl, and telangiectasias. Diffuse systemic scleroderma is rapidly progressing and affects a large area of the skin and one or more internal organs, frequently the kidneys, esophagus, heart and/or lungs.

Scleroderma affects the small blood vessels known as arterioles, in all organs. First, the endothelial cells of the arteriole die off apoptotically, along with smooth muscle cells. These cells are replaced by collagen and other fibrous material. Inflammatory cells, particularly CD4+ helper T cells, infiltrate the arteriole, and cause further damage.

The skin manifestations of scleroderma can be painful, can impair use of the affected area (e.g., use of the hands, fingers, toes, feet, etc.) and can be disfiguring. Skin ulceration may occur, and such ulcers may be prone to infection or even gangrene. The ulcerated skin may be difficult or slow to heal. Difficulty in healing skin ulcerations may be particularly exacerbated in patients with impaired circulation, such as those with Raynaud's phenomenon. In certain embodiments, the methods of the present disclosure are used to treat scleroderma, for example skin symptoms of scleroderma. In certain embodiments, treating scleroderma comprises treating skin ulceration, such as digital ulcers. Administration of MASP-2 inhibitory agent such as anti-MASP-2 antibodies can be used to reduce the fibrotic and/or inflammatory symptoms of scleroderma in affected tissue and/or organs.

In addition to skin symptoms/manifestations, scleroderma may also affect the heart, kidney, lungs, joints, and digestive tract. In certain embodiments, treating scleroderma includes treating symptoms of the disease in any one or more of these tissues, such as by reducing fibrotic and/or inflammatory symptoms. Lung problems are amongst the most serious complications of scleroderma and are responsible for much of the mortality associated with the disease. The two predominant lung conditions associated with scleroderma are pulmonary fibrosis and pulmonary hypertension. A patient with lung involvement may have either or both conditions. Lung fibrosis associated with scleroderma is one example of pulmonary fibrosis that can be treated with MASP-2 inhibitory agents. Scleroderma involving the lung causes scarring (pulmonary fibrosis). Such pulmonary fibrosis occurs in about 70% of scleroderma patients, although its progression is typically slow and symptoms vary widely across patients in terms of severity. For patients that do have symptoms associated with pulmonary fibrosis, the symptoms include a dry cough, shortness of breath, and reduced ability to exercise. About 16% of patients with some level of pulmonary fibrosis develop severe pulmonary fibrosis. Patients with severe pulmonary fibrosis experience significant decline in lung function and alveolitis.

In certain embodiments, the methods of the present disclosure are used to treat scleroderma, for example lung fibrosis associated with scleroderma. Administration of MASP-2 inhibitory agents, such as MASP-2 inhibitory antibodies can be used to reduce the fibrotic symptoms of scleroderma in lung. For example, the methods can be used to improve lung function and/or to reduce the risk of death due to scleroderma.

Kidney involvement is also common in scleroderma patients. Renal fibrosis associated with scleroderma is an example of renal fibrosis that can be treated by administration of MASP-2 inhibitory agents, such as anti-MASP-2 antibodies. In certain embodiments, the methods of the present disclosure are used to treat scleroderma, for example kidney fibrosis associated with scleroderma. In one embodiment, administration of MASP-2 inhibitory antibodies can be used to reduce the fibrotic symptoms of scleroderma in kidney. For example, the methods can be used to improve kidney function, to reduce protein in the urine, to reduce hypertension, and/or to reduce the risk of renal crisis that may lead to fatal renal failure.

Systemic lupus erythematosus (SLE) is a chronic, inflammatory autoimmune disorder characterized by spontaneous B and T cell autoreactivity and multiorgan immune injury and may affect the skin, joints, kidneys, and other organs. Almost all people with SLE have joint pain and most develop arthritis. Frequently affected joints are the fingers, hands, wrists, and knees. General symptoms of SLE include: arthritis; fatigue; general discomfort, uneasiness or ill feeling (malaise); joint pain and swelling; muscle aches; nausea and vomiting: and skin rash. Additionally symptoms may also include: abdominal pain; blood in the urine; fingers that change color upon pressure or in the cold; numbness and tingling; and red spots on skin. In some patients, SLE has lung or kidney involvement. Without being bound by theory, inflammation and/or fibrosis in lung and kidney damages those organs and leads to symptoms associated with lung and/or kidney damage. In some cases, patients with SLE develop a particular kidney condition called lupus nephritis. In certain embodiments, the disclosure provides methods of treating SLE comprising administering an effective amount of a MASP-2 inhibitory agent such as an anti-MASP-2 antibody. Administering MASP-2 inhibitory antibodies can be used to decrease one or more symptoms of SLE. In certain embodiments, administering anti-MASP-2 antibodies is used to treat SLE in a patient with lupus nephritis. In such cases, treating SLE comprises treating lupus nephritis, such as by reducing symptoms of lupus nephritis. In certain embodiments, treating comprises treating the skin symptoms of SLE. In certain embodiments, treating comprises reducing one or more symptoms of lupus nephritis. In certain embodiments, treating comprises reducing, delaying or eliminating the need for dialysis. In certain embodiments, treating comprises reducing, delaying, or eliminating the need for kidney transplantation. In certain embodiments, treating comprises delaying or preventing progression of lupus nephritis to renal failure or end stage renal disease.

Lupus nephritis is an inflammation of the kidney, and is a severe complication of systemic lupus erythematosus (SLE). In the kidney, lupus nephritis can lead to debilitating loss of function. Patients with lupus nephritis may eventually develop kidney failure and require dialysis or kidney transplantation. Related complications that can also be treated using the methods of the disclosure include interstitial nephritis and nephrotic syndrome. Symptoms of lupus nephritis include: blood in the urine, foamy appearance to urine, high blood pressure, protein in the urine, fluid retention, and edema. Other symptoms include signs and symptoms of renal fibrosis and/or kidney failure. If left untreated, lupus nephritis may lead to kidney failure, and even end stage renal disease.

Accordingly, in certain embodiments, the disclosure provides a method of preventing, treating, reverting, inhibiting and/or reducing fibrosis and/or inflammation in a subject suffering from an autoimmune disease that causes or exacerbates fibrosis and/or inflammation comprising administering a MASP-2 inhibitory agent, such as a MASP-2 inhibitory antibody, to a subject in need thereof. This method includes administering a composition comprising an amount of a MASP-2 inhibitor effective to inhibit fibrosis.

The MASP-2 inhibitory composition may be administered locally to the region of fibrosis, such as by local application of the composition during surgery or local injection, either directly or remotely, for example, by catheter. Alternately, the MASP-2 inhibitory agent may be administered to the subject systemically, such as by intra-arterial, intravenous, intramuscular, inhalational, nasal, subcutaneous or other parenteral administration, or potentially by oral administration for non-peptidergic agents. Administration may be repeated as determined by a physician until the condition has been resolved or is controlled.

In certain embodiments, the MASP-2 inhibitory agents (e.g., MASP-2 inhibitory antibodies) are administered in combination with one or more agents or treatment modalities appropriate for the underlying autoimmune disease.

In some embodiments, the autoimmune disease that causes or exacerbates fibrosis and/or inflammation is selected from the group consisting of: scleroderma and systemic lupus erythematosus (SLE).

Central Nervous System Diseases and Conditions:

In certain embodiments, the disclosure provides a method of preventing, treating, reverting, inhibiting and/or reducing fibrosis and/or inflammation in a subject suffering from a disease or disorder of the central nervous system caused or exacerbated by fibrosis and/or inflammation comprising administering a MASP-2 inhibitory agent, such as an anti-MASP-2 antibody, to a subject in need thereof. This method includes administering a composition comprising an amount of a MASP-2 inhibitor effective to inhibit fibrosis and/or inflammation.

The MASP-2 inhibitory composition may be administered locally to the region of fibrosis, such as by local application of the composition during surgery or local injection, either directly or remotely, for example, by catheter. Alternately, the MASP-2 inhibitory agent may be administered to the subject systemically, such as by intra-arterial, intravenous, intramuscular, inhalational, nasal, subcutaneous or other parenteral administration, or potentially by oral administration for non-peptidergic agents. Administration may be repeated as determined by a physician until the condition has been resolved or is controlled.

In certain embodiments, the MASP-2 inhibitory agents (e.g., MASP-2 inhibitory antibodies) are administered in combination with one or more agents or treatment modalities appropriate for the underlying disease or disorder of the central nervous system.

In some embodiments, the disease or disorder of the central nervous system caused or exacerbated by fibrosis and/or inflammation is selected from the group consisting of: stroke, traumatic brain injury and spinal cord injury.

Skin Diseases and Conditions

In certain embodiments, the disclosure provides a method of preventing, treating, reverting, inhibiting and/or reducing fibrosis and/or inflammation in a subject suffering from a skin disease or disorder caused or exacerbated by fibrosis and/or inflammation comprising administering a MASP-2 inhibitory agent, such as a MASP-2 inhibitory antibody, to a subject in need thereof. This method includes administering a composition comprising an amount of a MASP-2 inhibitor effective to inhibit fibrosis and/or inflammation.

The MASP-2 inhibitory composition may be administered locally to the region of fibrosis, such as by local application of the composition to the skin, or local application during surgery or local injection, either directly or remotely, for example, by catheter. Alternately, the MASP-2 inhibitory agent may be administered to the subject systemically, such as by intra-arterial, intravenous, intramuscular, inhalational, nasal, subcutaneous or other parenteral administration, by topical administration, or potentially by oral administration for non-peptidergic agents. Administration may be repeated as determined by a physician until the condition has been resolved or is controlled.

In certain embodiments, the MASP-2 inhibitory agents (e.g., MASP-2 inhibitory antibodies) are administered in combination with one or more agents or treatment modalities appropriate for the underlying skin disease or disorder.

In some embodiments, the skin disease or disorder caused or exacerbated by fibrosis and/or inflammation is selected from the group consisting of: skin fibrosis, wound healing, scleroderma, systemic sclerosis, keloids, connective tissue diseases, scarring, and hypertrophic scars.

Musculoskeletal Bone and Soft-Tissue Disorders and Conditions

In certain embodiments, the disclosure provides a method of preventing, treating, reverting, inhibiting and/or reducing fibrosis and/or inflammation in a subject suffering from a bone or soft-tissue disease or disorder caused or exacerbated by fibrosis and/or inflammation comprising administering a MASP-2 inhibitory agent, such as a MASP-2 inhibitory antibody, to a subject in need thereof. This method includes administering a composition comprising an amount of a MASP-2 inhibitor effective to inhibit fibrosis and/or inflammation.

The MASP-2 inhibitory composition may be administered locally to the region of fibrosis, such as by local application of the composition to the bone or soft-tissue structure, or local application during surgery or local injection, either directly or remotely, for example, by catheter. Alternately, the MASP-2 inhibitory agent may be administered to the subject systemically, such as by intra-arterial, intravenous, intramuscular, inhalational, nasal, subcutaneous or other parenteral administration, by topical administration, or potentially by oral administration for non-peptidergic agents. Administration may be repeated as determined by a physician until the condition has been resolved or is controlled.

In certain embodiments, the MASP-2 inhibitory agents (e.g., MASP-2 inhibitory antibodies) are administered in combination with one or more agents or treatment modalities appropriate for the underlying bone or soft-tissue disease or disorder.

In some embodiments, the bone or soft-tissue disease or disorder caused or exacerbated by fibrosis and/or inflammation is selected from the group consisting of: osteoporosis and/or osteopenia associated with, for example, cystic fibrosis, myelodysplastic conditions with increased bone fibrosis, adhesive capsulitis, Dupuytren's contracture and myelofibrosis.

Joint Diseases and Conditions

In certain embodiments, the disclosure provides a method of preventing, treating, reverting, inhibiting and/or reducing fibrosis and/or inflammation in a subject suffering from a joint disease or disorder caused or exacerbated by fibrosis and/or inflammation comprising administering a MASP-2 inhibitory agent, such as a MASP-2 inhibitory antibody, to a subject in need thereof. This method includes administering a composition comprising an amount of a MASP-2 inhibitor effective to inhibit fibrosis and/or inflammation.

The MASP-2 inhibitory composition may be administered locally to the region of fibrosis, such as by local application of the composition to the joint, or local application during surgery or local injection, either directly or remotely, for example, by catheter. Alternately, the MASP-2 inhibitory agent may be administered to the subject systemically, such as by intra-arterial, intravenous, intramuscular, inhalational, nasal, subcutaneous or other parenteral administration, by topical administration, or potentially by oral administration for non-peptidergic agents. Administration may be repeated as determined by a physician until the condition has been resolved or is controlled.

In certain embodiments, the MASP-2 inhibitory agents (e.g., MASP-2 inhibitory antibodies) are administered in combination with one or more agents or treatment modalities appropriate for the underlying joint disease or disorder.

In some embodiments, the joint disease or disorder caused or exacerbated by fibrosis and/or inflammation is arthrofibrosis.

Digestive Diseases and Conditions

In certain embodiments, the disclosure provides a method of preventing, treating, reverting, inhibiting and/or reducing fibrosis and/or inflammation in a subject suffering from a digestive disease or disorder caused or exacerbated by fibrosis and/or inflammation comprising administering a MASP-2 inhibitory agent, such as a MASP-2 inhibitory antibody, to a subject in need thereof. This method includes administering a composition comprising an amount of a MASP-2 inhibitor effective to inhibit fibrosis and/or inflammation.

The MASP-2 inhibitory composition may be administered locally to the region of fibrosis, such as by local application during surgery or local injection, either directly or remotely, for example, by catheter. Alternately, the MASP-2 inhibitory agent may be administered to the subject systemically, such as by intra-arterial, intravenous, intramuscular, inhalational, nasal, subcutaneous or other parenteral administration, by topical administration, or potentially by oral administration for non-peptidergic agents. Administration may be repeated as determined by a physician until the condition has been resolved or is controlled.

In certain embodiments, the MASP-2 inhibitory agents (e.g., MASP-2 inhibitory antibodies) are administered in combination with one or more agents or treatment modalities appropriate for the underlying digestive disease or disorder.

In some embodiments, the digestive disease or disorder caused or exacerbated by fibrosis and/or inflammation is selected from the group consisting of: Crohn's disease, ulcerative colitis and pancreatic fibrosis.

Ocular Diseases and Conditions

In certain embodiments, the disclosure provides a method of preventing, treating, reverting, inhibiting and/or reducing fibrosis and/or inflammation in a subject suffering from an ocular disease or disorder caused or exacerbated by fibrosis and/or inflammation comprising administering a MASP-2 inhibitory agent, such as a MASP-2 inhibitory antibody, to a subject in need thereof. This method includes administering a composition comprising an amount of a MASP-2 inhibitor effective to inhibit fibrosis and/or inflammation.

The MASP-2 inhibitory composition may be administered locally to the region of fibrosis, such as by local application during surgery or local injection, either directly or remotely, for example, by catheter. Alternately, the MASP-2 inhibitory agent may be administered to the subject systemically, such as by intra-arterial, intravenous, intramuscular, inhalational, nasal, subcutaneous or other parenteral administration, by topical administration to the eye (e.g., as eye drops), or potentially by oral administration for non-peptidergic agents. Administration may be repeated as determined by a physician until the condition has been resolved or is controlled.

In certain embodiments, the MASP-2 inhibitory agents (e.g., MASP-2 inhibitory antibodies) are administered in combination with one or more agents or treatment modalities appropriate for the underlying ocular disease or disorder.

In some embodiments, the ocular disease or disorder caused or exacerbated by fibrosis and/or inflammation is selected from the group consisting of: anterior subcapsular cataract, posterior capsule opacification, macular degeneration, and retinal and vitreal retinopathy.

Diseases and Conditions of the Reproductive Organs

In certain embodiments, the disclosure provides a method of preventing, treating, reverting, inhibiting and/or reducing fibrosis and/or inflammation in a subject suffering from a reproductive disease or disorder caused or exacerbated by fibrosis and/or inflammation comprising administering a MASP-2 inhibitory agent, such as a MASP-2 inhibitory antibody, to a subject in need thereof. This method includes administering a composition comprising an amount of a MASP-2 inhibitor effective to inhibit fibrosis and/or inflammation.

The MASP-2 inhibitory composition may be administered locally to the region of fibrosis, such as by local application during surgery or local injection, either directly or remotely, for example, by catheter. Alternately, the MASP-2 inhibitory agent may be administered to the subject systemically, such as by intra-arterial, intravenous, intramuscular, inhalational, nasal, subcutaneous or other parenteral administration, by topical administration, or potentially by oral administration for non-peptidergic agents. Administration may be repeated as determined by a physician until the condition has been resolved or is controlled.

In certain embodiments, the MASP-2 inhibitory agents (e.g., MASP-2 inhibitory antibodies) are administered in combination with one or more agents or treatment modalities appropriate for the underlying reproductive disease or disorder.

In some embodiments, the reproductive disease or disorder caused or exacerbated by fibrosis and/or inflammation is selected from the group consisting of: endometriosis and Peyronie's disease.

Scarring Associated with Trauma

In certain embodiments, the disclosure provides a method of preventing, treating, reverting, inhibiting and/or reducing fibrosis and/or inflammation in a subject suffering from a disease or condition resulting from scarring associated with trauma comprising administering a MASP-2 inhibitory agent, such as a MASP-2 inhibitory antibody, to a subject in need thereof. This method includes administering a composition comprising an amount of a MASP-2 inhibitor effective to inhibit fibrosis and/or inflammation.

The MASP-2 inhibitory composition may be administered locally to the region of fibrosis, such as by local application during surgery or local injection, either directly or remotely, for example, by catheter. Alternately, the MASP-2 inhibitory agent may be administered to the subject systemically, such as by intra-arterial, intravenous, intramuscular, inhalational, nasal, subcutaneous or other parenteral administration, by topical administration, or potentially by oral administration for non-peptidergic agents.

Administration may be repeated as determined by a physician until the condition has been resolved or is controlled.

In certain embodiments, the MASP-2 inhibitory agents (e.g., MASP-2 inhibitory antibodies) are administered in combination with one or more agents or treatment modalities appropriate for the underlying disease or disorder.

In some embodiments, the scarring associated with trauma is selected from the group consisting of: surgical complications (e.g., surgical adhesions wherein scar tissue can form between internal organs causing contracture, pain and can cause infertility), chemotherapeutic drug-induced fibrosis, radiation-induced fibrosis and scarring associated with burns.

Additional Diseases and Disorders Caused or Exacerbated by Fibrosis and/or Inflammation In certain embodiments, the disclosure provides a method of preventing, treating, reverting, inhibiting and/or reducing fibrosis and/or inflammation in a subject suffering from a disease or disorder caused or exacerbated by fibrosis and/or inflammation selected from the group consisting of organ transplant, breast fibrosis, muscle fibrosis, retroperitoneal fibrosis, thyroid fibrosis, lymph node fibrosis, bladder fibrosis and pleural fibrosis, comprising administering a MASP-2 inhibitory agent, such as a MASP-2 inhibitory antibody, to a subject in need thereof. This method includes administering a composition comprising an amount of a MASP-2 inhibitor effective to inhibit fibrosis and/or inflammation.

The MASP-2 inhibitory composition may be administered locally to the region of fibrosis, such as by local application during surgery or local injection, either directly or remotely, for example, by catheter. Alternately, the MASP-2 inhibitory agent may be administered to the subject systemically, such as by intra-arterial, intravenous, intramuscular, inhalational, nasal, subcutaneous or other parenteral administration, by topical administration to the eye (e.g., as eye drops), or potentially by oral administration for non-peptidergic agents. Administration may be repeated as determined by a physician until the condition has been resolved or is controlled.

In certain embodiments, the MASP-2 inhibitory agents (e.g., MASP-2 inhibitory antibodies) are administered in combination with one or more agents or treatment modalities appropriate for the underlying disease or disorder.

In certain embodiments of any of the various methods and pharmaceutical compositions described herein, the MASP-2 inhibitory antibody selectively blocks the lectin pathway while leaving intact the classical pathway.

IV. MASP-2 Inhibitory Agents

In various aspects, the present invention provides methods of inhibiting the adverse effects of fibrosis and/or inflammation comprising administering a MASP-2 inhibitory agent to a subject in need thereof. MASP-2 inhibitory agents are administered in an amount effective to inhibit MASP-2-dependent complement activation in a living subject. In the practice of this aspect of the invention, representative MASP-2 inhibitory agents include: molecules that inhibit the biological activity of MASP-2 (such as small molecule inhibitors, anti-MASP-2 antibodies (e.g., MASP-2 inhibitory antibodies) or blocking peptides which interact with MASP-2 or interfere with a protein-protein interaction), and molecules that decrease the expression of MASP-2 (such as MASP-2 antisense nucleic acid molecules, MASP-2 specific RNAi molecules and MASP-2 ribozymes), thereby preventing MASP-2 from activating the lectin complement pathway. The MASP-2 inhibitory agents can be used alone as a primary therapy or in combination with other therapeutics as an adjuvant therapy to enhance the therapeutic benefits of other medical treatments.

The inhibition of MASP-2-dependent complement activation is characterized by at least one of the following changes in a component of the complement system that occurs as a result of administration of a MASP-2 inhibitory agent in accordance with the methods of the invention: the inhibition of the generation or production of MASP-2-dependent complement activation system products C4b, C3a, C5a and/or C5b-9 (MAC) (measured, for example, as described in Example 2), the reduction of C4 cleavage and C4b deposition (measured, for example as described in Example 2), or the reduction of C3 cleavage and C3b deposition (measured, for example, as described in Example 2).

According to the present invention, MASP-2 inhibitory agents are utilized that are effective in inhibiting fibrosis and/or inflammation, and exhibit a detectable antifibrotic activity and/or induce a decrease of fibrosis. Within the context of the invention, an anti-fibrotic activity may comprise at least one or more of the following: (1) reduction in inflammation, for example, as assessed by activation and recruitment of macrophages and endothelial cells; recruitment and activation of lymphocytes and/or eosinophils via secretion of a number of cytokines/chemokines; release of cytotoxic mediators and fibrogenic cytokines; (2) reduction of cell proliferation, ECM synthesis or angiogenesis, and/or (3) reduction in collagen deposition, as compared to the fibrotic activity in the absence of the MASP-2 inhibitory agent.

Assessment of an antifibrotic agent, such as a MASP-2 inhibitory agent, may be detected using any technique known to the skilled person. For example, assessment of an antifibrotic agent may be assessed in a UUO model (as described in Examples 12 and 14 herein). If a detectable antifibrotic activity and/or a reduction or decrease of fibrosis is assessed using a MASP-2 inhibitory agent, such MASP-2 inhibitory agent is said to be used as a medicament for preventing, treating, reverting, and/or inhibiting fibrosis.

The assessment of fibrosis may be carried out periodically, e.g., each week, or each month. The increase/decrease of fibrosis and/or presence of an antifibrotic activity may therefore be assessed periodically, e.g. each week, or month. This assessment is preferably carried out at several time points for a given subject or at one or several time points for a given subject and a healthy control. The assessment may be carried out at regular time intervals, e.g. each week, or each month. The assessment may therefore be assessed regularly, e.g. each week, or each month. When one assessment has led to the finding of a decrease of fibrosis or to the presence of an antifibrotic activity, a MASP-2 inhibitory agent, such as a MASP-2 inhibitory antibody, is said is exhibit a detectable antifibrotic activity and/or inducing a reduction or decrease of fibrosis.

MASP-2 inhibitory agents useful in the practice of this aspect of the invention include, for example, MASP-2 antibodies and fragments thereof, MASP-2 inhibitory peptides, small molecules, MASP-2 soluble receptors and expression inhibitors. MASP-2 inhibitory agents may inhibit the MASP-2-dependent complement activation system by blocking the biological function of MASP-2. For example, an inhibitory agent may effectively block MASP-2 protein-to-protein interactions, interfere with MASP-2 dimerization or assembly, block $Ca^{2+}$ binding, interfere with the MASP-2 serine protease active site, or may reduce MASP-2 protein expression.

In some embodiments, the MASP-2 inhibitory agents selectively inhibit MASP-2 complement activation, leaving the C1q-dependent complement activation system functionally intact.

In one embodiment, a MASP-2 inhibitory agent useful in the methods of the invention is a specific MASP-2 inhibitory agent that specifically binds to a polypeptide comprising SEQ ID NO:6 with an affinity of at least ten times greater than to other antigens in the complement system. In another embodiment, a MASP-2 inhibitory agent specifically binds to a polypeptide comprising SEQ ID NO:6 with a binding affinity of at least 100 times greater than to other antigens in the complement system. In one embodiment, the MASP-2 inhibitory agent specifically binds to at least one of (i) the CCP1-CCP2 domain (aa 300-431 of SEQ ID NO:6) or the serine protease domain of MASP-2 (aa 445-682 of SEQ ID NO:6) and inhibits MASP-2-dependent complement activation. In one embodiment, the MASP-2 inhibitory agent is a MASP-2 monoclonal antibody, or fragment thereof that specifically binds to MASP-2. The binding affinity of the MASP-2 inhibitory agent can be determined using a suitable binding assay.

The MASP-2 polypeptide exhibits a molecular structure similar to MASP-1, MASP-3, and C1r and C1s, the proteases of the C1 complement system. The cDNA molecule set forth in SEQ ID NO:4 encodes a representative example of MASP-2 (consisting of the amino acid sequence set forth in SEQ ID NO:5) and provides the human MASP-2 polypeptide with a leader sequence (aa 1-15) that is cleaved after secretion, resulting in the mature form of human MASP-2 (SEQ ID NO:6). As shown in FIG. 2, the human MASP 2 gene encompasses twelve exons. The human MASP-2 cDNA is encoded by exons B, C, D, F, G, H, L J, K AND L. An alternative splice results in a 20 kDa protein termed MBL-associated protein 19 ("MAp19", also referred to as "sMAP") (SEQ ID NO:2), encoded by (SEQ ID NO: 1) arising from exons B, C, D and E as shown in FIG. 2. The cDNA molecule set forth in SEQ ID NO:50 encodes the murine MASP-2 (consisting of the amino acid sequence set forth in SEQ ID NO:51) and provides the murine MASP-2 polypeptide with a leader sequence that is cleaved after secretion, resulting in the mature form of murine MASP-2 (SEQ ID NO:52). The cDNA molecule set forth in SEQ ID NO:53 encodes the rat MASP-2 (consisting of the amino acid sequence set forth in SEQ ID NO:54) and provides the rat MASP-2 polypeptide with a leader sequence that is cleaved after secretion, resulting in the mature form of rat MASP-2 (SEQ ID NO:55).

Those skilled in the art will recognize that the sequences disclosed in SEQ ID NO:4, SEQ ID NO:50 and SEQ ID NO:53 represent single alleles of human, murine and rat MASP-2 respectively, and that allelic variation and alternative splicing are expected to occur. Allelic variants of the nucleotide sequences shown in SEQ ID NO:4, SEQ ID NO:50 and SEQ ID NO:53, including those containing silent mutations and those in which mutations result in amino acid sequence changes, are within the scope of the present invention. Allelic variants of the MASP-2 sequence can be cloned by probing cDNA or genomic libraries from different individuals according to standard procedures.

Figure 2A:
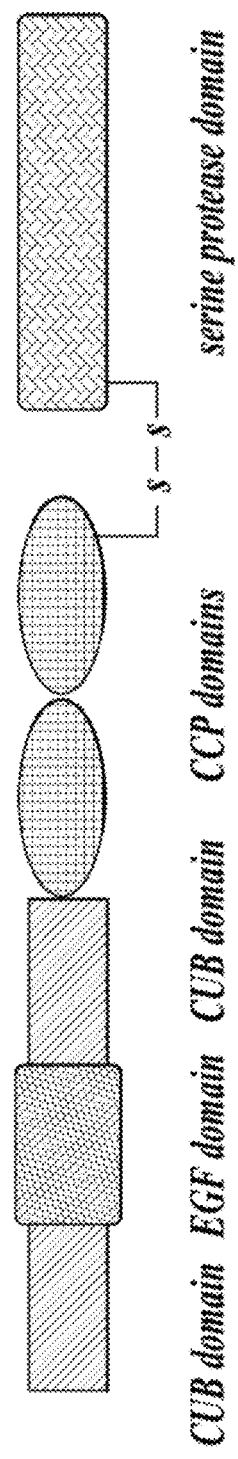
FIG. 2A is a schematic diagram illustrating the domain structure of human MASP-2 protein.
Figure 2B:
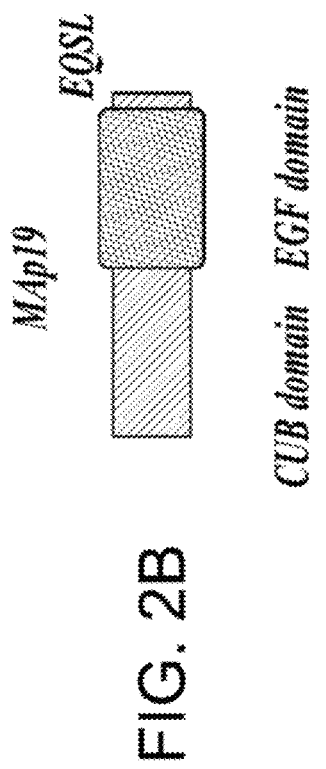
FIG. 2B is a schematic diagram illustrating the domain structure of human MAp19 protein.

The domains of the human MASP-2 protein (SEQ ID NO:6) are shown in FIGS. 1 and 2A and include an N-terminal C1r/C1s/sea urchin Vegf/bone morphogenic protein (CUBI) domain (aa 1-121 of SEQ ID NO:6), an epidermal growth factor-like domain (aa 122-166), a second CUBI domain (aa 167-293), as well as a tandem of complement control protein domains and a serine protease domain.

Alternative splicing of the AMASP 2 gene results in MAp19 shown in FIG. 1. MAp19 is a nonenzymatic protein containing the N-terminal CUBI-EGF region of MASP-2 with four additional residues (EQSL) derived from exon E as shown in FIG. 1.

Several proteins have been shown to bind to, or interact with MASP-2 through protein-to-protein interactions. For example, MASP-2 is known to bind to, and form $Ca^{2+}$ dependent complexes with, the lectin proteins MBL, H-ficolin and L-ficolin. Each MASP-2/lectin complex has been shown to activate complement through the MASP-2-dependent cleavage of proteins C4 and C2 (Ikeda, K., et al., *J. Biol. Chem.* 262:7451-7454, 1987; Matsushita, M., et al., *J. Exp. Med.* 176:1497-2284, 2000; Matsushita, M., et al., *J. Immunol.* 168:3502-3506, 2002). Studies have shown that the CUBI-EGF domains of MASP-2 are essential for the association of MASP-2 with MBL (Thielens, N. M., et al., *J. Immunol.* 166:5068, 2001). It has also been shown that the CUBIEGFCUBII domains mediate dimerization of MASP-2, which is required for formation of an active MBL complex (Wallis, R., et al., *J. Biol. Chem.* 275:30962-30969, 2000). Therefore, MASP-2 inhibitory agents can be identified that bind to or interfere with MASP-2 target regions known to be important for MASP-2-dependent complement activation.

Anti-MASP-2 Antibodies

In some embodiments of this aspect of the invention, the MASP-2 inhibitory agent comprises an anti-MASP-2 antibody that inhibits the MASP-2-dependent complement activation system. The anti-MASP-2 antibodies useful in this aspect of the invention include polyclonal, monoclonal or recombinant antibodies derived from any antibody producing mammal and may be multispecific, chimeric, humanized, anti-idiotype, and antibody fragments. Antibody fragments include Fab, Fab', F(ab)$_2$, F(ab')$_2$, Fv fragments, scFv fragments and single-chain antibodies as further described herein.

MASP-2 antibodies can be screened for the ability to inhibit MASP-2-dependent complement activation system and for antifibrotic activity and/or the ability to inhibit renal damage associated with proteinuria or Adriamycin-induced nephropathy using the assays described herein. Several MASP-2 antibodies have been described in the literature and some have been newly generated, some of which are listed below in TABLE 1. For example, as described in Examples 10 and 11 herein, anti-MASP-2 Fab2 antibodies have been identified that block MASP-2-dependent complement activation. As described in Example 12, and also described in WO2012/151481, which is hereby incorporated herein by reference, fully human MASP-2 scFv antibodies (e.g., OMS646) have been identified that block MASP-2-dependent complement activation. As described in Example 13, and also described in WO2014/144542, which is hereby incorporated herein by reference, SGMI-2 peptide-bearing MASP-2 antibodies and fragments thereof with MASP-2 inhibitory activity were generated by fusing the SGMI-2 peptide amino acid sequence (SEQ ID NO:72, 73 or 74) onto the amino or carboxy termini of the heavy and/or light chains of a human MASP-2 antibody (e.g., OMS646-SGMI-2).

Accordingly, in one embodiment, the MASP-2 inhibitory agent for use in the methods of the invention comprises a human antibody such as, for example OMS646. Accordingly, in one embodiment, a MASP-2 inhibitory agent for use in the compositions and methods of the claimed invention comprises a human antibody that binds a polypeptide consisting of human MASP-2 (SEQ ID NO:6), wherein the antibody comprises: (I) (a) a heavy-chain variable region comprising: i) a heavy-chain CDR-H1 comprising the amino acid sequence from 31-35 of SEQ ID NO:67; and ii) a heavy-chain CDR-H2 comprising the amino acid sequence from 50-65 of SEQ ID NO:67; and iii) a heavy-chain CDR-H3 comprising the amino acid sequence from 95-107 of SEQ ID NO:67 and b) a light-chain variable region comprising: i) a light-chain CDR-L1 comprising the amino acid sequence from 24-34 of SEQ ID NO:69; and ii) a light-chain CDR-L2 comprising the amino acid sequence from 50-56 of SEQ ID NO:69; and iii) a light-chain CDR-L3 comprising the amino acid sequence from 89-97 of SEQ ID NO:69 or (II) a variant thereof comprising a heavy-chain variable region with at least 90% identity to SEQ ID NO:67 (e.g., at least 91%, at least 92%, at least 93%, at least 94%, at least 95%, at least 96%, at least 97%, at least 98%, at least 99% identity to SEQ ID NO:67) and a light-chain variable region with at least 90% identity (e.g., at least 91%, at least 92%, at least 93%, at least 94%, at least 95%, at least 96%, at least 97%, at least 98%, at least 99% identity to SEQ ID NO:69.

In some embodiments, the method comprises administering to the subject a composition comprising an amount of a MASP-2 inhibitory antibody, or antigen binding fragment thereof, comprising a heavy-chain variable region comprising the amino acid sequence set forth as SEQ ID NO:67 and a light-chain variable region comprising the amino acid sequence set forth as SEQ ID NO:69.

In some embodiments, the method comprises administering to the subject a composition comprising a MASP-2 inhibitory antibody, or antigen binding fragment thereof, that specifically recognizes at least part of an epitope on human MASP-2 recognized by reference antibody OMS646 comprising a heavy-chain variable region as set forth in SEQ ID NO:67 and a light-chain variable region as set forth in SEQ ID NO:69. In one embodiment, the MASP-2 inhibitory agent for use in the methods of the invention comprises the human antibody OMS646.

TABLE 1

| EXEMPLARY MASP-2 SPECIFIC ANTIBODIES | | |
|---|---|---|
| ANTIGEN | ANTIBODY TYPE | REFERENCE |
| Recombinant MASP-2 | Rat Polyclonal | Peterson, S. V., et al., *Mol. Immunol.* 37: 803-811, 2000 |
| Recombinant human | Rat MoAb | Moller-Kristensen, M., et al., *J. of* |

TABLE 1-continued

EXEMPLARY MASP-2 SPECIFIC ANTIBODIES

| ANTIGEN | ANTIBODY TYPE | REFERENCE |
|---|---|---|
| CCP1/2-SP fragment (MoAb 8B5) | (subclass IgG1) | *Immunol. Methods* 282: 159-167, 2003 |
| Recombinant human MAp19 (MoAb 6G12) (cross reacts with MASP-2) | Rat MoAb (subclass IgG1) | Moller-Kristensen, M., et al., *J. of Immunol. Methods* 282: 159-167, 2003 |
| hMASP-2 | Mouse MoAb (S/P) Mouse MoAb (N-term) | Peterson, S. V., et al., *Mol. Immunol.* 35: 409, April 1998 |
| hMASP-2 (CCP1-CCP2-SP domain | rat MoAb: Nimoab101, produced by hybridoma cell line 03050904 (ECACC) | WO 2004/106384 |
| hMASP-2 (full length-his tagged) | murine MoAbs: NimoAb104, produced by hybridoma cell line M0545YM035 (DSMZ) NimoAb108, produced by hybridoma cell line M0545YM029 (DSMZ) NimoAb109 produced by hybridoma cell line M0545YM046 (DSMZ) NimoAb110 produced by hybridoma cell line M0545YM048 (DSMZ) | WO 2004/106384 |
| Rat MASP-2 (full-length) | MASP-2 Fab2 antibody fragments | Example 10 |
| hMASP-2 (full-length) | Fully human scFv clones | Example 12 and WO2012/151481 |
| hMASP-2 (full-length) | SGMI-2 peptide bearing MASP-2 antibodies | Example 13 and WO2014/144542 |

Anti-MASP-2 Antibodies with Reduced Effector Function

In some embodiments of this aspect of the invention, the anti-MASP-2 antibodies have reduced effector function in order to reduce inflammation that may arise from the activation of the classical complement pathway. The ability of IgG molecules to trigger the classical complement pathway has been shown to reside within the Fc portion of the molecule (Duncan, A. R., et al., *Nature* 332:738-740 1988). IgG molecules in which the Fc portion of the molecule has been removed by enzymatic cleavage are devoid of this effector function (see Harlow, *Antibodies: A Laboratory Manual*, Cold Spring Harbor Laboratory, New York, 1988). Accordingly, antibodies with reduced effector function can be generated as the result of lacking the Fc portion of the molecule by having a genetically engineered Fc sequence that minimizes effector function, or being of either the human $IgG_2$ or $IgG_4$ isotype.

Antibodies with reduced effector function can be produced by standard molecular biological manipulation of the Fc portion of the IgG heavy chains as described herein and also described in Jolliffe et al., *Int'l Rev. Immunol.* 10:241-250, 1993, and Rodrigues et al., *J. Immunol.* 151:6954-6961, 1998. Antibodies with reduced effector function also include human IgG2 and IgG4 isotypes that have a reduced ability to activate complement and/or interact with Fc receptors (Ravetch, J. V., et al., *Anmi. Rev. Immunol.* 9:457-492, 1991; Isaacs, J. D., et al., *J. Immunol.* 148:3062-3071, 1992; van de Winkel, J. G., et al., *Immunol. Today* 14:215-221, 1993). Humanized or fully human antibodies specific to human MASP-2 comprised of IgG2 or IgG4 isotypes can be produced by one of several methods known to one of ordinary skilled in the art, as described in Vaughan, T. J., et al., *Nature Biotechnical* 16:535-539, 1998.

Production of Anti-MASP-2 Antibodies

Anti-MASP-2 antibodies can be produced using MASP-2 polypeptides (e.g., full length MASP-2) or using antigenic MASP-2 epitope-bearing peptides (e.g., a portion of the MASP-2 polypeptide). Immunogenic peptides may be as small as five amino acid residues. For example, the MASP-2 polypeptide including the entire amino acid sequence of SEQ ID NO:6 may be used to induce anti-MASP-2 antibodies useful in the method of the invention. Particular MASP-2 domains known to be involved in protein-protein interactions, such as the CUBI, and CUBIEGF domains, as well as the region encompassing the serine-protease active site, may be expressed as recombinant polypeptides as described in Example 3 and used as antigens. In addition, peptides comprising a portion of at least 6 amino acids of the MASP-2 polypeptide (SEQ ID NO:6) are also useful to induce MASP-2 antibodies. Additional examples of MASP-2 derived antigens useful to induce MASP-2 antibodies are provided below in TABLE 2. The MASP-2 peptides and polypeptides used to raise antibodies may be isolated as natural polypeptides, or recombinant or synthetic peptides and catalytically inactive recombinant polypeptides, such as MASP-2A, as further described herein. In some embodiments of this aspect of the invention, anti-MASP-2 antibodies are obtained using a transgenic mouse strain as described herein.

Antigens useful for producing anti-MASP-2 antibodies also include fusion polypeptides, such as fusions of MASP-2 or a portion thereof with an immunoglobulin polypeptide or with maltose-binding protein. The polypeptide immunogen may be a full-length molecule or a portion thereof. If the polypeptide portion is hapten-like, such portion may be advantageously joined or linked to a macromolecular carrier (such as keyhole limpet hemocyanin (KLH), bovine serum albumin (BSA) or tetanus toxoid) for immunization.

TABLE 2

MASP-2 DERIVED ANTIGENS

| SEQ ID NO: | Amino Acid Sequence | |
|---|---|---|
| SEQ ID NO: 6 | | Human MASP-2 protein |
| SEQ ID NO: 51 | | Murine MASP-2 protein |
| SEQ ID NO: 8 | | CUBI domain of human MASP-2 (aa 1-121 of SEQ ID NO: 6) |
| SEQ ID NO: 9 | | CUBIEGF domains of human MASP-2 (aa 1-166 of SEQ ID NO: 6) |
| SEQ ID NO: 10 | | CUBIEGFCUBII domains of human MASP-2 (aa 1-293 of SEQ ID NO: 6) |
| SEQ ID NO: 11 | | EGF domain of human MASP-2 aa 122-166 of SEQ ID NO: 6) |
| SEQ ID NO: 12 | | Serine-Protease domain of human MASP-2 (aa 429-671 of SEQ ID NO: 6) |
| SEQ ID NO: 13 | GKDSCRGDAGG-ALVFL | Serine-Protease inactivated mutant form (aa 610-625 of SEQ ID NO: 6 with mutated Ser 618) |
| SEQ ID NO: 14 | TPLGPKWPEPV-FGRL | Human CUBI peptide |
| SEQ ID NO: 15 | TAPPGYRLRLY-FTHFDLELSHL-CEYDFVKLSSG-AKVLATLCGQ | Human CUBI peptide |
| SEQ ID NO: 16 | TFRSDYSN | MBL binding region in human CUBI domain |
| SEQ ID NO: 17 | FYSLGSSLDIT-FRSDYSNEKPF-TGF | MBL binding region in human CUBI domain |
| SEQ ID NO: 18 | IDECQVAPG | EGF peptide |
| SEQ ID NO: 19 | ANMLCAGLESG-GKDSCRGDSGG-ALV | Peptide from serine-protease active site |

Polyclonal Antibodies

Polyclonal antibodies against MASP-2 can be prepared by immunizing an animal with MASP-2 polypeptide or an immunogenic portion thereof using methods well known to those of ordinary skill in the art. See, for example, Green et al., "Production of Polyclonal Antisera," in *Immunochemical Protocols* (Manson, ed.), page 105. The immunogenicity of a MASP-2 polypeptide can be increased through the use of an adjuvant, including mineral gels, such as aluminum hydroxide or Freund's adjuvant (complete or incomplete), surface active substances such as lysolecithin, pluronic polyols, polyanions, oil emulsions, keyhole limpet hemocyanin and dinitrophenol. Polyclonal antibodies are typically raised in animals such as horses, cows, dogs, chicken, rats, mice, rabbits, guinea pigs, goats, or sheep. Alternatively, an anti-MASP-2 antibody useful in the present invention may also be derived from a subhuman primate. General techniques for raising diagnostically and therapeutically useful antibodies in baboons may be found, for example, in Goldenberg et al., International Patent Publication No. WO 91/11465, and in Losman, M. J., et al., *Int. J. Cancer* 46:310, 1990. Sera containing immunologically active antibodies are then produced from the blood of such immunized animals using standard procedures well known in the art.

Monoclonal Antibodies

In some embodiments, the MASP-2 inhibitory agent is an anti-MASP-2 monoclonal antibody. Anti-MASP-2 monoclonal antibodies are highly specific, being directed against a single MASP-2 epitope. As used herein, the modifier "monoclonal" indicates the character of the antibody as being obtained from a substantially homogenous population of antibodies, and is not to be construed as requiring production of the antibody by any particular method. Monoclonal antibodies can be obtained using any technique that provides for the production of antibody molecules by continuous cell lines in culture, such as the hybridoma method described by Kohler, G., et al., *Nature* 256:495, 1975, or they may be made by recombinant DNA methods (see, e.g., U.S. Pat. No. 4,816,567 to Cabilly). Monoclonal antibodies may also be isolated from phage antibody libraries using the techniques described in Clackson, T., et al., *Nature* 352:624-628, 1991, and Marks, J. D., et al., *J. Mol. Biol.* 222:581-597, 1991. Such antibodies can be of any immunoglobulin class including IgG, IgM, IgE, IgA, IgD and any subclass thereof.

For example, monoclonal antibodies can be obtained by injecting a suitable mammal (e.g., a BALB/c mouse) with a composition comprising a MASP-2 polypeptide or portion thereof. After a predetermined period of time, splenocytes are removed from the mouse and suspended in a cell culture medium. The splenocytes are then fused with an immortal cell line to form a hybridoma. The formed hybridomas are grown in cell culture and screened for their ability to produce a monoclonal antibody against MASP-2. Examples further describing the production of anti-MASP-2 monoclonal antibodies are provided herein (see also *Current Protocols in Immunology*, Vol. 1., John Wiley & Sons, pages 2.5.1-2.6.7, 1991.)

Human monoclonal antibodies may be obtained through the use of transgenic mice that have been engineered to produce specific human antibodies in response to antigenic challenge. In this technique, elements of the human immunoglobulin heavy and light chain locus are introduced into strains of mice derived from embryonic stem cell lines that contain targeted disruptions of the endogenous immunoglobulin heavy chain and light chain loci. The transgenic mice can synthesize human antibodies specific for human antigens, such as the MASP-2 antigens described herein, and the mice can be used to produce human MASP-2 antibody-secreting hybridomas by fusing B-cells from such animals to suitable myeloma cell lines using conventional Kohler-Milstein technology as further described herein. Transgenic mice with a human immunoglobulin genome are commercially available (e.g., from Abgenix, Inc., Fremont, Calif., and Medarex, Inc., Annandale, N.J.). Methods for obtaining human antibodies from transgenic mice are described, for example, by Green, L. L., et al., *Nature Genet.* 7:13, 1994; Lonberg, N., et al., *Nature* 368:856, 1994; and Taylor, L. D., et al., *Int. Immun.* 6:579, 1994.

Monoclonal antibodies can be isolated and purified from hybridoma cultures by a variety of well-established techniques. Such isolation techniques include affinity chromatography with Protein-A Sepharose, size-exclusion chromatography, and ion-exchange chromatography (see, for example, Coligan at pages 2.7.1-2.7.12 and pages 2.9.1-2.9.3; Baines et al., "Purification of Immunoglobulin G (IgG)," in *Methods in Molecular Biology*, The Humana Press, Inc., Vol. 10, pages 79-104, 1992).

Once produced, polyclonal, monoclonal or phage-derived antibodies are first tested for specific MASP-2 binding. A variety of assays known to those skilled in the art may be utilized to detect antibodies which specifically bind to MASP-2. Exemplary assays include Western blot or immunoprecipitation analysis by standard methods (e.g., as described in Ausubel et al.), immunoelectrophoresis, enzyme-linked immuno-sorbent assays, dot blots, inhibition or competition assays and sandwich assays (as described in Harlow and Land, *Antibodies: A Laboratory Manual*, Cold Spring Harbor Laboratory Press, 1988). Once antibodies are identified that specifically bind to MASP-2, the anti-MASP-2 antibodies are tested for the ability to function as a MASP-2 inhibitory agent in one of several assays such as, for example, a lectin-specific C4 cleavage assay (described in Example 2), a C3b deposition assay (described in Example 2) or a C4b deposition assay (described in Example 2).

The affinity of anti-MASP-2 monoclonal antibodies can be readily determined by one of ordinary skill in the art (see, e.g., Scatchard, A., *NY Acad. Sci.* 51:660-672, 1949). In one embodiment, the anti-MASP-2 monoclonal antibodies useful for the methods of the invention bind to MASP-2 with a binding affinity of <100 nM, preferably <10 nM and most preferably <2 nM.

Chimeric/Humanized Antibodies

Monoclonal antibodies useful in the method of the invention include chimeric antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies (U.S. Pat. No. 4,816,567, to Cabilly; and Morrison, S. L., et al., *Proc. Natl Acad. Sci. USA* 81:6851-6855, 1984).

One form of a chimeric antibody useful in the invention is a humanized monoclonal anti-MASP-2 antibody. Humanized forms of non-human (e.g., murine) antibodies are chimeric antibodies, which contain minimal sequence derived from non-human immunoglobulin. Humanized monoclonal antibodies are produced by transferring the non-human (e.g., mouse) complementarity determining regions (CDR), from the heavy and light variable chains of the mouse immunoglobulin into a human variable domain. Typically, residues of human antibodies are then substituted in the framework regions of the non-human counterparts. Furthermore, humanized antibodies may comprise residues that are not found in the recipient antibody or in the donor antibody. These modifications are made to further refine antibody performance. In general, the humanized antibody will comprise substantially all of at least one, and typically two variable domains, in which all or substantially all of the hypervariable loops correspond to those of a non-human immunoglobulin and all or substantially all of the Fv framework regions are those of a human immunoglobulin sequence. The humanized antibody optionally also will comprise at least a portion of an immunoglobulin constant region (Fc), typically that of a human immunoglobulin. For further details, see Jones, P. T., et al., *Nature* 321:522-525, 1986; Reichmann, L., et al., *Nature* 332:323-329, 1988; and Presta, *Curr. Op. Struct. Biol.* 2:593-596, 1992.

The humanized antibodies useful in the invention include human monoclonal antibodies including at least a MASP-2 binding CDRH3 region. In addition, the Fc portions may be replaced so as to produce IgA or IgM as well as human IgG antibodies. Such humanized antibodies will have particular clinical utility because they will specifically recognize human MASP-2 but will not evoke an immune response in humans against the antibody itself. Consequently, they are better suited for in vivo administration in humans, especially when repeated or long-term administration is necessary.

An example of the generation of a humanized anti-MASP-2 antibody from a murine anti-MASP-2 monoclonal antibody is provided herein in Example 6. Techniques for producing humanized monoclonal antibodies are also described, for example, by Jones, P. T., et al., *Nature* 321:522, 1986; Carter, P., et al., *Proc. Natl. Acad. Sci. USA* 89:4285, 1992; Sandhu, J. S., *Crit. Rev. Biotech.* 12:437, 1992; Singer, I. I., et al., *J. Immun.* 150:2844, 1993; Sudhir (ed.), *Antibody Engineering Protocols*, Humana Press, Inc., 1995; Kelley, "Engineering Therapeutic Antibodies," in Protein Engineering: Principles and Practice, Cleland et al. (eds.), John Wiley & Sons, Inc., pages 399-434, 1996; and by U.S. Pat. No. 5,693,762, to Queen, 1997. In addition, there are commercial entities that will synthesize humanized antibodies from specific murine antibody regions, such as Protein Design Labs (Mountain View, Calif.).

Recombinant Antibodies

Anti-MASP-2 antibodies can also be made using recombinant methods. For example, human antibodies can be made using human immunoglobulin expression libraries (available for example, from Stratagene, Corp., La Jolla, Calif.) to produce fragments of human antibodies ($V_H$, $V_L$, Fv, Fd, Fab or $F(ab')_2$). These fragments are then used to construct whole human antibodies using techniques similar to those for producing chimeric antibodies.

Anti-Idiotype Antibodies

Once anti-MASP-2 antibodies are identified with the desired inhibitory activity, these antibodies can be used to generate anti-idiotype antibodies that resemble a portion of MASP-2 using techniques that are well known in the art. See, e.g., Greenspan, N. S., et al., *FASEB J.* 7:437, 1993. For example, antibodies that bind to MASP-2 and competitively inhibit a MASP-2 protein interaction required for complement activation can be used to generate anti-idiotypes that resemble the MBL binding site on MASP-2 protein and therefore bind and neutralize a binding ligand of MASP-2 such as, for example, MBL.

Immunoglobulin Fragments

The MASP-2 inhibitory agents useful in the method of the invention encompass not only intact immunoglobulin molecules but also the well known fragments including Fab, Fab', $F(ab)_2$, $F(ab')_2$ and Fv fragments, scFv fragments, diabodies, linear antibodies, single-chain antibody molecules and multispecific antibodies formed from antibody fragments.

It is well known in the art that only a small portion of an antibody molecule, the paratope, is involved in the binding of the antibody to its epitope (see, e.g., Clark, W. R., *The Experimental Foundations of Modern Immunology*, Wiley & Sons, Inc., NY, 1986). The pFc and Fc regions of the antibody are effectors of the classical complement pathway, but are not involved in antigen binding. An antibody from which the pFc region has been enzymatically cleaved, or which has been produced without the pFc region, is designated an $F(ab')_2$ fragment and retains both of the antigen binding sites of an intact antibody. An isolated $F(ab')_2$ fragment is referred to as a bivalent monoclonal fragment because of its two antigen binding sites. Similarly, an antibody from which the Fc region has been enzymatically cleaved, or which has been produced without the Fc region, is designated a Fab fragment, and retains one of the antigen binding sites of an intact antibody molecule.

Antibody fragments can be obtained by proteolytic hydrolysis, such as by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent to produce 3.5S Fab' monovalent fragments. Optionally, the cleavage reaction can be performed using a blocking group for the sulfhydryl groups that result from cleavage of disulfide linkages. As an alternative, an enzymatic cleavage using pepsin produces two monovalent Fab fragments and an Fc fragment directly. These methods are described, for example, U.S. Pat. No. 4,331,647 to Goldenberg; Nisonoff, A., et al., *Arch. Biochem. Biophys.* 89:230, 1960; Porter, R. R., Biochem. J. 73:119, 1959; Edelman, et al., in *Methods in Enzymwology* 1:422, Academic Press, 1967; and by Coligan at pages 2.8.1-2.8.10 and 2.10.-2.10.4.

In some embodiments, the use of antibody fragments lacking the Fc region are preferred to avoid activation of the classical complement pathway which is initiated upon binding Fc to the Fcγ receptor. There are several methods by which one can produce a MoAb that avoids Fcγ receptor interactions. For example, the Fc region of a monoclonal antibody can be removed chemically using partial digestion by proteolytic enzymes (such as ficin digestion), thereby generating, for example, antigen-binding antibody fragments such as Fab or F(ab')$_2$ fragments (Mariani, M., et al., *Mol. Immunol.* 28:69-71, 1991). Alternatively, the human γ4 IgG isotype, which does not bind Fcγ receptors, can be used during construction of a humanized antibody as described herein. Antibodies, single chain antibodies and antigen-binding domains that lack the Fc domain can also be engineered using recombinant techniques described herein.

Single-Chain Antibody Fragments

Alternatively, one can create single peptide chain binding molecules specific for MASP-2 in which the heavy and light chain Fv regions are connected. The Fv fragments may be connected by a peptide linker to form a single-chain antigen binding protein (scFv). These single-chain antigen binding proteins are prepared by constructing a structural gene comprising DNA sequences encoding the $V_H$ and $V_L$ domains which are connected by an oligonucleotide. The structural gene is inserted into an expression vector, which is subsequently introduced into a host cell, such as *E. coli*. The recombinant host cells synthesize a single polypeptide chain with a linker peptide bridging the two V domains. Methods for producing scFvs are described for example, by Whitlow, et al., *"Methods: A Companion to Methods in Enzymology"* 2:97, 1991; Bird, et al., *Science* 242:423, 1988; U.S. Pat. No. 4,946,778, to Ladner; Pack, P., et al., *Bio Technology* 11:1271, 1993.

As an illustrative example, a MASP-2 specific scFv can be obtained by exposing lymphocytes to MASP-2 polypeptide in vitro and selecting antibody display libraries in phage or similar vectors (for example, through the use of immobilized or labeled MASP-2 protein or peptide). Genes encoding polypeptides having potential MASP-2 polypeptide binding domains can be obtained by screening random peptide libraries displayed on phage or on bacteria such as *E. coli*. These random peptide display libraries can be used to screen for peptides which interact with MASP-2. Techniques for creating and screening such random peptide display libraries are well known in the art (U.S. Pat. No. 5,223,409, to Lardner; U.S. Pat. No. 4,946,778, to Ladner; U.S. Pat. No. 5,403,484, to Lardner; U.S. Pat. No. 5,571,698, to Lardner; and Kay et al., *Phage Display of Peptides and Proteins* Academic Press, Inc., 1996) and random peptide display libraries and kits for screening such libraries are available commercially, for instance from CLONTECH Laboratories, Inc. (Palo Alto, Calif.), Invitrogen Inc. (San Diego, Calif.), New England Biolabs, Inc. (Ipswich, Mass.), and Pharmacia LKB Biotechnology Inc. (Piscataway, N.J.).

Another form of an anti-MASP-2 antibody fragment useful in this aspect of the invention is a peptide coding for a single complementarity-determining region (CDR) that binds to an epitope on a MASP-2 antigen and inhibits MASP-2-dependent complement activation. CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (see, for example, Larrick et al., *Methods: A Companion to Methods in Enzymology* 2:106, 1991; Courtenay-Luck, "Genetic Manipulation of Monoclonal Antibodies," in *Monoclonal Antibodies: Production, Engineering and Clinical Application*, Ritter et al. (eds.), page 166, Cambridge University Press, 1995; and Ward et al., "Genetic Manipulation and Expression of Antibodies," in Monoclonal Antibodies: Principles and Applications, Birch et al. (eds.), page 137, Wiley-Liss, Inc., 1995).

The MASP-2 antibodies described herein are administered to a subject in need thereof to inhibit MASP-2-dependent complement activation. In some embodiments, the MASP-2 inhibitory agent is a high-affinity human or humanized monoclonal anti-MASP-2 antibody with reduced effector function.

Peptide Inhibitors

In some embodiments of this aspect of the invention, the MASP-2 inhibitory agent comprises isolated MASP-2 peptide inhibitors, including isolated natural peptide inhibitors and synthetic peptide inhibitors that inhibit the MASP-2-dependent complement activation system. As used herein, the term "isolated MASP-2 peptide inhibitors" refers to peptides that inhibit MASP-2 dependent complement activation by binding to, competing with MASP-2 for binding to another recognition molecule (e.g., MBL, H-ficolin, M-ficolin, or L-ficolin) in the lectin pathway, and/or directly interacting with MASP-2 to inhibit MASP-2-dependent complement activation that are substantially pure and are essentially free of other substances with which they may be found in nature to an extent practical and appropriate for their intended use.

Peptide inhibitors have been used successfully in vivo to interfere with protein-protein interactions and catalytic sites. For example, peptide inhibitors to adhesion molecules structurally related to LFA-1 have recently been approved for clinical use in coagulopathies (Ohman, E. M., et al., *European Heart J.* 16:50-55, 1995). Short linear peptides (<30 amino acids) have been described that prevent or interfere with integrin-dependent adhesion (Murayama, O., et al., *J Biochem.* 120:445-51, 1996). Longer peptides, ranging in length from 25 to 200 amino acid residues, have also been used successfully to block integrin-dependent adhesion (Zhang, L., et al., *J. Biol. Chem.* 271(47):29953-57, 1996). In general, longer peptide inhibitors have higher affinities and/or slower off-rates than short peptides and may therefore be more potent inhibitors. Cyclic peptide inhibitors have also been shown to be effective inhibitors of integrins in vivo for the treatment of human inflammatory disease (Jackson, D. Y., et al., *J. Med. Chem.* 40:3359-68, 1997). One method of producing cyclic peptides involves the synthesis of peptides in which the terminal amino acids of the peptide are cysteines, thereby allowing the peptide to exist in a cyclic form by disulfide bonding between the terminal amino acids, which has been shown to improve affinity and half-life in vivo for the treatment of hematopoietic neoplasms (e.g., U.S. Pat. No. 6,649,592, to Larson).

Synthetic MASP-2 Peptide Inhibitors

MASP-2 inhibitory peptides useful in the methods of this aspect of the invention are exemplified by amino acid sequences that mimic the target regions important for MASP-2 function. The inhibitory peptides useful in the practice of the methods of the invention range in size from about 5 amino acids to about 300 amino acids. TABLE 3 provides a list of exemplary inhibitory peptides that may be useful in the practice of this aspect of the present invention. A candidate MASP-2 inhibitory peptide may be tested for the ability to function as a MASP-2 inhibitory agent in one of several assays including, for example, a lectin specific C4 cleavage assay (described in Example 2), and a C3b deposition assay (described in Example 2).

In some embodiments, the MASP-2 inhibitory peptides are derived from MASP-2 polypeptides and are selected from the full length mature MASP-2 protein (SEQ ID NO:6), or from a particular domain of the MASP-2 protein such as, for example, the CUBI domain (SEQ ID NO:8), the CUBIEGF domain (SEQ ID NO:9), the EGF domain (SEQ ID NO: 11), and the serine protease domain (SEQ ID NO:12). As previously described, the CUBEGFCUBII regions have been shown to be required for dimerization and binding with MBL (Thielens et al., supra). In particular, the peptide sequence TFRSDYN (SEQ ID NO:16) in the CUBI domain of MASP-2 has been shown to be involved in binding to MBL in a study that identified a human carrying a homozygous mutation at Asp105 to Gly105, resulting in the loss of MASP-2 from the MBL complex (Stengaard-Pedersen, K., et al., *New England J. Med.* 349:554-560, 2003).

In some embodiments, MASP-2 inhibitory peptides are derived from the lectin proteins that bind to MASP-2 and are involved in the lectin complement pathway. Several different lectins have been identified that are involved in this pathway, including mannan-binding lectin (MBL), L-ficolin, M-ficolin and H-ficolin. (Ikeda, K., et al., *J. Biol. Chem.* 262:7451-7454, 1987; Matsushita, M., et al., *J. Exp. Med.* 176:1497-2284, 2000; Matsushita, M., et al., *J. Immunol.* 168:3502-3506, 2002). These lectins are present in serum as oligomers of homotrimeric subunits, each having N-terminal collagen-like fibers with carbohydrate recognition domains. These different lectins have been shown to bind to MASP-2, and the lectin/MASP-2 complex activates complement through cleavage of proteins C4 and C2. H-ficolin has an amino-terminal region of 24 amino acids, a collagen-like domain with 11 Gly-Xaa-Yaa repeats, a neck domain of 12 amino acids, and a fibrinogen-like domain of 207 amino acids (Matsushita, M., et al., *J. Immunol.* 168:3502-3506, 2002). H-ficolin binds to GlcNAc and agglutinates human erythrocytes coated with LPS derived from *S. typhimurium, S. minnesota* and *E. coli.* H-ficolin has been shown to be associated with MASP-2 and MAp19 and activates the lectin pathway. Id. L-ficolin/P35 also binds to GlcNAc and has been shown to be associated with MASP-2 and MAp19 in human serum and this complex has been shown to activate the lectin pathway (Matsushita, M., et al., *J. Immunol.* 164:2281, 2000). Accordingly, MASP-2 inhibitory peptides useful in the present invention may comprise a region of at least 5 amino acids selected from the MBL protein (SEQ ID NO:21), the H-ficolin protein (Genbank accession number NM_173452), the M-ficolin protein (Genbank accession number 000602) and the L-ficolin protein (Genbank accession number NM_015838).

More specifically, scientists have identified the MASP-2 binding site on MBL to be within the 12 Gly-X-Y triplets "GKD GRD GTK GEK GEP GQG LRG LQG POG KLG POG NOG PSG SOG PKG QKG DOG KS" (SEQ ID NO:26) that lie between the hinge and the neck in the C-terminal portion of the collagen-like domain of MBP (Wallis, R., et al., *J. Biol. Chem.* 279:14065, 2004). This MASP-2 binding site region is also highly conserved in human H-ficolin and human L-ficolin. A consensus binding site has been described that is present in all three lectin proteins comprising the amino acid sequence "OGK-X-GP" (SEQ ID NO:22) where the letter "O" represents hydroxyproline and the letter "X" is a hydrophobic residue (Wallis et al., 2004, supra). Accordingly, in some embodiments, MASP-2 inhibitory peptides useful in this aspect of the invention are at least 6 amino acids in length and comprise SEQ ID NO:22. Peptides derived from MBL that include the amino acid sequence "GLR GLQ GPO GKL GPO G" (SEQ ID NO:24) have been shown to bind MASP-2 in vitro (Wallis, et al., 2004, .supra). To enhance binding to MASP-2, peptides can be synthesized that are flanked by two GPO triplets at each end ("GPO GPO GLR GLQ GPO GKL GPO GGP OGP O" SEQ ID NO:25) to enhance the formation of triple helices as found in the native MBL protein (as further described in Wallis, R., et al., *J. Biol. Chem.* 279:14065, 2004).

MASP-2 inhibitory peptides may also be derived from human H-ficolin that include the sequence "GAO GSO GEK GAO GPQ GPO GPO GKM GPK GEO GDO" (SEQ ID NO:27) from the consensus MASP-2 binding region in H-ficolin. Also included are peptides derived from human L-ficolin that include the sequence "GCO GLO GAO GDK GEA GTN GKR GER GPO GPO GKA GPO GPN GAO GEO" (SEQ ID NO:28) from the consensus MASP-2 binding region in L-ficolin.

MASP-2 inhibitory peptides may also be derived from the C4 cleavage site such as "LQRALEILPNRVTIKANRPFLVFI" (SEQ ID NO:29) which is the C4 cleavage site linked to the C-terminal portion of antithrombin III (Glover, G. I., et al., *Mol. Immunol.* 25:1261 (1988)).

TABLE 3

EXEMPLARY MASP-2 INHIBITORY PEPTIDES

| SEQ ID NO | Source |
|---|---|
| SEQ ID NO: 6 | Human MASP-2 protein |
| SEQ ID NO: 8 | CUBI domain of MASP-2 (aa 1-121 of SEQ ID NO: 6) |
| SEQ ID NO: 9 | CUBIEGF domains of MASP-2 (aa 1-166 of SEQ ID NO: 6) |

TABLE 3-continued

EXEMPLARY MASP-2 INHIBITORY PEPTIDES

| SEQ ID NO | Source |
| --- | --- |
| SEQ ID NO: 10 | CUBIEGFCUBII domains of MASP-2 (aa 1-293 of SEQ ID NO: 6) |
| SEQ ID NO: 11 | EGF domain of MASP-2 (aa 122-166) |
| SEQ ID NO: 12 | Serine-protease domain of MASP-2 (aa 429-671) |
| SEQ ID NO: 16 | MBL binding region in MASP-2 |
| SEQ ID NO: 3 | Human MAp19 |
| SEQ ID NO: 21 | Human MBL protein |
| SEQ ID NO: 22<br>OGK-X-GP,<br>Where "O" = hydroxyproline and "X" is a hydrophobic amino acid residue | Synthetic peptide Consensus binding site from Human MBL and Human ficolins |
| SEQ ID NO: 23<br>OGKLG | Human MBL core binding site |
| SEQ ID NO: 24<br>GLR GLQ GPO GKL GPO G | Human MBP Triplets 6-10-demonstrated binding to MASP-2 |
| SEQ ID NO: 25<br>GPOGPOGLRGLQGPO GKLGPOGGPOGPO | Human MBP Triplets with GPO added to enhance formation of triple helices |
| SEQ ID NO: 26<br>GKDGRDGTKGEKGEP GQGLRGLQGPOGKLG POGNOGPSGSOGPKG QKGDOGKS | Human MBP Triplets 1-17 |
| SEQ ID NO: 27<br>GAOGSOGEKGAOGPQ GPOGPOGKMGPKGEO GDO | Human H-Ficolin (Hataka) |
| SEQ ID NO: 28<br>GCOGLOGAOGDKGE AGTNGKRGERGPOGP OGKAGPOGPINGAOGE O | Human L-Ficolin P35 |
| SEQ ID NO: 29<br>LQRAIEILPNRVTIKA NRPFLVFI | Human C4 cleavage site |
| SEQ ID NO: 72<br>LEVTCEPGTTFKDKCNT CRCGSDGKSAVCTKLW CNQ | SGMI-2L (full-length) |
| SEQ ID NO: 73<br>TCEPGTTFKDKCNTCRC GSDGKSAVCTKLWCNQ | SGMI-2M (medium truncated version) |
| SEQ ID NO: 74<br>TCRCGSDGKSAVCTKL WCNQ | SGMI-2S (short truncated version) |

Note:
The letter "O" represents hydroxyproline. The letter "X" is a hydrophobic residue.

Peptides derived from the C4 cleavage site as well as other peptides that inhibit the MASP-2 serine protease site can be chemically modified so that they are irreversible protease inhibitors. For example, appropriate modifications may include, but are not necessarily limited to, halomethyl ketones (Br, Cl, I, F) at the C-terminus, Asp or Glu, or appended to functional side chains; haloacetyl (or other α-haloacetyl) groups on amino groups or other functional side chains; epoxide or imine-containing groups on the amino or carboxy termini or on functional side chains; or imidate esters on the amino or carboxy termini or on functional side chains. Such modifications would afford the advantage of permanently inhibiting the enzyme by covalent attachment of the peptide. This could result in lower effective doses and/or the need for less frequent administration of the peptide inhibitor.

In addition to the inhibitory peptides described above, MASP-2 inhibitory peptides useful in the method of the invention include peptides containing the MASP-2-binding CDRH3 region of anti-MASP-2 MoAb obtained as described herein. The sequence of the CDR regions for use in synthesizing the peptides may be determined by methods known in the art. The heavy chain variable region is a peptide that generally ranges from 100 to 150 amino acids in length. The light chain variable region is a peptide that generally ranges from 80 to 130 amino acids in length. The CDR sequences within the heavy and light chain variable regions include only approximately 3-25 amino acid sequences that may be easily sequenced by one of ordinary skill in the art.

Those skilled in the art will recognize that substantially homologous variations of the MASP-2 inhibitory peptides described above will also exhibit MASP-2 inhibitory activity. Exemplary variations include, but are not necessarily limited to, peptides having insertions, deletions, replacements, and/or additional amino acids on the carboxy-terminus or amino-terminus portions of the subject peptides and mixtures thereof. Accordingly, those homologous peptides having MASP-2 inhibitory activity are considered to be useful in the methods of this invention. The peptides described may also include duplicating motifs and other modifications with conservative substitutions. Conservative variants are described elsewhere herein, and include the exchange of an amino acid for another of like charge, size or hydrophobicity and the like.

MASP-2 inhibitory peptides may be modified to increase solubility and/or to maximize the positive or negative charge in order to more closely resemble the segment in the intact protein. The derivative may or may not have the exact primary amino acid structure of a peptide disclosed herein so long as the derivative functionally retains the desired property of MASP-2 inhibition. The modifications can include amino acid substitution with one of the commonly known twenty amino acids or with another amino acid, with a derivatized or substituted amino acid with ancillary desirable characteristics, such as resistance to enzymatic degradation or with a D-amino acid or substitution with another molecule or compound, such as a carbohydrate, which mimics the natural confirmation and function of the amino acid, amino acids or peptide; amino acid deletion; amino acid insertion with one of the commonly known twenty amino acids or with another amino acid, with a derivatized or substituted amino acid with ancillary desirable characteristics, such as resistance to enzymatic degradation or with a D-amino acid or substitution with another molecule or compound, such as a carbohydrate, which mimics the natural confirmation and function of the amino acid, amino acids or peptide; or substitution with another molecule or compound, such as a carbohydrate or nucleic acid monomer, which mimics the natural conformation, charge distribution and function of the parent peptide. Peptides may also be modified by acetylation or amidation.

The synthesis of derivative inhibitory peptides can rely on known techniques of peptide biosynthesis, carbohydrate biosynthesis and the like. As a starting point, the artisan may rely on a suitable computer program to determine the conformation of a peptide of interest. Once the conformation of peptide disclosed herein is known, then the artisan can determine in a rational design fashion what sort of substitutions can be made at one or more sites to fashion a derivative that retains the basic conformation and charge distribution of the parent peptide but which may possess characteristics which are not present or are enhanced over those found in the parent peptide. Once candidate derivative molecules are identified, the derivatives can be tested to determine if they function as MASP-2 inhibitory agents using the assays described herein.

Screening for MASP-2 Inhibitory Peptides

One may also use molecular modeling and rational molecular design to generate and screen for peptides that mimic the molecular structures of key binding regions of MASP-2 and inhibit the complement activities of MASP-2. The molecular structures used for modeling include the CDR regions of anti-MASP-2 monoclonal antibodies, as well as the target regions known to be important for MASP-2 function including the region required for dimerization, the region involved in binding to MBL, and the serine protease active site as previously described. Methods for identifying peptides that bind to a particular target are well known in the art. For example, molecular imprinting may be used for the de novo construction of macromolecular structures such as peptides that bind to a particular molecule. See, for example, Shea, K. J., "Molecular Imprinting of Synthetic Network Polymers: The De Novo synthesis of Macromolecular Binding and Catalytic Sties," TRIP 2(5) 1994.

As an illustrative example, one method of preparing mimics of MASP-2 binding peptides is as follows. Functional monomers of a known MASP-2 binding peptide or the binding region of an anti-MASP-2 antibody that exhibits MASP-2 inhibition (the template) are polymerized. The template is then removed, followed by polymerization of a second class of monomers in the void left by the template, to provide a new molecule that exhibits one or more desired properties that are similar to the template. In addition to preparing peptides in this manner, other MASP-2 binding molecules that are MASP-2 inhibitory agents such as polysaccharides, nucleosides, drugs, nucleoproteins, lipoproteins, carbohydrates, glycoproteins, steroid, lipids and other biologically active materials can also be prepared. This method is useful for designing a wide variety of biological mimics that are more stable than their natural counterparts because they are typically prepared by free radical polymerization of function monomers, resulting in a compound with a nonbiodegradable backbone.

Peptide Synthesis

The MASP-2 inhibitory peptides can be prepared using techniques well known in the art, such as the solid-phase synthetic technique initially described by Merrifield, in *J. Amer. Chem. Soc.* 85:2149-2154, 1963. Automated synthesis may be achieved, for example, using Applied Biosystems 431A Peptide Synthesizer (Foster City, Calif.) in accordance with the instructions provided by the manufacturer. Other techniques may be found, for example, in Bodanszky, M., et al., *Peptide Synthesis*, second edition, John Wiley & Sons, 1976, as well as in other reference works known to those skilled in the art.

The peptides can also be prepared using standard genetic engineering techniques known to those skilled in the art. For example, the peptide can be produced enzymatically by inserting nucleic acid encoding the peptide into an expression vector, expressing the DNA, and translating the DNA into the peptide in the presence of the required amino acids. The peptide is then purified using chromatographic or electrophoretic techniques, or by means of a carrier protein that can be fused to, and subsequently cleaved from, the peptide by inserting into the expression vector in phase with the peptide encoding sequence a nucleic acid sequence encoding the carrier protein. The fusion protein-peptide may be isolated using chromatographic, electrophoretic or immunological techniques (such as binding to a resin via an antibody to the carrier protein). The peptide can be cleaved using chemical methodology or enzymatically, as by, for example, hydrolases.

The MASP-2 inhibitory peptides that are useful in the method of the invention can also be produced in recombinant host cells following conventional techniques. To express a MASP-2 inhibitory peptide encoding sequence, a nucleic acid molecule encoding the peptide must be operably linked to regulatory sequences that control transcriptional expression in an expression vector and then introduced into a host cell. In addition to transcriptional regulatory sequences, such as promoters and enhancers, expression vectors can include translational regulatory sequences and a marker gene, which are suitable for selection of cells that carry the expression vector.

Nucleic acid molecules that encode a MASP-2 inhibitory peptide can be synthesized with "gene machines" using protocols such as the phosphoramidite method. If chemically synthesized double-stranded DNA is required for an application such as the synthesis of a gene or a gene fragment, then each complementary strand is made separately. The production of short genes (60 to 80 base pairs) is technically straightforward and can be accomplished by synthesizing the complementary strands and then annealing them. For the production of longer genes, synthetic genes (double-stranded) are assembled in modular form from single-stranded fragments that are from 20 to 100 nucleotides in length. For reviews on polynucleotide synthesis, see, for example, Glick and Pasternak, "Molecular Biotechnology, Principles and Applications of Recombinant DNA", ASM Press, 1994; Itakura, K., et al., *Annu. Rev. Biochem.* 53:323, 1984, and Climie, S., et al., *Proc. Natl Acad. Sci. USA* 87:633, 1990.

Small Molecule Inhibitors

In some embodiments, MASP-2 inhibitory agents are small molecule inhibitors including natural and synthetic substances that have a low molecular weight, such as for example, peptides, peptidomimetics and nonpeptide inhibitors (including oligonucleotides and organic compounds). Small molecule inhibitors of MASP-2 can be generated based on the molecular structure of the variable regions of the anti-MASP-2 antibodies.

Small molecule inhibitors may also be designed and generated based on the MASP-2 crystal structure using computational drug design (Kuntz I.D., et al., *Science* 257: 1078, 1992). The crystal structure of rat MASP-2 has been described (Feinberg, H., et al., *EMBO J.* 22:2348-2359, 2003). Using the method described by Kuntz et al., the MASP-2 crystal structure coordinates are used as an input for a computer program such as DOCK, which outputs a list of small molecule structures that are expected to bind to MASP-2. Use of such computer programs is well known to one of skill in the art. For example, the crystal structure of the HIV-1 protease inhibitor was used to identify unique nonpeptide ligands that are HIV-1 protease inhibitors by evaluating the fit of compounds found in the Cambridge Crystallographic database to the binding site of the enzyme using the program DOCK (Kuntz, I. D., et al., *J. Mol. Biol.* 161:269-288, 1982; DesJarlais, R. L., et al., *PNAS* 87:6644-6648, 1990).

The list of small molecule structures that are identified by a computational method as potential MASP-2 inhibitors are screened using a MASP-2 binding assay such as described in Example 10. The small molecules that are found to bind to MASP-2 are then assayed in a functional assay such as described in Example 2 to determine if they inhibit MASP-2-dependent complement activation.

MASP-2 Soluble Receptors

Other suitable MASP-2 inhibitory agents are believed to include MASP-2 soluble receptors, which may be produced using techniques known to those of ordinary skill in the art.

Expression Inhibitors of MASP-2

In another embodiment of this aspect of the invention, the MASP-2 inhibitory agent is a MASP-2 expression inhibitor capable of inhibiting MASP-2-dependent complement activation. In the practice of this aspect of the invention, representative MASP-2 expression inhibitors include MASP-2 antisense nucleic acid molecules (such as antisense mRNA, antisense DNA or antisense oligonucleotides), MASP-2 ribozymes and MASP-2 RNAi molecules.

Anti-sense RNA and DNA molecules act to directly block the translation of MASP-2 mRNA by hybridizing to MASP-2 mRNA and preventing translation of MASP-2 protein. An antisense nucleic acid molecule may be constructed in a number of different ways provided that it is capable of interfering with the expression of MASP-2. For example, an antisense nucleic acid molecule can be constructed by inverting the coding region (or a portion thereof) of MASP-2 cDNA (SEQ ID NO:4) relative to its normal orientation for transcription to allow for the transcription of its complement.

The antisense nucleic acid molecule is usually substantially identical to at least a portion of the target gene or genes. The nucleic acid, however, need not be perfectly identical to inhibit expression. Generally, higher homology can be used to compensate for the use of a shorter antisense nucleic acid molecule. The minimal percent identity is typically greater than about 65%, but a higher percent identity may exert a more effective repression of expression of the endogenous sequence. Substantially greater percent identity of more than about 80% typically is preferred, though about 95% to absolute identity is typically most preferred.

The antisense nucleic acid molecule need not have the same intron or exon pattern as the target gene, and non-coding segments of the target gene may be equally effective in achieving antisense suppression of target gene expression as coding segments. A DNA sequence of at least about 8 or so nucleotides may be used as the antisense nucleic acid molecule, although a longer sequence is preferable. In the present invention, a representative example of a useful inhibitory agent of MASP-2 is an antisense MASP-2 nucleic acid molecule which is at least ninety percent identical to the complement of the MASP-2 cDNA consisting of the nucleic acid sequence set forth in SEQ ID NO:4. The nucleic acid sequence set forth in SEQ ID NO:4 encodes the MASP-2 protein consisting of the amino acid sequence set forth in SEQ ID NO:5.

The targeting of antisense oligonucleotides to bind MASP-2 mRNA is another mechanism that may be used to reduce the level of MASP-2 protein synthesis. For example, the synthesis of polygalacturonase and the muscarine type 2 acetylcholine receptor is inhibited by antisense oligonucleotides directed to their respective mRNA sequences (U.S. Pat. No. 5,739,119, to Cheng, and U.S. Pat. No. 5,759,829, to Shewmaker). Furthermore, examples of antisense inhibition have been demonstrated with the nuclear protein cyclin, the multiple drug resistance gene (MDG1), ICAM-1, E-selectin, STK-1, striatal $GABA_A$ receptor and human EGF (see, e.g., U.S. Pat. No. 5,801,154, to Baracchini; U.S. Pat.

No. 5,789,573, to Baker; U.S. Pat. No. 5,718,709, to Considine; and U.S. Pat. No. 5,610,288, to Reubenstein).

A system has been described that allows one of ordinary skill to determine which oligonucleotides are useful in the invention, which involves probing for suitable sites in the target mRNA using RNAse H cleavage as an indicator for accessibility of sequences within the transcripts. Scherr, M., et al., *Nucleic Acids Res.* 26:5079-5085, 1998; Lloyd, et al., *Nucleic Acids Res.* 29:3665-3673, 2001. A mixture of antisense oligonucleotides that are complementary to certain regions of the MASP-2 transcript is added to cell extracts expressing MASP-2, such as hepatocytes, and hybridized in order to create an RNAse H vulnerable site. This method can be combined with computer-assisted sequence selection that can predict optimal sequence selection for antisense compositions based upon their relative ability to form dimers, hairpins, or other secondary structures that would reduce or prohibit specific binding to the target mRNA in a host cell. These secondary structure analysis and target site selection considerations may be performed using the OLIGO primer analysis software (Rychlik, I., 1997) and the BLASTN 2.0.5 algorithm software (Altschul, S. F., et al., *Nucl. Acids Res.* 25:3389-3402, 1997). The antisense compounds directed towards the target sequence preferably comprise from about 8 to about 50 nucleotides in length. Antisense oligonucleotides comprising from about 9 to about 35 or so nucleotides are particularly preferred. The inventors contemplate all oligonucleotide compositions in the range of 9 to 35 nucleotides (i.e., those of 9, 10, 11, 12, 13, 14, 15, 16, 17, 18, 19, 20, 21, 22, 23, 24, 25, 26, 27, 28, 29, 30, 31, 32, 33, 34, or 35 or so bases in length) are highly preferred for the practice of antisense oligonucleotide-based methods of the invention. Highly preferred target regions of the MASP-2 mRNA are those that are at or near the AUG translation initiation codon, and those sequences that are substantially complementary to 5' regions of the mRNA, e.g., between the −10 and +10 regions of the MASP-2 gene nucleotide sequence (SEQ ID NO:4). Exemplary MASP-2 expression inhibitors are provided in TABLE 4.

trative embodiments, the antisense compounds of the invention differ from native DNA by the modification of the phosphodiester backbone to extend the life of the antisense oligonucleotide in which the phosphate substituents are replaced by phosphorothioates. Likewise, one or both ends of the oligonucleotide may be substituted by one or more acridine derivatives that intercalate between adjacent base-pairs within a strand of nucleic acid.

Another alternative to antisense is the use of "RNA interference" (RNAi). Double-stranded RNAs (dsRNAs) can provoke gene silencing in mammals in vivo. The natural function of RNAi and co-suppression appears to be protection of the genome against invasion by mobile genetic elements such as retrotransposons and viruses that produce aberrant RNA or dsRNA in the host cell when they become active (see, e.g., Jensen, J., et al., *Nat. Genet.* 21:209-12, 1999). The double-stranded RNA molecule may be prepared by synthesizing two RNA strands capable of forming a double-stranded RNA molecule, each having a length from about 19 to 25 (e.g., 19-23 nucleotides). For example, a dsRNA molecule useful in the methods of the invention may comprise the RNA corresponding to a sequence and its complement listed in TABLE 4. Preferably, at least one strand of RNA has a 3' overhang from 1-5 nucleotides. The synthesized RNA strands are combined under conditions that form a double-stranded molecule. The RNA sequence may comprise at least an 8 nucleotide portion of SEQ ID NO:4 with a total length of 25 nucleotides or less. The design of siRNA sequences for a given target is within the ordinary skill of one in the art. Commercial services are available that design siRNA sequence and guarantee at least 70% knockdown of expression (Qiagen, Valencia, Calif.).

The dsRNA may be administered as a pharmaceutical composition and carried out by known methods, wherein a nucleic acid is introduced into a desired target cell. Commonly used gene transfer methods include calcium phosphate, DEAE-dextran, electroporation, microinjection and viral methods. Such methods are taught in Ausubel et al., *Current Protocols in Molecular Biology*, John Wiley & Sons, Inc., 1993.

TABLE 4

EXEMPLARY EXPRESSION INHIBITORS OF MASP-2

| | |
|---|---|
| SEQ ID NO: 30 (nucleotides 22-680 of SEQ ID NO: 4) | Nucleic acid sequence of MASP-2 cDNA SEQ ID NO: 4) encoding CUBIEGF |
| SEQ ID NO: 31 5'CGGGCACACCATGAGGCTGCTG ACCCTCCTGGGC3 | Nucleotides 12-45 of SEQ ID NO: 4 including the MASP-2 translation start site sense) |
| SEQ ID NO: 32 5'GACATTACCITCCGCTCCGACTC CAACGAGAAG3' | Nucleotides 361-396 of SEQ ID NO: 4 encoding a region comprising the MASP-2 MBL binding site (sense) |
| SEQ ID NO: 33 5'AGCACTCCCTGAATACCCACGGCC GTATCCCAAA3' | Nucleotides 610-642 of SEQ ID NO: 4 encoding a region comprising the CUBII domain |

As noted above, the term "oligonucleotide" as used herein refers to an oligomer or polymer of ribonucleic acid (RNA) or deoxyribonucleic acid (DNA) or mimetics thereof. This term also covers those oligonucleobases composed of naturally occurring nucleotides, sugars and covalent internucleoside (backbone) linkages as well as oligonucleotides having non-naturally occurring modifications. These modifications allow one to introduce certain desirable properties that are not offered through naturally occurring oligonucleotides, such as reduced toxic properties, increased stability against nuclease degradation and enhanced cellular uptake. In illus- Ribozymes can also be utilized to decrease the amount and/or biological activity of MASP-2, such as ribozymes that target MASP-2 mRNA. Ribozymes are catalytic RNA molecules that can cleave nucleic acid molecules having a sequence that is completely or partially homologous to the sequence of the ribozyme. It is possible to design ribozyme transgenes that encode RNA ribozymes that specifically pair with a target RNA and cleave the phosphodiester backbone at a specific location, thereby functionally inactivating the target RNA. In carrying out this cleavage, the ribozyme is not itself altered, and is thus capable of recycling and cleaving other molecules. The inclusion of ribozyme sequences within antisense RNAs confers RNA-cleaving activity upon them, thereby increasing the activity of the antisense constructs.

Ribozymes useful in the practice of the invention typically comprise a hybridizing region of at least about nine nucleotides, which is complementary in nucleotide sequence to at least part of the target MASP-2 mRNA, and a catalytic region that is adapted to cleave the target MASP-2 mRNA (see generally, EPA No. 0 321 201; WO88/04300; Haseloff, J., et al., *Nature* 334:585-591, 1988; Fedor, M. J., et al., *Proc. Natl. Acad. Sci. USA* 87:1668-1672, 1990; Cech, T. R., et al., *Ann. Rev. Biochem.* 55:599-629, 1986).

Ribozymes can either be targeted directly to cells in the form of RNA oligonucleotides incorporating ribozyme sequences, or introduced into the cell as an expression vector encoding the desired ribozymal RNA. Ribozymes may be used and applied in much the same way as described for antisense polynucleotides.

Anti-sense RNA and DNA, ribozymes and RNAi molecules useful in the methods of the invention may be prepared by any method known in the art for the synthesis of DNA and RNA molecules. These include techniques for chemically synthesizing oligodeoxyribonucleotides and oligoribonucleotides well known in the art, such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various well known modifications of the DNA molecules may be introduced as a means of increasing stability and half-life. Useful modifications include, but are not limited to, the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone.

V. Pharmaceutical Compositions and Delivery Methods Dosing

In another aspect, the invention provides compositions for inhibiting the adverse effects of MASP-2-dependent complement activation in a subject suffering from a disease or condition as disclosed herein, comprising administering to the subject a composition comprising a therapeutically effective amount of a MASP-2 inhibitory agent and a pharmaceutically acceptable carrier. The MASP-2 inhibitory agents can be administered to a subject in need thereof, at therapeutically effective doses to treat or ameliorate conditions associated with MASP-2-dependent complement activation. A therapeutically effective dose refers to the amount of the MASP-2 inhibitory agent sufficient to result in amelioration of symptoms associated with the disease or condition.

Toxicity and therapeutic efficacy of MASP-2 inhibitory agents can be determined by standard pharmaceutical procedures employing experimental animal models, such as the murine MASP-2-/- mouse model expressing the human MASP-2 transgene described in Example 1. Using such animal models, the NOAEL (no observed adverse effect level) and the MED (the minimally effective dose) can be determined using standard methods. The dose ratio between NOAEL and MED effects is the therapeutic ratio, which is expressed as the ratio NOAEL/MED. MASP-2 inhibitory agents that exhibit large therapeutic ratios or indices are most preferred. The data obtained from the cell culture assays and animal studies can be used in formulating a range of dosages for use in humans. The dosage of the MASP-2 inhibitory agent preferably lies within a range of circulating concentrations that include the MED with little or no toxicity. The dosage may vary within this range depending upon the dosage form employed and the route of administration utilized.

In some embodiments, therapeutic efficacy of the MASP-2 inhibitory agents for treating, inhibiting, alleviating or preventing fibrosis in a mammalian subject suffering, or at risk of developing a disease or disorder caused or exacerbated by fibrosis and/or inflammation is determined by one or more of the following: a reduction in one of more markers of inflammation and scarring (e.g., TGFβ-1, CTFF, IL-6, apoptosis, fibronectin, laminin, collagens, EMT, infiltrating macrophages) in renal tissue; a reduction in the release of soluble markers of inflammation and fibrotic renal disease into urine and plasma (e.g., by the measurement of renal excretory functions).

For any compound formulation, the therapeutically effective dose can be estimated using animal models. For example, a dose may be formulated in an animal model to achieve a circulating plasma concentration range that includes the MED. Quantitative levels of the MASP-2 inhibitory agent in plasma may also be measured, for example, by high performance liquid chromatography.

In addition to toxicity studies, effective dosage may also be estimated based on the amount of MASP-2 protein present in a living subject and the binding affinity of the MASP-2 inhibitory agent. It has been shown that MASP-2 levels in normal human subjects is present in serum in low levels in the range of 500 ng/ml, and MASP-2 levels in a particular subject can be determined using a quantitative assay for MASP-2 described in Moller-Kristensen M., et al., *J. Immunol. Methods* 282:159-167, 2003.

Generally, the dosage of administered compositions comprising MASP-2 inhibitory agents varies depending on such factors as the subject's age, weight, height, sex, general medical condition, and previous medical history. As an illustration, MASP-2 inhibitory agents, such as anti-MASP-2 antibodies, can be administered in dosage ranges from about 0.010 to 10.0 mg/kg, preferably 0.010 to 1.0 mg/kg, more preferably 0.010 to 0.1 mg/kg of the subject body weight. In some embodiments the composition comprises a combination of anti-MASP-2 antibodies and MASP-2 inhibitory peptides.

Therapeutic efficacy of MASP-2 inhibitory compositions and methods of the present invention in a given subject, and appropriate dosages, can be determined in accordance with complement assays well known to those of skill in the art. Complement generates numerous specific products. During the last decade, sensitive and specific assays have been developed and are available commercially for most of these activation products, including the small activation fragments C3a, C4a, and C5a and the large activation fragments iC3b, C4d, Bb, and sC5b-9. Most of these assays utilize monoclonal antibodies that react with new antigens (neoantigens) exposed on the fragment, but not on the native proteins from which they are formed, making these assays very simple and specific. Most rely on ELISA technology, although radioimmunoassay is still sometimes used for C3a and C5a. These latter assays measure both the unprocessed fragments and their 'desArg' fragments, which are the major forms found in the circulation. Unprocessed fragments and $C5_{desArg}$ are rapidly cleared by binding to cell surface receptors and are hence present in very low concentrations, whereas $C3a_{desArg}$ does not bind to cells and accumulates in plasma. Measurement of C3a provides a sensitive, pathway-independent indicator of complement activation. Alternative pathway activation can be assessed by measuring the Bb fragment. Detection of the fluid-phase product of membrane attack pathway activation, sC5b-9, provides evidence that complement is being activated to completion. Because both the lectin and classical pathways generate the same activation products, C4a and C4d, measurement of these two fragments does not provide any information about which of these two pathways has generated the activation products.

The inhibition of MASP-2-dependent complement activation is characterized by at least one of the following changes in a component of the complement system that occurs as a result of administration of a MASP-2 inhibitory agent in accordance with the methods of the invention: the inhibition of the generation or production of MASP-2-dependent complement activation system products C4b, C3a, C5a and/or C5b-9 (MAC) (measured, for example, as described in measured, for example, as described in Example 2, the reduction of C4 cleavage and C4b deposition (measured, for example as described in Example 10), or the reduction of C3 cleavage and C3b deposition (measured, for example, as described in Example 10).

Additional Agents

In certain embodiments, methods of preventing, treating, reverting and/or inhibiting fibrosis and/or inflammation include administering an MASP-2 inhibitory agent (e.g., a MASP-2 inhibitory antibody) as part of a therapeutic regimen along with one or more other drugs, biologics, or therapeutic interventions appropriate for inhibiting fibrosis and/or inflammation. In certain embodiments, the additional drug, biologic, or therapeutic intervention is appropriate for particular symptoms associated with a disease or disorder caused or exacerbated by fibrosis and/or inflammation. By way of example, MASP-2 inhibitory antibodies may be administered as part of a therapeutic regimen along with one or more immunosuppressive agents, such as methotrexate, cyclophosphamide, azathioprine, and mycophenolate mofetil. By way of further example, MASP-2 inhibitory antibodies may be administered as part of a therapeutic regimen along with one or more agents designed to increase blood flow (e.g., nifedipine, amlodipine, diltiazem, felodipine, or nicardipine). By way of further example, MASP-2 inhibitory antibodies may be administered as part of a therapeutic regimen along with one or more agents intended to decrease fibrosis, such as d-penicillamine, colchicine, PUVA, Relaxin, cyclosporine, TGF beta blockers and/or p38 MAPK blockers. By way of further example, MASP-2 inhibitory antibodies may be administered as part of a therapeutic regimen along with steroids or broncho-dilators.

The compositions and methods comprising MASP-2 inhibitory agents (e.g., MASP-2 inhibitory antibodies) may optionally comprise one or more additional therapeutic agents, which may augment the activity of the MASP-2 inhibitory agent or that provide related therapeutic functions in an additive or synergistic fashion. For example, in the context of treating a subject suffering from a disease or disorder caused or exacerbated by fibrosis and/or inflammation one or more MASP-2 inhibitory agents may be administered in combination (including co-administration) with one or more additional antifibrotic agents and/or one or more anti-inflammatory and/or immunosuppressive agents.

MASP-2 inhibitory agents (e.g., MASP-2 inhibitory antibodies) can be used in combination with other therapeutic agents such as general immunosuppressive drugs such as corticosteroids, immunosuppressive or cytotoxic agents, and/or antifibrotic agents.

Pharmaceutical Carriers and Delivery Vehicles

In general, the MASP-2 inhibitory agent compositions of the present invention, combined with any other selected therapeutic agents, are suitably contained in a pharmaceutically acceptable carrier. The carrier is non-toxic, biocompatible and is selected so as not to detrimentally affect the biological activity of the MASP-2 inhibitory agent (and any other therapeutic agents combined therewith). Exemplary pharmaceutically acceptable carriers for peptides are described in U.S. Pat. No. 5,211,657 to Yamada. The anti-MASP-2 antibodies and inhibitory peptides useful in the invention may be formulated into preparations in solid, semi-solid, gel, liquid or gaseous forms such as tablets, capsules, powders, granules, ointments, solutions, depositories, inhalants and injections allowing for oral, parenteral or surgical administration. The invention also contemplates local administration of the compositions by coating medical devices and the like.

Suitable carriers for parenteral delivery via injectable, infusion or irrigation and topical delivery include distilled water, physiological phosphate-buffered saline, normal or lactated Ringer's solutions, dextrose solution, Hank's solution, or propanediol. In addition, sterile, fixed oils may be employed as a solvent or suspending medium. For this purpose any biocompatible oil may be employed including synthetic mono- or diglycerides. In addition, fatty acids such as oleic acid find use in the preparation of injectables. The carrier and agent may be compounded as a liquid, suspension, polymerizable or non-polymerizable gel, paste or salve.

The carrier may also comprise a delivery vehicle to sustain (i.e., extend, delay or regulate) the delivery of the agent(s) or to enhance the delivery, uptake, stability or pharmacokinetics of the therapeutic agent(s). Such a delivery vehicle may include, by way of non-limiting example, microparticles, microspheres, nanospheres or nanoparticles composed of proteins, liposomes, carbohydrates, synthetic organic compounds, inorganic compounds, polymeric or copolymeric hydrogels and polymeric micelles. Suitable hydrogel and micelle delivery systems include the PEO:PHB:PEO copolymers and copolymer/cyclodextrin complexes disclosed in WO 2004/009664 A2 and the PEO and PEO/cyclodextrin complexes disclosed in U.S. Patent Application Publication No. 2002/0019369 A1. Such hydrogels may be injected locally at the site of intended action, or subcutaneously or intramuscularly to form a sustained release depot.

For intra-articular delivery, the MASP-2 inhibitory agent may be carried in above-described liquid or gel carriers that are injectable, above-described sustained-release delivery vehicles that are injectable, or a hyaluronic acid or hyaluronic acid derivative.

For oral administration of non-peptidergic agents, the MASP-2 inhibitory agent may be carried in an inert filler or diluent such as sucrose, cornstarch, or cellulose.

For topical administration, the MASP-2 inhibitory agent may be carried in ointment, lotion, cream, gel, drop, suppository, spray, liquid or powder, or in gel or microcapsular delivery systems via a transdermal patch.

Various nasal and pulmonary delivery systems, including aerosols, metered-dose inhalers, dry powder inhalers, and nebulizers, are being developed and may suitably be adapted for delivery of the present invention in an aerosol, inhalant, or nebulized delivery vehicle, respectively.

For intrathecal (IT) or intracerebroventricular (ICV) delivery, appropriately sterile delivery systems (e.g., liquids; gels, suspensions, etc.) can be used to administer the present invention.

The compositions of the present invention may also include biocompatible excipients, such as dispersing or wetting agents, suspending agents, diluents, buffers, penetration enhancers, emulsifiers, binders, thickeners, flavouring agents (for oral administration).

Pharmaceutical Carriers for Antibodies and Peptides

More specifically with respect to anti-MASP-2 antibodies and inhibitory peptides, exemplary formulations can be parenterally administered as injectable dosages of a solution or suspension of the compound in a physiologically acceptable diluent with a pharmaceutical carrier that can be a sterile liquid such as water, oils, saline, glycerol or ethanol. Additionally, auxiliary substances such as wetting or emulsifying agents, surfactants, pH buffering substances and the like can be present in compositions comprising anti-MASP-2 antibodies and inhibitory peptides. Additional components of pharmaceutical compositions include petroleum (such as of animal, vegetable or synthetic origin), for example, soybean oil and mineral oil. In general, glycols such as propylene glycol or polyethylene glycol are preferred liquid carriers for injectable solutions.

The anti-MASP-2 antibodies and inhibitory peptides can also be administered in the form of a depot injection or implant preparation that can be formulated in such a manner as to permit a sustained or pulsatile release of the active agents.

Pharmaceutically Acceptable Carriers for Expression Inhibitors

More specifically with respect to expression inhibitors useful in the methods of the invention, compositions are provided that comprise an expression inhibitor as described above and a pharmaceutically acceptable carrier or diluent. The composition may further comprise a colloidal dispersion system.

Pharmaceutical compositions that include expression inhibitors may include, but are not limited to, solutions, emulsions, and liposome-containing formulations. These compositions may be generated from a variety of components that include, but are not limited to, preformed liquids, self-emulsifying solids and self-emulsifying semisolids. The preparation of such compositions typically involves combining the expression inhibitor with one or more of the following: buffers, antioxidants, low molecular weight polypeptides, proteins, amino acids, carbohydrates including glucose, sucrose or dextrins, chelating agents such as EDTA, glutathione and other stabilizers and excipients. Neutral buffered saline or saline mixed with non-specific serum albumin are examples of suitable diluents.

In some embodiments, the compositions may be prepared and formulated as emulsions which are typically heterogeneous systems of one liquid dispersed in another in the form of droplets (see, Idson, in *Pharmaceutical Dosage Forms*, Vol. 1, Rieger and Banker (eds.), Marcek Dekker, Inc., N.Y., 1988). Examples of naturally occurring emulsifiers used in emulsion formulations include acacia, beeswax, lanolin, lecithin and phosphatides.

In one embodiment, compositions including nucleic acids can be formulated as microemulsions. A microemulsion, as used herein refers to a system of water, oil, and amphiphile, which is a single optically isotropic and thermodynamically stable liquid solution (see Rosoff in Pharmaceutical Dosage Forms, Vol. 1). The method of the invention may also use liposomes for the transfer and delivery of antisense oligonucleotides to the desired site.

Pharmaceutical compositions and formulations of expression inhibitors for topical administration may include transdermal patches, ointments, lotions, creams, gels, drops, suppositories, sprays, liquids and powders. Conventional pharmaceutical carriers, as well as aqueous, powder or oily bases and thickeners and the like may be used.

Modes of Administration

The pharmaceutical compositions comprising MASP-2 inhibitory agents may be administered in a number of ways depending on whether a local or systemic mode of administration is most appropriate for the condition being treated. Further, the compositions of the present invention can be delivered by coating or incorporating the compositions on or into an implantable medical device.

Systemic Delivery

As used herein, the terms "systemic delivery" and "systemic administration" are intended to include but are not limited to oral and parenteral routes including intramuscular (IM), subcutaneous, intravenous (IV), intra-arterial, inhalational, sublingual, buccal, topical, transdermal, nasal, rectal, vaginal and other routes of administration that effectively result in dispersement of the delivered agent to a single or multiple sites of intended therapeutic action. Preferred routes of systemic delivery for the present compositions include intravenous, intramuscular, subcutaneous and inhalational. It will be appreciated that the exact systemic administration route for selected agents utilized in particular compositions of the present invention will be determined in part to account for the agent's susceptibility to metabolic transformation pathways associated with a given route of administration. For example, peptidergic agents may be most suitably administered by routes other than oral.

MASP-2 inhibitory antibodies and polypeptides can be delivered into a subject in need thereof by any suitable means. Methods of delivery of MASP-2 antibodies and polypeptides include administration by oral, pulmonary, parenteral (e.g., intramuscular, intraperitoneal, intravenous (IV) or subcutaneous injection), inhalation (such as via a fine powder formulation), transdermal, nasal, vaginal, rectal, or sublingual routes of administration, and can be formulated in dosage forms appropriate for each route of administration.

By way of representative example, MASP-2 inhibitory antibodies and peptides can be introduced into a living body by application to a bodily membrane capable of absorbing the polypeptides, for example the nasal, gastrointestinal and rectal membranes. The polypeptides are typically applied to the absorptive membrane in conjunction with a permeation enhancer. (See, e.g., Lee, V. H. L., *Crit. Rev. Ther. Drug Carrier Sys.* 5:69, 1988; Lee, V. H. L., *J. Controlled Release* 13:213, 1990; Lee, V. H. L., Ed., *Peptide and Protein Drug Delivery*, Marcel Dekker, New York (1991); DeBoer, A. G., et al., *J. Controlled Release* 13:241, 1990.) For example, STDHF is a synthetic derivative of fusidic acid, a steroidal surfactant that is similar in structure to the bile salts, and has been used as a permeation enhancer for nasal delivery. (Lee, W. A., *Biopharm.* 22, November/December 1990.)

The MASP-2 inhibitory antibodies and polypeptides may be introduced in association with another molecule, such as a lipid, to protect the polypeptides from enzymatic degradation. For example, the covalent attachment of polymers, especially polyethylene glycol (PEG), has been used to protect certain proteins from enzymatic hydrolysis in the body and thus prolong half-life (Fuertges, F., et al., *J. Controlled Release* 11:139, 1990). Many polymer systems have been reported for protein delivery (Bae, Y. H., et al., *J. Controlled Release* 9:271, 1989; Hori, R., et al., *Pharm. Res.* 6:813, 1989; Yamakawa, I., et al., *J. Pharm. Sci.* 79:505, 1990; Yoshihiro, I., et al., *J. Controlled Release* 10:195, 1989; Asano, M., et al., *J. Controlled Release* 9:111, 1989; Rosenblatt, J., et al., *J. Controlled Release* 9:195, 1989; Makino, K., *J. Controlled Release* 12:235, 1990; Takakura, Y., et al., *J Pharm. Sci.* 78:117, 1989; Takakura, Y., et al., *J. Pharm. Sci.* 78:219, 1989).

Recently, liposomes have been developed with improved serum stability and circulation half-times (see, e.g., U.S. Pat. No. 5,741,516, to Webb). Furthermore, various methods of liposome and liposome-like preparations as potential drug carriers have been reviewed (see, e.g., U.S. Pat. No. 5,567,434, to Szoka; U.S. Pat. No. 5,552,157, to Yagi; U.S. Pat. No. 5,565,213, to Nakamori; U.S. Pat. No. 5,738,868, to Shinkarenko; and U.S. Pat. No. 5,795,587, to Gao).

For transdermal applications, the MASP-2 inhibitory antibodies and polypeptides may be combined with other suitable ingredients, such as carriers and/or adjuvants. There are no limitations on the nature of such other ingredients, except that they must be pharmaceutically acceptable for their intended administration, and cannot degrade the activity of the active ingredients of the composition. Examples of suitable vehicles include ointments, creams, gels, or suspensions, with or without purified collagen. The MASP-2 inhibitory antibodies and polypeptides may also be impregnated into transdermal patches, plasters, and bandages, preferably in liquid or semi-liquid form.

The compositions of the present invention may be systemically administered on a periodic basis at intervals determined to maintain a desired level of therapeutic effect. For example, compositions may be administered, such as by subcutaneous injection, every two to four weeks or at less frequent intervals. The dosage regimen will be determined by the physician considering various factors that may influence the action of the combination of agents. These factors will include the extent of progress of the condition being treated, the patient's age, sex and weight, and other clinical factors. The dosage for each individual agent will vary as a function of the MASP-2 inhibitory agent that is included in the composition, as well as the presence and nature of any drug delivery vehicle (e.g., a sustained release delivery vehicle). In addition, the dosage quantity may be adjusted to account for variation in the frequency of administration and the pharmacokinetic behavior of the delivered agent(s).

Local Delivery

As used herein, the term "local" encompasses application of a drug in or around a site of intended localized action, and may include for example topical delivery to the skin or other affected tissues, ophthalmic delivery, intrathecal (IT), intracerebroventricular (ICV), intra-articular, intracavity, intracranial or intravesicular administration, placement or irrigation. Local administration may be preferred to enable administration of a lower dose, to avoid systemic side effects, and for more accurate control of the timing of delivery and concentration of the active agents at the site of local delivery. Local administration provides a known concentration at the target site, regardless of interpatient variability in metabolism, blood flow, etc. Improved dosage control is also provided by the direct mode of delivery.

Local delivery of a MASP-2 inhibitory agent may be achieved in the context of surgical methods for treating disease or disorder caused or exacerbated by fibrosis and/or inflammation such as for example during procedures such as surgery.

Treatment Regimens

In prophylactic applications, the pharmaceutical compositions comprising a MASP-2 inhibitory agent (e.g., a MASP-2 inhibitory antibody) are administered to a subject susceptible to, or otherwise at risk of developing a disease or disorder caused or exacerbated by fibrosis and/or inflammation in an amount sufficient to inhibit fibrosis and/or inflammation and thereby eliminate or reduce the risk of developing symptoms of the condition. In some embodiments, the pharmaceutical compositions are administered to a subject suspected of, or already suffering from, a disease or disorder caused or exacerbated by fibrosis and/or inflammation in a therapeutically effective amount sufficient to relieve, or at least partially reduce, the symptoms of the condition. In both prophylactic and therapeutic regimens, compositions comprising MASP-2 inhibitory agents may be administered in several dosages until a sufficient therapeutic outcome has been achieved in the subject. Application of the MASP-2 inhibitory compositions of the present invention may be carried out by a single administration of the composition, or a limited sequence of administrations, for treatment of an acute condition associated with fibrosis and/or inflammation. Alternatively, the composition may be administered at periodic intervals over an extended period of time for treatment of chronic conditions associated with fibrosis and/or inflammation.

In both prophylactic and therapeutic regimens, compositions comprising MASP-2 inhibitory agents may be administered in several dosages until a sufficient therapeutic outcome has been achieved in the subject. In one embodiment of the invention, the MASP-2 inhibitory agent comprises a MASP-2 antibody, which suitably may be administered to an adult patient (e.g., an average adult weight of 70 kg) in a dosage of from 0.1 mg to 10,000 mg, more suitably from 1.0 mg to 5,000 mg, more suitably 10.0 mg to 2,000 mg, more suitably 10.0 mg to 1,000 mg and still more suitably from 50.0 mg to 500 mg. For pediatric patients, dosage can be adjusted in proportion to the patient's weight. Application of the MASP-2 inhibitory compositions of the present invention may be carried out by a single administration of the composition, or a limited sequence of administrations, for treatment of a subject suffering from or at risk for developing a disease or disorder caused or exacerbated by fibrosis and/or inflammation. Alternatively, the composition may be administered at periodic intervals such as daily, biweekly, weekly, every other week, monthly or bimonthly over an extended period of time for treatment of a subject suffering from or at risk for developing a disease or disorder caused or exacerbated by fibrosis and/or inflammation.

In both prophylactic and therapeutic regimens, compositions comprising MASP-2 inhibitory agents may be administered in several dosages until a sufficient therapeutic outcome has been achieved in the subject.

In some embodiments, a subject is identified to be at risk for developing a disease or disorder caused or exacerbated by fibrosis or inflammation by determining that the subject has one or more symptoms of impaired kidney function, as assessed, for example, by measuring serum creatinine levels, serum creatinine clearance, blood urea nitrogen levels, protein in the urine, and/or by measuring one or more biomarkers associated with a renal disease or injury.

Methods for assessing renal function are well known in the art and include, but art not limited to, measurements of blood systemic and glomerular capillary pressure, proteinuria (e.g., albuminuria), microscopic and macroscopic hematuria, serum creatinine level (e.g., one formula for estimating renal function in humans equates a creatinine level of 2.0 mg/dl to 50 percent of normal kidney function and 4.0 mg/dl to 25 percent), decline in the glomerular filtration rate (e.g., rate of creatinine clearance), and degree of tubular damage. For example, assessment of kidney function may include evaluating at least one kidney function using biological and/or physiological parameters such as serum creatinine level, creatinine clearance rate, 24-hour urinary protein secretion, glomerular filtration rate, urinary albumin creatinine ratio, albumin excretion rate, and renal biopsy (e.g., determining the degree of renal fibrosis by measuring deposition of collagen and/or fibronectin).

VI. Examples

The following examples merely illustrate the best mode now contemplated for practicing the invention, but should not be construed to limit the invention. All literature citations herein are expressly incorporated by reference.

Example 1

This example describes the generation of a mouse strain deficient in MASP-2 (MASP-2−/−) but sufficient of MAp19 (MAp19+/+).

Figure 3:
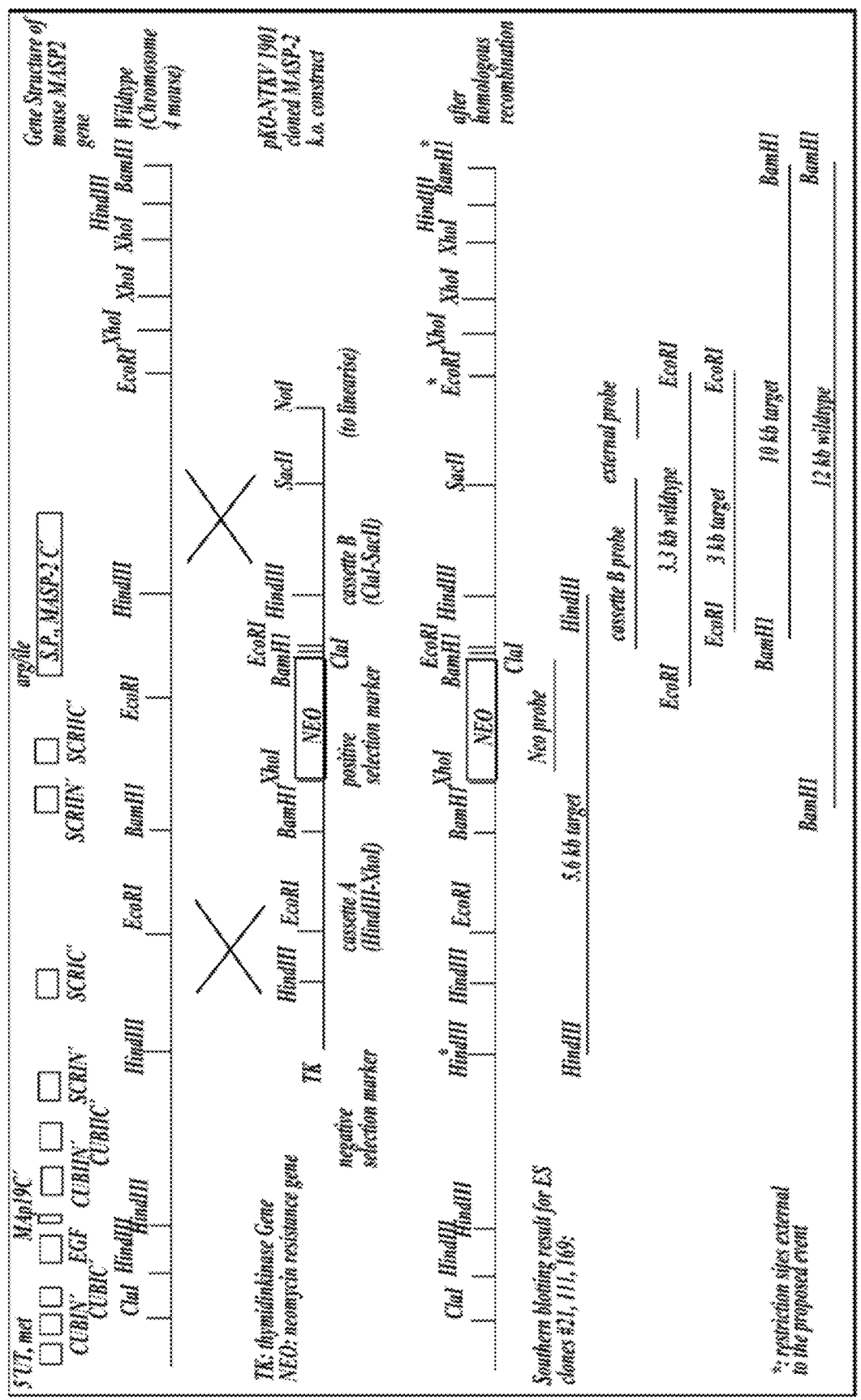
FIG. 3 is a diagram illustrating the murine MASP-2 knockout strategy.

Materials and Methods: The targeting vector pKO-NTKV 1901 was designed to disrupt the three exons coding for the C-terminal end of murine MASP-2, including the exon that encodes the serine protease domain, as shown in FIG. 3. PKO-NTKV 1901 was used to transfect the murine ES cell line E14.1a (SV129 Ola). Neomycin-resistant and Thymidine Kinase-sensitive clones were selected. 600 ES clones were screened and, of these, four different clones were identified and verified by southern blot to contain the expected selective targeting and recombination event as shown in FIG. 3. Chimeras were generated from these four positive clones by embryo transfer. The chimeras were then backcrossed in the genetic background C57/BL6 to create transgenic males. The transgenic males were crossed with females to generate F1s with 50% of the offspring showing heterozygosity for the disrupted MASP-2 gene. The heterozygous mice were intercrossed to generate homozygous MASP-2 deficient offspring, resulting in heterozygous and wild-type mice in the ration of 1:2:1, respectively.

Results and Phenotype:

The resulting homozygous MASP-2−/− deficient mice were found to be viable and fertile and were verified to be MASP-2 deficient by southern blot to confirm the correct targeting event, by Northern blot to confirm the absence of MASP-2 mRNA, and by Western blot to confirm the absence of MASP-2 protein (data not shown). The presence of MAp19 mRNA and the absence of MASP-2 mRNA were further confirmed using time-resolved RT-PCR on a Light-Cycler machine. The MASP-2−/− mice do continue to express MAp19, MASP-1, and MASP-3 mRNA and protein as expected (data not shown). The presence and abundance of mRNA in the MASP-2−/− mice for Properdin, Factor B, Factor D, C4, C2, and C3 was assessed by LightCycler analysis and found to be identical to that of the wild-type littermate controls (data not shown). The plasma from homozygous MASP-2−/− mice is totally deficient of lectin-pathway-mediated complement activation as further described in Example 2.

Generation of a MASP-2−/− strain on a pure C57BL6 Background: The MASP-2−/− mice were back-crossed with a pure C57BL6 line for nine generations prior to use of the MASP-2−/− strain as an experimental animal model.

Figure 4:
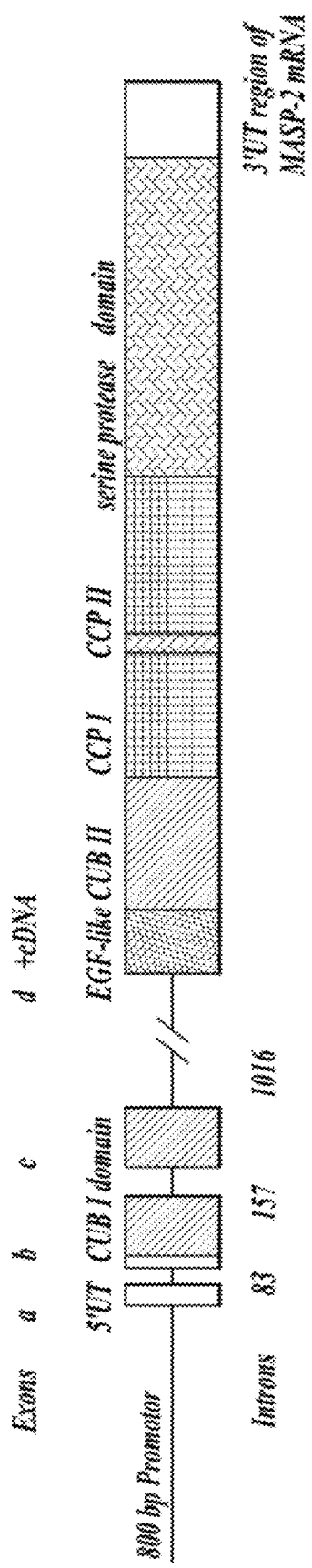
FIG. 4 is a diagram illustrating the human MASP-2 minigene construct.

A transgenic mouse strain that is murine MASP-2−/−, MAp19+/+ and that expresses a human MASP-2 transgene (a murine MASP-2 knock-out and a human MASP-2 knock-in) was also generated as follows:

Materials and Methods:

A minigene encoding human MASP-2 called "mini hMASP-2" (SEQ ID NO:49) as shown in FIG. 4 was constructed which includes the promoter region of the human MASP 2 gene, including the first 3 exons (exon 1 to exon 3) followed by the cDNA sequence that represents the coding sequence of the following 8 exons, thereby encoding the full-length MASP-2 protein driven by its endogenous promoter. The mini hMASP-2 construct was injected into fertilized eggs of MASP-2−/− in order to replace the deficient murine MASP 2 gene by transgenically expressed human MASP-2.

Example 2

This example demonstrates that MASP-2 is required for complement activation via the lectin pathway.

Methods and Materials:

Lectin Pathway Specific C4 Cleavage Assay:

A C4 cleavage assay has been described by Petersen, et al., *J. Immunol. Methods* 257:107 (2001) that measures lectin pathway activation resulting from lipoteichoic acid (LTA) from *S. aureus*, which binds L-ficolin. The assay described by Petersen et al., (2001) was adapted to measure lectin pathway activation via MBL by coating the plate with LPS and mannan or zymosan prior to adding serum from MASP-2−/− mice as described below. The assay was also modified to remove the possibility of C4 cleavage due to the classical pathway. This was achieved by using a sample dilution buffer containing 1 M NaCl, which permits high affinity binding of lectin pathway recognition components to their ligands but prevents activation of endogenous C4, thereby excluding the participation of the classical pathway by dissociating the C1 complex. Briefly described, in the modified assay serum samples (diluted in high salt (1 M NaCl) buffer) are added to ligand-coated plates, followed by the addition of a constant amount of purified C4 in a buffer with a physiological concentration of salt. Bound recognition complexes containing MASP-2 cleave the C4, resulting in C4b deposition.

Assay Methods:

1) Nunc Maxisorb microtiter plates (MaxiSorb, Nunc, Cat. No. 442404, Fisher Scientific) were coated with 1 μg/ml mannan (M7504 Sigma) or any other ligand (e.g., such as those listed below) diluted in coating buffer (15 mM $Na_2CO_3$, 35 mM $NaHCO_3$, pH 9.6).

The following reagents were used in the assay:
a. mannan (1 μg/well mannan (M7504 Sigma) in 100 μl coating buffer):
b. zymosan (1 μg/well zymosan (Sigma) in 100 μl coating buffer),
c. LTA (1 μg/well in 100 μl coating buffer or 2 μg/well in 20 μl methanol)
d. 1 μg of the H-ficolin specific Mab 4H5 in coating buffer
e. PSA from *Aerococcus viridans* (2 μg/well in 100 μl coating buffer)
f. 100 μl/well of formalin-fixed *S. aureus* DSM20233 ($OD_{550}$=0.5) in coating buffer.

2) The plates were incubated overnight at 4° C.

3) After overnight incubation, the residual protein binding sites were saturated by incubated the plates with 0.1%

HSA-TBS blocking buffer (0.1% (w/v) HSA in 10 mM Tris-CL, 140 mM NaCl, 1.5 mM NaN$_3$, pH 7.4) for 1-3 hours, then washing the plates 3× with TBS/tween/Ca$^{2+}$ (TBS with 0.05% Tween 20 and 5 mM CaCl$_2$, 1 mM MgCl$_2$, pH 7.4).

4) Serum samples to be tested were diluted in MBL-binding buffer (1 M NaCl) and the diluted samples were added to the plates and incubated overnight at 4° C. Wells receiving buffer only were used as negative controls.

5) Following incubation overnight at 4° C., the plates were washed 3× with TBS/tween/Ca$^{2+}$. Human C4 (100 µl/well of 1 µg/ml diluted in BBS (4 mM barbital, 145 mM NaCl, 2 mM CaCl$_2$, 1 mM MgCl$_2$, pH 7.4)) was then added to the plates and incubated for 90 minutes at 37° C. The plates were washed again 3× with TBS/tween/Ca$^{2+}$.

6) C4b deposition was detected with an alkaline phosphatase-conjugated chicken anti-human C4c (diluted 1:1000 in TBS/tween/Ca$^{2+}$), which was added to the plates and incubated for 90 minutes at room temperature. The plates were then washed again 3× with TBS/tween/Ca$^{2+}$.

7) Alkaline phosphatase was detected by adding 100 µl of p-nitrophenyl phosphate substrate solution, incubating at room temperature for 20 minutes, and reading the OD$_{405}$ in a microtiter plate reader.

Figure 5A:
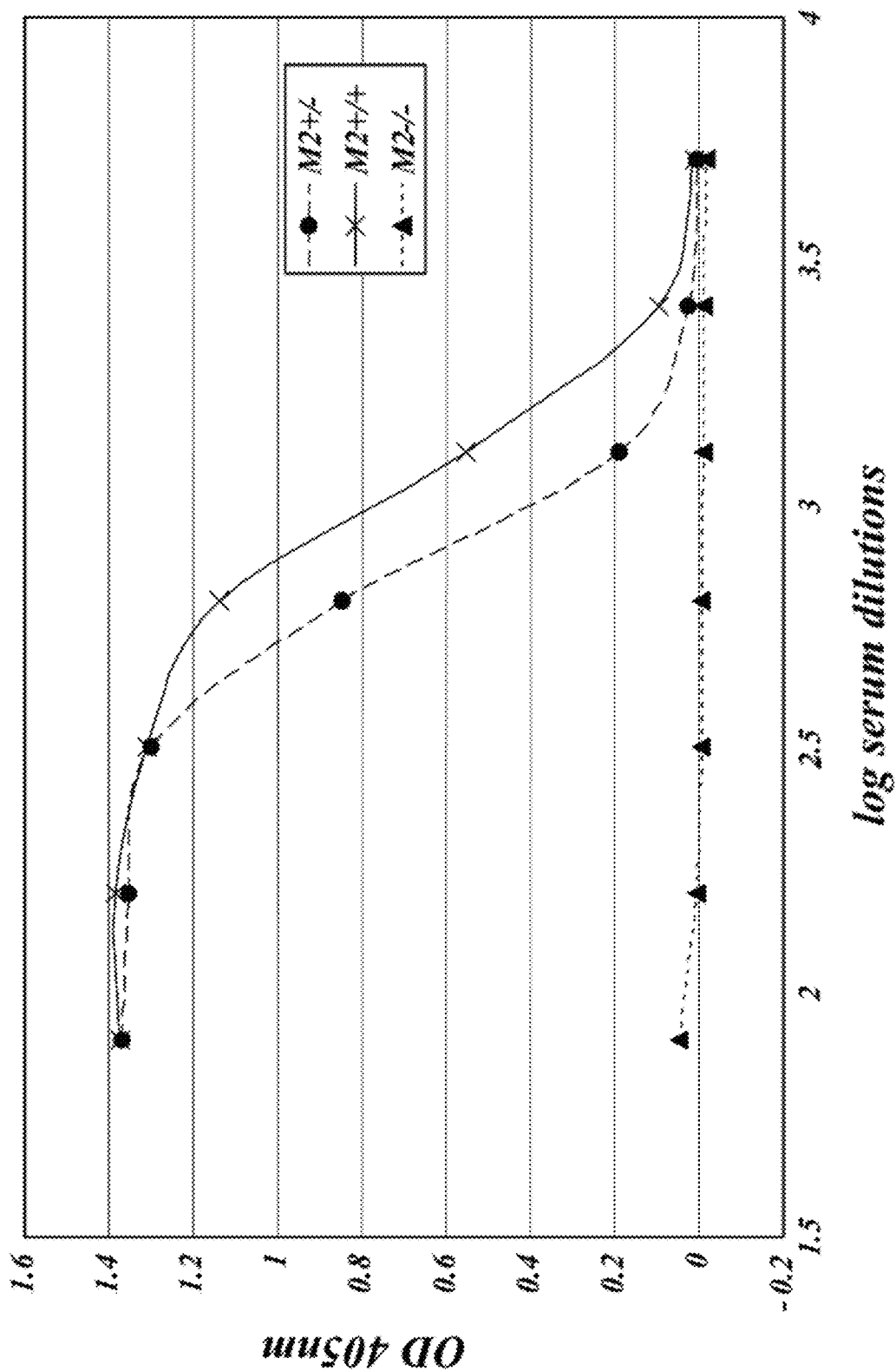
FIG. 5A presents results demonstrating that MASP-2-deficiency leads to the loss of lectin-pathway-mediated C4 activation as measured by lack of C4b deposition on mannan, as described in Example 2.
Figure 5B:
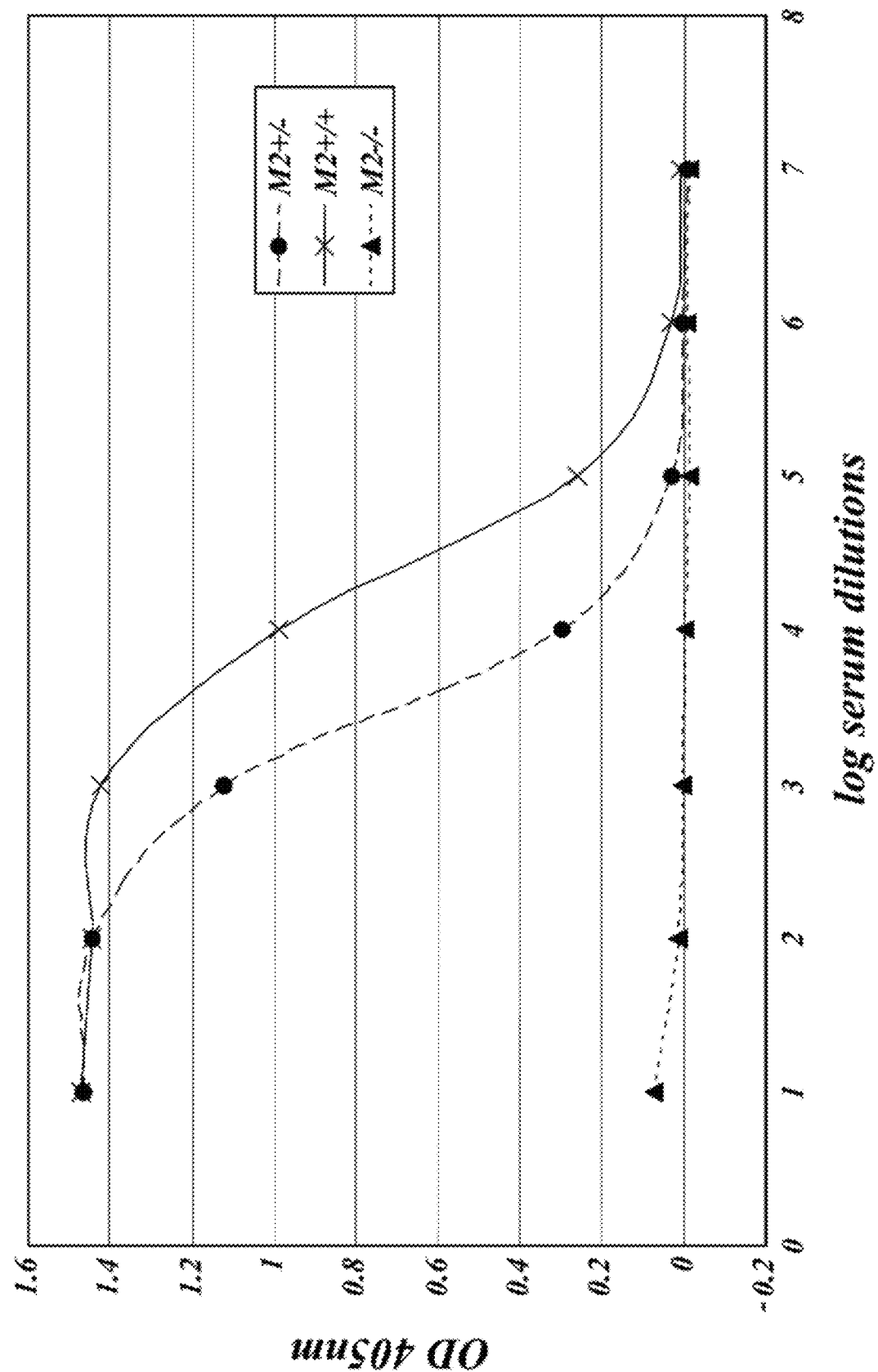
FIG. 5B presents results demonstrating that MASP-2-deficiency leads to the loss of lectin-pathway-mediated C4 activation as measured by lack of C4b deposition on zymosan, as described in Example 2.
Figure 5C:
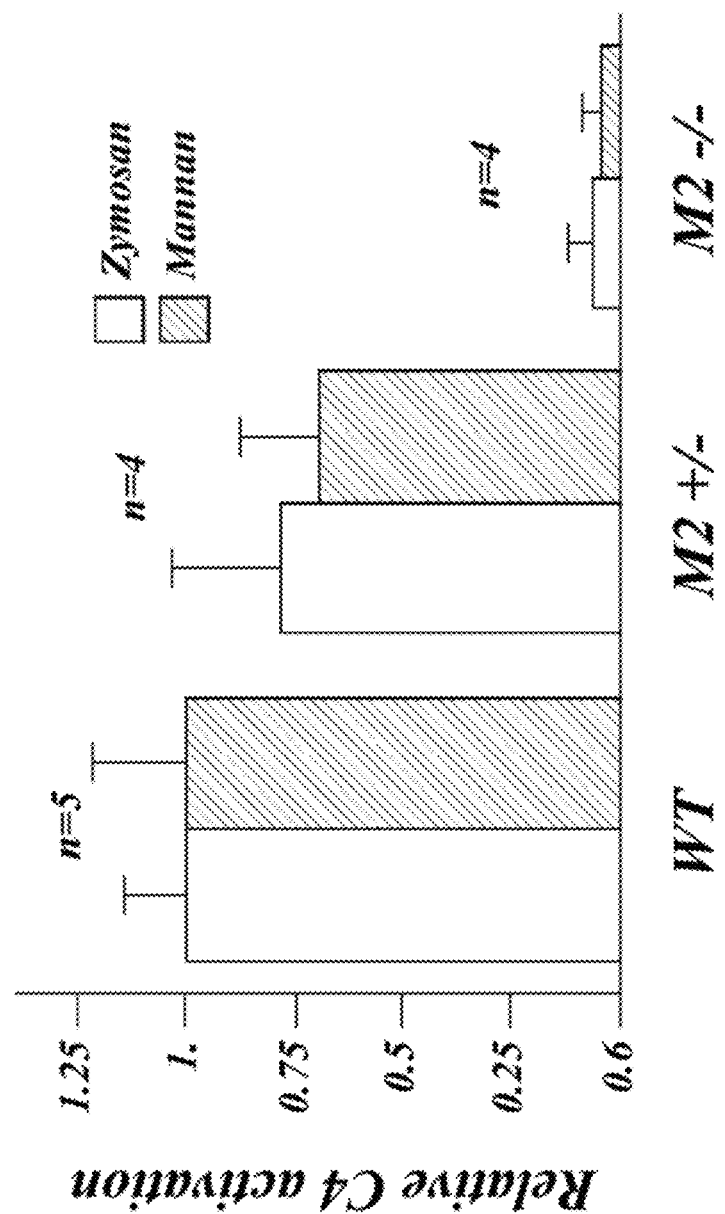
FIG. 5C presents results demonstrating the relative C4 activation levels of serum samples obtained from MASP-2+/−; MASP-2−/− and wild-type strains as measure by C4b deposition on mannan and on zymosan, as described in Example 2.

Results:

FIGS. 5A-B show the amount of C4b deposition on mannan (FIG. 5A) and zymosan (FIG. 5B) in serum dilutions from MASP-2+/+(crosses), MASP-2+/−(closed circles) and MASP-2−/− (closed triangles). FIG. 5C shows the relative C4 convertase activity on plates coated with zymosan (white bars) or mannan (shaded bars) from MASP-2−/+ mice (n=5) and MASP-2−/− mice (n=4) relative to wild-type mice (n=5) based on measuring the amount of C4b deposition normalized to wild-type serum. The error bars represent the standard deviation. As shown in FIGS. 5A-C, plasma from MASP-2−/− mice is totally deficient in lectin-pathway-mediated complement activation on mannan and on zymosan coated plates. These results clearly demonstrate that MASP-2 is an effector component of the lectin pathway.

Recombinant MASP-2 Reconstitutes Lectin Pathway-Dependent C4 Activation in Serum from the MASP-2−/− Mice In order to establish that the absence of MASP-2 was the direct cause of the loss of lectin pathway-dependent C4 activation in the MASP-2−/− mice, the effect of adding recombinant MASP-2 protein to serum samples was examined in the C4 cleavage assay described above. Functionally active murine MASP-2 and catalytically inactive murine MASP-2A (in which the active-site serine residue in the serine protease domain was substituted for the alanine residue) recombinant proteins were produced and purified as described below in Example 3. Pooled serum from 4 MASP-2−/− mice was pre-incubated with increasing protein concentrations of recombinant murine MASP-2 or inactive recombinant murine MASP-2A and C4 convertase activity was assayed as described above.

Figure 6:
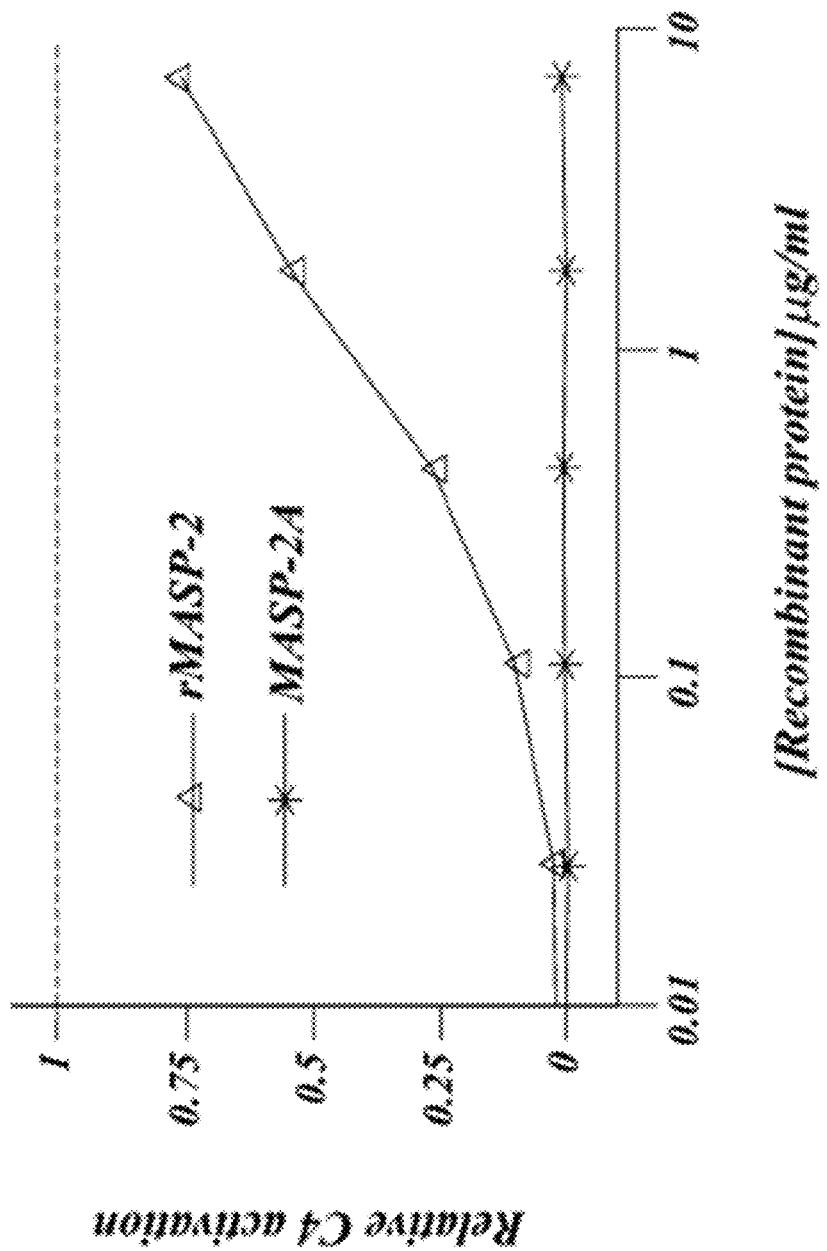
FIG. 6 presents results demonstrating that the addition of murine recombinant MASP-2 to MASP-2−/− serum samples recovers lectin-pathway-mediated C4 activation in a protein concentration dependent manner, as measured by C4b deposition on mannan, as described in Example 2.

Results:

As shown in FIG. 6, the addition of functionally active murine recombinant MASP-2 protein (shown as open triangles) to serum obtained from the MASP-2−/− mice restored lectin pathway-dependent C4 activation in a protein concentration dependent manner, whereas the catalytically inactive murine MASP-2A protein (shown as stars) did not restore C4 activation. The results shown in FIG. 6 are normalized to the C4 activation observed with pooled wild-type mouse serum (shown as a dotted line).

Example 3

This example describes the recombinant expression and protein production of recombinant full-length human, rat and murine MASP-2, MASP-2 derived polypeptides, and catalytically inactivated mutant forms of MASP-2

Expression of Full-Length Human, Murine and Rat MASP-2:

The full length cDNA sequence of human MASP-2 (SEQ ID NO: 4) was also subcloned into the mammalian expression vector pCI-Neo (Promega), which drives eukaryotic expression under the control of the CMV enhancer/promoter region (described in Kaufman R. J. et al., *Nucleic Acids Research* 19:4485-90, 1991; Kaufman, *Methods in Enzymology*, 185:537-66 (1991)). The full length mouse cDNA (SEQ ID NO:50) and rat MASP-2 cDNA (SEQ ID NO:53) were each subcloned into the pED expression vector. The MASP-2 expression vectors were then transfected into the adherent Chinese hamster ovary cell line DXB1 using the standard calcium phosphate transfection procedure described in Maniatis et al., 1989. Cells transfected with these constructs grew very slowly, implying that the encoded protease is cytotoxic.

In another approach, the minigene construct (SEQ ID NO:49) containing the human cDNA of MASP-2 driven by its endogenous promoter is transiently transfected into Chinese hamster ovary cells (CHO). The human MASP-2 protein is secreted into the culture media and isolated as described below.

Expression of Full-Length Catalytically Inactive MASP-2:

Rationale: MASP-2 is activated by autocatalytic cleavage after the recognition subcomponents MBL or ficolins (either L-ficolin, H-ficolin or M-ficolin) bind to their respective carbohydrate pattern. Autocatalytic cleavage resulting in activation of MASP-2 often occurs during the isolation procedure of MASP-2 from serum, or during the purification following recombinant expression. In order to obtain a more stable protein preparation for use as an antigen, a catalytically inactive form of MASP-2, designed as MASP-2A was created by replacing the serine residue that is present in the catalytic triad of the protease domain with an alanine residue in rat (SEQ ID NO:55 Ser617 to Ala617); in mouse (SEQ ID NO:52 Ser617 to Ala617); or in human (SEQ ID NO:6 Ser618 to Ala618).

In order to generate catalytically inactive human and murine MASP-2A proteins, site-directed mutagenesis was carried out using the oligonucleotides shown in TABLE 5. The oligonucleotides in TABLE 5 were designed to anneal to the region of the human and murine cDNA encoding the enzymatically active serine and oligonucleotide contain a mismatch in order to change the serine codon into an alanine codon. For example, PCR oligonucleotides SEQ ID NOS: 56-59 were used in combination with human MASP-2 cDNA (SEQ ID NO:4) to amplify the region from the start codon to the enzymatically active serine and from the serine to the stop codon to generate the complete open reading from of the mutated MASP-2A containing the Ser618 to Ala618 mutation. The PCR products were purified after agarose gel electrophoresis and band preparation and single adenosine overlaps were generated using a standard tailing procedure. The adenosine tailed MASP-2A was then cloned into the pGEM-T easy vector, transformed into *E. coli*.

A catalytically inactive rat MASP-2A protein was generated by kinasing and annealing SEQ ID NO:64 and SEQ ID NO:65 by combining these two oligonucleotides in equal molar amounts, heating at 100° C. for 2 minutes and slowly cooling to room temperature. The resulting annealed fragment has Pst1 and Xba1 compatible ends and was inserted in place of the Pst1-Xba1 fragment of the wild-type rat MASP-2 cDNA (SEQ ID NO:53) to generate rat MASP-2A.

5'GAGGTGACGCAGGAGGGGCATTAGTGTTT 3' (SEQ ID NO: 64)

5'CTAGAAACACTAATGCCCCTCCTGCGTCACCTCTGCA 3' (SEQ ID NO: 65)

The human, murine and rat MASP-2A were each further subcloned into either of the mammalian expression vectors pED or pCI-Neo and transfected into the Chinese Hamster ovary cell line DXB1 as described below.

In another approach, a catalytically inactive form of MASP-2 is constructed using the method described in Chen et al., *J. Biol. Chem.*, 276(28):25894-25902, 2001. Briefly, the plasmid containing the full-length human MASP-2 cDNA (described in Thiel et al., *Nature* 386:506, 1997) is digested with Xho1 and EcoR1 and the MASP-2 cDNA (described herein as SEQ ID NO:4) is cloned into the corresponding restriction sites of the pFastBac1 baculovirus transfer vector (Life Technologies, NY). The MASP-2 serine protease active site at Ser618 is then altered to Ala618 by substituting the double-stranded oligonucleotides encoding the peptide region amino acid 610-625 (SEQ ID NO:13) with the native region amino acids 610 to 625 to create a MASP-2 full length polypeptide with an inactive protease domain.

Construction of Expression Plasmids Containing Polypeptide Regions Derived from Human MASP-2.

The following constructs are produced using the MASP-2 signal peptide (residues 1-15 of SEQ ID NO:5) to secrete various domains of MASP-2. A construct expressing the human MASP-2 CUBI domain (SEQ ID NO:8) is made by PCR amplifying the region encoding residues 1-121 of MASP-2 (SEQ ID NO:6) (corresponding to the N-terminal CUBI domain). A construct expressing the human MASP-2 CUBIEGF domain (SEQ ID NO:9) is made by PCR amplifying the region encoding residues 1-166 of MASP-2 (SEQ ID NO:6) (corresponding to the N-terminal CUBIEGF domain). A construct expressing the human MASP-2 CUBIEGFCUBII domain (SEQ ID NO: 10) is made by PCR amplifying the region encoding residues 1-293 of MASP-2 (SEQ ID NO:6) (corresponding to the N-terminal CUBIEGFCUBII domain). The above mentioned domains are amplified by PCR using Vent$_R$ polymerase and pBS-MASP-2 as a template, according to established PCR methods. The 5' primer sequence of the sense primer (5'-CGGATCCATGAGGCTGCTGACCCTC-3' SEQ ID NO:34) introduces a BamHI restriction site (underlined) at the 5' end of the PCR products. Antisense primers for each of the MASP-2 domains, shown below in TABLE 5, are designed to introduce a stop codon (boldface) followed by an EcoRI site (underlined) at the end of each PCR product. Once amplified, the DNA fragments are digested with BamHI and EcoRI and cloned into the corresponding sites of the pFastBac1 vector. The resulting constructs are characterized by restriction mapping and confirmed by dsDNA sequencing.

TABLE 5

MASP-2 PCR PRIMERS

| MASP-2 domain | 5' PCR Primer | 3' PCR Primer |
|---|---|---|
| SEQ ID NO: 8 CUBI (aa 1-121 of SEQ ID NO: 6) | 5'CGGGATCCATGAG GCTGCTGACCCTC-3' (SEQ ID NO: 34) | 5'GGAATTCCTAGGCTGCA TA (SEQ ID NO: 35) |
| SEQ ID NO: 9 CUBIEGF (aa 1-166 of SEQ ID NO: 6) | 5'CGGGATCCATGAG GCTGCTGACCCTC-3' (SEQ ID NO: 34) | 5'GGAATTCCTACAGGGCG CT-3' (SEQ ID NO: 36) |
| SEQ ID NO: 10 CUBIEGFCUBII (aa 1-293 of SEQ ID NO: 6) | 5'CGGGATCCATGAG GCTGCTGACCCTC-3' (SEQ ID NO: 34) | 5'GGAATTCCTAGTAGTGG AT 3' (SEQ ID NO: 37) |
| SEQ ID NO: 4 human MASP-2 | 5'ATGAGGCTGCTGA CCCTCCTGGGCCTTC 3' (SEQ ID NO: 56) hMASP-2_forward | 5'TTAAAATCACTAATTAT GTTCTCGATC 3' (SEQ ID NO: 59) hMASP-2_reverse |
| SEQ ID NO: 4 human MASP-2 cDNA | 5'CAGAGGTGACGCA GGAGGGGCAC 3' (SEQ ID NO: 58) hMASP-2_ala_forward | 5'GTGCCCCTCCTGCGTCA CCTCTG 3' (SEQ ID NO: 57) hMASP-2_ala_reverse |
| SEQ ID NO: 50 Murine MASP-2 (DNA | 5'ATGAGGCTACTCA TCTTCCTGG3' (SEQ ID NO: 60) mMASP-2_forward | 5'TTAGAAATTACTTATTAT GTTGTCAATCC3' (SEQ ID NO: 63) mMASP-2_reverse |
| SEQ ID NO: 50 Murine MASP-2 cDNA | 5'CCCCCCCTGCGTC ACCTCTGCAG3' (SEQ ID NO: 62) mMASP-2_ala_forward | 5'CTGCAGAGGTGACGCAG GGGGG 3' (SEQ ID NO: 61) mMASP-2_ala_reverse |

Recombinant Eukaryotic Expression of MASP-2 and Protein Production of Enzymatically Inactive Mouse, Rat, and Human MASP-2A.

The MASP-2 and MASP-2A expression constructs described above were transfected into DXB1 cells using the standard calcium phosphate transfection procedure (Maniatis et al., 1989). MASP-2A was produced in serum-free medium to ensure that preparations were not contaminated with other serum proteins. Media was harvested from confluent cells every second day (four times in total). The level of recombinant MASP-2A averaged approximately 1.5 mg/liter of culture medium for each of the three species.

MASP-2A Protein Purification:

The MASP-2A (Ser-Ala mutant described above) was purified by affinity chromatography on MBP-A-agarose columns. This strategy enabled rapid purification without the use of extraneous tags. MASP-2A (100-200 ml of medium diluted with an equal volume of loading buffer (50 mM Tris-Cl, pH 7.5, containing 150 mM NaCl and 25 mM $CaCl_2$) was loaded onto an MBP-agarose affinity column (4 ml) pre-equilibrated with 10 ml of loading buffer. Following washing with a further 10 ml of loading buffer, protein was eluted in 1 ml fractions with 50 mM Tris-Cl, pH 7.5, containing 1.25 M NaCl and 10 mM EDTA. Fractions containing the MASP-2A were identified by SDS-polyacrylamide gel electrophoresis. Where necessary, MASP-2A was purified further by ion-exchange chromatography on a MonoQ column (HR 5/5). Protein was dialyzed with 50 mM Tris-Cl pH 7.5, containing 50 mM NaCl and loaded onto the column equilibrated in the same buffer. Following washing, bound MASP-2A was eluted with a 0.05-1 M NaCl gradient over 10 ml.

Results:

Yields of 0.25-0.5 mg of MASP-2A protein were obtained from 200 ml of medium. The molecular mass of 77.5 kDa determined by MALDI-MS is greater than the calculated value of the unmodified polypeptide (73.5 kDa) due to glycosylation. Attachment of glycans at each of the N-glycosylation sites accounts for the observed mass. MASP-2A migrates as a single band on SDS-polyacrylamide gels, demonstrating that it is not proteolytically processed during biosynthesis. The weight-average molecular mass determined by equilibrium ultracentrifugation is in agreement with the calculated value for homodimers of the glycosylated polypeptide.

Production of Recombinant Human MASP-2 Polypeptides

Another method for producing recombinant MASP-2 and MASP2A derived polypeptides is described in Thielens, N. M., et al., *J. Immunol.* 166:5068-5077, 2001. Briefly, the *Spodoptera frugiperda* insect cells (Ready-Plaque Sf9 cells obtained from Novagen, Madison, Wis.) are grown and maintained in Sf900II serum-free medium (Life Technologies) supplemented with 50 IU/ml penicillin and 50 mg/ml streptomycin (Life Technologies). The *Trichoplusia ni* (High Five) insect cells (provided by Jadwiga Chroboczek, Institut de Biologie Structurale, Grenoble, France) are maintained in TC100 medium (Life Technologies) containing 10% FCS (Dominique Dutscher, Brumath, France) supplemented with 50 IU/ml penicillin and 50 mg/ml streptomycin. Recombinant baculoviruses are generated using the Bac-to-Bac System® (Life Technologies). The bacmid DNA is purified using the Qiagen midiprep purification system (Qiagen) and is used to transfect Sf9 insect cells using cellfectin in Sf900 II SFM medium (Life Technologies) as described in the manufacturer's protocol. Recombinant virus particles are collected 4 days later, titrated by virus plaque assay, and amplified as described by King and Possee, in *The Baculovirus Expression System: A Laboratory Guide*, Chapman and Hall Ltd., London, pp. 111-114, 1992.

High Five cells ($1.75 \times 10^7$ cells/175-$cm^2$ tissue culture flask) are infected with the recombinant viruses containing MASP-2 polypeptides at a multiplicity of infection of 2 in Sf900 II SFM medium at 28° C. for 96 h. The supernatants are collected by centrifugation and diisopropyl phosphorofluoridate is added to a final concentration of 1 mM.

The MASP-2 polypeptides are secreted in the culture medium. The culture supernatants are dialyzed against 50 mM NaCl, 1 mM $CaCl_2$, 50 mM triethanolamine hydrochloride, pH 8.1, and loaded at 1.5 ml/min onto a Q-Sepharose Fast Flow column (Amersham Pharmacia Biotech) (2.8×12 cm) equilibrated in the same buffer. Elution is conducted by applying a 1.2 liter linear gradient to 350 mM NaCl in the same buffer. Fractions containing the recombinant MASP-2 polypeptides are identified by Western blot analysis, precipitated by addition of $(NH_4)_2SO_4$ to 60% (w/v), and left overnight at 4° C. The pellets are resuspended in 145 mM NaCl, 1 mM $CaCl_2$, 50 mM triethanolamine hydrochloride, pH 7.4, and applied onto a TSK G3000 SWG column (7.5×600 mm) (Tosohaas, Montgomeryville, Pa.) equilibrated in the same buffer. The purified polypeptides are then concentrated to 0.3 mg/ml by ultrafiltration on Microsep microconcentrators (m.w. cut-off=10,000) (Filtron, Karlstein, Germany).

Example 4

This example describes a method of producing polyclonal antibodies against MASP-2 polypeptides.

Materials and Methods:

MASP-2 Antigens:

Polyclonal anti-human MASP-2 antiserum is produced by immunizing rabbits with the following isolated MASP-2 polypeptides: human MASP-2 (SEQ ID NO:6) isolated from serum; recombinant human MASP-2 (SEQ ID NO:6), MASP-2A containing the inactive protease domain (SEQ ID NO:13), as described in Example 3; and recombinant CUBI (SEQ ID NO:8), CUBEGFI (SEQ ID NO:9), and CUBEGFCUBII (SEQ ID NO:10) expressed as described above in Example 3.

Polyclonal Antibodies:

Six-week old Rabbits, primed with BCG (*bacillus* Calmette-Guerin vaccine) are immunized by injecting 100 μg of MASP-2 polypeptide at 100 gig/ml in sterile saline solution. Injections are done every 4 weeks, with antibody titer monitored by ELISA assay as described in Example 5. Culture supernatants are collected for antibody purification by protein A affinity chromatography.

Example 5

This example describes a method for producing murine monoclonal antibodies against rat or human MASP-2 polypeptides.

Materials and Methods:

Male A/J mice (Harlan, Houston, Tex.), 8-12 weeks old, are injected subcutaneously with 100 gig human or rat rMASP-2 or rMASP-2A polypeptides (made as described in Example 3) in complete Freund's adjuvant (Difco Laboratories, Detroit, Mich.) in 200 μl of phosphate buffered saline (PBS) pH 7.4. At two-week intervals the mice are twice injected subcutaneously with 50 μg of human or rat rMASP-2 or rMASP-2A polypeptide in incomplete Freund's adjuvant. On the fourth week the mice are injected with 50 μg of human or rat rMASP-2 or rMASP-2A polypeptide in PBS and are fused 4 days later.

For each fusion, single cell suspensions are prepared from the spleen of an immunized mouse and used for fusion with Sp2/0 myeloma cells. $5 \times 10^8$ of the Sp2/0 and $5 \times 10^8$ spleen cells are fused in a medium containing 50% polyethylene glycol (M.W. 1450) (Kodak, Rochester, N.Y.) and 5% dimethylsulfoxide (Sigma Chemical Co., St. Louis, Mo.). The cells are then adjusted to a concentration of $1.5 \times 10^5$ spleen cells per 200 μl of the suspension in Iscove medium (Gibco, Grand Island, N.Y.), supplemented with 10% fetal bovine serum, 100 units/ml of penicillin, 100 μg/ml of streptomycin, 0.1 mM hypoxanthine, 0.4 µM aminopterin and 16 µM thymidine. Two hundred microliters of the cell suspension are added to each well of about twenty 96-well microculture plates. After about ten days culture supernatants are withdrawn for screening for reactivity with purified factor MASP-2 in an ELISA assay.

ELISA Assay:

Wells of Immulon® 2 (Dynatech Laboratories, Chantilly, Va.) microtest plates are coated by adding 50 µl of purified hMASP-2 at 50 ng/ml or rat rMASP-2 (or rMASP-2A) overnight at room temperature. The low concentration of MASP-2 for coating enables the selection of high-affinity antibodies. After the coating solution is removed by flicking the plate, 200 µl of BLOTTO (non-fat dry milk) in PBS is added to each well for one hour to block the non-specific sites. An hour later, the wells are then washed with a buffer PBST (PBS containing 0.05% Tween 20). Fifty microliters of culture supernatants from each fusion well is collected and mixed with 50 µl of BLOTTO and then added to the individual wells of the microtest plates. After one hour of incubation, the wells are washed with PBST. The bound murine antibodies are then detected by reaction with horseradish peroxidase (HRP) conjugated goat anti-mouse IgG (Fc specific) (Jackson ImmunoResearch Laboratories, West Grove, Pa.) and diluted at 1:2,000 in BLOTTO. Peroxidase substrate solution containing 0.1% 3,3,5,5 tetramethyl benzidine (Sigma, St. Louis, Mo.) and 0.0003% hydrogen peroxide (Sigma) is added to the wells for color development for 30 minutes. The reaction is terminated by addition of 50 µl of 2M $H_2SO_4$ per well. The Optical Density at 450 nm of the reaction mixture is read with a BioTek ELISA Reader (BioTek® Instruments, Winooski, Vt.).

MASP-2 Binding Assay:

Culture supernatants that test positive in the MASP-2 ELISA assay described above can be tested in a binding assay to determine the binding affinity the MASP-2 inhibitory agents have for MASP-2. A similar assay can also be used to determine if the inhibitory agents bind to other antigens in the complement system.

Polystyrene microtiter plate wells (96-well medium binding plates, Corning Costar, Cambridge, Mass.) are coated with MASP-2 (20 ng/100 µl/well, Advanced Research Technology, San Diego, Calif.) in phosphate-buffered saline (PBS) pH 7.4 overnight at 4° C. After aspirating the MASP-2 solution, wells are blocked with PBS containing 1% bovine serum albumin (BSA; Sigma Chemical) for 2 h at room temperature. Wells without MASP-2 coating serve as the background controls. Aliquots of hybridoma supernatants or purified anti-MASP-2 MoAbs, at varying concentrations in blocking solution, are added to the wells. Following a 2 h incubation at room temperature, the wells are extensively rinsed with PBS. MASP-2-bound anti-MASP-2 MoAb is detected by the addition of peroxidase-conjugated goat anti-mouse IgG (Sigma Chemical) in blocking solution, which is allowed to incubate for 1 h at room temperature. The plate is rinsed again thoroughly with PBS, and 100 µl of 3,3',5,5'-tetramethyl benzidine (TMB) substrate (Kirkegaard and Perry Laboratories, Gaithersburg, Md.) is added. The reaction of TMB is quenched by the addition of 100 µl of 1M phosphoric acid, and the plate is read at 450 nm in a microplate reader (SPECTRA MAX 250, Molecular Devices, Sunnyvale, Calif.).

The culture supernatants from the positive wells are then tested for the ability to inhibit complement activation in a functional assay such as the C4 cleavage assay as described in Example 2. The cells in positive wells are then cloned by limiting dilution. The MoAbs are tested again for reactivity with hMASP-2 in an ELISA assay as described above. The selected hybridomas are grown in spinner flasks and the spent culture supernatant collected for antibody purification by protein A affinity chromatography.

Example 6

This example describes the generation and production of humanized murine anti-MASP-2 antibodies and antibody fragments.

A murine anti-MASP-2 monoclonal antibody is generated in Male A/J mice as described in Example 5. The murine antibody is then humanized as described below to reduce its immunogenicity by replacing the murine constant regions with their human counterparts to generate a chimeric IgG and Fab fragment of the antibody, which is useful for inhibiting the adverse effects of MASP-2-dependent complement activation in human subjects in accordance with the present invention.

1. Cloning of Anti-MASP-2 Variable Region Genes from Murine Hybridoma Cells.

Total RNA is isolated from the hybridoma cells secreting anti-MASP-2 MoAb (obtained as described in Example 7) using RNAzol following the manufacturer's protocol (Biotech, Houston, Tex.). First strand cDNA is synthesized from the total RNA using oligo dT as the primer. PCR is performed using the immunoglobulin constant C region-derived 3' primers and degenerate primer sets derived from the leader peptide or the first framework region of murine $V_H$ or $V_K$ genes as the 5' primers. Anchored PCR is carried out as described by Chen and Platsucas (Chen, P. F., *Scand. J. Immunol.* 35:539-549, 1992). For cloning the $V_K$ gene, double-stranded cDNA is prepared using a Not1-MAK1 primer (5'-TGCGGCCGCTGTAGGTGCTGTCTTT-3' SEQ ID NO:38). Annealed adaptors AD1 (5'-GGAATTCACTCGTTATTCTCGGA-3' SEQ ID NO:39) and AD2 (5'-TCCGAGAATAACGAGTG-3' SEQ ID NO:40) are ligated to both 5' and 3' termini of the double-stranded cDNA. Adaptors at the 3' ends are removed by Nod digestion. The digested product is then used as the template in PCR with the AD1 oligonucleotide as the 5' primer and MAK2 (5'-CATTGAAAGCTTTGGGGTAGAAGTTGTTC-3' SEQ ID NO:41) as the 3' primer. DNA fragments of approximately 500 bp are cloned into pUC19. Several clones are selected for sequence analysis to verify that the cloned sequence encompasses the expected murine immunoglobulin constant region. The Not1-MAK1 and MAK2 oligonucleotides are derived from the $V_K$ region and are 182 and 84 bp, respectively, downstream from the first base pair of the C kappa gene. Clones are chosen that include the complete $V_K$ and leader peptide.

For cloning the $V_H$ gene, double-stranded cDNA is prepared using the Not1 MAG1 primer (5'-CGCGGCCGCAGCTGCTCAGAGTGTAGA-3' SEQ ID NO:42). Annealed adaptors AD1 and AD2 are ligated to both 5' and 3' termini of the double-stranded cDNA. Adaptors at the 3' ends are removed by Not1 digestion. The digested product are used as the template in PCR with the AD1 oligonucleotide and MAG2 (5'-CGGTAAGCTTCACTGGCTCAGGGAAATA-3' SEQ ID NO:43) as primers. DNA fragments of 500 to 600 bp in length are cloned into pUC19. The Not1-MAG1 and MAG2 oligonucleotides are derived from the murine Cγ.7.1 region, and are 180 and 93 bp, respectively, downstream from the first bp of the murine Cγ.7.1 gene. Clones are chosen that encompass the complete $V_H$ and leader peptide.

2. Construction of Expression Vectors for Chimeric MASP-2 IgG and Fab.

The cloned $V_H$ and $V_K$ genes described above are used as templates in a PCR reaction to add the Kozak consensus sequence to the 5' end and the splice donor to the 3' end of the nucleotide sequence. After the sequences are analyzed to confirm the absence of PCR errors, the $V_H$ and $V_K$ genes are inserted into expression vector cassettes containing human C.γ1 and C. kappa respectively, to give pSV2neoV$_H$-huCγ1 and pSV2neoV-huCγ. CsCl gradient-purified plasmid DNAs of the heavy- and light-chain vectors are used to transfect COS cells by electroporation. After 48 hours, the culture supernatant is tested by ELISA to confirm the presence of approximately 200 ng/ml of chimeric IgG. The cells are harvested and total RNA is prepared. First strand cDNA is synthesized from the total RNA using oligo dT as the primer. This cDNA is used as the template in PCR to generate the Fd and kappa DNA fragments. For the Fd gene, PCR is carried out using 5'-AAGAAGCTTGCCGCCACCATG-GATTGGCTGTGGAACT-3' (SEQ ID NO:44) as the 5' primer and a CH1-derived 3' primer (5'-CGGGATCCT-CAAACTTTCTTGTCCACCTTGG-3' SEQ ID NO:45). The DNA sequence is confirmed to contain the complete $V_H$ and the CH1 domain of human IgG1. After digestion with the proper enzymes, the Fd DNA fragments are inserted at the HindIII and BamHI restriction sites of the expression vector cassette pSV2dhfr-TUS to give pSV2dhfrFd. The pSV2 plasmid is commercially available and consists of DNA segments from various sources: pBR322 DNA (thin line) contains the pBR322 origin of DNA replication (pBR ori) and the lactamase ampicillin resistance gene (Amp); SV40 DNA, represented by wider hatching and marked, contains the SV40 origin of DNA replication (SV40 ori), early promoter (5' to the dhfr and neo genes), and polyadenylation signal (3' to the dhfr and neo genes). The SV40-derived polyadenylation signal (pA) is also placed at the 3' end of the Fd gene.

For the kappa gene, PCR is carried out using 5'-AAGAAAGCTTGCCGCCACCATGTTCT-CACTAGCTCT-3' (SEQ ID NO:46) as the 5' primer and a CK-derived 3' primer (5'-CGGGATCCTTCTC-CCTCTAACACTCT-3' SEQ ID NO:47). DNA sequence is confirmed to contain the complete $V_K$ and human CK regions. After digestion with proper restriction enzymes, the kappa DNA fragments are inserted at the HindIII and BamHI restriction sites of the expression vector cassette pSV2neo-TUS to give pSV2neoK. The expression of both Fd and .kappa genes are driven by the HCMV-derived enhancer and promoter elements. Since the Fd gene does not include the cysteine amino acid residue involved in the inter-chain disulfide bond, this recombinant chimeric Fab contains non-covalently linked heavy- and light-chains. This chimeric Fab is designated as cFab.

To obtain recombinant Fab with an inter-heavy and light chain disulfide bond, the above Fd gene may be extended to include the coding sequence for additional 9 amino acids (EPKSCDKTH SEQ ID NO:48) from the hinge region of human IgG1. The BstEII-BamHI DNA segment encoding 30 amino acids at the 3' end of the Fd gene may be replaced with DNA segments encoding the extended Fd, resulting in pSV2dhfrFd/9aa.

3. Expression and Purification of Chimeric Anti-MASP-2 IgG

To generate cell lines secreting chimeric anti-MASP-2 IgG, NSO cells are transfected with purified plasmid DNAs of pSV2neoV$_H$-huC.γ1 and pSV2neoV-huC kappa by electroporation. Transfected cells are selected in the presence of 0.7 mg/ml G418. Cells are grown in a 250 ml spinner flask using serum-containing medium.

Culture supernatant of 100 ml spinner culture is loaded on a 10-ml PROSEP-A column (Bioprocessing, Inc., Princeton, N.J.). The column is washed with 10 bed volumes of PBS. The bound antibody is eluted with 50 mM citrate buffer, pH 3.0. Equal volume of 1 M Hepes, pH 8.0 is added to the fraction containing the purified antibody to adjust the pH to 7.0. Residual salts are removed by buffer exchange with PBS by Millipore membrane ultrafiltration (M.W. cut-off: 3,000). The protein concentration of the purified antibody is determined by the BCA method (Pierce).

4. Expression and Purification of Chimeric Anti-MASP-2 Fab

To generate cell lines secreting chimeric anti-MASP-2 Fab, CHO cells are transfected with purified plasmid DNAs of pSV2dhfrFd (or pSV2dhfrFd/9aa) and pSV2neokappa, by electroporation. Transfected cells are selected in the presence of G418 and methotrexate. Selected cell lines are amplified in increasing concentrations of methotrexate. Cells are single-cell subcloned by limiting dilution. High-producing single-cell subcloned cell lines are then grown in 100 ml spinner culture using serum-free medium.

Chimeric anti-MASP-2 Fab is purified by affinity chromatography using a mouse anti-idiotypic MoAb to the MASP-2 MoAb. An anti-idiotypic MASP-2 MoAb can be made by immunizing mice with a murine anti-MASP-2 MoAb conjugated with keyhole limpet hemocyanin (KLH) and screening for specific MoAb binding that can be competed with human MASP-2. For purification, 100 ml of supernatant from spinner cultures of CHO cells producing cFab or cFab/9aa are loaded onto the affinity column coupled with an anti-idiotype MASP-2 MoAb. The column is then washed thoroughly with PBS before the bound Fab is eluted with 50 mM diethylamine, pH 11.5. Residual salts are removed by buffer exchange as described above. The protein concentration of the purified Fab is determined by the BCA method (Pierce).

The ability of the chimeric MASP-2 IgG, cFab, and cFAb/9aa to inhibit MASP-2-dependent complement pathways may be determined by using the inhibitory assays described in Example 2 or Example 7.

Example 7

This example describes an in vitro C4 cleavage assay used as a functional screen to identify MASP-2 inhibitory agents capable of blocking MASP-2-dependent complement activation via L-ficolin/P35, H-ficolin, M-ficolin or mannan.

C4 Cleavage Assay:

A C4 cleavage assay has been described by Petersen, S. V., et al., *J. Immunol. Methods* 257:107, 2001, which measures lectin pathway activation resulting from lipoteichoic acid (LTA) from *S. aureus* which binds L-ficolin.

Reagents:

Formalin-fixed *S. aureus* (DSM20233) is prepared as follows: bacteria is grown overnight at 37° C. in tryptic soy blood medium, washed three times with PBS, then fixed for 1 h at room temperature in PBS/0.5% formalin, and washed a further three times with PBS, before being resuspended in coating buffer (15 mM Na$_2$Co$_3$, 35 mM NaHCO$_3$, pH 9.6).

Assay:

The wells of a Nunc MaxiSorbI microtiter plate (Nalgene Nunc International, Rochester, N.Y.) are coated with: 100 µl of formalin-fixed *S. aureus* DSM20233 (OD$_{550}$=0.5) in coating buffer with 1 µg of L-ficolin in coating buffer. After overnight incubation, wells are blocked with 0.1% human serum albumin (HSA) in TBS (10 mM Tris-HCl, 140 mM NaCl, pH 7.4), then are washed with TBS containing 0.05% Tween 20 and 5 mM $CaCl_2$ (wash buffer). Human serum samples are diluted in 20 mM Tris-HCl, 1 M NaCl, 10 mM $CaCl_2$, 0.05% Triton X-100, 0.1% HSA, pH 7.4, which prevents activation of endogenous C4 and dissociates the C1 complex (composed of C1q, C1r and C1s). MASP-2 inhibitory agents, including anti-MASP-2 MoAbs and inhibitory peptides are added to the serum samples in varying concentrations. The diluted samples are added to the plate and incubated overnight at 4° C. After 24 hours, the plates are washed thoroughly with wash buffer, then 0.1 µg of purified human C4 (obtained as described in Dodds, A.W., *Methods Enzymol.* 223:46, 1993) in 100 µl of 4 mM barbital, 145 mM NaCl, 2 mM $CaCl_2$, 1 mM $MgCl_2$, pH 7.4 is added to each well. After 1.5 h at 37° C., the plates are washed again and C4b deposition is detected using alkaline phosphatase-conjugated chicken anti-human C4c (obtained from Immunsystem, Uppsala, Sweden) and measured using the colorimetric substrate p-nitrophenyl phosphate.

C4 Assay on Mannan:

The assay described above is adapted to measure lectin pathway activation via MBL by coating the plate with LSP and mannan prior to adding serum mixed with various MASP-2 inhibitory agents.

C4 Assay on H-Ficolin (Hakata Ag):

The assay described above is adapted to measure lectin pathway activation via H-ficolin by coating the plate with LPS and H-ficolin prior to adding serum mixed with various MASP-2 inhibitory agents.

Example 8

The following assay demonstrates the presence of classical pathway activation in wild-type and MASP-2-/- mice.

Methods:

Immune complexes were generated in situ by coating microtiter plates (MaxiSorb®, Nunc, cat. No. 442404, Fisher Scientific) with 0.1% human serum albumin in 10 mM Tris, 140 mM NaCl, pH 7.4 for 1 hours at room temperature followed by overnight incubation at 4° C. with sheep anti whole serum antiserum (Scottish Antibody Production Unit, Carluke, Scotland) diluted 1:1000 in TBS/tween/$Ca^{2+}$. Serum samples were obtained from wild-type and MASP-2-/- mice and added to the coated plates. Control samples were prepared in which C1q was depleted from wild-type and MASP-2-/- serum samples.

C1q-depleted mouse serum was prepared using protein-A-coupled Dynabeads® (Dynal Biotech, Oslo, Norway) coated with rabbit anti-human C1q IgG (Dako, Glostrup, Denmark), according to the supplier's instructions. The plates were incubated for 90 minutes at 37° C. Bound C3b was detected with a polyclonal anti-human-C3c Antibody (Dako A 062) diluted in TBS/tw/$Ca^{++}$ at 1:1000. The secondary antibody is goat anti-rabbit IgG.

Figure 7:
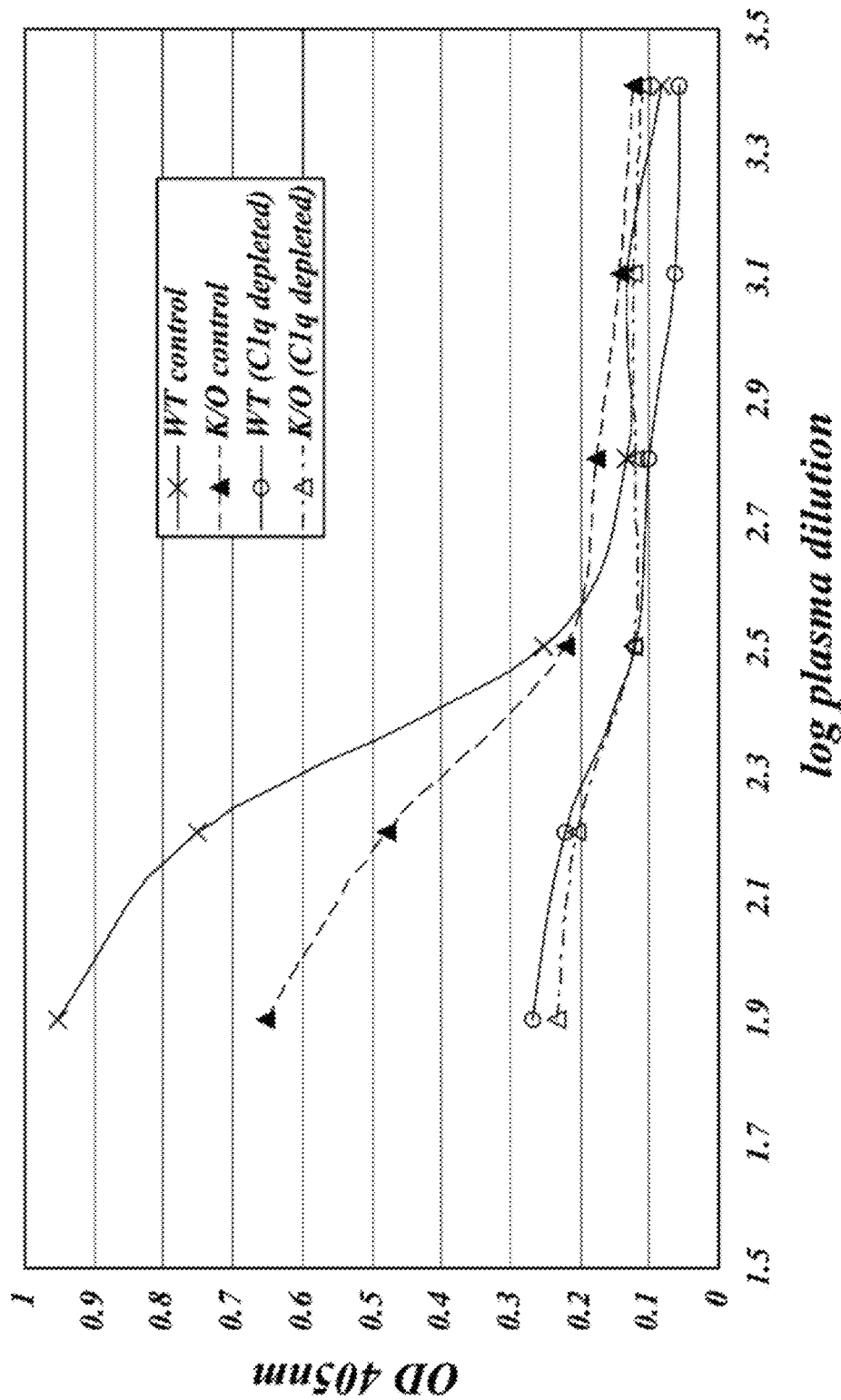
FIG. 7 presents results demonstrating that the classical pathway is functional in the MASP-2−/− strain, as described in Example 8.

Results:

FIG. 7 shows the relative C3b deposition levels on plates coated with IgG in wild-type serum, MASP-2-/- serum, C1q-depleted wild-type and C1q-depleted MASP-2-/- serum. These results demonstrate that the classical pathway is intact in the MASP-2-/- mouse strain.

Example 9

The following assay is used to test whether a MASP-2 inhibitory agent blocks the classical pathway by analyzing the effect of a MASP-2 inhibitory agent under conditions in which the classical pathway is initiated by immune complexes.

Methods:

To test the effect of a MASP-2 inhibitory agent on conditions of complement activation where the classical pathway is initiated by immune complexes, triplicate 50 µl samples containing 90% NHS are incubated at 37° C. in the presence of 10 µg/ml immune complex (IC) or PBS, and parallel triplicate samples (+/-IC) are also included which contain 200 nM anti-properdin monoclonal antibody during the 37° C. incubation. After a two hour incubation at 37° C., 13 mM EDTA is added to all samples to stop further complement activation and the samples are immediately cooled to 5° C. The samples are then stored at -70° C. prior to being assayed for complement activation products (C3a and sC5b-9) using ELISA kits (Quidel, Catalog Nos. A015 and A009) following the manufacturer's instructions.

Example 10

This example describes the identification of high affinity anti-MASP-2 Fab2 antibody fragments that block MASP-2 activity.

Background and Rationale:

MASP-2 is a complex protein with many separate functional domains, including: binding site(s) for MBL and ficolins, a serine protease catalytic site, a binding site for proteolytic substrate C2, a binding site for proteolytic substrate C4, a MASP-2 cleavage site for autoactivation of MASP-2 zymogen, and two $Ca^{++}$ binding sites. Fab2 antibody fragments were identified that bind with high affinity to MASP-2, and the identified Fab2 fragments were tested in a functional assay to determine if they were able to block MASP-2 functional activity.

To block MASP-2 functional activity, an antibody or Fab2 antibody fragment must bind and interfere with a structural epitope on MASP-2 that is required for MASP-2 functional activity. Therefore, many or all of the high affinity binding anti-MASP-2 Fab2s may not inhibit MASP-2 functional activity unless they bind to structural epitopes on MASP-2 that are directly involved in MASP-2 functional activity.

A functional assay that measures inhibition of lectin pathway C3 convertase formation was used to evaluate the "blocking activity" of anti-MASP-2 Fab2s. It is known that the primary physiological role of MASP-2 in the lectin pathway is to generate the next functional component of the lectin-mediated complement pathway, namely the lectin pathway C3 convertase. The lectin pathway C3 convertase is a critical enzymatic complex (C4bC2a) that proteolytically cleaves C3 into C3a and C3b. MASP-2 is not a structural component of the lectin pathway C3 convertase (C4bC2a); however, MASP-2 functional activity is required in order to generate the two protein components (C4b, C2a) that comprise the lectin pathway C3 convertase. Furthermore, all of the separate functional activities of MASP-2 listed above appear to be required in order for MASP-2 to generate the lectin pathway C3 convertase. For these reasons, a preferred assay to use in evaluating the "blocking activity" of anti-MASP-2 Fab2s is believed to be a functional assay that measures inhibition of lectin pathway C3 convertase formation.

Generation of High Affinity Fab2s:

A phage display library of human variable light and heavy chain antibody sequences and automated antibody selection technology for identifying Fab2s that react with selected ligands of interest was used to create high affinity Fab2s to rat MASP-2 protein (SEQ ID NO:55). A known amount of rat MASP-2 (~1 mg, >85% pure) protein was utilized for antibody screening. Three rounds of amplification were utilized for selection of the antibodies with the best affinity. Approximately 250 different hits expressing antibody fragments were picked for ELISA screening. High affinity hits were subsequently sequenced to determine uniqueness of the different antibodies.

Fifty unique anti-MASP-2 antibodies were purified and 250 µg of each purified Fab2 antibody was used for characterization of MASP-2 binding affinity and complement pathway functional testing, as described in more detail below.

Assays Used to Evaluate the Inhibitory (Blocking) Activity of Anti-MASP-2 Fab2s

1. Assay to Measure Inhibition of Formation of Lectin Pathway C3 Convertase:

Background: The lectin pathway C3 convertase is the enzymatic complex (C4bC2a) that proteolytically cleaves C3 into the two potent proinflammatory fragments, anaphylatoxin C3a and opsonic C3b. Formation of C3 convertase appears to a key step in the lectin pathway in terms of mediating inflammation. MASP-2 is not a structural component of the lectin pathway C3 convertase (C4bC2a); therefore anti-MASP-2 antibodies (or Fab2) will not directly inhibit activity of preexisting C3 convertase. However, MASP-2 serine protease activity is required in order to generate the two protein components (C4b, C2a) that comprise the lectin pathway C3 convertase. Therefore, anti-MASP-2 Fab2 which inhibit MASP-2 functional activity (i.e., blocking anti-MASP-2 Fab2) will inhibit de novo formation of lectin pathway C3 convertase. C3 contains an unusual and highly reactive thioester group as part of its structure. Upon cleavage of C3 by C3 convertase in this assay, the thioester group on C3b can form a covalent bond with hydroxyl or amino groups on macromolecules immobilized on the bottom of the plastic wells via ester or amide linkages, thus facilitating detection of C3b in the ELISA assay.

Yeast mannan is a known activator of the lectin pathway. In the following method to measure formation of C3 convertase, plastic wells coated with mannan were incubated 30 min at 37° C. with diluted rat serum to activate the lectin pathway. The wells were then washed and assayed for C3b immobilized onto the wells using standard ELISA methods.

The amount of C3b generated in this assay is a direct reflection of the de novo formation of lectin pathway C3 convertase. Anti-MASP-2 Fab2s at selected concentrations were tested in this assay for their ability to inhibit C3 convertase formation and consequent C3b generation.

Methods:

96-well Costar Medium Binding plates were incubated overnight at 5° C. with mannan diluted in 50 mM carbonate buffer, pH 9.5 at 1 µg/50 µL/well. After overnight incubation, each well was washed three times with 200 µL PBS. The wells were then blocked with 100 µL/well of 1% bovine serum albumin in PBS and incubated for one hour at room temperature with gentle mixing. Each well was then washed three times with 200 µL of PBS. The anti-MASP-2 Fab2 samples were diluted to selected concentrations in Ca and Mg$^{++}$ containing GVB buffer (4.0 mM barbital, 141 mM NaCl, 1.0 mM MgCl$_2$, 2.0 mM CaCl$_2$, 0.1% gelatin, pH 7.4) at 5 C. A 0.5% rat serum was added to the above samples at 5° C. and 100 µL was transferred to each well. Plates were covered and incubated for 30 minutes in a 37 C waterbath to allow complement activation. The reaction was stopped by transferring the plates from the 37° C. waterbath to a container containing an ice-water mix. Each well was washed five times with 200 µL with PBS-Tween 20 (0.05% Tween 20 in PBS), then washed two times with 200 µL PBS. A 100 µL/well of 1:10,000 dilution of the primary antibody (rabbit anti-human C3c, DAKO A0062) was added in PBS containing 2.0 mg/ml bovine serum albumin and incubated 1 hr at room temperature with gentle mixing. Each well was washed 5×200 µL PBS. 100 µL/well of 1:10,000 dilution of the secondary antibody (peroxidase-conjugated goat anti-rabbit IgG, American Qualex A102PU) was added in PBS containing 2.0 mg/ml bovine serum albumin and incubated for one hour at room temperature on a shaker with gentle mixing. Each well was washed five times with 200 µL with PBS. 100 L/well of the peroxidase substrate TMB (Kirkegaard & Perry Laboratories) was added and incubated at room temperature for 10 min. The peroxidase reaction was stopped by adding 100 µL/well of 1.0 M H$_3$PO$_4$ and the OD$_{450}$ was measured.

2. Assay to Measure Inhibition of MASP-2-Dependent C4 Cleavage

Background: The serine protease activity of MASP-2 is highly specific and only two protein substrates for MASP-2 have been identified; C2 and C4. Cleavage of C4 generates C4a and C4b. Anti-MASP-2 Fab2 may bind to structural epitopes on MASP-2 that are directly involved in C4 cleavage (e.g., MASP-2 binding site for C4; MASP-2 serine protease catalytic site) and thereby inhibit the C4 cleavage functional activity of MASP-2.

Yeast mannan is a known activator of the lectin pathway. In the following method to measure the C4 cleavage activity of MASP-2, plastic wells coated with mannan were incubated for 30 minutes at 37° C. with diluted rat serum to activate the lectin pathway. Since the primary antibody used in this ELISA assay only recognizes human C4, the diluted rat serum was also supplemented with human C4 (1.0 µg/ml). The wells were then washed and assayed for human C4b immobilized onto the wells using standard ELISA methods. The amount of C4b generated in this assay is a measure of MASP-2 dependent C4 cleavage activity. Anti-MASP-2 Fab2 at selected concentrations were tested in this assay for their ability to inhibit C4 cleavage.

Methods:

96-well Costar Medium Binding plates were incubated overnight at 5° C. with mannan diluted in 50 mM carbonate buffer, pH 9.5 at 1.0 µg/50 µL/well. Each well was washed 3× with 200 µL PBS. The wells were then blocked with 100 µL/well of 1% bovine serum albumin in PBS and incubated for one hour at room temperature with gentle mixing. Each well was washed 3× with 200 µL of PBS. Anti-MASP-2 Fab2 samples were diluted to selected concentrations in Ca$^{++}$ and Mg$^{++}$ containing GVB buffer (4.0 mM barbital, 141 mM NaCl, 1.0 mM MgCl$_2$, 2.0 mM CaCl$_2$, 0.1% gelatin, pH 7.4) at 5° C. 1.0 µg/ml human C4 (Quidel) was also included in these samples. 0.5% rat serum was added to the above samples at 5° C. and 100 µL was transferred to each well. The plates were covered and incubated for 30 minutes in a 37° C. waterbath to allow complement activation. The reaction was stopped by transferring the plates from the 37° C. waterbath to a container containing an ice-water mix. Each well was washed 5×200 µL with PBS-Tween 20 (0.05% Tween 20 in PBS), then each well was washed with 2× with 200 µL PBS. 100 µL/well of 1:700 dilution of biotin-conjugated chicken anti-human C4c (Immunsystem AB, Uppsala, Sweden) was added in PBS containing 2.0 mg/ml bovine serum albumin (BSA) and incubated one hour at room temperature with gentle mixing. Each well was washed 5×200 µL PBS. 100 L/well of 0.1

μg/ml of peroxidase-conjugated streptavidin (Pierce Chemical #21126) was added in PBS containing 2.0 mg/ml BSA and incubated for one hour at room temperature on a shaker with gentle mixing. Each well was washed 5×200 μL with PBS. 100 μL/well of the peroxidase substrate TMB (Kirkegaard & Perry Laboratories) was added and incubated at room temperature for 16 min. The peroxidase reaction was stopped by adding 100 μL/well of 1.0 M $H_3PO_4$ and the $OD_{450}$ was measured.

3. Binding Assay of Anti-Rat MASP-2 Fab2 to 'Native' Rat MASP-2

Background: MASP-2 is usually present in plasma as a MASP-2 dimer complex that also includes specific lectin molecules (mannose-binding protein (MBL) and ficolins). Therefore, if one is interested in studying the binding of anti-MASP-2 Fab2 to the physiologically relevant form of MASP-2, it is important to develop a binding assay in which the interaction between the Fab2 and 'native' MASP-2 in plasma is used, rather than purified recombinant MASP-2. In this binding assay the 'native' MASP-2-MBL complex from 10% rat serum was first immobilized onto mannan-coated wells. The binding affinity of various anti-MASP-2 Fab2s to the immobilized 'native' MASP-2 was then studied using a standard ELISA methodology.

Methods:

96-well Costar High Binding plates were incubated overnight at 5° C. with mannan diluted in 50 mM carbonate buffer, pH 9.5 at 1 μg/50 μL/well. Each well was washed 3× with 200 μL PBS. The wells were blocked with 100 μL/well of 0.5% nonfat dry milk in PBST (PBS with 0.05% Tween 20) and incubated for one hour at room temperature with gentle mixing. Each well was washed 3× with 200 μL of TBS/Tween/$Ca^+$ Wash Buffer (Tris-buffered saline, 0.05% Tween 20, containing 5.0 mM $CaCl_2$, pH 7.4. 10% rat serum in High Salt Binding Buffer (20 mM Tris, 1.0 M NaCl, 10 mM $CaCl_2$, 0.05% Triton-X100, 0.1% (w/v) bovine serum albumin, pH 7.4) was prepared on ice. 100 L/well was added and incubated overnight at 5° C. Wells were washed 3× with 200 μL of TBS/Tween/$Ca^{++}$ Wash Buffer. Wells were then washed 2× with 200 μL PBS. 100 μL/well of selected concentration of anti-MASP-2 Fab2 diluted in $Ca^{++}$ and $Mg^{++}$ containing GVB Buffer (4.0 mM barbital, 141 mM NaCl, 1.0 mM $MgCl_2$, 2.0 mM $CaCl_2$, 0.1% gelatin, pH 7.4) was added and incubated for one hour at room temperature with gentle mixing. Each well was washed 5×200 μL PBS. 100 μL/well of HRP-conjugated goat anti-Fab2 (Biogenesis Cat No 0500-0099) diluted 1:5000 in 2.0 mg/ml bovine serum albumin in PBS was added and incubated for one hour at room temperature with gentle mixing. Each well was washed 5×200 μL PBS. 100 μL/well of the peroxidase substrate TMB (Kirkegaard & Perry Laboratories) was added and incubated at room temperature for 70 min. The peroxidase reaction was stopped by adding 100 μL/well of 1.0 M $H_3PO_4$ and $OD_{450}$ was measured.

Results:

Approximately 250 different Fab2s that reacted with high affinity to the rat MASP-2 protein were picked for ELISA screening. These high affinity Fab2s were sequenced to determine the uniqueness of the different antibodies, and 50 unique anti-MASP-2 antibodies were purified for further analysis. 250 μg of each purified Fab2 antibody was used for characterization of MASP-2 binding affinity and complement pathway functional testing. The result of this analysis is shown below in TABLE 6.

TABLE 6

ANTI-MASP-2 FAB2 THAT BLOCK LECTIN PATHWAY COMPLEMENT ACTIVATION

| Fab2 antibody # | C3 Convertase ($IC_{50}$ (nM)) | $K_d$ | C4 Cleavage $IC_{50}$ (nM) |
|---|---|---|---|
| 88 | 0.32 | 4.1 | ND |
| 41 | 0.35 | 0.30 | 0.81 |
| 11 | 0.46 | 0.86 | <2 nM |
| 86 | 0.53 | 1.4 | ND |
| 81 | 0.54 | 2.0 | ND |
| 66 | 0.92 | 4.5 | ND |
| 57 | 0.95 | 3.6 | <2 nM |
| 40 | 1.1 | 7.2 | 0.68 |
| 58 | 1.3 | 2.6 | ND |
| 60 | 1.6 | 3.1 | ND |
| 52 | 1.6 | 5.8 | <2 nM |
| 63 | 2.0 | 6.6 | ND |
| 49 | 2.8 | 8.5 | <2 nM |
| 89 | 3.0 | 2.5 | ND |
| 71 | 3.0 | 10.5 | ND |
| 87 | 6.0 | 2.5 | ND |
| 67 | 10.0 | 7.7 | ND |

Figure 8A:
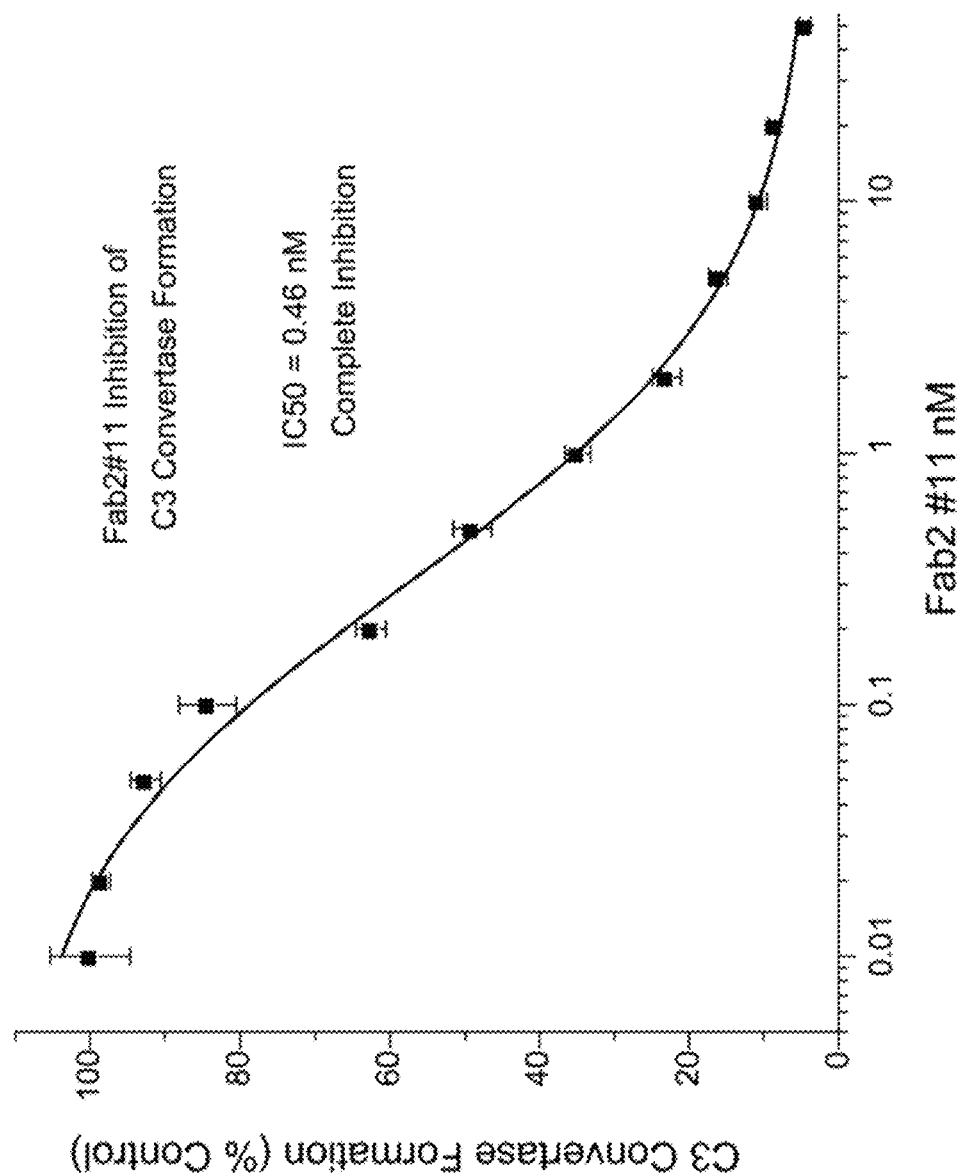
FIG. 8A presents results demonstrating that anti-MASP-2 Fab2 antibody #11 inhibits C3 convertase formation, as described in Example 10.

As shown above in TABLE 6, of the 50 anti-MASP-2 Fab2s tested, seventeen Fab2s were identified as MASP-2 blocking Fab2 that potently inhibit C3 convertase formation with $IC_{50}$ equal to or less than 10 nM Fab2s (a 34% positive hit rate). Eight of the seventeen Fab2s identified have $IC_{50}$s in the subnanomolar range. Furthermore, all seventeen of the MASP-2 blocking Fab2s shown in TABLE 6 gave essentially complete inhibition of C3 convertase formation in the lectin pathway C3 convertase assay. FIG. 8A graphically illustrates the results of the C3 convertase formation assay for Fab2 antibody #11, which is representative of the other Fab2 antibodies tested, the results of which are shown in TABLE 6. This is an important consideration, since it is theoretically possible that a "blocking" Fab2 may only fractionally inhibit MASP-2 function even when each MASP-2 molecule is bound by the Fab2.

Although mannan is a known activator of the lectin pathway, it is theoretically possible that the presence of anti-mannan antibodies in the rat serum might also activate the classical pathway and generate C3b via the classical pathway C3 convertase. However, each of the seventeen blocking anti-MASP-2 Fab2s listed in this example potently inhibits C3b generation (>95%), thus demonstrating the specificity of this assay for lectin pathway C3 convertase.

Figure 8B:
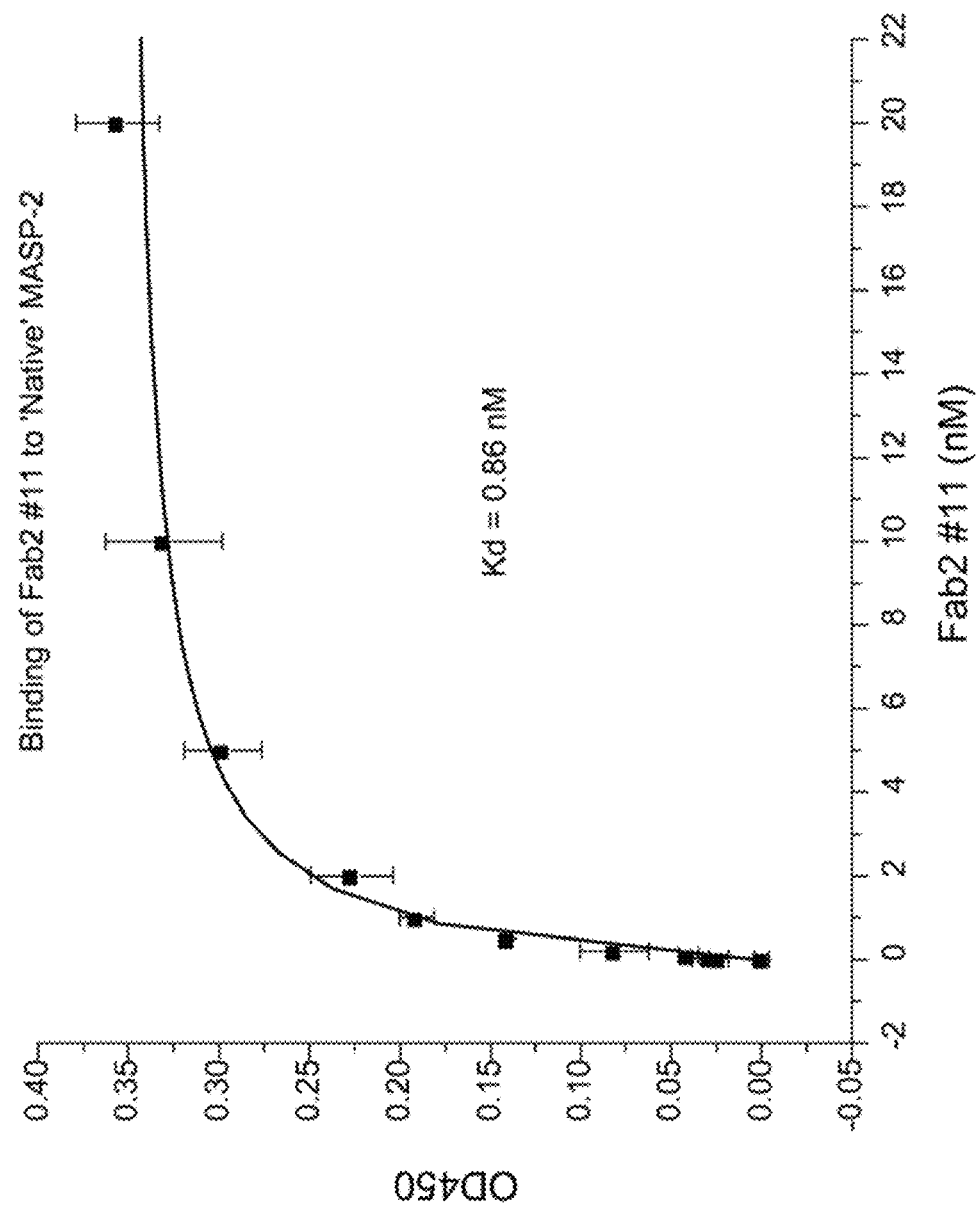
FIG. 8B presents results demonstrating that anti-MASP-2 Fab2 antibody #11 binds to native rat MASP-2, as described in Example 10.

Binding assays were also performed with all seventeen of the blocking Fab2s in order to calculate an apparent $K_d$ for each. The results of the binding assays of anti-rat MASP-2 Fab2s to native rat MASP-2 for six of the blocking Fab2s are also shown in TABLE 6. FIG. 8B graphically illustrates the results of a binding assay with the Fab2 antibody #11. Similar binding assays were also carried out for the other Fab2s, the results of which are shown in TABLE 6. In general, the apparent $K_d$s obtained for binding of each of the six Fab2s to 'native' MASP-2 corresponds reasonably well with the $IC_{50}$ for the Fab2 in the C3 convertase functional assay. There is evidence that MASP-2 undergoes a conformational change from an 'inactive' to an 'active' form upon activation of its protease activity (Feinberg et al., *EMBO J* 22:2348-59 (2003); Gal et al., *J. Biol. Chem.* 280:33435-44 (2005)). In the normal rat plasma used in the C3 convertase formation assay, MASP-2 is present primarily in the 'inactive' zymogen conformation. In contrast, in the binding assay, MASP-2 is present as part of a complex with MBL bound to immobilized mannan; therefore, the MASP-2 would be in the 'active' conformation (Petersen et al., *J.*

*Immunol Methods* 257:107-16, 2001). Consequently, one would not necessarily expect an exact correspondence between the $IC_{50}$ and $K_d$ for each of the seventeen blocking Fab2 tested in these two functional assays since in each assay the Fab2 would be binding a different conformational form of MASP-2. Never-the-less, with the exception of Fab2 #88, there appears to be a reasonably close correspondence between the $IC_{50}$ and apparent $K_d$ for each of the other sixteen Fab2 tested in the two assays (see TABLE 6).

Figure 8C:
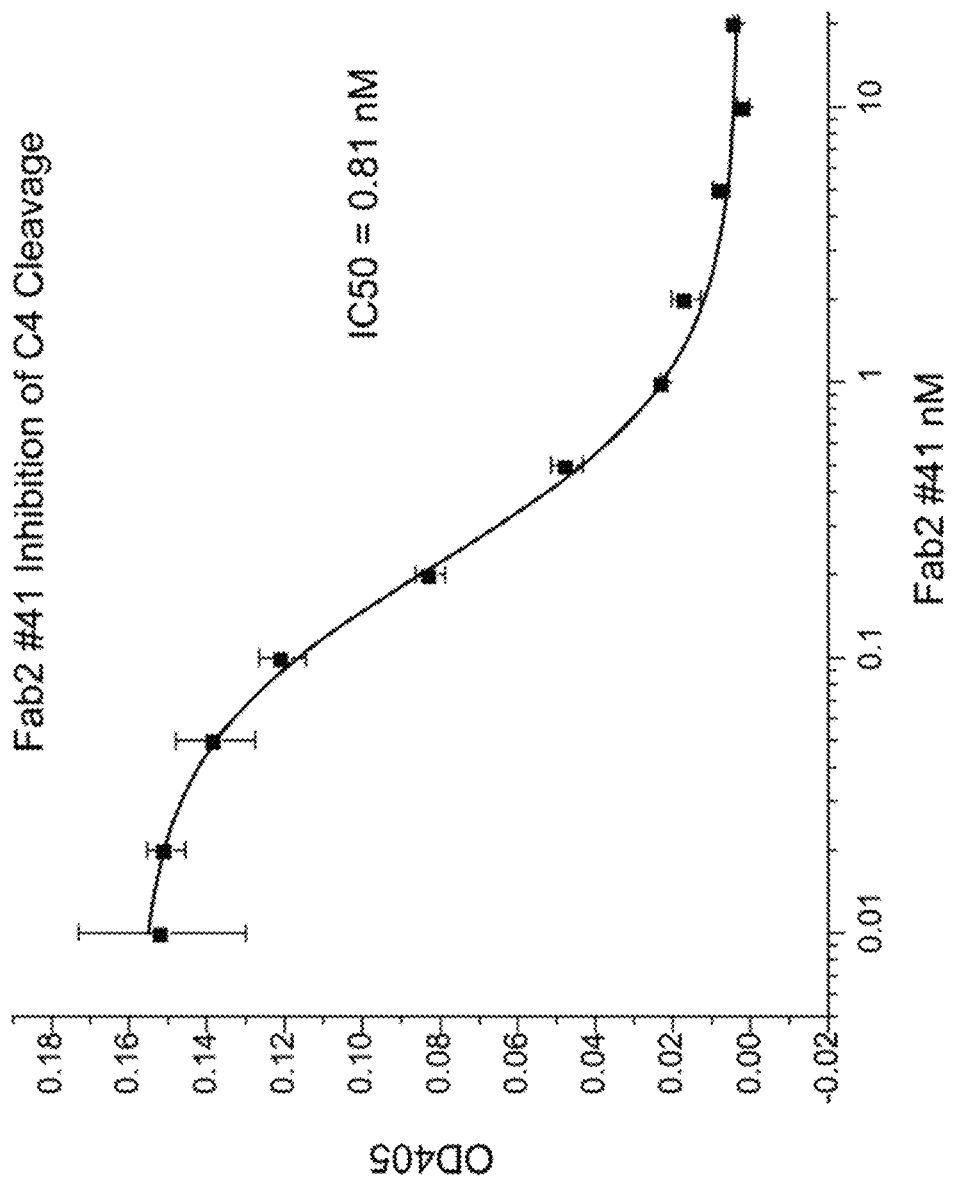
FIG. 8C presents results demonstrating that anti-MASP-2 Fab2 antibody #41 inhibits C4 cleavage, as described in Example 10.
Figure 9:
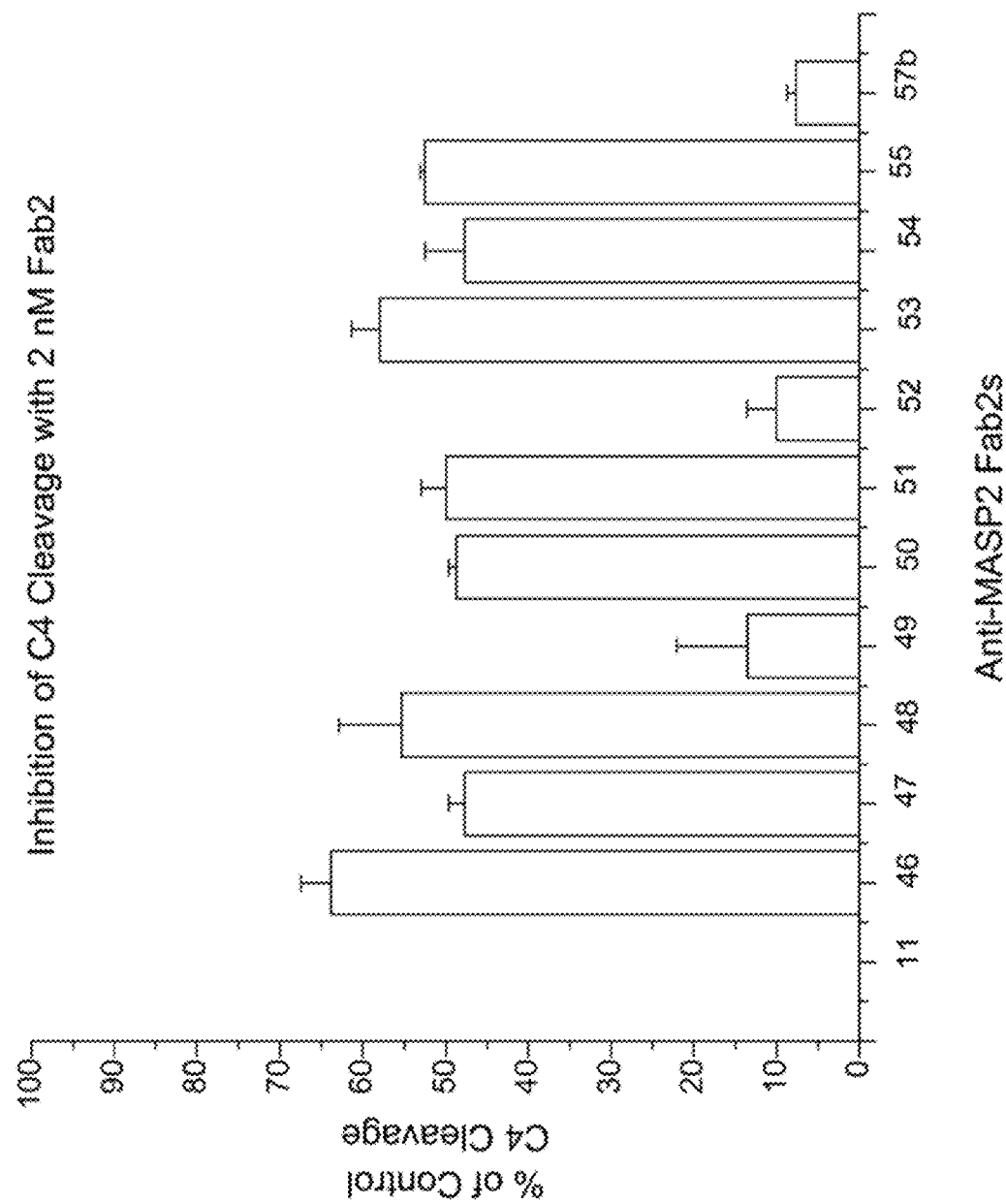
FIG. 9 presents results demonstrating that all of the anti-MASP-2 Fab2 antibodies tested that inhibited C3 convertase formation also were found to inhibit C4 cleavage, as described in Example 10.

Several of the blocking Fab2s were evaluated for inhibition of MASP-2 mediated cleavage of C4. FIG. 8C graphically illustrates the results of a C4 cleavage assay, showing inhibition with Fab2 #41, with an $IC_{50}$=0.81 nM (see TABLE 6). As shown in FIG. 9, all of the Fab2s tested were found to inhibit C4 cleavage with $IC_{50}$s similar to those obtained in the C3 convertase assay (see TABLE 6).

Although mannan is a known activator of the lectin pathway, it is theoretically possible that the presence of anti-mannan antibodies in the rat serum might also activate the classical pathway and thereby generate C4b by C1s-mediated cleavage of C4. However, several anti-MASP-2 Fab2s have been identified which potently inhibit C4b generation (>95%), thus demonstrating the specificity of this assay for MASP-2 mediated C4 cleavage. C4, like C3, contains an unusual and highly reactive thioester group as part of its structure. Upon cleavage of C4 by MASP-2 in this assay, the thioester group on C4b can form a covalent bond with hydroxyl or amino groups on macromolecules immobilized on the bottom of the plastic wells via ester or amide linkages, thus facilitating detection of C4b in the ELISA assay.

These studies clearly demonstrate the creation of high affinity Fab2s to rat MASP-2 protein that functionally block both C4 and C3 convertase activity, thereby preventing lectin pathway activation.

Example 11

This Example describes the epitope mapping for several of the blocking anti-rat MASP-2 Fab2 antibodies that were generated as described in Example 10.

Figure 10:
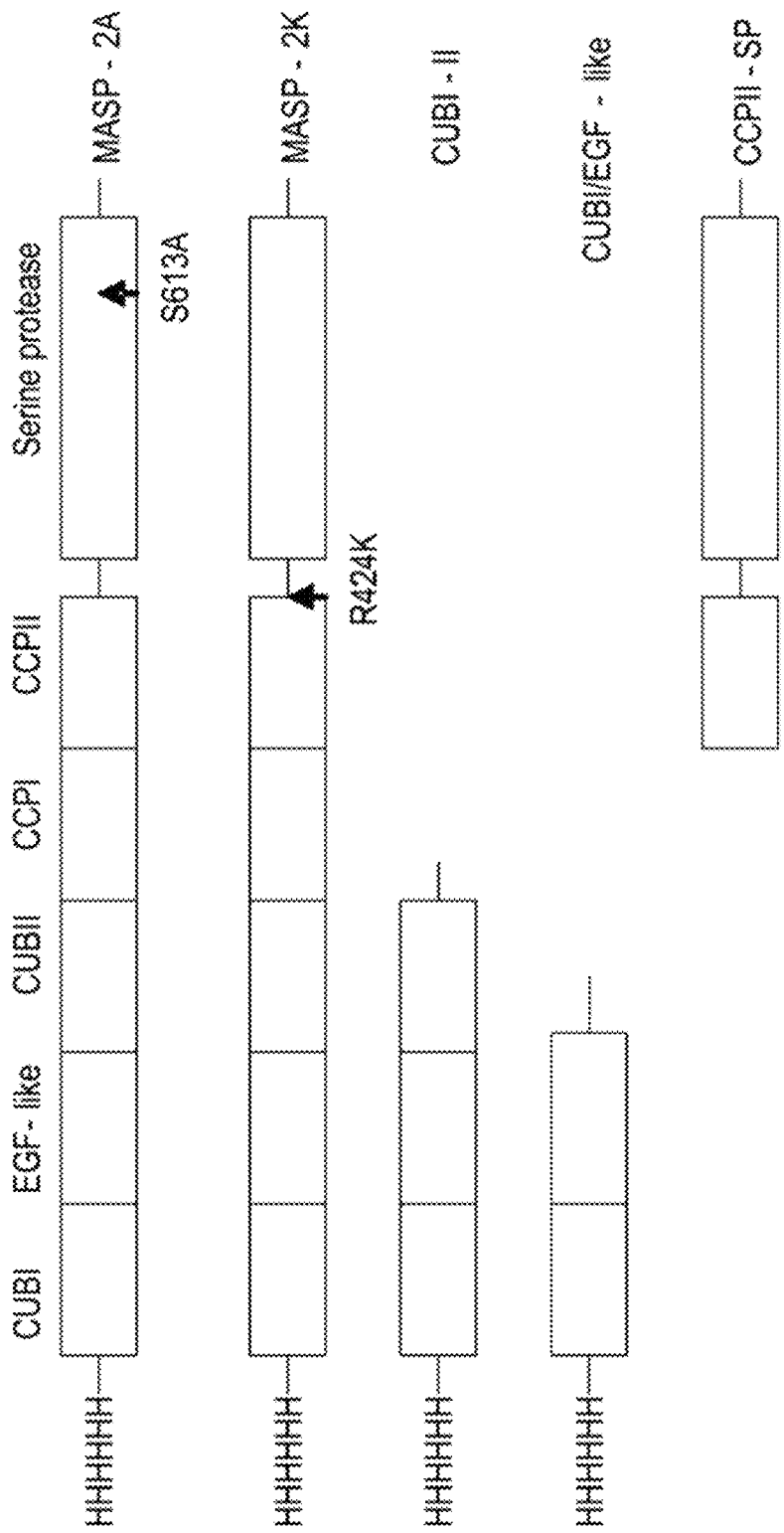
FIG. 10 is a diagram illustrating the recombinant polypeptides derived from rat MASP-2 that were used for epitope mapping of the MASP-2 blocking Fab2 antibodies, as described in Example 11.

Methods:

As shown in FIG. 10, the following proteins, all with N-terminal 6x His tags were expressed in CHO cells using the pED4 vector:

rat MASP-2A, a full length MASP-2 protein, inactivated by altering the serine at the active center to alanine (S613A);

rat MASP-2K, a full-length MASP-2 protein altered to reduce autoactivation (R424K);

CUBI-II, an N-terminal fragment of rat MASP-2 that contains the CUBI, EGF-like and CUBII domains only; and CUBI/EGF-like, an N-terminal fragment of rat MASP-2 that contains the CUBI and EGF-like domains only.

These proteins were purified from culture supernatants by nickel-affinity chromatography, as previously described (Chen et al., *J. Biol. Chem.* 276:25894-02 (2001)).

A C-terminal polypeptide (CCPII-SP), containing CCPII and the serine protease domain of rat MASP-2, was expressed in *E. coli* as a thioredoxin fusion protein using pTrxFus (Invitrogen). Protein was purified from cell lysates using Thiobond affinity resin. The thioredoxin fusion partner was expressed from empty pTrxFus as a negative control.

All recombinant proteins were dialyzed into TBS buffer and their concentrations determined by measuring the OD at 280 nm.

Dot Blot Analysis:

Serial dilutions of the five recombinant MASP-2 polypeptides described above and shown in FIG. 10 (and the thioredoxin polypeptide as a negative control for CCPII-serine protease polypeptide) were spotted onto a nitrocellulose membrane. The amount of protein spotted ranged from 100 ng to 6.4 µg, in five-fold steps. In later experiments, the amount of protein spotted ranged from 50 ng down to 16 µg, again in five-fold steps. Membranes were blocked with 5% skimmed milk powder in TBS (blocking buffer) then incubated with 1.0 µg/ml anti-MASP-2 Fab2s in blocking buffer (containing 5.0 mM $Ca^{2+}$). Bound Fab2s were detected using HRP-conjugated anti-human Fab (AbD/Serotec; diluted 1/10,000) and an ECL detection kit (Amersham). One membrane was incubated with polyclonal rabbit-anti human MASP-2 Ab (described in Stover et al., *J Immunol* 163:6848-59 (1999)) as a positive control. In this case, bound Ab was detected using HRP-conjugated goat anti-rabbit IgG (Dako; diluted 1/2,000).

MASP-2 Binding Assay

ELISA plates were coated with 1.0 gig/well of recombinant MASP-2A or CUBI-II polypeptide in carbonate buffer (pH 9.0) overnight at 4° C. Wells were blocked with 1% BSA in TBS, then serial dilutions of the anti-MASP-2 Fab2s were added in TBS containing 5.0 mM $Ca^{2+}$. The plates were incubated for one hour at RT. After washing three times with TBS/tween/$Ca^{2+}$, HRP-conjugated anti-human Fab (AbD/Serotec) diluted 1/10,000 in TBS/$Ca^{2+}$ was added and the plates incubated for a further one hour at RT. Bound antibody was detected using a TMB peroxidase substrate kit (Biorad).

Results:

Results of the dot blot analysis demonstrating the reactivity of the Fab2s with various MASP-2 polypeptides are provided below in TABLE 7. The numerical values provided in TABLE 7 indicate the amount of spotted protein required to give approximately half-maximal signal strength. As shown, all of the polypeptides (with the exception of the thioredoxin fusion partner alone) were recognized by the positive control Ab (polyclonal anti-human MASP-2 sera, raised in rabbits).

TABLE 7

REACTIVITY WITH VARIOUS RECOMBINANT RAT MASP-2 POLYPEPTIDES ON DOT BLOTS

| Fab2 Antibody # | MASP-2A | CUBI-II | CUBI/EGF-like | CCPII-SP | Thioredoxin |
|---|---|---|---|---|---|
| 40 | 0.16 ng | NR | NR | 0.8 ng | NR |
| 41 | 0.16 ng | NR | NR | 0.8 ng | NR |
| 11 | 0.16 ng | NR | NR | 0.8 ng | NR |
| 49 | 0.16 ng | NR | NR | >20 ng | NR |
| 52 | 0.16 ng | NR | NR | 0.8 ng | NR |
| 57 | 0.032 ng | NR | NR | NR | NR |

TABLE 7-continued

REACTIVITY WITH VARIOUS RECOMBINANT RAT
MASP-2 POLYPEPTIDES ON DOT BLOTS

| Fab2 Antibody # | MASP-2A | CUBI-II | CUBI/EGF-like | CCPII-SP | Thioredoxin |
|---|---|---|---|---|---|
| 58 | 0.4 ng | NR | NR | 2.0 ng | NR |
| 60 | 0.4 ng | 0.4 ng | NR | NR | NR |
| 63 | 0.4 ng | NR | NR | 2.0 ng | NR |
| 66 | 0.4 ng | NR | NR | 2.0 ng | NR |
| 67 | 0.4 ng | NR | NR | 2.0 ng | NR |
| 71 | 0.4 ng | NR | NR | 2.0 ng | NR |
| 81 | 0.4 ng | NR | NR | 2.0 ng | NR |
| 86 | 0.4 ng | NR | NR | 10 ng | NR |
| 87 | 0.4 ng | NR | NR | 2.0 ng | NR |
| Positive Control | <0.032 ng | 0.16 ng | 0.16 ng | <0.032 ng | NR |

NR = No reaction.
The positive control antibody is polyclonal anti-human MASP-2 sera, raised in rabbits.

Figure 11:
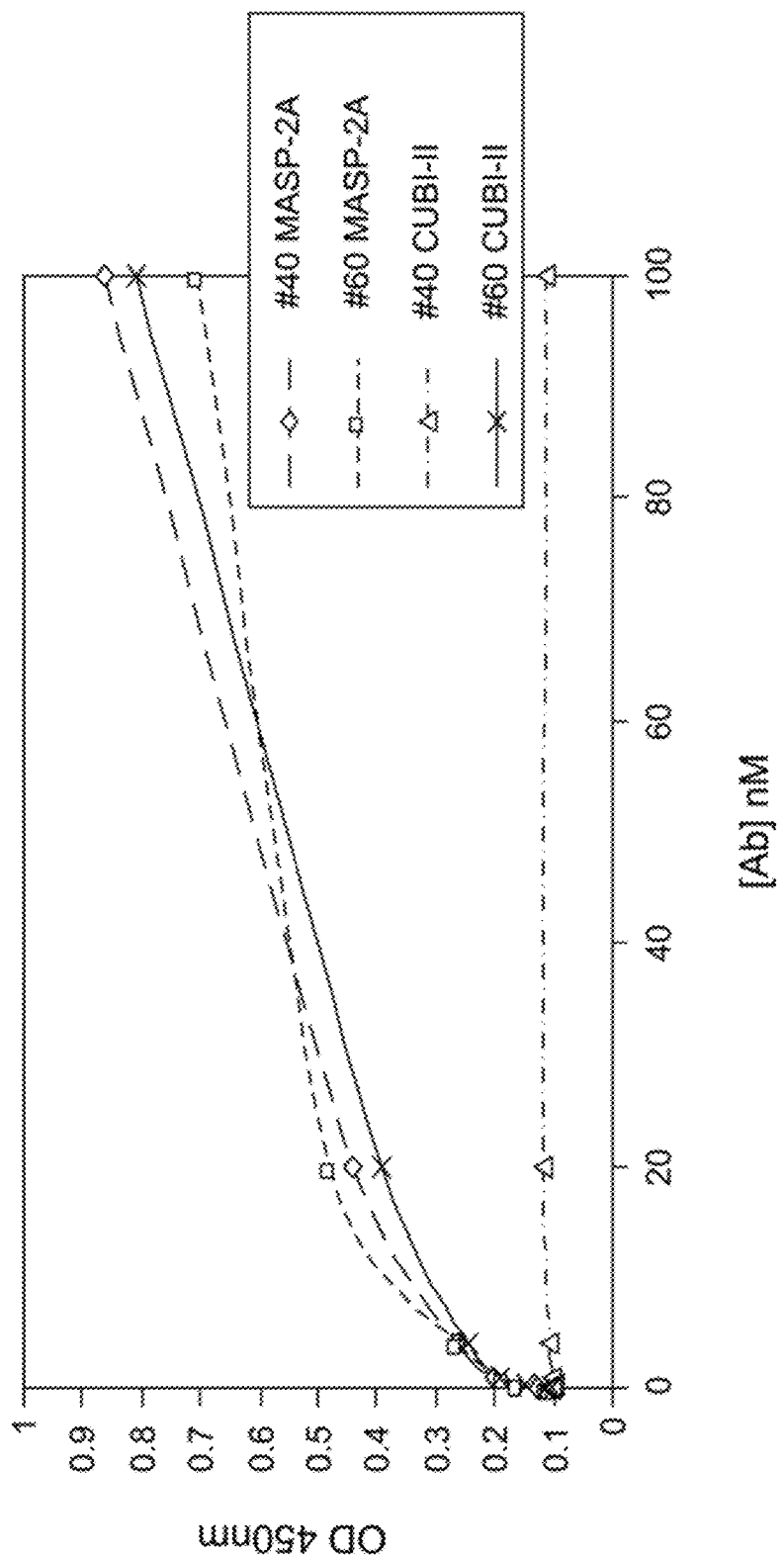
FIG. 11 presents results demonstrating the binding of anti-MASP-2 Fab2 #40 and #60 to rat MASP-2 polypeptides, as described in Example 11.

All of the Fab2s reacted with MASP-2A as well as MASP-2K (data not shown). The majority of the Fab2s recognized the CCPII-SP polypeptide but not the N-terminal fragments. The two exceptions are Fab2 #60 and Fab2 #57. Fab2 #60 recognizes MASP-2A and the CUBI-II fragment, but not the CUBI/EGF-like polypeptide or the CCPII-SP polypeptide, suggesting it binds to an epitope in CUBII, or spanning the CUBII and the EGF-like domain. Fab2 #57 recognizes MASP-2A but not any of the MASP-2 fragments tested, indicating that this Fab2 recognizes an epitope in CCP1. Fab2 #40 and #49 bound only to complete MASP-2A. In the ELISA binding assay shown in FIG. 11, Fab2 #60 also bound to the CUBI-II polypeptide, albeit with a slightly lower apparent affinity.

These finding demonstrate the identification of unique blocking Fab2s to multiple regions of the MASP-2 protein.

Example 12

This example describes the identification, using phage display, of fully human scFv antibodies that bind to MASP-2 and inhibit lectin-mediated complement activation while leaving the classical (C1q-dependent) pathway component of the immune system intact.

Overview:

Fully human, high-affinity MASP-2 antibodies were identified by screening a phage display library. The variable light and heavy chain fragments of the antibodies were isolated in both a scFv format and in a full-length IgG format. The human MASP-2 antibodies are useful for inhibiting cellular injury associated with lectin pathway-mediated complement pathway activation while leaving the classical (C1q-dependent) pathway component of the immune system intact. In some embodiments, the subject MASP-2 inhibitory antibodies have the following characteristics: (a) high affinity for human MASP-2 (e.g., a $K_D$ of 10 nM or less), and (b) inhibit MASP-2-dependent complement activity in 90% human serum with an $IC_{50}$ of 30 nM or less.

Methods:

Expression of Full-Length Catalytically Inactive MASP-2:

The full-length cDNA sequence of human MASP-2 (SEQ ID NO: 4), encoding the human MASP-2 polypeptide with leader sequence (SEQ ID NO:5) was subcloned into the mammalian expression vector pCI-Neo (Promega), which drives eukaryotic expression under the control of the CMV enhancer/promoter region (described in Kaufman R. J. et al., Nucleic Acids Research 19:4485-90, 1991; Kaufman, Methods in Enzymology, 185:537-66 (1991)). In order to generate catalytically inactive human MASP-2A protein, site-directed mutagenesis was carried out as described in US2007/0172483, hereby incorporated herein by reference. The PCR products were purified after agarose gel electrophoresis and band preparation and single adenosine overlaps were generated using a standard tailing procedure. The adenosine-tailed MASP-2A was then cloned into the pGEM-T easy vector and transformed into E. coli. The human MASP-2A was further subcloned into either of the mammalian expression vectors pED or pCI-Neo.

The MASP-2A expression construct described above was transfected into DXB1 cells using the standard calcium phosphate transfection procedure (Maniatis et al., 1989). MASP-2A was produced in serum-free medium to ensure that preparations were not contaminated with other serum proteins. Media was harvested from confluent cells every second day (four times in total). The level of recombinant MASP-2A averaged approximately 1.5 mg/liter of culture medium. The MASP-2A (Ser-Ala mutant described above) was purified by affinity chromatography on MBP-A-agarose columns MASP-2A ELISA on ScFv Candidate Clones Identified by Panning/scFv Conversion and Filter Screening A phage display library of human immunoglobulin light- and heavy-chain variable region sequences was subjected to antigen panning followed by automated antibody screening and selection to identify high-affinity scFv antibodies to human MASP-2 protein. Three rounds of panning the scFv phage library against HIS-tagged or biotin-tagged MASP-2A were carried out. The third round of panning was eluted first with MBL and then with TEA (alkaline). To monitor the specific enrichment of phages displaying scFv fragments against the target MASP-2A, a polyclonal phage ELISA against immobilized MASP-2A was carried out. The scFv genes from panning round 3 were cloned into a pHOG expression vector and run in a small-scale filter screening to look for specific clones against MASP-2A.

Bacterial colonies containing plasmids encoding scFv fragments from the third round of panning were picked, gridded onto nitrocellulose membranes and grown overnight on non-inducing medium to produce master plates. A total of 18,000 colonies were picked and analyzed from the third panning round, half from the competitive elution and half from the subsequent TEA elution. Panning of the scFv phagemid library against MASP-2A followed by scFv conversion and a filter screen yielded 137 positive clones. 108/137 clones were positive in an ELISA assay for MASP-2 binding (data not shown), of which 45 clones were further analyzed for the ability to block MASP-2 activity in normal human serum.

Assay to Measure Inhibition of Formation of Lectin Pathway C3 Convertase

A functional assay that measures inhibition of lectin pathway C3 convertase formation was used to evaluate the "blocking activity" of the MASP-2 scFv candidate clones. MASP-2 serine protease activity is required in order to generate the two protein components (C4b, C2a) that comprise the lectin pathway C3 convertase. Therefore, a MASP-2 scFv that inhibits MASP-2 functional activity (i.e., a blocking MASP-2 scFv), will inhibit de novo formation of lectin pathway C3 convertase. C3 contains an unusual and highly reactive thioester group as part of its structure. Upon cleavage of C3 by C3 convertase in this assay, the thioester group on C3b can form a covalent bond with hydroxyl or amino groups on macromolecules immobilized on the bottom of the plastic wells via ester or amide linkages, thus facilitating detection of C3b in the ELISA assay.

Yeast mannan is a known activator of the lectin pathway. In the following method to measure formation of C3 convertase, plastic wells coated with mannan were incubated with diluted human serum to activate the lectin pathway. The wells were then washed and assayed for C3b immobilized onto the wells using standard ELISA methods. The amount of C3b generated in this assay is a direct reflection of the de novo formation of lectin pathway C3 convertase. MASP-2 scFv clones at selected concentrations were tested in this assay for their ability to inhibit C3 convertase formation and consequent C3b generation.

Methods:

The 45 candidate clones identified as described above were expressed, purified and diluted to the same stock concentration, which was again diluted in $Ca^{++}$ and $Mg^{++}$ containing GVB buffer (4.0 mM barbital, 141 mM NaCl, 1.0 mM $MgCl_2$, 2.0 mM $CaCl_2$, 0.1% gelatin, pH 7.4) to assure that all clones had the same amount of buffer. The scFv clones were each tested in triplicate at the concentration of 2 μg/mL. The positive control was OMS100 Fab2 and was tested at 0.4 g/mL. C3c formation was monitored in the presence and absence of the scFv/IgG clones.

Mannan was diluted to a concentration of 20 μg/mL (1 μg/well) in 50 mM carbonate buffer (15 mM $Na_2CO_3$+35 mM $NaHCO_3$+1.5 mM $NaN_3$), pH 9.5 and coated on an ELISA plate overnight at 4° C. The next day, the mannan-coated plates were washed 3 times with 200 μl PBS. 100 μl of 1% HSA blocking solution was then added to the wells and incubated for 1 hour at room temperature. The plates were washed 3 times with 200 μl PBS, and stored on ice with 200 μl PBS until addition of the samples.

Normal human serum was diluted to 0.5% in CaMgGVB buffer, and scFv clones or the OMS100 Fab2 positive control were added in triplicates at 0.01 μg/mL; 1 μg/mL (only OMS100 control) and 10 μg/mL to this buffer and preincubated 45 minutes on ice before addition to the blocked ELISA plate. The reaction was initiated by incubation for one hour at 37° C. and was stopped by transferring the plates to an ice bath. C3b deposition was detected with a Rabbit α-Mouse C3c antibody followed by Goat α-Rabbit HRP. The negative control was buffer without antibody (no antibody=maximum C3b deposition), and the positive control was buffer with EDTA (no C3b deposition). The background was determined by carrying out the same assay except that the wells were mannan-free. The background signal against plates without mannan was subtracted from the signals in the mannan-containing wells. A cut-off criterion was set at half of the activity of an irrelevant scFv clone (VZV) and buffer alone.

Results:

Based on the cut-off criterion, a total of 13 clones were found to block the activity of MASP-2. All 13 clones producing >50% pathway suppression were selected and sequenced, yielding 10 unique clones. All ten clones were found to have the same light chain subclass, λ3, but three different heavy chain subclasses: VH2, VH3 and VH6. In the functional assay, five out of the ten candidate scFv clones gave $IC_{50}$ nM values less than the nM target criteria using 0.5% human serum.

To identify antibodies with improved potency, the three mother scFv clones, identified as described above, were subjected to light-chain shuffling. This process involved the generation of a combinatorial library consisting of the $V_H$ of each of the mother clones paired up with a library of naïve, human lambda light chains (VL) derived from six healthy donors. This library was then screened for scFv clones with improved binding affinity and/or functionality.

TABLE 8

Comparison of functional potency in $IC_{50}$ (nM) of the lead daughter clones and their respective mother clones (all in scFv format)

| scFv clone | 1% human serum C3 assay ($IC_{50}$ nM) | 90% human serum C3 assay ($IC_{50}$ nM) | 90% human serum C4 assay ($IC_{50}$ nM) |
|---|---|---|---|
| 17D20mc | 38 | nd | nd |
| 17D20m_d3521N11 | 26 | >1000 | 140 |
| 17N16mc | 68 | nd | nd |
| 17N16m_d17N9 | 48 | 15 | 230 |

Presented below are the heavy-chain variable region ($V_H$) sequences for the mother clones and daughter clones shown above in TABLE 8.

The Kabat CDRs (31-35 (H1), 50-65 (H2) and 95-107 (H3)) are bolded; and the Chothia CDRs (26-32 (H1), 52-56 (H2) and 95-101 (H3)) are underlined.

17D20_35VH-21N11VL heavy chain variable region (VH) (SEQ ID NO: 67, encoded by SEQ ID NO: 66)
QVTLKESGPVLVKPTETLTLTCTVSGFSLSRGKMGVSWIRQPPGKALEWL
AHIFSSDEKSYRTSLKSRLTISKDTSKNQVVLTMTNMDPVDTATYYCARI
RRGGIDYWGQGTLVTVSS d17N9 heavy chain variable region (VH) (SEQ ID NO: 68)
QVQLQQSGPGLVKPSQTLSLTCAISGDSVSSTSAAWNWIRQSPSRGLEWL
GRTYYRSKWYNDYAVSVKSRITINPDTSKNQFSLQLNSVTPEDTAVYYCA
RDPFGVPFDIWGQGTMVTVSS Presented below are the light-chain variable region (VL) sequences for the mother clones and daughter clones shown above in TABLE 8.

The Kabat CDRs (24-34 (L1); 50-56 (L2); and 89-97 (L3) are bolded; and the Chothia CDRs (24-34 (L1); 50-56 (L2) and 89-97 (L3) are underlined. These regions are the same whether numbered by the Kabat or Chothia system.

17D20m_d3521N11 light chain variable region (VL) (SEQ ID NO: 69, encoded by SEQ ID NO: 70)
QPVLTQPPSLSVSPGQTASITCSGEKLGDKYAYWYQQKPGQSPVLVMYQD
KQRPSGIPERFSGSNSGNTATLTISGTQAMDEADYYCQAWDSSTAVFGGG
TKLTVL -continued 17N16m_d17N9 light chain variable region (VL)
(SEQ ID NO: 71)
SYELIQPPSVSVAPGQTATITCAGDNLGKKRVHWYQQRPGQAPVLVIYD**D
SDRPSGIPDRFSASNSGNTATLTITRGEAGDEADYYCQVWDIATDHV**VFG
GGTKLTVLAAAGSEQKLISE The MASP-2 antibodies OMS100 and MoAb_d3521N11VL, (comprising a heavy chain variable region set forth as SEQ ID NO:67 and a light chain variable region set forth as SEQ ID NQ:69, also referred to as "OMS646" and "mAb6"), which have both been demonstrated to bind to human MASP-2 with high affinity and have the ability to block functional complement activity, were analyzed with regard to epitope binding by dot blot analysis. The results show that OMS646 and OMS100 antibodies are highly specific for MASP-2 and do not bind to MASP-1/3. Neither antibody bound to MAp19 nor to MASP-2 fragments that did not contain the CCP1 domain of MASP-2, leading to the conclusion that the binding sites encompass CCP1.

The MASP-2 antibody OMS646 was determined to avidly bind to recombinant MASP-2 (Kd 60-250 µM) with >5000 fold selectivity when compared to C1s, C1r or MASP-1 (see TABLE 9 below):

TABLE 9

Affinity and Specificity of OMS646 MASP-2 antibody-MASP-2 interaction as assessed by solid phase ELISA studies

| Antigen | $K_D$ (pM) |
|---|---|
| MASP-1 | >500,000 |
| MASP-2 | 62 ± 73* |
| MASP-3 | >500,000 |
| Purified human C1r | >500,000 |
| Purified human C1s | ~500,000 |

*Mean ± SD; n = 12

OMS646 Specifically Blocks Lectin-Dependent Activation of Terminal Complement Components Methods:

The effect of OMS646 on membrane attack complex (MAC) deposition was analyzed using pathway-specific conditions for the lectin pathway, the classical pathway and the alternative pathway. For this purpose, the Wieslab Comp300 complement screening kit (Wieslab, Lund, Sweden) was used following the manufacturer's instructions.

Figure 12A:
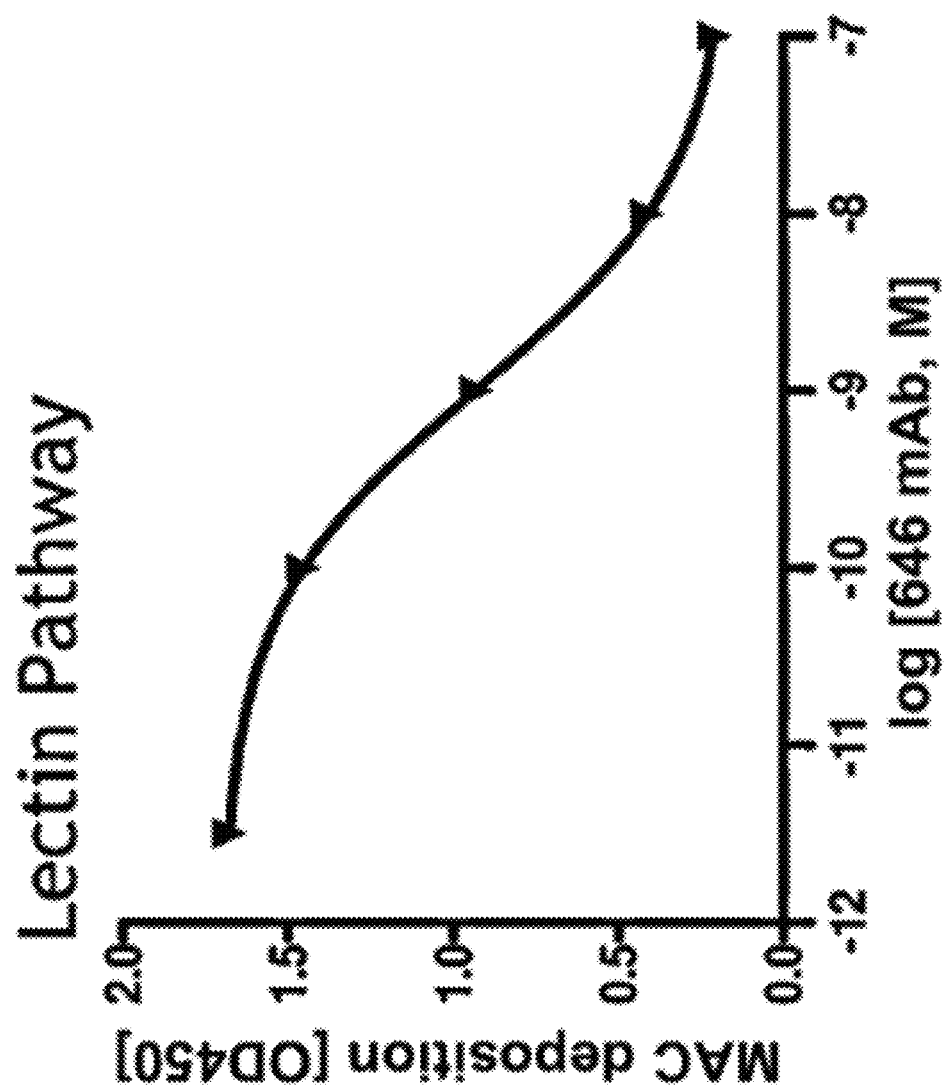
FIG. 12A graphically illustrates the level of MAC deposition in the presence or absence of human MASP-2 monoclonal antibody (OMS646) under lectin pathway-specific assay conditions, demonstrating that OMS646 inhibits lectin-mediated MAC deposition with an $IC_{50}$ value of approximately 1 nM, as described in Example 12.
Figure 12B:
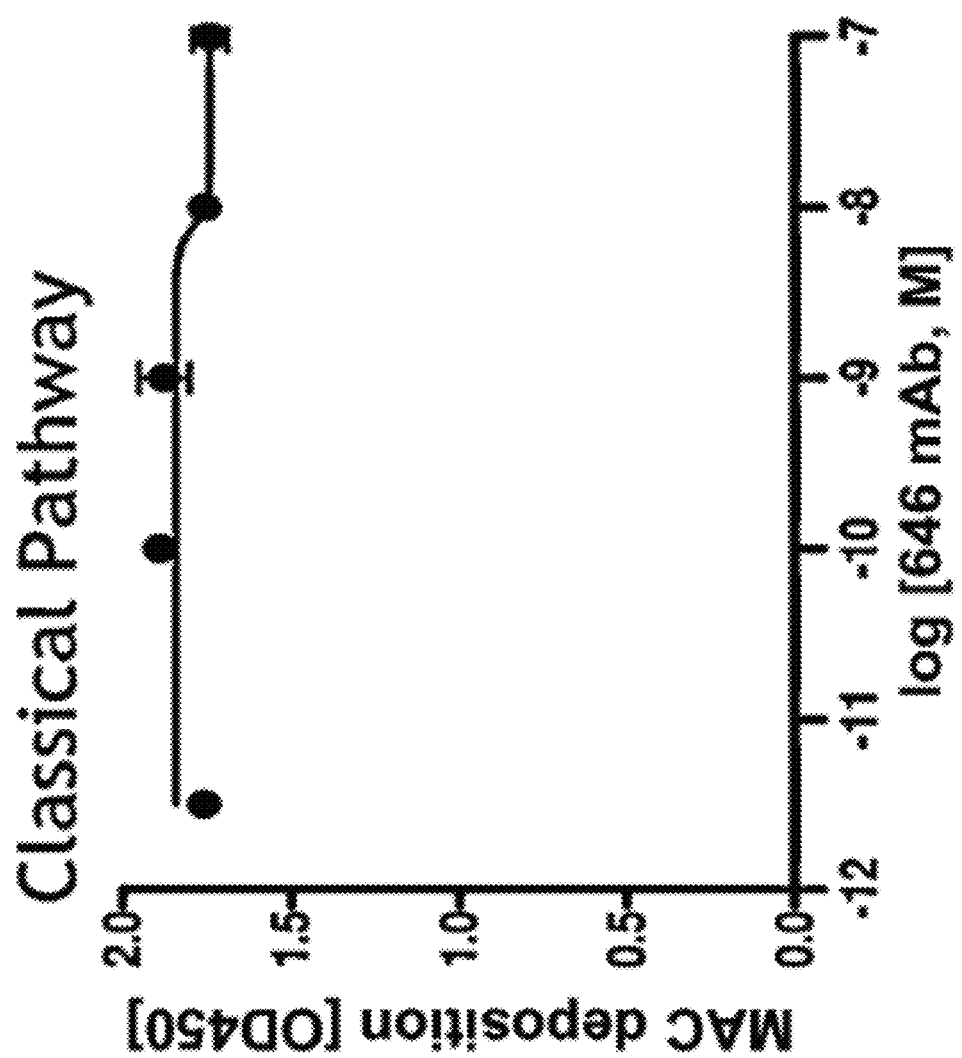
FIG. 12B graphically illustrates the level of MAC deposition in the presence or absence of human MASP-2 monoclonal antibody (OMS646) under classical pathway-specific assay conditions, demonstrating that OMS646 does not inhibit classical pathway-mediated MAC deposition, as described in Example 12.
Figure 12C:
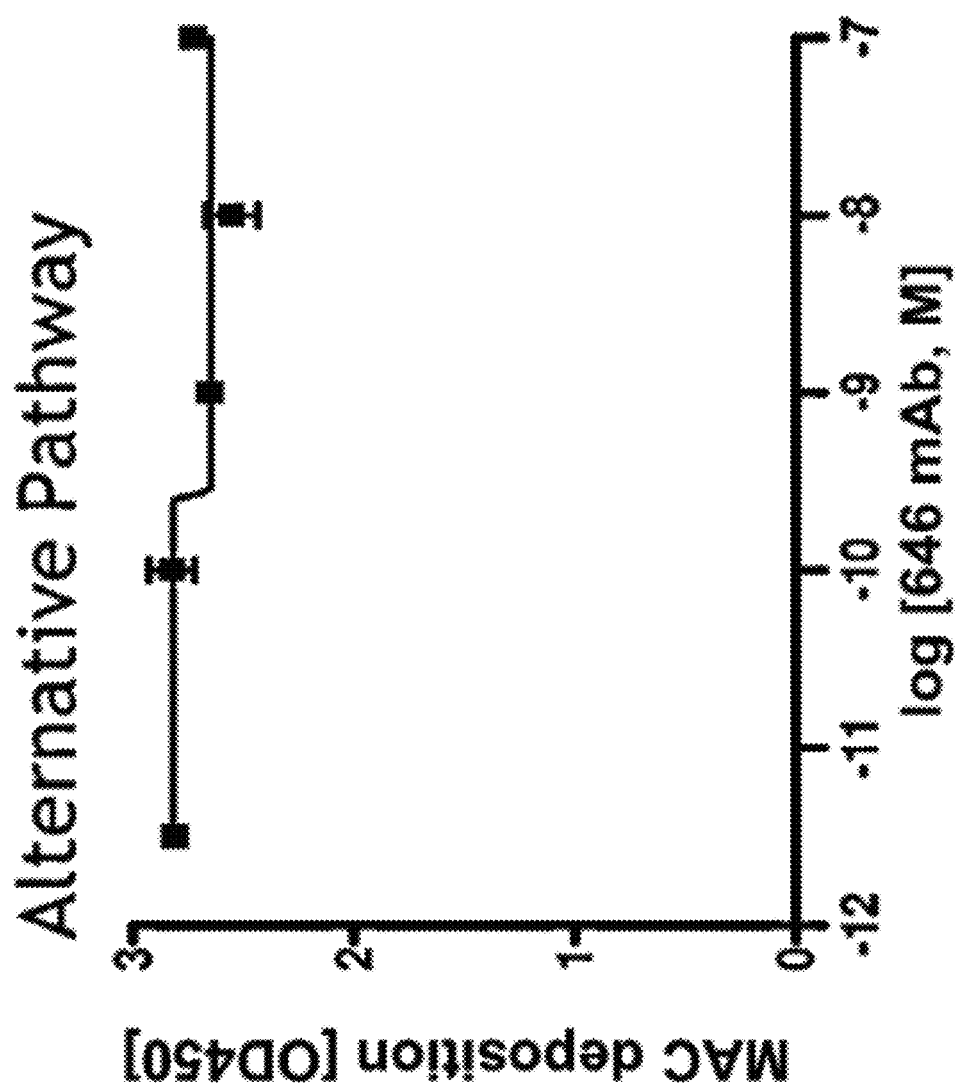
FIG. 12C graphically illustrates the level of MAC deposition in the presence or absence of human MASP-2 monoclonal antibody (OMS646) under alternative pathway-specific assay conditions, demonstrating that OMS646 does not inhibit alternative pathway-mediated MAC deposition, as described in Example 12.

Results:

FIG. 12A graphically illustrates the level of MAC deposition in the presence or absence of anti-MASP-2 antibody (OMS646) under lectin pathway-specific assay conditions. FIG. 12B graphically illustrates the level of MAC deposition in the presence or absence of anti-MASP-2 antibody (OMS646) under classical pathway-specific assay conditions. FIG. 12C graphically illustrates the level of MAC deposition in the presence or absence of anti-MASP-2 antibody (OMS646) under alternative pathway-specific assay conditions.

As shown in FIG. 12A, OMS646 blocks lectin pathway-mediated activation of MAC deposition with an $IC_{50}$ value of approximately 1 nM. However, OMS646 had no effect on MAC deposition generated from classical pathway-mediated activation (FIG. 12B) or from alternative pathway-mediated activation (FIG. 12C).

Pharmacokinetics and Pharmacodynamics of OMS646 Following Intravenous (IV) or Subcutaneous (SC) Administration to Mice The pharmacokinetics (PK) and pharmacodynamics (PD) of OMS646 were evaluated in a 28 day single dose PK/PD study in mice. The study tested dose levels of 5 mg/kg and 15 mg/kg of OMS646 administered subcutaneously (SC), as well as a dose level of 5 mg/kg OMS646 administered intravenously (IV).

Figure 13:
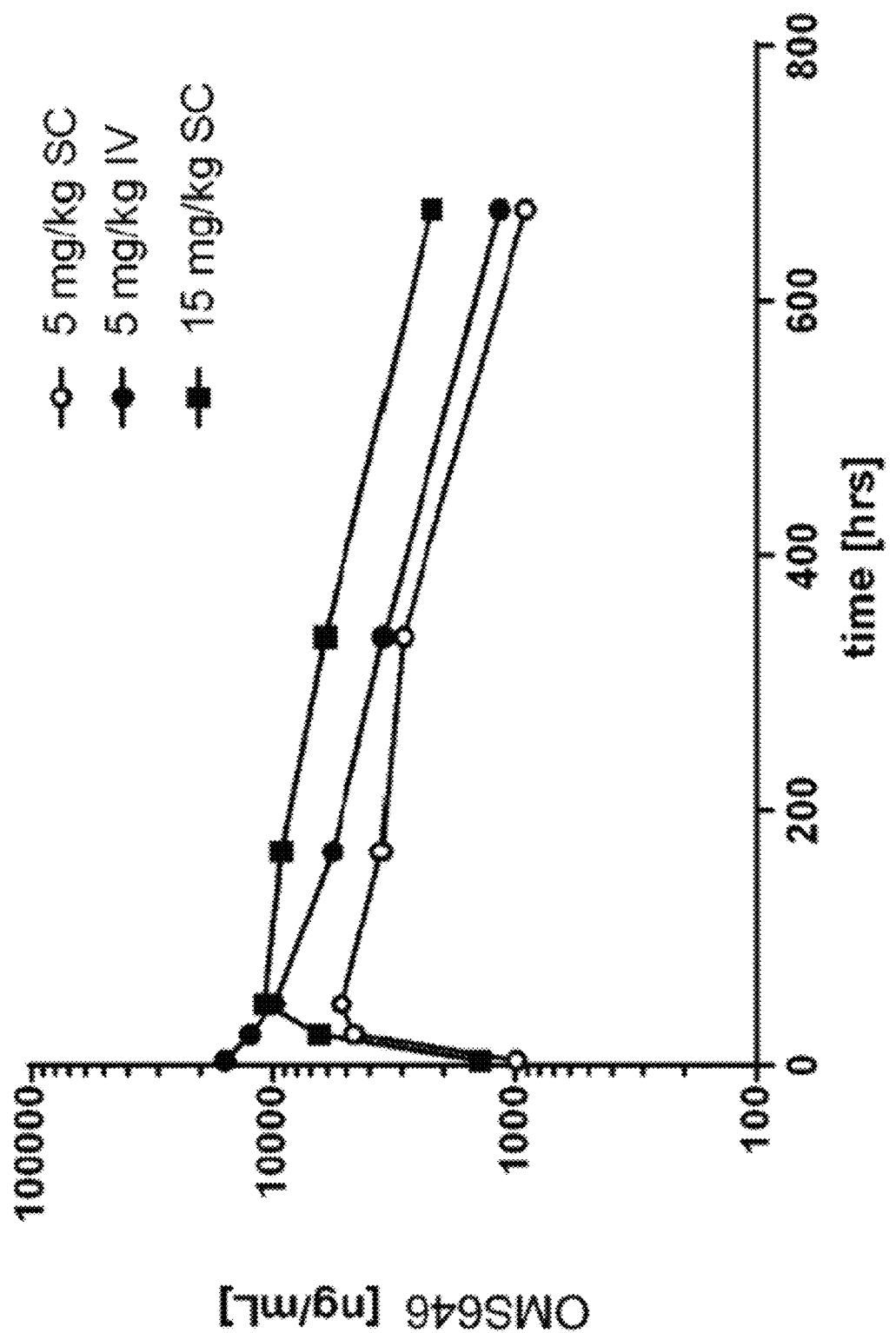
FIG. 13 graphically illustrates the pharmacokinetic (PK) profile of human MASP-2 monoclonal antibody (OMS646) in mice, showing the OMS646 concentration (mean of n=3 animals/groups) as a function of time after administration at the indicated dose, as described in Example 12.

With regard to the PK profile of OMS646, FIG. 13 graphically illustrates the OMS646 concentration (mean of n=3 animals/groups) as a function of time after administration of OMS646 at the indicated dose. As shown in FIG. 13, at 5 mg/kg SC, OMS646 reached the maximal plasma concentration of 5-6 µg/mL approximately 1-2 days after dosing. The bioavailability of OMS646 at 5 mg/kg SC was approximately 60%. As further shown in FIG. 13, at 15 mg/kg SC, OMS646 reached a maximal plasma concentration of 10-12 µg/mL approximately 1 to 2 days after dosing. For all groups, the OMS646 was cleared slowly from systemic circulation with a terminal half-life of approximately 8-10 days. The profile of OMS646 is typical for human antibodies in mice.

Figure 14A:
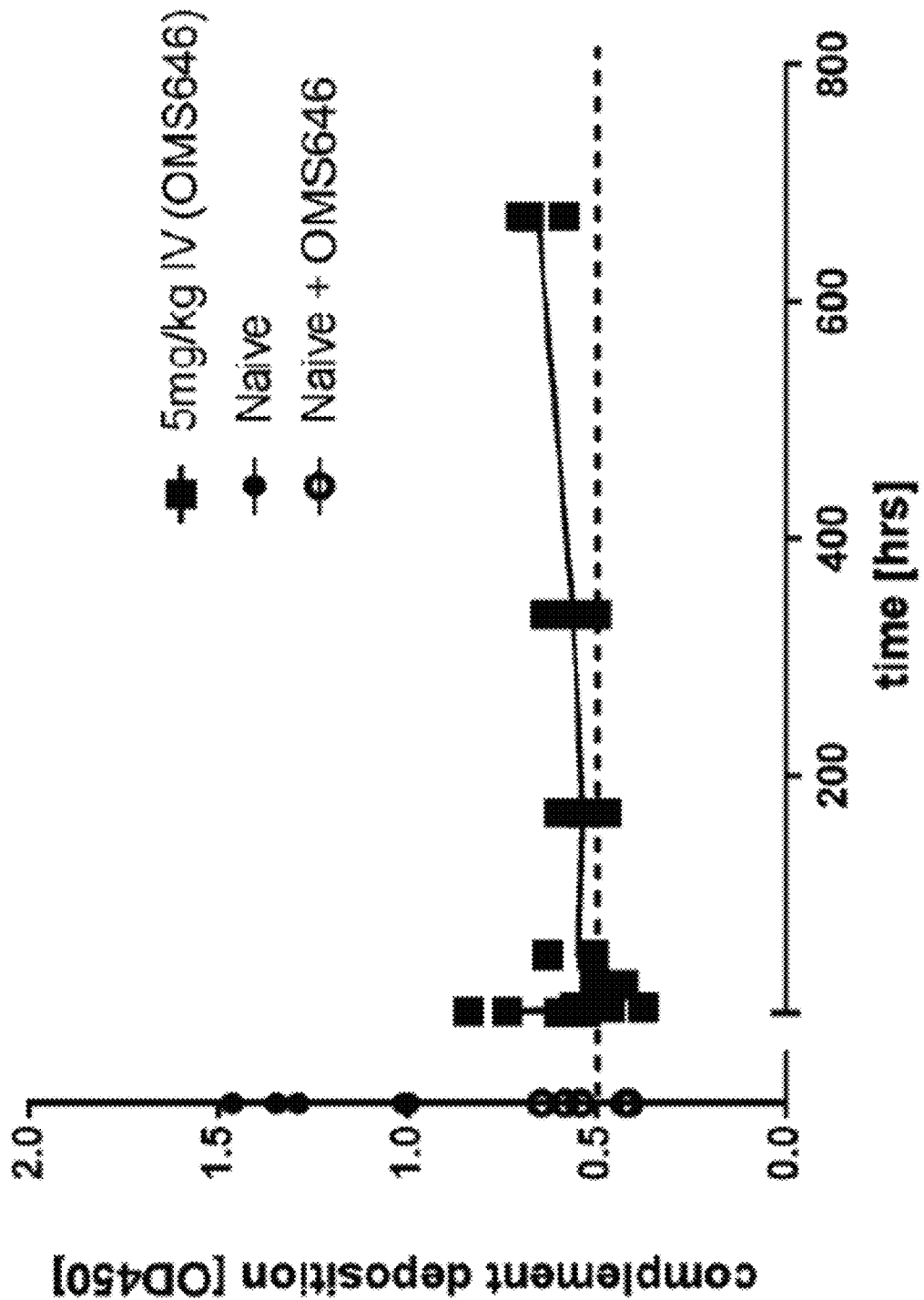
FIG. 14A graphically illustrates the pharmacodynamic (PD) response of human MASP-2 monoclonal antibody (OMS646), measured as a drop in systemic lectin pathway activity, in mice following intravenous administration, as described in Example 12.
Figure 14B:
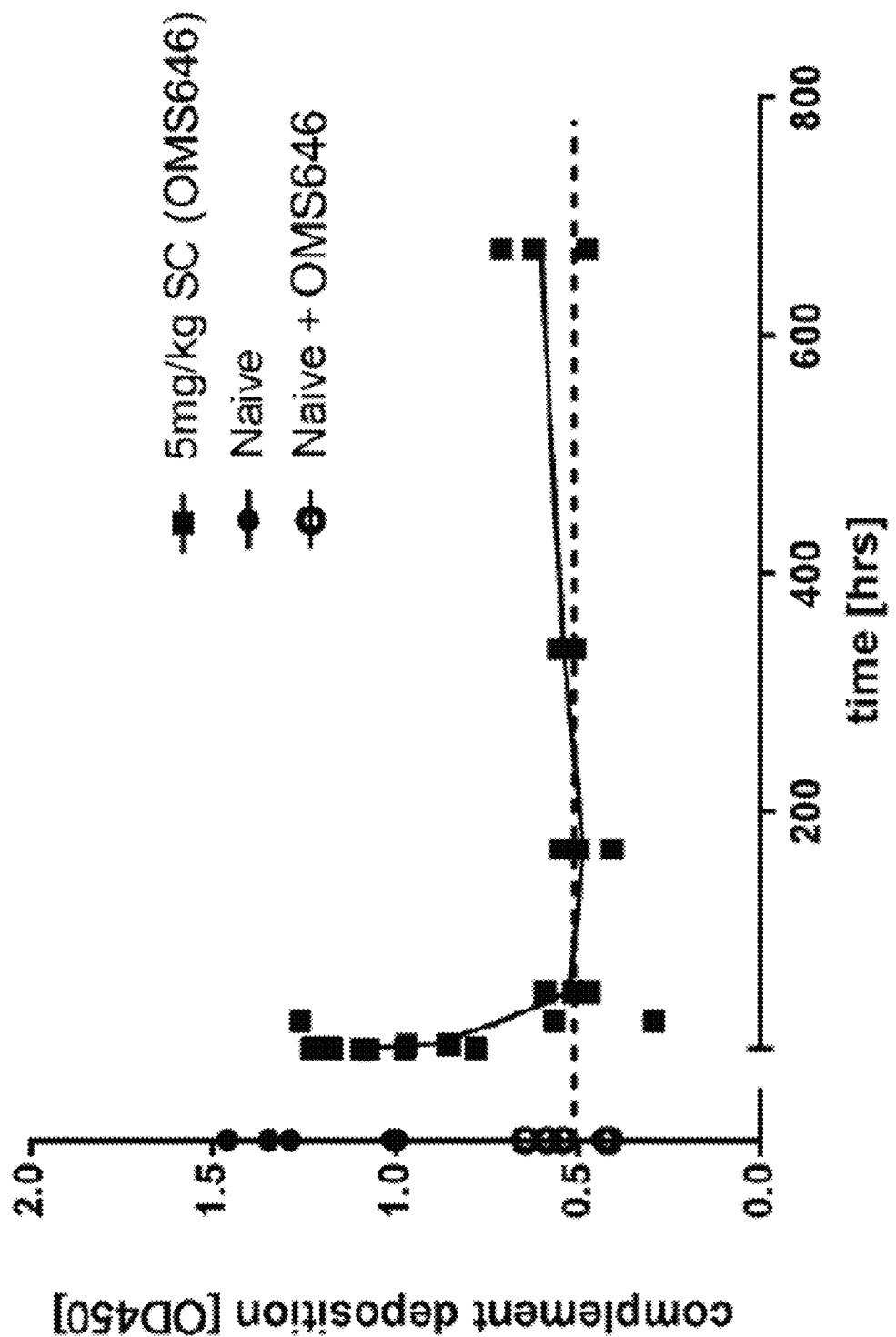
FIG. 14B graphically illustrates the pharmacodynamic (PD) response of human MASP-2 monoclonal antibody (OMS646), measured as a drop in systemic lectin pathway activity, in mice following subcutaneous administration, as described in Example 12.

The PD activity of OMS646 is graphically illustrated in FIGS. 14A and 14B. FIGS. 14A and 14B show the PD response (drop in systemic lectin pathway activity) for each mouse in the 5 mg/kg IV (FIG. 14A) and 5 mg/kg SC (FIG. 14B) groups. The dashed line indicates the baseline of the assay (maximal inhibition, naïve mouse serum spiked in vitro with excess OMS646 prior to assay). As shown in FIG. 14A, following IV administration of 5 mg/kg of OMS646, systemic lectin pathway activity immediately dropped to near undetectable levels, and lectin pathway activity showed only a modest recovery over the 28 day observation period. As shown in FIG. 14B, in mice dosed with 5 mg/kg of OMS646 SC, time-dependent inhibition of lectin pathway activity was observed. Lectin pathway activity dropped to near-undetectable levels within 24 hours of drug administration and remained at low levels for at least 7 days. Lectin pathway activity gradually increased with time, but did not revert to pre-dose levels within the 28 day observation period. The lectin pathway activity versus time profile observed after administration of 15 mg/kg SC was similar to the 5 mg/kg SC dose (data not shown), indicating saturation of the PD endpoint. The data further indicated that weekly doses of 5 mg/kg of OMS646, administered either IV or SC, is sufficient to achieve continuous suppression of systemic lectin pathway activity in mice.

Example 13

This Example describes the generation of recombinant antibodies that inhibit MASP-2 comprising a heavy chain and/or a light chain variable region comprising one or more CDRs that specifically bind to MASP-2 and at least one SGMI core peptide sequence (also referred to as an SGMI-peptide bearing MASP-2 antibody or antigen binding fragment thereof).

Background/Rationale:

The generation of specific inhibitors of MASP-2, termed SGMI-2, is described in Heja et al., *J Biol Chem* 287:20290 (2012) and Heja et al., *PNAS* 109:10498 (2012), each of which is hereby incorporated herein by reference. SGMI-2 is a 36 amino acid peptide which was selected from a phage library of variants of the *Schistocerca gregaria* protease inhibitor 2 in which six of the eight positions of the protease binding loop were fully randomized. Subsequent in vitro evolution yielded mono-specific inhibitors with single digit nM K$_I$ values (Heja et al., *J. Biol. Chem.* 287:20290, 2012). Structural studies revealed that the optimized protease binding loop forms the primary binding site that defines the specificity of the two inhibitors. The amino acid sequences of the extended secondary and internal binding regions are common to the two inhibitors and contribute to the contact interface (Heja et al., 2012. *J. Biol. Chem.* 287:20290). Mechanistically, SGMI-2 blocks the lectin pathway of complement activation without affecting the classical pathway (Heja et al., 2012. *Proc. Natl. Acad. Sci.* 109:10498).

The amino acid sequences of the SGMI-2 inhibitors are set forth below:

```
SGMI-2-full-length:
                                    (SEQ ID NO: 72)
LEVTCEPGTTFKDKCNTCRCGSDGKSAVCTKLWCNQ SGMI-2-medium:
                                    (SEQ ID NO: 73)
TCEPGTTFKDKCNTCRCGSDGKSAVCTKLWCNQ SGMI-2-short:
                                    (SEQ ID NO: 74)
...TCRCGSDGKSAVCTKLNCNQ
```

As described in this Example, and also described in WO2014/144542, SGMI-2 peptide-bearing MASP-2 antibodies and fragments thereof were generated by fusing the SGMI-2 peptide amino acid sequence (e.g., SEQ ID NO: 72, 73 or 74) onto the amino or carboxy termini of the heavy and/or light chains of a human MASP-2 antibody. The SGMI-2 peptide-bearing MASP-2 antibodies and fragments have enhanced inhibitory activity, as compared to the naked MASP-2 scaffold antibody that does not contain the SGMI-2 peptide sequence, when measured in a C3b or C4b deposition assay using human serum, as described in WO2014/144542, and also have enhanced inhibitory activity as compared to the naked MASP-2 scaffold antibody when measured in a mouse model in vivo. Methods of generating SGMI-2 peptide bearing MASP-2 antibodies are described below.

Methods:

Expression constructs were generated to encode four exemplary SGMI-2 peptide bearing MASP-2 antibodies wherein the SGMI-2 peptide was fused either to the N- or C-terminus of the heavy or light chain of a representative MASP-2 inhibitory antibody OMS646 (generated as described in Example 12).

TABLE 10

MASP-2 antibody/SGMI-2 fusions

| Antibody reference | Peptide Location on Antibody | | | | SEQ ID NO: |
| --- | --- | --- | --- | --- | --- |
| | H-N | H-C | L-N | L-C | |
| HL-M2 (naked MASP-2 OMS646) | — | — | — | — | 67 + 70 |
| H-M2-SGMI-2-N | SGMI-2 | — | — | — | 75 + 70 |
| H-M2-SGMI-2-C | — | SGMI-2 | — | — | 76 + 70 |
| L-M2-SGMI-2-N | — | — | SGMI-2 | — | 67 + 77 |
| L-M2-SGMI-2-C | — | — | — | SGMI-2 | 67 + 78 |

Abbreviations in Table 10:
"H-N" = amino terminus of heavy chain
"H-C" = carboxyl terminus of heavy chain
"L-N" = amino terminus of light chain
"L-C" = carboxyl terminus of light chain
"M2" = MASP-2 ab scaffold (representative OMS646)

For the N-terminal fusions shown in TABLE 10, a peptide linker ('GTGGGSGSSS' SEQ ID NO: 79) was added between the SGMI-2 peptide and the variable region.

For the C-terminal fusions shown in TABLE 10, a peptide linker ('AAGGSG' SEQ ID NO: 80) was added between the constant region and the SGMI-2 peptide, and a second peptide "GSGA" (SEQ ID NO: 81) was added at the C-terminal end of the fusion polypeptide to protect C-terminal SGMI-2 peptides from degradation.

Amino acid sequences are provided below for the following representative MASP-2 antibody/SGMI-2 fusions:

H-M2ab6-SGMI-2-N (SEQ ID NO: 75, encoded by SEQ ID NO: 82):

LEVTCEPGTTFKDKCNTCRCGSDGKSAVCTKLWCNQ*GTGGSGSSS*QVTLK

ESGPVLVKPTETLTLTCTVSGFSLSRGKMGVSWIRQPPGKALEWLAHIFS

SDEKSYRTSLKSRLTISKDTSKNQVVLTMTNMDPVDTATYYCARIRRGGI

DYWGQGTLVTVSSASTKGPSVFPLAPCSRSTSESTAALGCLVKDYFPEPV

TVSWNSGALTSGVHTFPAVLQSSGLYSLSSVVTVPSSSLGTKTYTCNVDH

KPSNTKVDKRVESKYGPPCPPCPAPEFLGGPSVFLFPPKPKDTLMISRTP

EVTCVVVDVSQEDPEVQFNWYVDGVEVHNAKTKPREEQFNSTYRVVSVLT

VLHQDWLNGKEYKCKVSNKGLPSSIEKTISKAKGQPREPQVYTLPPSQEE

MTKNQVSLTCLVKGFYPSDIAVEWESNGQPENNYKTTPPVLDSDGSFFLY

SRLTVDKSRWQEGNVFSCSVMHEALHNHYTQKSLSLSLGK

[491 aa protein, aa 1-36=SGMI-2 (underlined), aa37-46=linker (italicized); aa47-164=heavy chain variable region of MASP-2 ab #6 (underlined); aa165-491=IgG4 constant region with hinge mutation.]

H-M2ab6-SGMI-2-C (SEQ ID NO: 76, encoded by SEQ ID No: 83):

QVTLKESGPVLVKPTETLTLTCTVSGFSLSRGKMGVSWIRQPPGKALEWL

AHIFSSDEKSYRTSLKSRLTISKDTSKNQVVLTMTNMDPVDTATYYCARI

RRGGIDYWGQGTLVTVSSASTKGPSVFPLAPCSRSTSESTAALGCLVKDY

FPEPVTVSWNSGALTSGVHTFPAVLQSSGLYSLSSVVTVPSSSLGTKTYT

CNVDHKPSNTKVDKRVESKYGPPCPPCPAPEFLGGPSVFLFPPKPKDTLM

ISRTPEVTCVVVDVSQEDPEVQFNWYVDGVEVHNAKTKPREEQFNSTYRV

VSVLTVLHQDWLNGKEYKCKVSNKGLPSSIEKTISKAKGQPREPQVYTLP

PSQEEMTKNQVSLTCLVKGFYPSDIAVEWESNGQPENNYKTTPPVLDSDG

SFFLYSRLTVDKSRWQEGNVFSCSVMHEALHNHYTQKSLSLSLGKA*AGGS*

*G*LEVTCEPGTTFKDKCNTCRCGSDGKSAVCTKLWCNQ*GSGA*

[491aa protein, aa1-118=heavy chain variable region of MASP-2 ab #6 (underlined); aa 119-445=IgG4 constant region with hinge mutation; aa 446-451=1$^{st}$ linker (italicized); aa 452-487=SGMI-2; aa488-491=2$^{nd}$ linker (italicized).]

L-M2ab6-SGMI-2-N (SEQ ID NO: 77, encoded by SEQ ID NO: 84):
LEVTCEPGTTFKDKCNTCRCGSDGKSAVCTKLWCNQ*GTGGGSGSSS*QPVL

TQPPSLSVSPGQTASITCSGEKLGDKYAYWYQQKPGQSPVLVMYQDKQRP

SGIPERFSGSNSGNTATLTISGTQAMDEADYYCQAWDSSTAVFGGGEKLT

VLGQPKAAPSVTLFPPSSEELQANKATLVCLISDFYPGAVTVAWKADSSP

VKAGVETTTPSKQSNNKYAASSYLSLTPEQWKSHRSYSCQVTHEGSTVEK

TVAPTECS

[258aa protein, aa1-36=SGMI-2 (underlined); aa37-46=linker (italicized); aa47-152=light chain variable region of MASP-2 ab #6 (underlined); aa153-258=human Ig lambda constant region]

L-M2ab6-SGMI-2-C (SEQ ID NO: 78, encoded by SEQ ID NO: 85):
QPVLTQPPSLSVSPGQTASITCSGEKLGDKYAYWYQQKPGQSPVLVMYQD

KQRPSGIPERFSGSNSGNTATLTISGTQAMDEADYYCQAWDSSTAVFGGG

TKLTVLGQPKAAPSVTLFPPSSEELQANKATLVCLISDFYPGAVTVAWKA

DSSPVKAGVETTTPSKQSNNKYAASSYLSLTPEQWKSHRSYSCQVTHEGS

TVEKTVAPTECS*AAGGSG*LEVTCEPGTTFKDKCNTCRCGSDGKSAVCTKL

WCNQ*GSGA*

[258aa protein, aa1-106=light chain variable region of MASP-2 ab #6 (underlined); aa 107-212=human Ig lambda constant region; aa 213-218=1$^{st}$ linker; aa219-254=SGMI-2; aa255-258=2$^{nd}$ linker]

Functional Assays:

The four MASP-2-SGMI-2 fusion antibody constructs were transiently expressed in Expi293F cells (Invitrogen), purified by Protein A affinity chromatography, and tested in 10% normal human serum for inhibition of C3b deposition in a mannan-coated bead assay as described below.

Testing the MASP-2-SGMI-2 Fusions in the Mannan-Coated Bead Assay for C3b Deposition The MASP-2-SGMI-2 fusion antibodies assessed for lectin pathway inhibition in an assay of C3b deposition on mannan-coated beads. This assay, which determines degree of activity by flow cytometry, offers greater resolution than the Wieslab® assay. The lectin pathway bead assay was carried out as follows: mannan was adsorbed to 7 μM-diameter polystyrene beads (Bangs Laboratories, Fishers, Ind., USA) overnight at 4° C. in carbonate-bicarbonate buffer (pH 9.6). The beads were washed in PBS and exposed to 10% human serum, or 10% serum pre-incubated with antibodies or inhibitors. The serum-bead mixture was incubated at room temperature for one hour while agitating. Following the serum incubation, the beads were washed, and C3b deposition on the beads was measured by detection with an anti-C3c rabbit polyclonal antibody (Dako North America; Carpinteria, Calif., USA) and a PE-Cy5 conjugated goat anti-rabbit secondary antibody (Southern Biotech; Birmingham, Ala., USA). Following the staining procedure, the beads were analyzed using a FACSCalibur flow cytometer. The beads were gated as a uniform population using forward and side scatter, and C3b deposition was apparent as FL3-positive particles (FL-3, or "FL-3 channel" indicates the 3rd or red channel on the cytometer). The Geometric Mean Fluorescence Intensity (MFI) for the population for each experimental condition was plotted relative to the antibody/inhibitor concentration to evaluate lectin pathway inhibition.

The $IC_{50}$ values were calculated using the GraphPad PRISM software. Specifically, $IC_{50}$ values were obtained by applying a variable slope (four parameter), nonlinear fit to log (antibody) versus mean fluorescence intensity curves obtained from the cytometric assay.

The results are shown in TABLE 11.

TABLE 11

| C3b deposition (mannan-coated bead assay) in 10% human serum | |
|---|---|
| Construct | $IC_{50}$ (nM) |
| Naked N2 ab (mAb#6) | ≥3.63 nM |
| H-M2-SGMI-2-N | 2.11 nM |
| L-M2-SGMI-2-C | 1.99 nM |
| H-M2-SGMI-2-N | 2.24 nM |
| L-M2-SGMI-2-N | 3.71 nM |

Results:

The control, non-SGMI-containing MASP-2 "naked" scaffold antibody (mAb #6), was inhibitory in this assay, with an IC50 value of ≥3.63 nM, which is consistent with the inhibitory results observed in Example 12. Remarkably, as shown in TABLE 11, all of the SGMI-2-MASP-2 antibody fusions that were tested improved the potency of the MASP-2 scaffold antibody in this assay, suggesting that increased valency may also be beneficial in the inhibition of C3b deposition.

Testing the MASP-2-SGMI-2 Fusions in the Mannan-Coated Bead Assay for C4b Deposition Assay with 10% Human Serum A C4b deposition assay was carried out with 10% human serum using the same assay conditions as described above for the C3b deposition assay with the following modifications. C4b detection and flow cytometric analysis was carried out by staining the deposition reaction with an anti-C4b mouse monoclonal antibody (1:500, Quidel) and staining with a secondary goat anti-mouse $F(ab')_2$ conjugated to PE Cy5 (1:200, Southern Biotech) prior to flow cytometric analysis.

Results:

The SGMI-2-bearing MASP-2-N-terminal antibody fusions (H-M2-SGMI-2-N: IC50=0.34 nM), L-M2-SGMI-2-N: IC50=0.41 nM)), both had increased potency as compared to the MASP-2 scaffold antibody (HL-M2: IC50=0.78 nM).

Similarly, the single SGMI-2 bearing C-terminal MASP-2 antibody fusions (H-M2-SGMI-2-C: $IC_{50}$=0.45 nM and L-M2-SGMI-2C: $IC_{50}$=0.47 nM) both had increased potency as compared to the MASP-2 scaffold antibody (HL-M2: $IC_{50}$=1.2 nM).

Testing the MASP-2-SGMI-2 Fusions in the Mannan-Coated Bead Assay for C3b Deposition with 10% Mouse Serum.

A mannan-coated bead assay for C3b deposition was carried out as described above with 10% mouse serum. Similar to the results observed in human serum, it was determined that the SGMI-2-bearing MASP-2 fusions had increased potency as compared to the MASP-2 scaffold antibody in mouse serum.

Summary of Results: The results in this Example demonstrate that all of the SGMI-2-MASP-2 antibody fusions that were tested improved the potency of the MASP-2 scaffold antibody.

Example 14

This Example provides results that were generated using a Unilateral Ureteric Obstruction (UUO) model of renal fibrosis in MASP-2−/− deficient and MASP-2+/+ sufficient mice to evaluate the role of the lectin pathway in renal fibrosis.

Background/Rationale:

Renal fibrosis and inflammation are prominent features of late stage kidney disease. Renal tubulointerstitial fibrosis is progressive process involving sustained cell injury, aberrant healing, activation of resident and infiltrating kidney cells, cytokine release, inflammation and phenotypic activation of kidney cells to produce extracellular matrix. Renal tubulointerstitial (TI) fibrosis is the common end point of multiple renal pathologies and represents a key target for potential therapies aimed at preventing progressive renal functional impairment in chronic kidney disease (CKD). Renal TI injury is closely linked to declining renal function in glomerular diseases (Risdon R. A. et al., *Lancet* 1: 363-366, 1968; Schainuck L. I. et al, Hum Pathol 1: 631-640, 1970; Nath K. A., *Am J Kid Dis* 20:1-17, 1992), and is characteristic of CKD where there is an accumulation of myofibroblasts, and the potential space between tubules and peritubular capillaries becomes occupied by matrix composed of collagens and other proteoglycans. The origin of TI myofibroblasts remains intensely controversial, but fibrosis is generally preceded by inflammation characterized initially by TI accumulation of T lymphocytes and then later by macrophages (Liu Y. et al., *Nat Rev Nephrol* 7:684-696, 2011; Duffield J. S., *J Clin Invest* 124:2299-2306, 2014).

The rodent model of UUO generates progressive renal fibrosis, a hallmark of progressive renal disease of virtually any etiology (Chevalier et al., *Kidney International* 75:1145-1152, 2009). It has been reported that C3 gene expression was increased in wild-type mice following UUO, and that collagen deposition was significantly reduced in C3−/− knockout mice following UUO as compared to wild-type mice, suggesting a role of complement activation in renal fibrosis (Fearn et al., *Mol Immunol* 48:1666-1733, 2011). It has also been reported that C5 deficiency led to a significant amelioration of major components of renal fibrosis in a model of tubulointerstitial injury (Boor P. et al., *J of Am Soc of Nephrology:* 18:1508-1515, 2007). However, prior to the study described herein carried out by the present inventors, the particular complement components involved in renal fibrosis were not well defined. Therefore, the following study was carried out to evaluate MASP-2 (−/−) and MASP-2 (+/+) male mice in a unilateral ureteral obstruction (UUO) model.

Methods:

A MASP-2−/− mouse was generated as described in Example 1 and backcrossed for generations with C57BL/6. Male wild-type (WT) C57BL/6 mice, and homozygous MASP-2 deficient (MASP-2−/−) mice on a C57BL/6 background were kept under standardized conditions of 12/12 day/night cycle, fed on standard food pellets and given free access to food and water. Ten-week-old mice, 6 per group, were anesthetized with 2.5% isoflurane in 1.5 L/min oxygen. The right ureters of two groups of ten-week-old male C56/BL6 mice, wild-type and MASP-2−/− were surgically ligated. The right kidney was exposed through a 1 cm flank incision. The right ureter was completely obstructed at two points using a 6/0 polyglactin suture. Buprenorphine analgesia was provided perioperatively every 12 hours for up to 5 doses depending on pain scoring. Local bupivacaine anesthetic was given once during the surgery.

Mice were sacrificed 7 days after the surgery and kidney tissues were collected, fixed and embedded in paraffin blocks. Blood was collected from the mice by cardiac puncture under anesthesia, and mice were culled by exsanguination after nephrectomy. Blood was allowed to clot on ice for 2 hours and serum was separated by centrifugation and kept frozen as aliquots at −80° C.

Immunohistochemistry of Kidney Tissue

To measure the degree of kidney fibrosis as indicated by collagen deposition, 5 micron paraffin embedded kidney sections were stained with picrosirius red, a collagen-specific stain, as described in Whittaker P. et al., *Basic Res Cardiol* 89:397-410, 1994. Briefly described, kidney sections were de-paraffinized, rehydrated and collagen stained for 1 hour with picrosirius red aqueous solution (0.5 gm Sirius red, Sigma, Dorset UK) in 500 mL saturated aqueous solution of picric acid. Slides were washed twice in acidified water (0.5% glacial acetic acid in distilled water) for 5 minutes each, then dehydrated and mounted.

To measure the degree of inflammation as indicated by macrophage infiltration, kidney sections were stained with macrophage-specific antibody F4/80 as follows. Formalin fixed, paraffin embedded, 5 micron kidney sections were deparaffinized and rehydrated. Antigen retrieval was performed in citrate buffer at 95° C. for 20 minutes followed by quenching of endogenous peroxidase activity by incubation in 3% $H_2O_2$ for 10 minutes. Tissue sections were incubated in blocking buffer (10% heat inactivated normal goat serum with 1% bovine serum albumin in phosphate buffered saline (PBS)) for 1 hour at room temperature followed by avidin/biotin blocking. Tissue sections were washed in PBS three times for 5 minutes after each step. F4/80 macrophage primary antibody (Santa Cruz, Dallas, Tex., USA) diluted 1:100 in blocking buffer was applied for 1 hour. A biotinylated goat anti-rat secondary antibody, diluted 1:200, was then applied for 30 minutes followed by horse radish peroxidase (HRP) conjugated enzyme for 30 minutes. Staining color was developed using diaminobenzidine (DAB) substrate (Vector Labs, Peterborough UK) for 10 minutes and slides were washed in water, dehydrated and mounted without counter staining to facilitate the computer based analysis.

Image Analysis

The percentage of kidney cortical staining was determined as described in Furness P. N. et al., *J Clin Pathol* 50:118-122, 1997. Briefly described, 24 bit color images were captured from sequential non-overlapping fields of renal cortex just beneath the renal capsule around the entire periphery of the section of kidney. After each image capture NIH Image was used to extract the red channel as an 8 bit monochrome image. Unevenness in the background illumination was subtracted using a pre-recorded image of the illuminated microscope field with no section in place. The image was subjected to a fixed threshold to identify areas of the image corresponding to the staining positivity. The percentage of black pixels was then calculated, and after all the images around the kidney had been measured in this way the average percentage was recorded, providing a value corresponding to the percentage of stained area in the kidney section.

Gene Expression Analysis

Expression of several genes relevant to renal inflammation and fibrosis in mouse kidney were measured by quantitative PCT (qPCR) as follows. Total RNA was isolated from kidney cortex using Trizol® (ThermoFisher Scientific, Paisley, UK) according to the manufacturer's instructions. Extracted RNA was treated with the Turbo DNA-free kit (ThermoFisher Scientific) to eliminate DNA contamination, and then first strand cDNA was synthesized using AMV Reverse Transcription System (Promega, Madison, Wis., USA). The cDNA integrity was confirmed by a single qPCR reaction using TaqMan GAPDH Assay (Applied Biosystems, Paisley UK) followed by qPCR reaction using Custom TaqMan Array 96-well Plates (Life Technologies, Paisley, UK).

Twelve genes were studied in this analysis:
Collagen type IV alpha 1 (col4α1; assay ID: Mm01210125_m1)
Transforming growth factor beta-1 (TGFβ-1; assay ID: Mm01178820_m1);
Cadherin 1 (Cdh1; Assay ID: Mm01247357_m1);
Fibronectin 1 (Fn1; Assay ID: Mm01256744_m1);
Interleukin 6 (IL6; Assay ID Mm00446191_m1);
Interleukin 10 (IL10; Assay ID Mm00439614_m1);
Interleukin 12a (IL12a; Assay ID Mm00434165_m1);
Vimentin (Vim; Assay ID Mm01333430_m1);
Actinin alpha 1 (Actn1; Assay ID Mm01304398_m1);
Tumor necrosis factor-α (TNF-α; Assay ID Mm00443260_g1)
Complement component 3 (C3; Assay ID Mm00437838_m1);
Interferon gamma (Ifn-γ; Assay ID Mm01168134)

The following housekeeping control genes were used:
Glyceraldehyde-3-phosphate dehydrogenase (GAPDH; Assay ID Mm99999915_g1);
Glucuronidase beta (Gusβ; Assay ID Mm00446953_m1);
Eukaryotic 18S rRNA (18S; Assay ID Hs99999901_s1);
Hypoxanthine guanine phosphoribosyl transferase (HPRT; Assay ID Mm00446968_m1)

Twenty μL reactions were amplified using TaqMan Fast Universal Master Mix (Applied Biosystems) for 40 cycles. Real time PCR amplification data were analyzed using Applied Biosystems 7000 SDS v1.4 software.

Results:

Following unilateral ureteric obstruction (UUO), obstructed kidneys experience an influx of inflammatory cells, particularly macrophages, followed by the prompt development of fibrosis as evidenced by the accumulation of collagen alongside tubular dilatation and attenuation of the proximal tubular epithelium (see Chevalier R. L. et al., *Kidney Int* 75:1145-1152, 2009).

Figure 15:
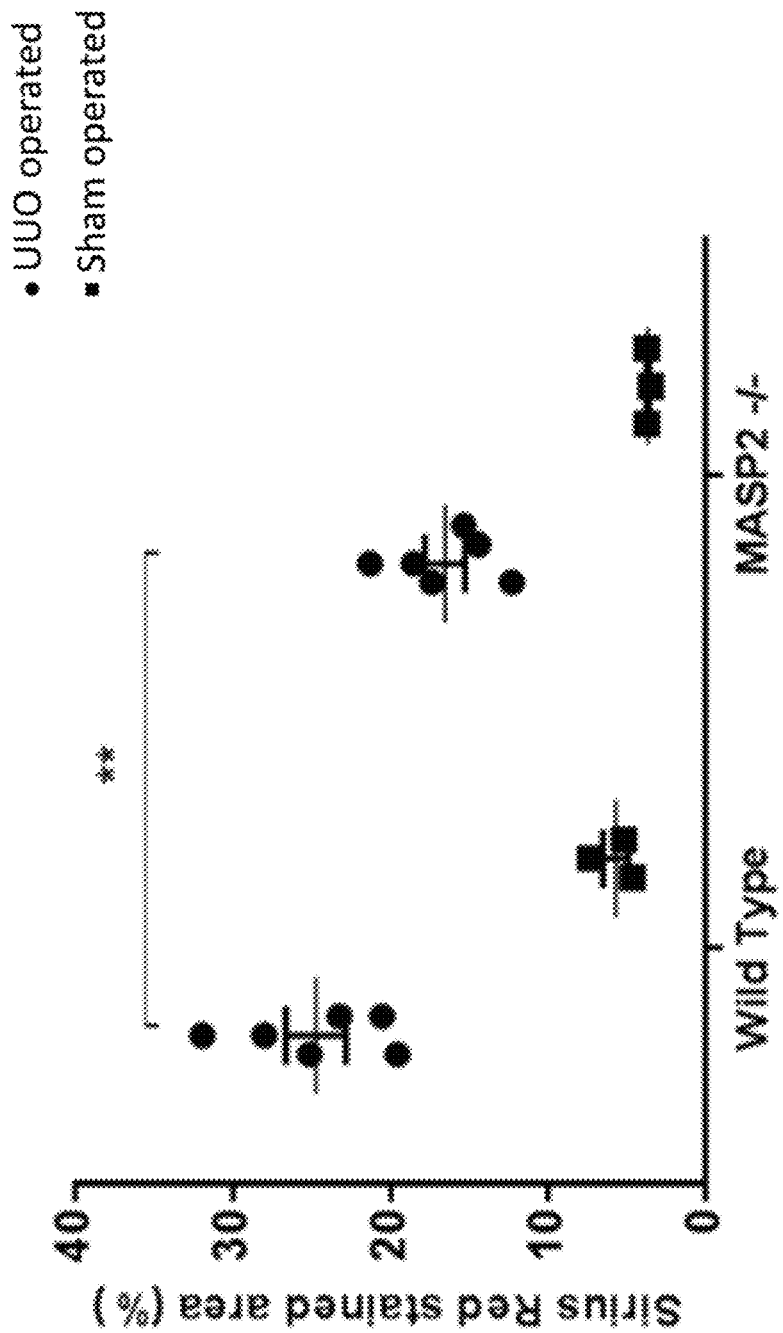
FIG. 15 graphically illustrates the results of computer-based image analysis of kidney tissue sections stained with Sirius red, wherein the tissue sections were obtained from wild-type and MASP-2−/− mice following 7 days of unilateral ureteric obstruction (UUO) and sham-operated wild-type and MASP-2−/− mice, as described in Example 14.

FIG. 15 graphically illustrates the results of computer-based image analysis of kidney tissue sections stained with Sirius red, wherein the tissue sections were obtained from wild-type and MASP-2−/− mice following 7 days of ureteric obstruction (UUO) or from sham-operated control mice. As shown in FIG. 15, kidney sections of wild-type mice following 7 days of ureteric obstruction showed significantly greater collagen deposition compared to MASP-2−/− mice (p value=0.0096). The mean values ±standard error of means for UUO operated mice in wild-type and MASP-2−/− groups were 24.79±1.908 (n=6) and 16.58±1.3 (n=6), respectively. As further shown in FIG. 15, the tissue sections from the sham-operated control wild-type and the sham operated control MASP-2−/− mice showed very low levels of collagen staining, as expected.

Figure 16:
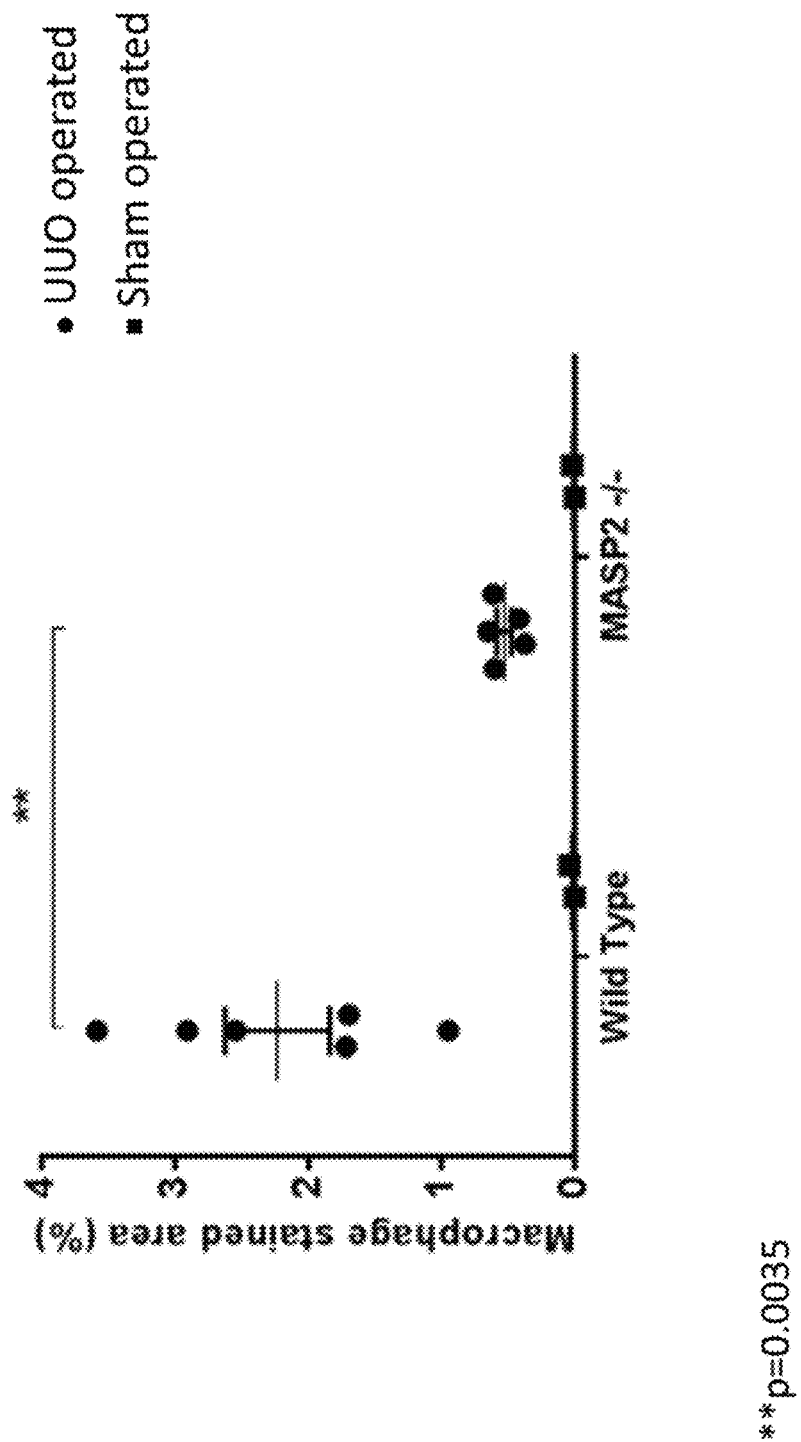
FIG. 16 graphically illustrates the results of computer-based image analysis of kidney tissue sections stained with the F4/80 macrophage-specific antibody, wherein the tissue sections were obtained from wild-type and MASP-2−/− mice following 7 days of unilateral ureteric obstruction (UUO) and sham-operated wild-type and MASP-2−/− mice, as described in Example 14.

FIG. 16 graphically illustrates the results of computer-based image analysis of kidney tissue sections stained with the F4/80 macrophage-specific antibody, wherein the tissue sections were obtained from wild-type and MASP-2−/− mice following 7 days of ureteric obstruction or from sham-operated control mice. As shown in FIG. 16, compared to wild-type mice, the tissue obtained from UUO kidneys from MASP-2−/− mice exhibited significantly less macrophage infiltration following 7 days of ureteric obstruction (% macrophage area stained in WT:2.23±0.4 vs MASP-2−/−: 0.53±0.06, p=0.0035). As further shown in FIG. 16, the tissue sections from the sham-operated wild-type and the sham-operated MASP-2−/− mice showed no detectable macrophage staining.

Figure 17:
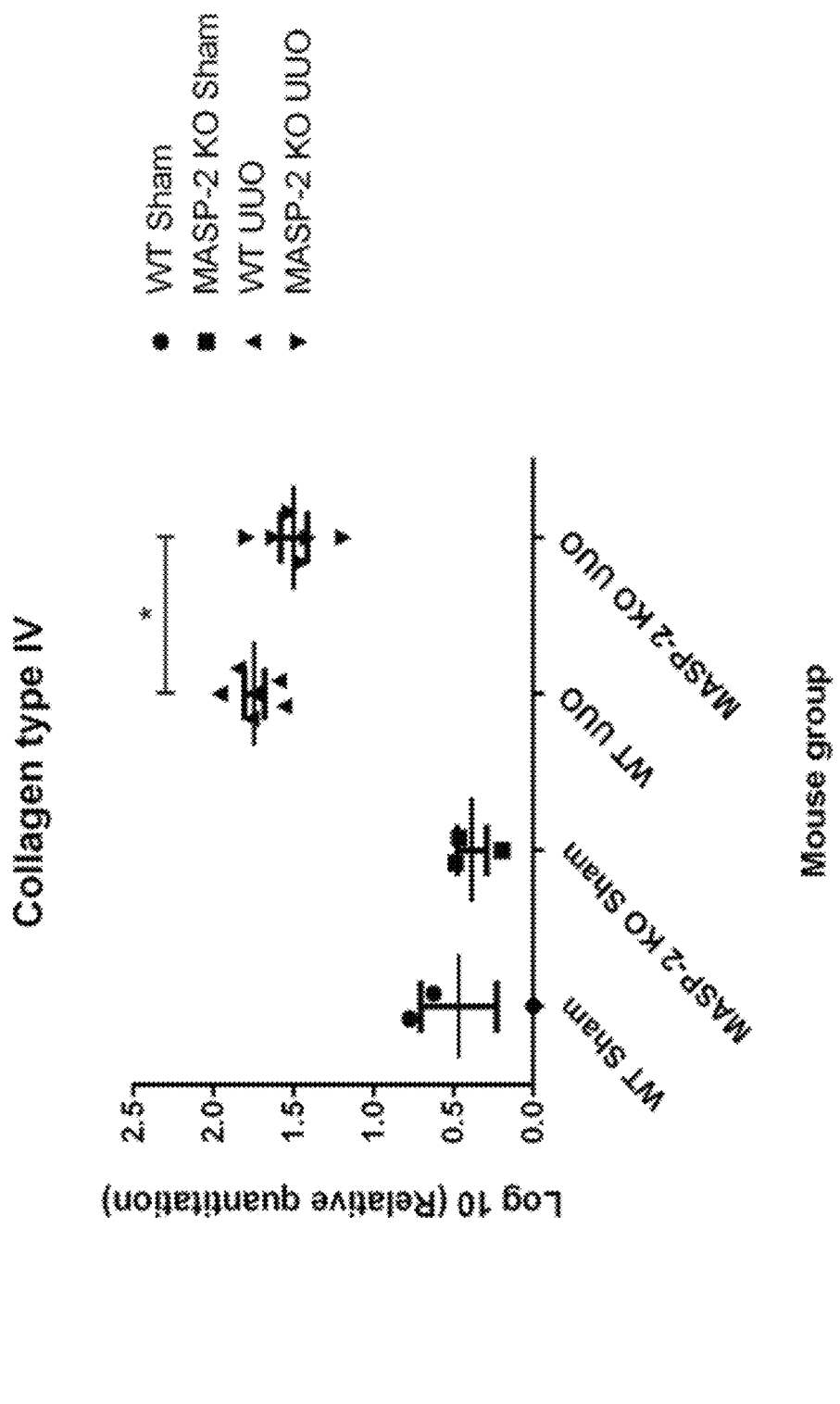
FIG. 17 graphically illustrates the relative mRNA expression levels of collagen-4, as measured by quantitative PCR (qPCR), in kidney tissue sections obtained from wild-type and MASP-2−/− mice following 7 days of unilateral ureteric obstruction (UUO) and sham-operated wild-type and MASP-2−/− mice, as described in Example 14.
Figure 18:
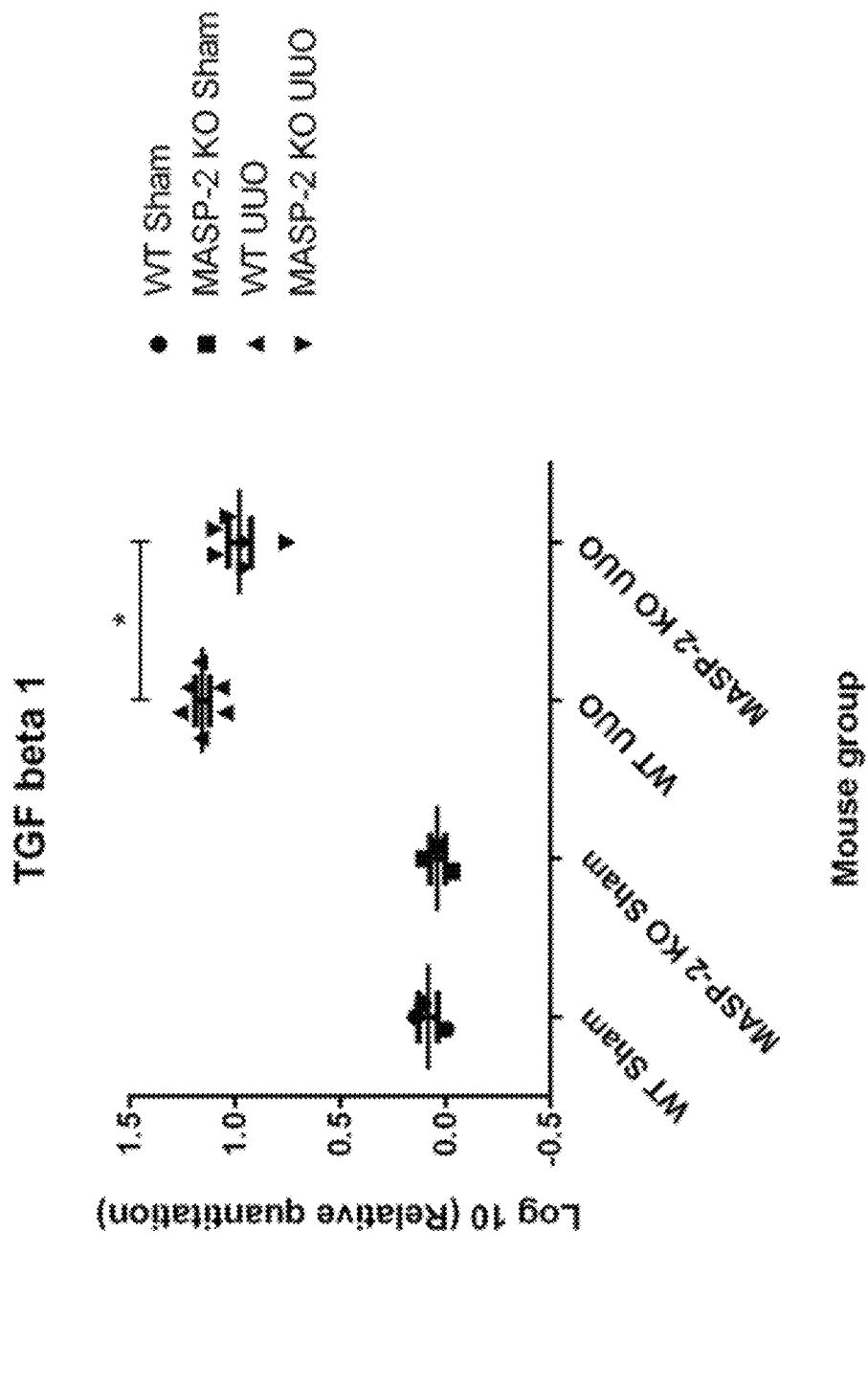
FIG. 18 graphically illustrates the relative mRNA expression levels of Transforming Growth Factor Beta-1 (TGFβ-1), as measured by qPCR, in kidney tissue sections obtained from wild-type and MASP-2−/− mice following 7 days of unilateral ureteric obstruction (UUO) and sham-operated wild-type and MASP-2−/− mice, as described in Example 14.

Gene expression analysis of a variety of genes linked to renal inflammation and fibrosis was carried out in the kidney tissue sections obtained from wild-type and MASP-2−/− mice following 7 days of ureteric obstruction and sham-operated wild-type and MASP-2−/− mice. The data shown in FIGS. 17-20 are the Log 10 of relative quantitation to a wild-type sham operated sample and bars represent the standard error of means. With regard to the results of the gene expression analysis of the fibrosis-related genes, FIG. 17 graphically illustrates the relative mRNA expression levels of collagen type IV alpha 1 (collagen-4), as measured by qPCR in kidney tissue sections obtained from wild-type and MASP-2−/− mice following 7 days of ureteric obstruction and sham-operated control mice. FIG. 18 graphically illustrates the relative mRNA expression levels of Transforming Growth Factor Beta-1 (TGFβ-1), as measured by qPCR in kidney tissue sections obtained from wild-type and MASP-2−/− mice following 7 days of ureteric obstruction and sham-operated control mice. As shown in FIGS. 17 and 18, the obstructed kidneys from the wild-type mice demonstrated significantly increased expression of the fibrosis-related genes Collagen-type IV (FIG. 17) and TGFβ 3-1 (FIG. 18), as compared to the sham-operated kidneys in wild-type mice, demonstrating that these fibrosis-related genes are induced after UUO injury in wild-type mice, as expected. In contrast, as further shown in FIGS. 17 and 18, the obstructed kidneys from the MASP-2−/− subjected to the UUO injury exhibited a significant reduction in the expression of Collagen-type IV (FIG. 17, p=0.0388) and a significant reduction in the expression of TGFβ-1 (FIG. 18, p=0.0174), as compared to the wild-type mice subjected to the UUO injury.

Figure 19:
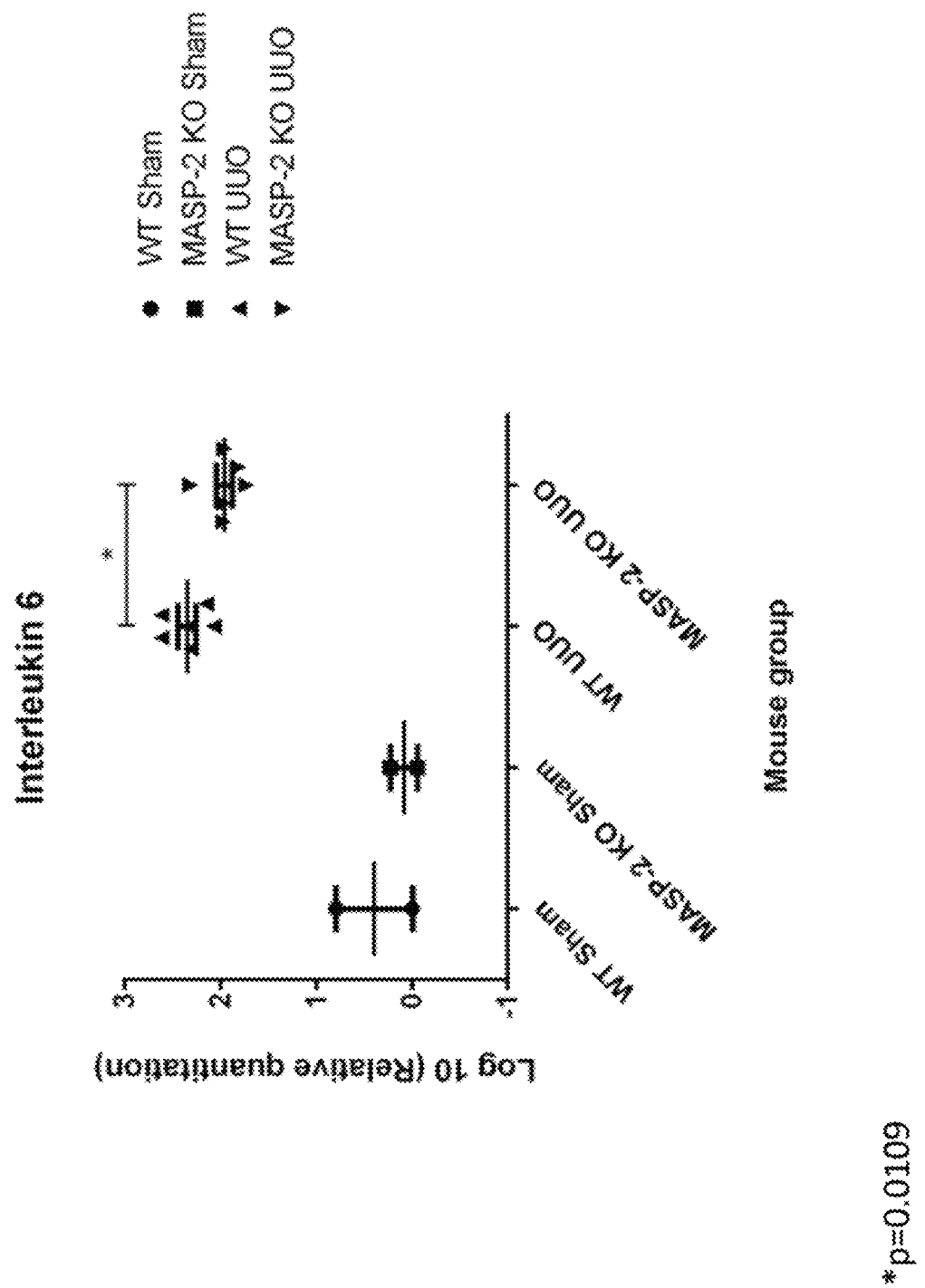
FIG. 19 graphically illustrates the relative mRNA expression levels of Interleukin-6 (IL-6), as measured by qPCR, in kidney tissue sections obtained from wild-type and MASP-2−/− mice following 7 days of unilateral ureteric obstruction (UUO) and sham-operated wild-type and MASP-2−/− mice, as described in Example 14.
Figure 20:
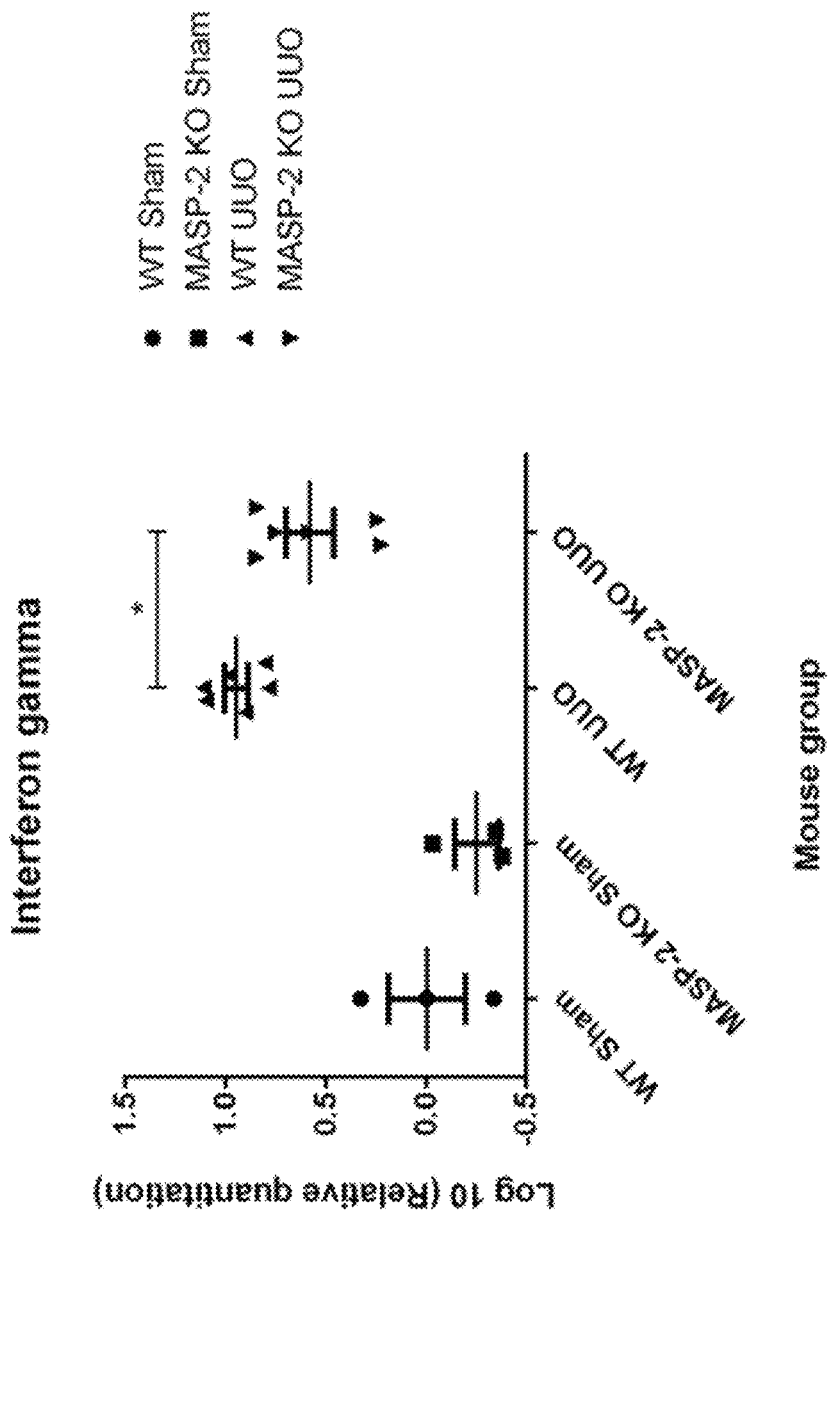
FIG. 20 graphically illustrates the relative mRNA expression levels of Interferon-T, as measured by qPCR, in kidney tissue sections obtained from wild-type and MASP-2−/− mice following 7 days of unilateral ureteric obstruction (UUO) and sham-operated wild-type and MASP-2−/− mice, as described in Example 14.

With regard to the results of the gene expression analysis of the inflammation-related genes, FIG. 19 graphically illustrates the relative mRNA expression levels of Interleukin-6 (IL-6), as measured by qPCR in kidney tissue sections obtained from wild-type and MASP-2−/− mice following 7 days of ureteric obstruction and sham-operated control mice. FIG. 20 graphically illustrates the relative mRNA expression levels of Interferon-γ, as measured by qPCR in kidney tissue sections obtained from wild-type and MASP-2−/− mice following 7 days of ureteric obstruction and sham-operated control mice. As shown in FIGS. 19 and 20, the obstructed kidneys from the wild-type mice demonstrated significantly increased expression of the inflammation-related genes Interleukin-6 (FIG. 19) and Interferon-γ (FIG. 20), as compared to the sham-operated kidneys in wild-type mice, demonstrating that these inflammation-related genes are induced after UUO injury in wild-type mice. In contrast, as further shown in FIGS. 19 and 20, the obstructed kidneys from the MASP-2−/− subjected to the UUO injury exhibited a significant reduction in the expression of Interleukin-6 (FIG. 19, p=0.0109) and Interferon-γ (FIG. 20, p=0.0182) as compared to the wild-type mice subjected to the UUO injury.

It is noted that gene expression for Vim, Actn-1, TNFα, C3 and IL-10 were all found to be significantly up-regulated in the UUO kidneys obtained from both the wild-type and the MASP-2−/− mice, with no significant difference in the expression levels of these particular genes between the wild-type and MASP-2−/− mice (data not shown). The gene expression levels of Cdh-1 and IL-12a did not change in obstructed kidneys from animals in any group (data not shown).

DISCUSSION

The UUO model in rodents is recognized to induce an early, active and profound injury in the obstructed kidney with reduced renal blood flow, interstitial inflammation and rapid fibrosis within one to two weeks following obstruction and has been used extensively to understand common mechanisms and mediators of inflammation and fibrosis in the kidney (see e.g., Chevalier R. L., *Kidney Int* 75:1145-1152, 2009; Yang H. et al., *Drug Discov Today Dis Models* 7:13-19, 2010).

The results described in this Example demonstrate that there is a significant reduction in collagen deposition and macrophage infiltration in UUO operated kidneys in the MASP-2(-/-) mice versus the wild-type (+/+) control mice. The unexpected results showing a significant reduction of renal injury at both the histological and gene expression levels in the MASP-2-/- animals demonstrates that the lectin pathway of complement activation contributes significantly to the development of inflammation and fibrosis in the obstructed kidney. While not wishing to be bound by a particular theory, it is believed that the lectin pathway contributes critically to the pathophysiology of fibrotic disease by triggering and maintaining pro-inflammatory stimuli that perpetuate a vicious cycle where cellular injury drives inflammation which in turn causes further cellular injury, scarring and tissue loss. In view of these results, it is expected that that inhibition or blockade of MASP-2 with an inhibitor would have a preventive and/or therapeutic effect in the inhibition or prevention of renal fibrosis, and for the inhibition or prevention of fibrosis in general (i.e., independent of the tissue or organ).

Example 15

This Example describes analysis of a monoclonal MASP-2 inhibitory antibody for efficacy in the Unilateral Ureteric Obstruction (UUO) model, a murine model of renal fibrosis.

Background/Rationale:

Amelioration of renal tubulointerstitial fibrosis, the common end point of multiple renal pathologies, represents a key target for therapeutic strategies aimed at preventing progressive renal diseases. Given the paucity of new and existing treatments targeting inflammatory pro-fibrotic pathways in renal disease, there is a pressing need to develop new therapies. Many patients with proteinuric renal disease exhibit tubulointerstitial inflammation and progressive fibrosis which closely parallels declining renal function. Proteinuria per se induces tubulointerstitial inflammation and the development of proteinuric nephropathy (Brunskill N. J. et al., *J Am Soc Nephrol* 15:504-505, 2004). Regardless of the primary renal disease, tubulointerstitial inflammation and fibrosis is invariably seen in patients with progressive renal impairment and is closely correlated with declining excretory function (Risdon R. A. et al., *Lancet* 1:363-366, 1968; Schainuck L. I., et al., *Hum Pathol* 1: 631-640, 1970). Therapies with the potential to interrupt the key common cellular pathways leading to fibrosis hold the promise of wide applicability in renal disorders.

As described in Example 14, in the UUO model of non-proteinuric renal fibrosis it was determined that MASP-2-/- mice exhibited significantly less renal fibrosis and inflammation compared to wild-type control animals, as shown by inflammatory cell infiltrates (75% reduction), and histological markers of fibrosis such as collagen (one third reduction), thereby establishing a key role of the lectin pathway in renal fibrosis.

As described in Example 13, a monoclonal MASP-2 antibody (OMS646-SGMI-2 fusion, comprising an SGMI-2 peptide fused to the C-terminus of the heavy chain of OMS646) was generated that specifically blocks the function of the human lectin pathway has also been shown to block the lectin pathway in mice. In this example, OMS646-SGMI-2 was analyzed in the UUO mouse model of renal fibrosis in wild-type mice to determine if a specific inhibitor of MASP-2 is able to inhibit renal fibrosis.

Methods:

This study evaluated the effect of a MASP-2 inhibitory antibody (10 mg/kg OMS646-SGMI-2), compared to a human IgG4 isotype control antibody (10 mg/kg ET904), and a vehicle control in male WT C57BL/6 mice. The antibodies (10 mg/kg) were administered to groups of 9 mice by intraperitoneal (ip) injection on day 7, day 4 and day 1 prior to UUO surgery and again on day 2 post-surgery. Blood samples were taken prior to antibody administration and at the end of the experiment to assess lectin pathway functional activity.

The UUO surgery, tissue collection and staining with Sirius red and macrophage-specific antibody F4/80 were carried out using the methods described in Example 14.

Hydroxyproline content of mouse kidneys was measured using a specific colorimetric assay test kit (Sigma) according to manufacturer's instructions.

To assess the pharmacodynamic effect of the MASP-2 inhibitory mAb in mice, systemic lectin pathway activity was evaluated by quantitating lectin-induced C3 activation in minimally diluted serum samples collected at the indicated time after MASP-2 mAb or control mAb i.p. administration to mice. Briefly described, 7 µM diameter polystyrene microspheres (Bangs Laboratories, Fisher Ind., USA) were coated with mannan by overnight incubation with 30 µg/mL mannan (Sigma) in sodium bicarbonate buffer (pH 9.6), then washed, blocked with 1% fetal bovine serum in PBS and resuspended in PBS at a final concentration of $1 \times 10^1$ beads/mL. Complement deposition reactions were initiated by the addition of 2.5 µL of mannan-coated beads (~250,000 beads) to 50 µL of minimally diluted mouse serum samples (90% final serum concentration), followed by incubation for 40 minutes at 4° C. Following termination of the deposition reaction by the addition of 250 µL of ice-cold flow cytometry buffer (FB: PBS containing 0.1% fetal bovine serum), beads were collected by centrifugation and washed two more times with 300 µL of ice-cold FB.

To quantify lectin-induced C3 activation, beads were incubated for 1 hour at 4° C. with 50 µL of rabbit anti-human C3c antibody (Dako, Carpenteria, Calif., USA) diluted in FB. Following two washes with FB to remove unbound material, the beads were incubated for 30 minutes at 4° C. with 50 µL of goat anti-rabbit antibody conjugated to PE-Cy5 (Southern Biotech, Birmingham, Ala., USA) diluted in FB. Following two washes with FB to remove unbound material, the beads were resuspended in FB and analyzed by a FACS Calibur cytometer. The beads were gated as a uniform population using forward and side scatter, and C3b deposition in each sample was quantitated as mean fluorescent intensity (MFI).

Figure 21:
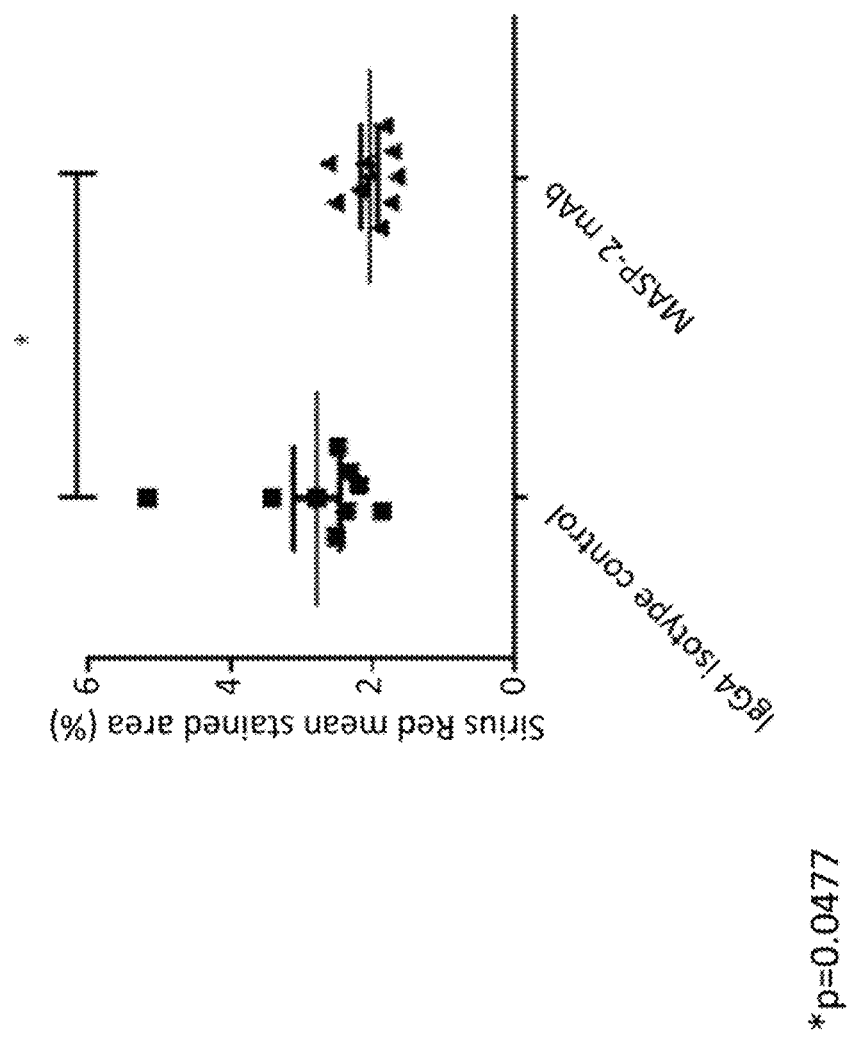
FIG. 21 graphically illustrates the results of computer-based image analysis of kidney tissue sections stained with Siruis red, wherein the tissue sections were obtained following 7 days of unilateral ureteric obstruction (UUO) from wild-type mice treated with a MASP-2 inhibitory antibody and an isotype control antibody, as described in Example 15.

Results:

Assessment of Collagen Deposition:

FIG. 21 graphically illustrates the results of computer-based image analysis of kidney tissue sections stained with Siruis red, wherein the tissue sections were obtained following 7 days of ureteric obstruction from wild-type mice treated with either a MASP-2 inhibitory antibody or an isotype control antibody. As shown in FIG. 21, tissue sections from kidneys harvested 7 days after obstruction (UUO) obtained from wild-type mice treated with MASP-2 inhibitory antibody showed a significant reduction (p=0.0477) in collagen deposition as compared with the amount of collagen deposition in tissue sections from obstructed kidneys obtained from wild-type mice treated with an IgG4 isotype control.

Assessment of Hydroxy Proline Content:

Hydroxy proline was measured in kidney tissues as an indicator of collagen content. Hydroxy proline is a parameter which is highly indicative of the pathophysiological progression of disease induced in this model.

Figure 22:
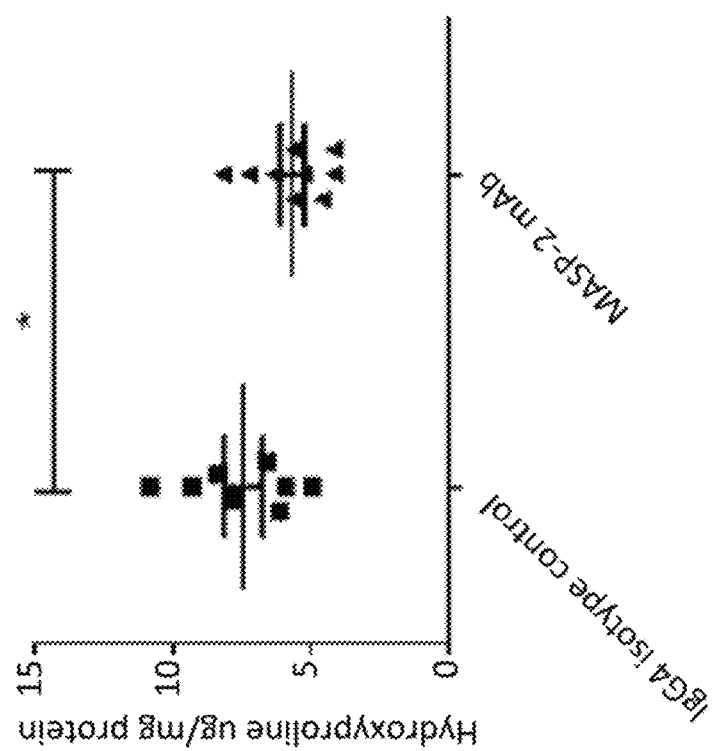
FIG. 22 graphically illustrates the hydroxyl proline content from kidneys harvested 7 days after unilateral ureteric obstruction (UUO) obtained from wild-type mice treated with MASP-2 inhibitory antibody as compared with the level of hydroxyl proline in tissue from obstructed kidneys obtained from wild-type mice treated with an IgG4 isotype control, as described in Example 15.

FIG. 22 graphically illustrates the hydroxyl proline content from kidneys harvested 7 days after obstruction (UUO) obtained from wild-type mice treated with either a MASP-2 inhibitory antibody or an isotype control antibody. As shown in FIG. 22, the obstructed kidney tissues from mice treated with MASP-2 inhibitory antibody demonstrated significantly less hydroxyl proline, an indicator of collagen content, than the kidneys from mice treated with the IgG4 isotype control mAb (p=0.0439).

Assessment of Inflammation:

Obstructed kidneys from wild-type, isotype control antibody-treated animals, and wild-type animals treated with MASP-2 inhibitory antibody demonstrated a brisk infiltrate of macrophages. Careful quantification revealed no significant difference in macrophage percentage stained area between these two groups (data not shown). However, despite equivalent numbers of infiltrating macrophages, the obstructed kidneys from the MASP-2 inhibitory antibody-injected animals exhibited significantly less fibrosis as judged by Sirius red staining, compared to obstructed kidneys from isotype control injected animals, which result is consistent with the results that obstructed kidney tissues from mice treated with MASP-2 inhibitory antibody had significantly less hydroxyl proline than the kidneys treated with the IgG4 isotype control mAb.

DISCUSSION

The results described in this Example demonstrate that the use of a MASP-2 inhibitory antibody provides protection against renal fibrosis in the UUO model, which is consistent with the results described in Example 14 demonstrating that MASP-2−/− mice have significantly reduced renal fibrosis and inflammation in the UUO model as compared to wild-type mice. The results in this Example showing reduced fibrosis in the mice treated with the MASP-2 inhibitory antibody. The finding of reduced fibrosis in the UUO kidneys in animals with a reduction or blockade of MASP-2-dependent lectin pathway activity is highly significant novel finding. Taken together, the results presented in Example 14 and in this Example demonstrate a beneficial effect of MASP-2 inhibition on renal tubulointerstitial inflammation, tubular cell injury, profibrotic cytokine release and scarring. The relief of renal fibrosis remains a key goal for renal therapeutics. The UUO model is a severe model of accelerated renal fibrosis, and an intervention that reduces fibrosis in this model, such as the use of MASP-2 inhibitory antibodies, is likely to be used to inhibit or prevent renal fibrosis. The results from the UUO model are likely to be transferable to renal disease characterized by glomerular and/or proteinuric tubular injury.

Example 16

This Example provides results that were generated using a protein overload proteinurea model of renal fibrosis, inflammation and tubulointerstitial injury in MASP-2−/− and wild-type mice to evaluate the role of the lectin pathway in proteinuric nephropathy.

Background/Rationale:

Proteinuria is a risk factor for the development of renal fibrosis and loss of renal excretory function, regardless of the primary renal disease (Tryggvason K. et al., *J Intern Med* 254:216-224, 2003, Williams M., *Am J. Nephrol* 25:77-94, 2005). The concept of proteinuric nephropathy describes the toxic effects of excess protein entering the proximal tubule as a result of the impaired glomerular permselectivity (Brunskill N. J., *J Am Soc Nephrol* 15:504-505, 2004, Baines R. J., *Nature Rev Nephrol* 7:177-180, 2011). This phenomenon, common to many glomerular diseases, results in a pro-inflammatory scarring environment in the kidney and is characterized by alterations in proximal tubular cell growth, apoptosis, gene transcription and inflammatory cytokine production as a consequence of dysregulated signaling pathways stimulated by proteinuric tubular fluid. Proteinuric nephropathy is generally recognized to be a key contributor to progressive renal injury common to diverse primary renal pathologies.

Chronic kidney disease affects greater than 15% of the adult population in the United States and accounts for approximately 750,000 deaths each year worldwide (Lozano R. et al., *Lancet vol* 380, Issue 9859:2095-2128, 2012). Proteinuria is an indicator of chronic kidney disease as well as a factor promoting disease progression. Many patients with proteinuric renal disease exhibit tubulointerstitial inflammation and progressive fibrosis which closely parallels declining renal function. Proteinuria per se induces tubulointerstitial inflammation and the development of proteinuric nephropathy (Brunskill N. J. et al., *J Am Soc Nephrol* 15:504-505, 2004). In proteinuric kidney diseases, excessive amounts of albumin and other macromolecules are filtered through the glomeruli and reabsorbed by proximal tubular epithelial cells. This causes an inflammatory vicious cycle mediated by complement activation leading to cytokine and leukocyte infiltrates that cause tubule-interstitial injury and fibrosis, thereby exacerbating proteinuria and leading to loss of renal function and eventually progression to end-stage renal failure (see, e.g., Clark et al., *Canadian Medical Association Journal* 178:173-175, 2008). Therapies that modulate this detrimental cycle of inflammation and proteinuria are expected to improve outcomes in chronic kidney disease.

In view of the beneficial effects of MASP-2 inhibition in the UUO model of tubulointersitital injury, the following experiment was carried out to determine if MASP-2 inhibition would reduce renal injury in a protein overload model. This study employed protein overload to induce proteinuric kidney disease as described in Ishola et al., *European Renal Association* 21:591-597, 2006.

Methods:

A MASP-2−/− mouse was generated as described in Example 1 and backcrossed for generations with BALB/c.

The current study compared the results of wild-type and MASP-2-/- BALB/c mice in a protein overload proteinuria model as follows.

One week prior to the experiment, mice were unilaterally nephrectomised before protein overload challenge in order to see an optimal response. The proteinuria inducing agent used was a low endotoxin bovine serum albumin (BSA, Sigma) given i.p. in normal saline to WT (n=7) and MASP-2-/- mice (n=7) at the following doses: one dose each of 2 mg BSA/gm, 4 mg BSA/gm, 6 mg BSA/gm, 8 mg BSA/gm, 10 mg BSA/gm and 12 mg BSA/gm body weight, and 9 doses of 15 mg BSA/gm body weight, for a total of 15 doses administered i.p. over a period of 15 days. The control WT (n=4) and MASP-2-/- (n=4) mice received saline only administered i.p. After administration of the last dose, animals were caged separately in metabolic cages for 24 hours to collect urine. Blood was collected by cardiac puncture under anesthesia, blood was allowed to clot on ice for 2 hours and serum was separated by centrifugation. Serum and urine samples were collected at the end of the experiment on day 15, stored and frozen for analysis.

Mice were sacrificed 24 hours after the last BSA administration on day 15 and various tissues were collected for analysis. Kidneys were harvested and processed for H&E and immunostaining. Immunohistochemistry staining was carried out as follows. Formalin fixed, paraffin-embedded 5 micron kidney tissue sections from each mouse were deparaffinized and rehydrated. Antigen retrieval was performed in citrate buffer at 95° C. for 20 minutes followed by incubating tissues in 3% $H_2O_2$ for 10 minutes. Tissues were then incubated in blocking buffer (10% serum from the species the secondary antibody was raised in and 1% BSA in PBS) with 10% avidin solution for 1 hour at room temperature. Sections were washed in PBS three times, 5 minutes each, after each step. Primary antibody was then applied in blocking buffer with 10% biotin solution for 1 hour at a concentration of 1:100 for the antibodies F4/80 (Santa Cruz cat # sc-25830), TGFβ (Santa Cruz cat # sc-7892), IL-6 (Santa Cruz cat # sc-1265) and at 1:50 for the TNFα antibody (Santa Cruz cat # sc-1348). A biotinylated secondary antibody was then applied for 30 minutes at a concentration of 1:200 for the F4/80, TGFβ and IL-6 sections and 1:100 for the TNFα section followed by HRP conjugate enzyme for another 30 minutes. The color was developed using diaminobenzidine (DAB) substrate kit (Vector labs) for 10 minutes and slides were washed in water, dehydrated and mounted without counter staining to facilitate computer-based image analysis. Stained tissue sections from the renal cortex were analyzed by digital image capture followed by quantification using automated image analysis software.

Apoptosis was assessed in the tissue sections by staining with terminal deoxynucleotidyl transferase dUTP nick end labeling (TUNEL) as follows. Apoptotic cells in the kidney sections were stained using ApopTag® Peroxidase kit (Millipore) as follows. Parrafin embedded, formalin fixed kidney sections from each mouse were deparaffinized, rehydrated and then protein permeabilized using proteinase K (20 μg/mL) which was applied to each specimen for 15 minutes at room temperature. Specimens were washed in PBS between steps. Endogenous peroxidase activity was quenched by incubating tissues in 3% $H_2O_2$ for 10 minutes. Tissues were then incubated in equilibration buffer followed by incubation with TdT enzyme for 1 hour at 37° C. After washing in stop/wash buffer for 10 minutes, anti-digoxignenin conjugate was applied for 30 minutes at room temperature followed by washing. Color was developed in DAB substrate kit for 4 minutes followed by washing in water. Tissues were counter stained in haematoxylin and mounted in DBX. The frequency of TUNEL stained (brown colored) apoptotic cells were manually counted in serially selected 20 high power fields from the cortex using Leica DBXM light microscope.

Results:

Assessment of Proteinuria

To confirm the presence of proteinuria in the mice, the total protein in serum was analyzed at day 15 and the total excreted proteins in urine was measured in urine samples collected over a 24 hour period on day 15 of the study.

Figure 23:
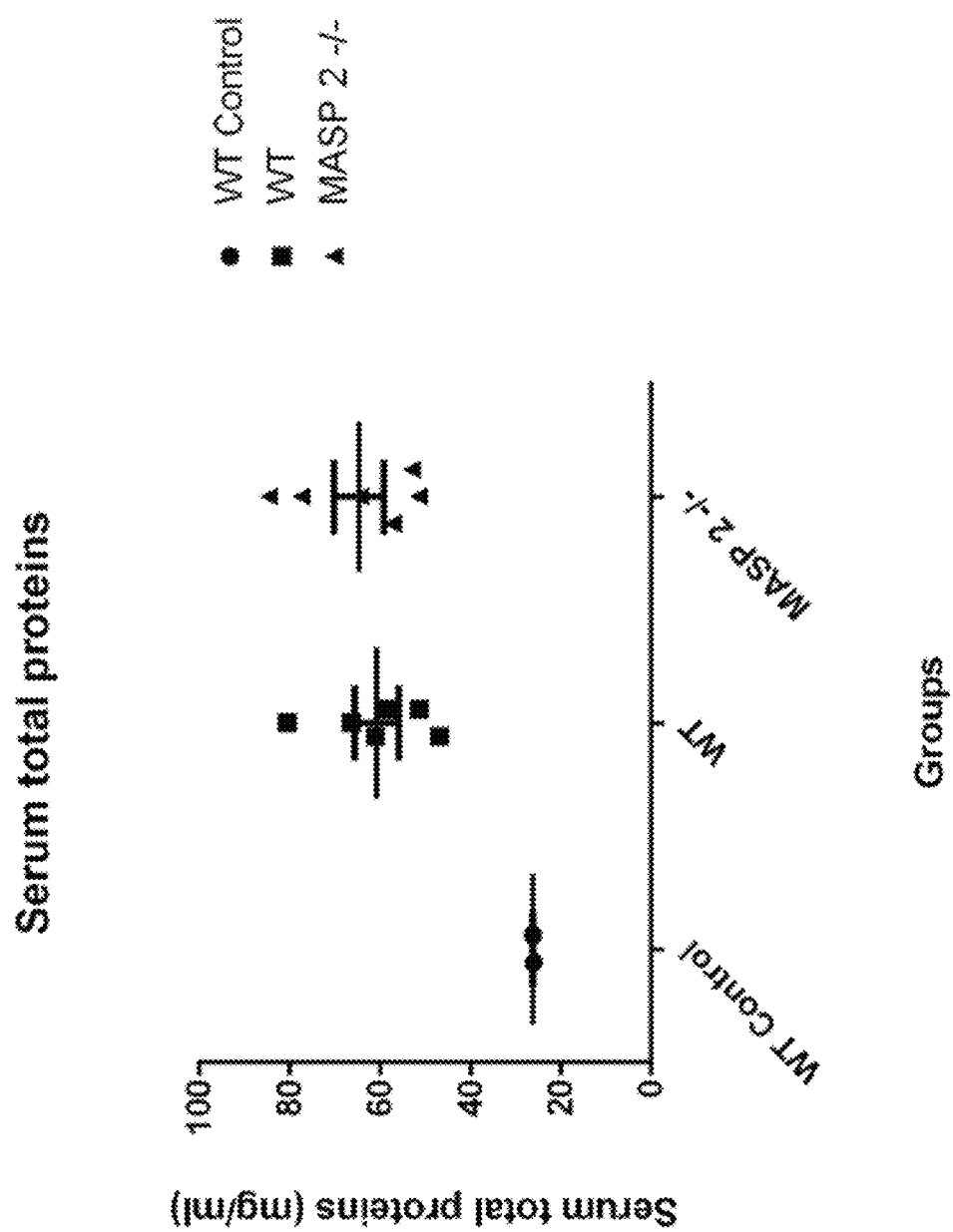
FIG. 23 graphically illustrates the total amount of serum proteins (mg/ml) measured on day 15 of the protein overload study in wild-type control mice (n=2) that received saline only, wild-type mice that received BSA (n=6) and MASP-2−/− mice that received BSA (n=6), as described in Example 16.

FIG. 23 graphically illustrates the total amount of serum proteins (mg/ml) measured at day 15 in the wild-type control mice (n=2) that received saline only, the wild-type mice that received BSA (n=6) and the MASP-2-/- mice that received BSA (n=6). As shown in FIG. 23, administration of BSA increased the serum total protein level in both wild-type and MASP-2-/- groups to more than double the concentration of the control group that received only saline, with no significant difference between the treated groups.

Figure 24:
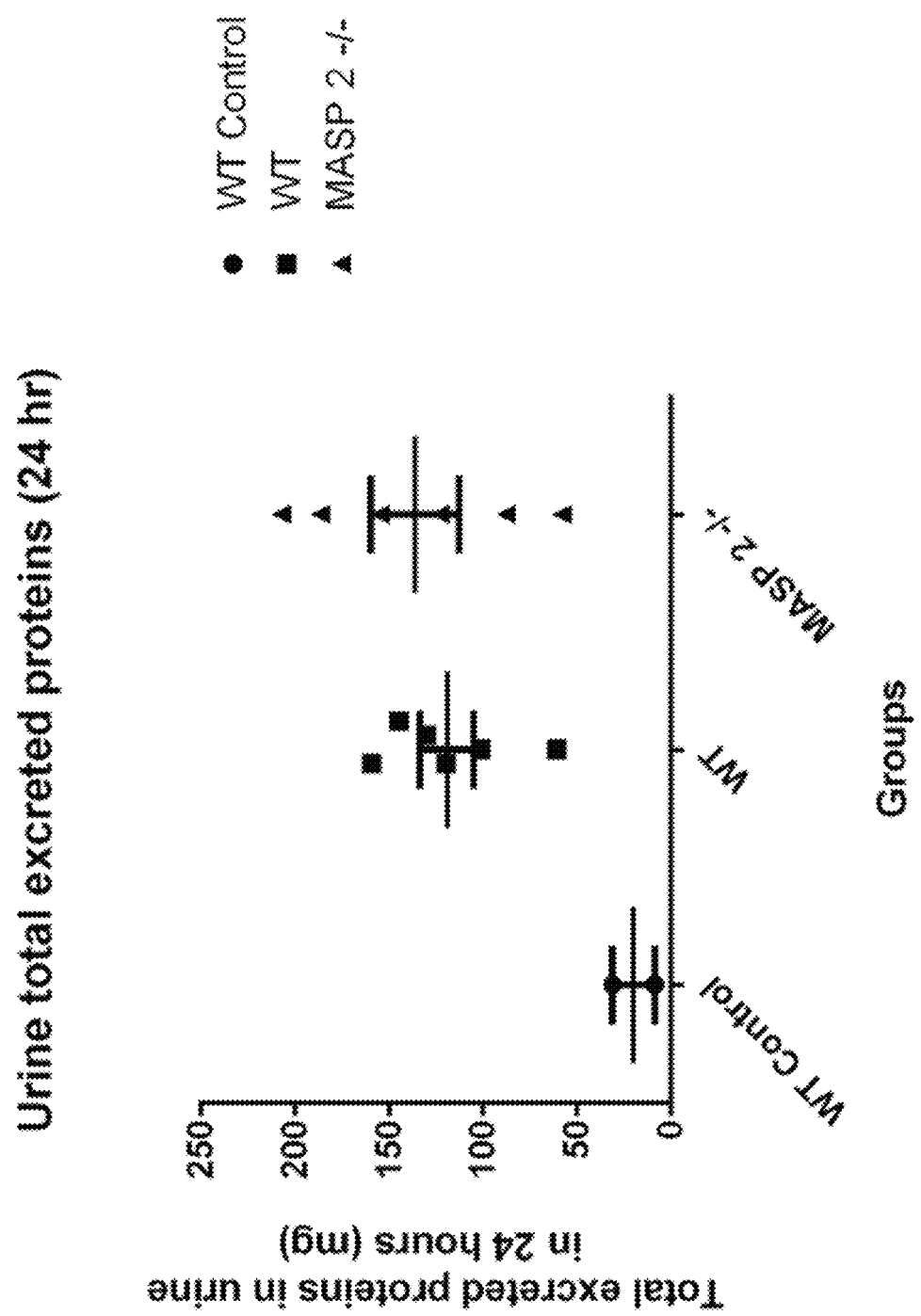
FIG. 24 graphically illustrates the total amount of excreted protein (mg) in urine collected over a 24 hour period on day 15 of the protein overload study from wild-type control mice (n=2) that received saline only, wild-type that received BSA (n=6) and MASP-2−/− mice that received BSA (n=6), as described in Example 16.

FIG. 24 graphically illustrates the total amount of excreted protein (mg) in urine collected over a 24 hour period on day 15 of the study from the wild-type control mice (n=2) that received saline only, the wild-type mice that received BSA (n=6) and the MASP-2-/- mice that received BSA (n=6). As shown in FIG. 24, on day 15 of this study, there was an approximately six-fold increase in total excreted proteins in urine in the BSA treated groups as compared to the sham-treated control group that received saline only. The results shown in FIGS. 23 and 24 demonstrate that the proteinuria model was working as expected.

Assessment of Histological Changes in the Kidney

Figure 25:
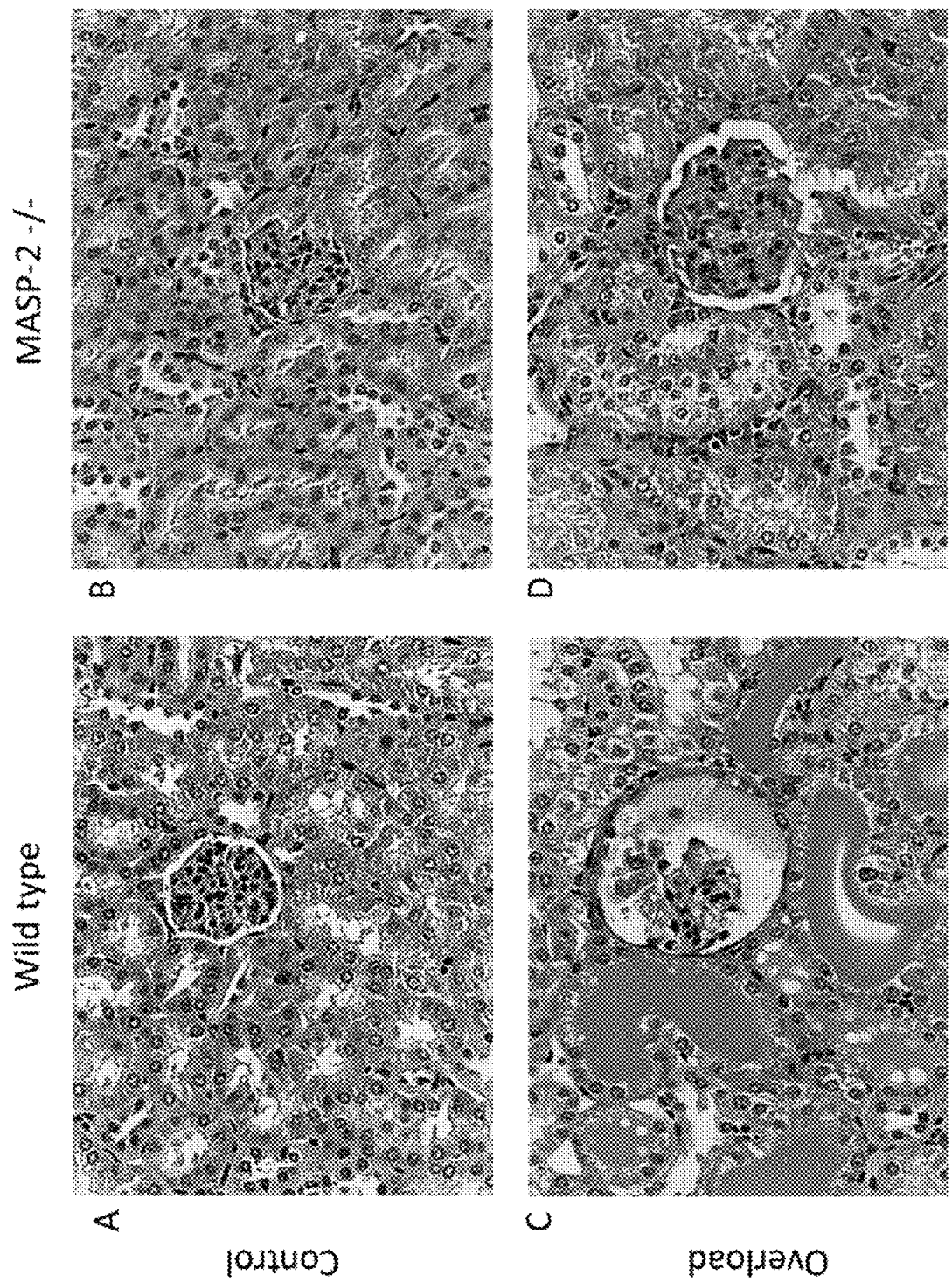
FIG. 25 shows representative hematoxylin and eosin (H&E) stained renal tissue sections from the following groups of mice on day 15 of the protein overload study as follows: (panel A) wild-type control mice; (panel B) MASP-2−/− control mice, (panel C) wild-type mice treated with BSA; and (panel D) MASP-2−/− mice treated with bovine serum albumin (BSA), as described in Example 16.

FIG. 25 shows representative H&E stained renal tissue sections that were harvested on day 15 of the protein overload study from the following groups of mice: (panel A) wild-type control mice; (panel B) MASP-2-/- control mice; (panel C) wild-type mice treated with BSA; and (panel D) MASP-2-/- mice treated with BSA. As shown in FIG. 25, there is a much higher degree of tissue preservation in the MASP-2-/- overload group (panel D) compared to the wild-type overload group (panel C) at the same level of protein overload challenge. For example, Bowman's capsules in the wild-type mice treated with BSA (overload) were observed to be greatly expanded (panel C) as compared to Bowman's capsules in the wild-type control group (panel A). In contrast, Bowman's capsules in the MASP-2-/- mice (overload) treated with the same level of BSA (panel D) retained morphology similar to the MASP-2-/- control mice (panel B) and wild-type control mice (panel A). As further shown in FIG. 25, large protein cast structures have accumulated in proximal and distal tubules of the wild-type kidney sections (panel C), which are larger and more abundant as compared to MASP-2-/- mice (panel D).

It is also noted that analysis of renal sections from this study by transmitting electron microscope showed that the mice treated with BSA had overall damage to the ciliary borders of distal and proximal tubular cells, with cellular content and nuclei bursting into the tubule lumen. In contrast, the tissue was preserved in the MASP-2-/- mice treated with BSA.

Assessment of Macrophage Infiltration in the Kidney

To measure the degree of inflammation, as indicated by macrophage infiltration, the tissue sections of the harvested kidneys were also stained with macrophage-specific antibody F4/80 using methods as described in Boor et al., *J of Am Soc of Nephrology* 18:1508-1515, 2007.

Figure 26:
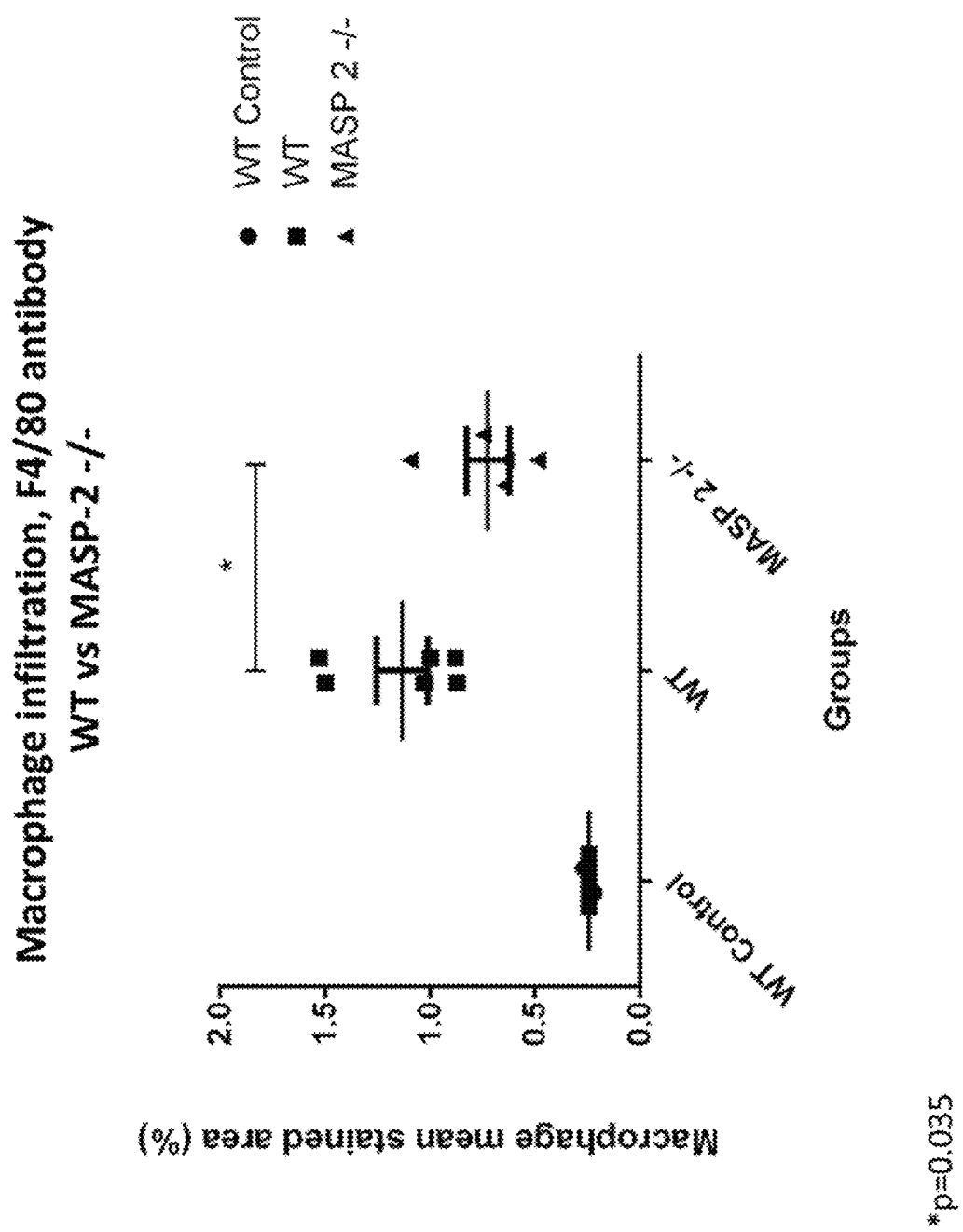
FIG. 26 graphically illustrates the results of computer-based image analysis of kidney tissue sections stained with macrophage-specific antibody F4/80, showing the macrophage mean stained area (%), wherein the tissue sections were obtained on day 15 of the protein overload study from wild-type control mice (n=2), wild-type mice treated with BSA (n=6), and MASP-2−/− mice treated with BSA (n=5), as described in Example 16.

FIG. 26 graphically illustrates the results of computer-based image analysis of kidney tissue sections stained with macrophage-specific antibody F4/80, showing the macrophage mean stained area (%), wherein the tissue sections were obtained at day 15 of the protein overload study from wild-type control mice (n=2), wild-type mice treated with BSA (n=6), and MASP-2−/− mice treated with BSA (n=5). As shown in FIG. 26, kidney tissue sections stained with F4/80 anti-macrophage antibody showed that while both groups treated with BSA showed a significant increase in the kidney macrophage infiltration (measured as % F4/80 antibody-stained area) compared to the wild-type sham control, a significant reduction in macrophage infiltration was observed in tissue sections from BSA-treated MASP-2−/− mice as compared with macrophage infiltration in tissue sections from BSA-treated wild-type mice (p value=0.0345).

Figure 27A:
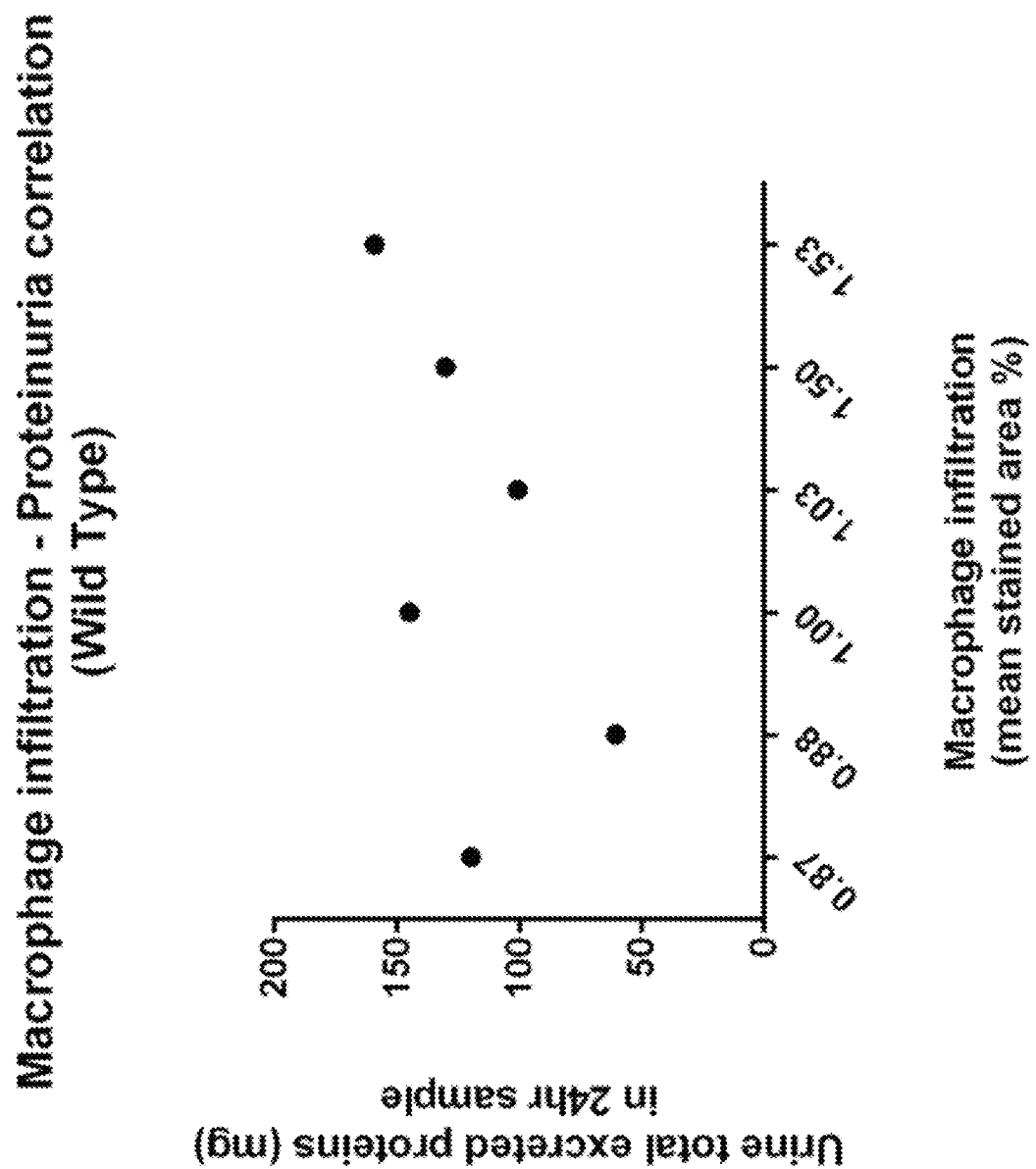
FIG. 27A graphically illustrates the analysis for the presence of a macrophage-proteinuria correlation in each wild-type mouse (n=6) treated with BSA by plotting the total excreted proteins measured in urine from a 24-hour sample versus the macrophage infiltration (mean stained area %), as described in Example 16.

FIG. 27A graphically illustrates the analysis for the presence of a macrophage-proteinuria correlation in each wild-type mouse (n=6) treated with BSA by plotting the total excreted proteins measured in urine from a 24 hour sample versus the macrophage infiltration (mean stained area %). As shown in FIG. 27A, most of the samples from the wild-type kidneys showed a positive correlation between the level of proteinuria present and the degree of macrophage infiltration.

Figure 27B:
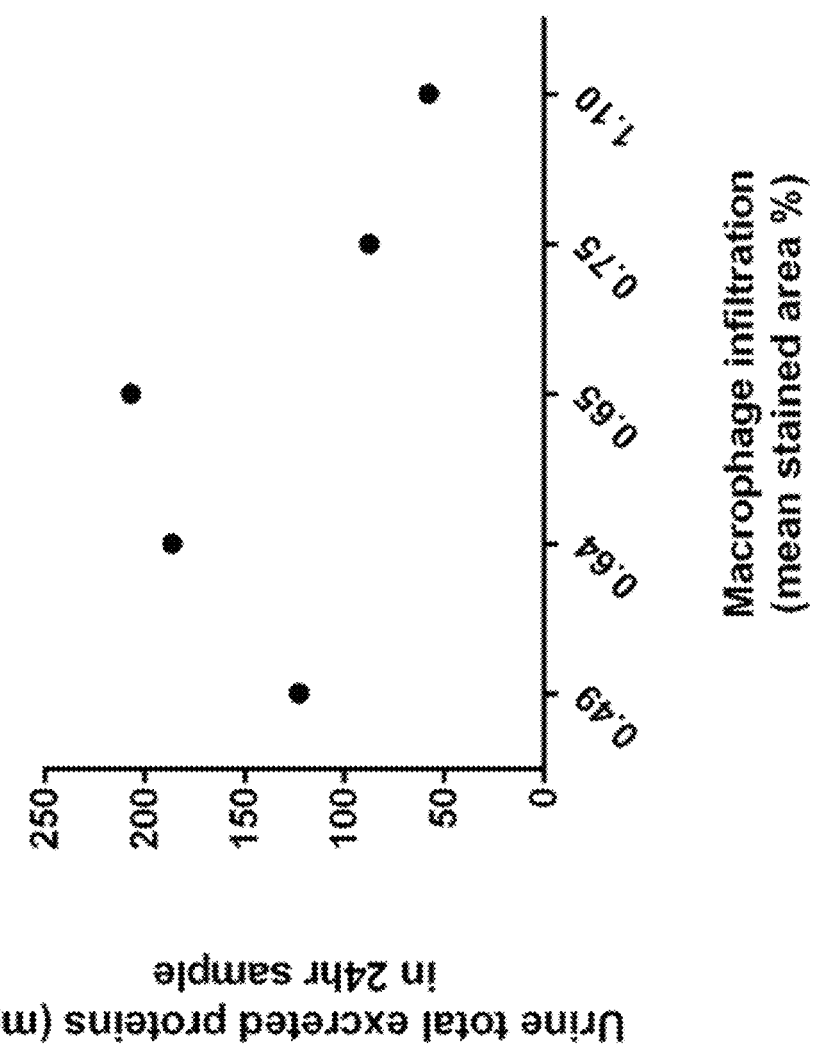
FIG. 27B graphically illustrates the analysis for the presence of a macrophage-proteinuria correlation in each MASP-2−/− mouse (n=5) treated with BSA by plotting the total excreted proteins in urine in a 24-hour sample versus the macrophage infiltration (mean stained area %), as described in Example 16.

FIG. 27B graphically illustrates the analysis for the presence of a macrophage-proteinuria correlation in each MASP-2−/− mouse (n=5) treated with BSA by plotting the total excreted proteins in urine in a 24 hour sample versus the macrophage infiltration (mean stained area %). As shown in FIG. 27B, the positive correlation observed in wild-type mice between the level of proteinuria and the degree of macrophage infiltration (shown in FIG. 27A) was not observed in MASP-2−/− mice. While not wishing to be bound by any particular theory, these results may indicate the presence of a mechanism of inflammation clearance at high levels of proteinuria in MASP-2−/− mice.

Assessment of Cytokine Infiltration

Interleukin 6 (IL-6), Transforming Growth Factor Beta (TGFβ) and Tumor Necrosis Factor Alpha (TNFα) are pro-inflammatory cytokines known to be up-regulated in proximal tubules of wild-type mice in a model of proteinuria (Abbate M. et al., *Journal of the American Society of Nephrology*: JASN, 17: 2974-2984, 2006; David S. et al., Nephrology, Didalysis, Transplantation, Official Publication of the European Dialysis and Transplant Association—*European Renal Association* 12: 51-56, 1997). The tissue sections of kidneys were stained with cytokine-specific antibodies as described above.

Figure 28:
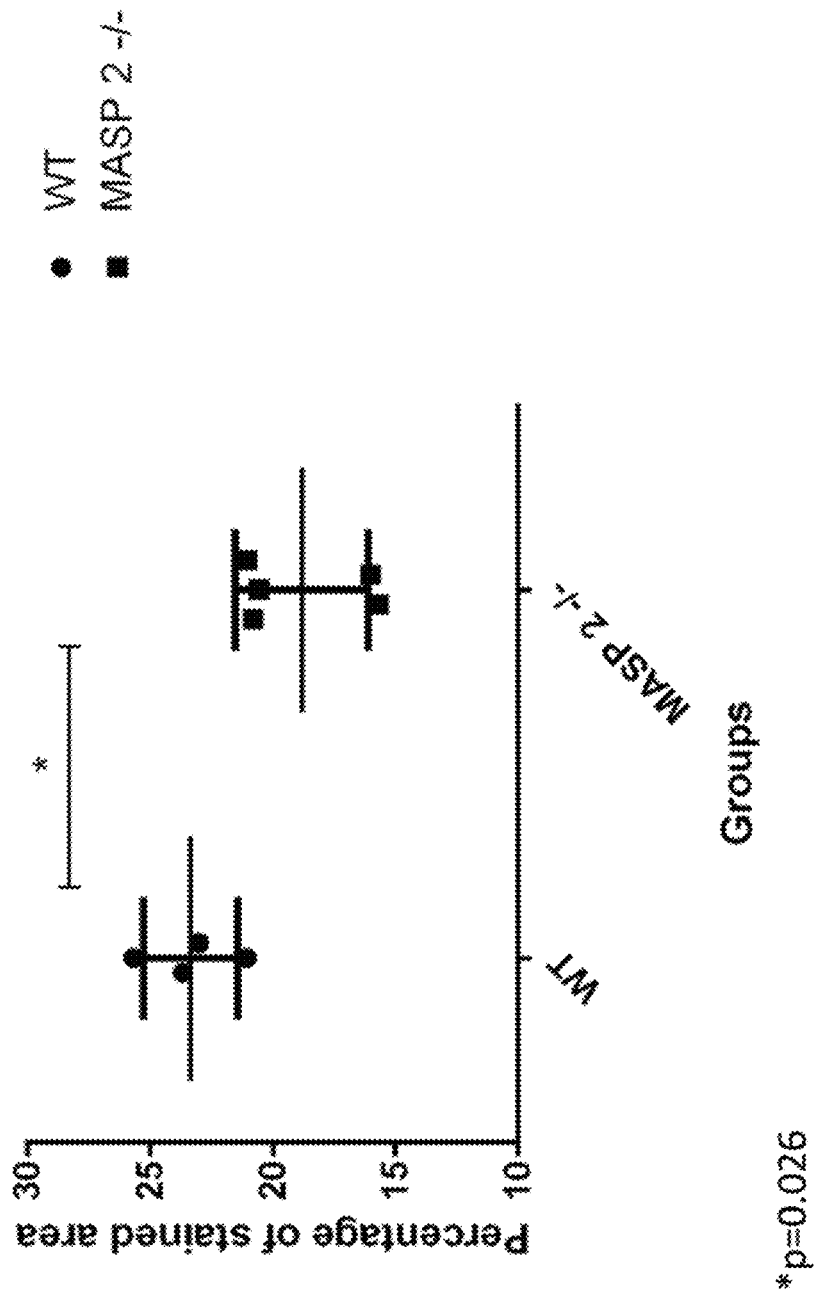
FIG. 28 graphically illustrates the results of computer-based image analysis of stained tissue sections with anti-TGFβ antibody (measured as % TGFβ antibody-stained area) in wild-type mice treated with BSA (n=4) and MASP-2−/− mice treated with BSA (n=5), as described in Example 16.

FIG. 28 graphically illustrates the results of computer-based image analysis of stained tissue sections with anti-TGFβ antibody (measured as % TGFβ antibody-stained area) in wild-type mice treated with BSA (n=4) and MASP-2−/− mice treated with BSA (n=5). As shown in FIG. 28, a significant increase in the staining of TGFβ was observed in the wild-type BSA treated (overload) group as compared to the MASP-2−/− BSA treated (overload) group (p=0.026).

Figure 29:
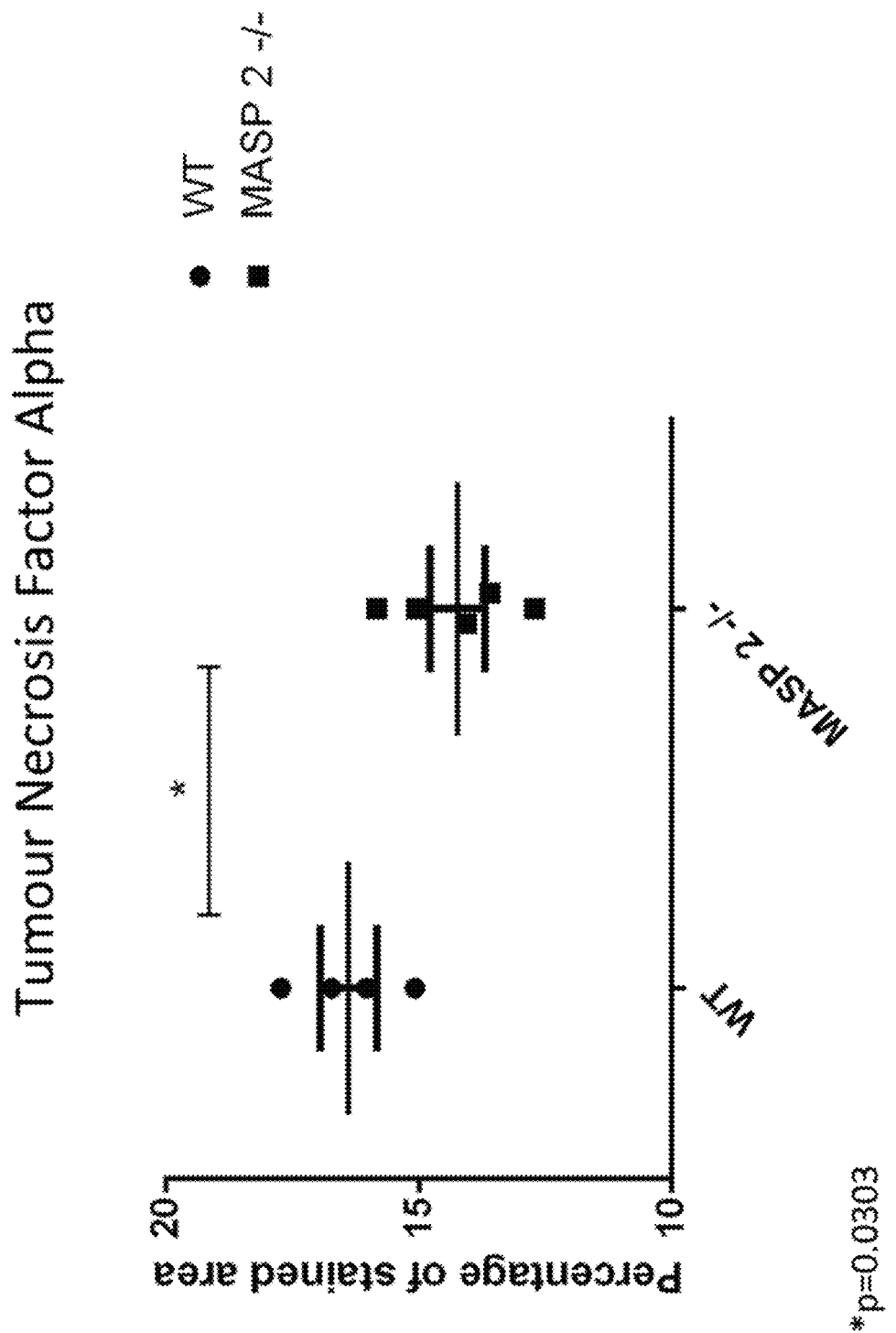
FIG. 29 graphically illustrates the results of computer-based image analysis of stained tissue sections with anti-TNFα antibody (measured as % TNFα antibody-stained area) in wild-type mice treated with BSA (n=4) and MASP-2−/− mice treated with BSA (n=5), as described in Example 16.

FIG. 29 graphically illustrates the results of computer-based image analysis of stained tissue sections with anti-TNFα antibody (measured as % TNFα antibody-stained area) in wild-type mice treated with BSA (n=4) and MASP-2−/− mice treated with BSA (n=5). As shown in FIG. 29, a significant increase in the staining of TNFα was observed in the wild-type BSA treated (overload) group as compared to the MASP-2−/− BSA treated (overload) group (p=0.0303).

Figure 30:
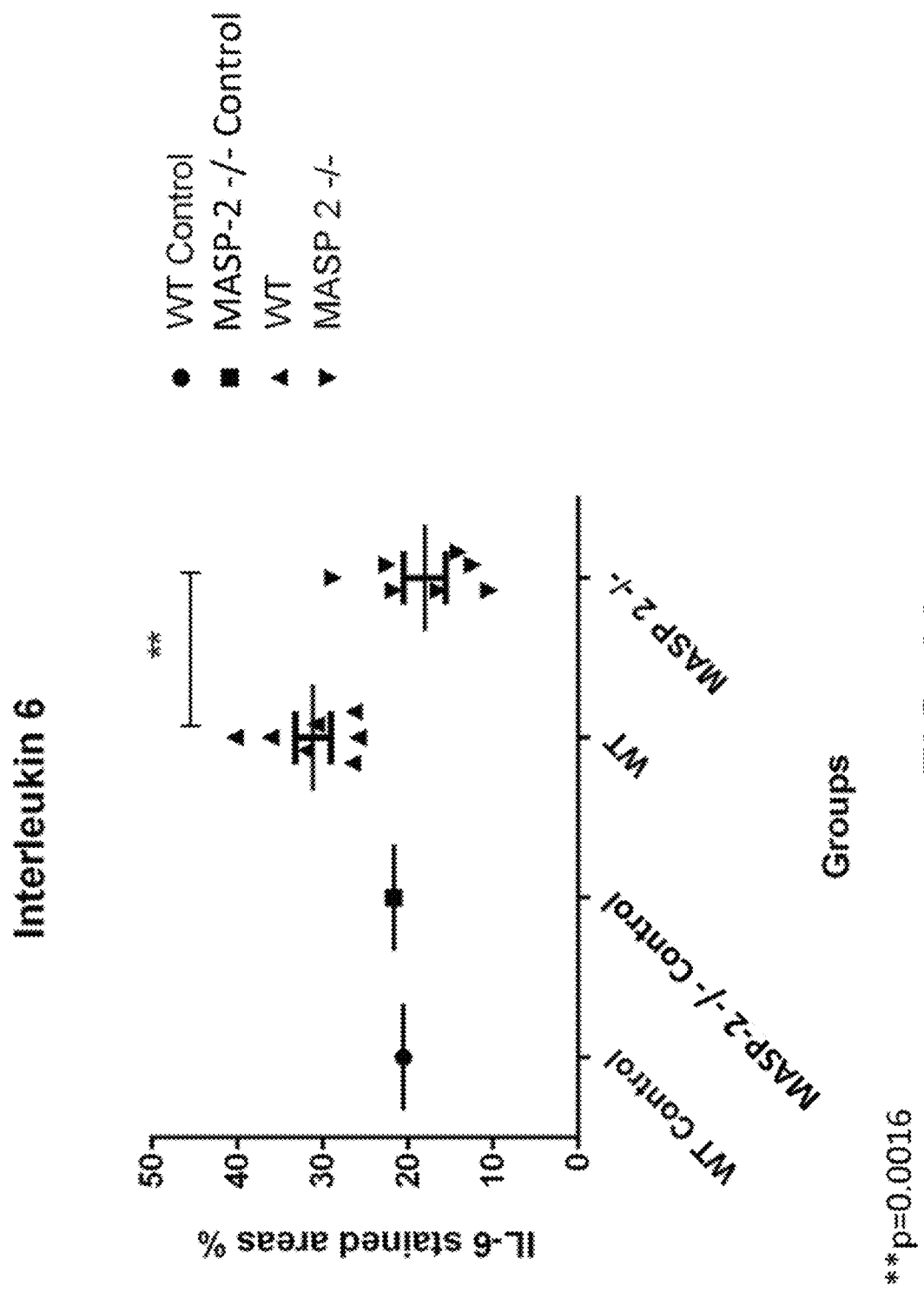
FIG. 30 graphically illustrates the results of computer-based image analysis of stained tissue sections with anti-IL-6 antibody (measured as % IL-6 antibody-stained area) in wild-type control mice, MASP-2−/− control mice, wild-type mice treated with BSA (n=7) and MASP-2−/− mice treated with BSA (n=7), as described in Example 16.

FIG. 30 graphically illustrates the results of computer-based image analysis of stained tissue sections with anti-IL-6 antibody (measured as % IL-6 antibody-stained area) in wild-type control mice, MASP-2−/− control mice, wild-type mice treated with BSA (n=7) and MASP-2−/− mice treated with BSA (n=7). As shown in FIG. 30, a highly significant increase in the staining of IL-6 was observed in the wild-type BSA treated group as compared to the MASP-2−/− BSA treated group (p=0.0016).

Assessment of Apoptosis

Apoptosis was assessed in the tissue sections by staining with terminal deoxynucleotidyl transferase dUTP nick end labeling (TUNEL) and the frequency of TUNEL stained apoptotic cells were counted in serially selected 20 high power fields (HPFs) from the cortex.

Figure 31:
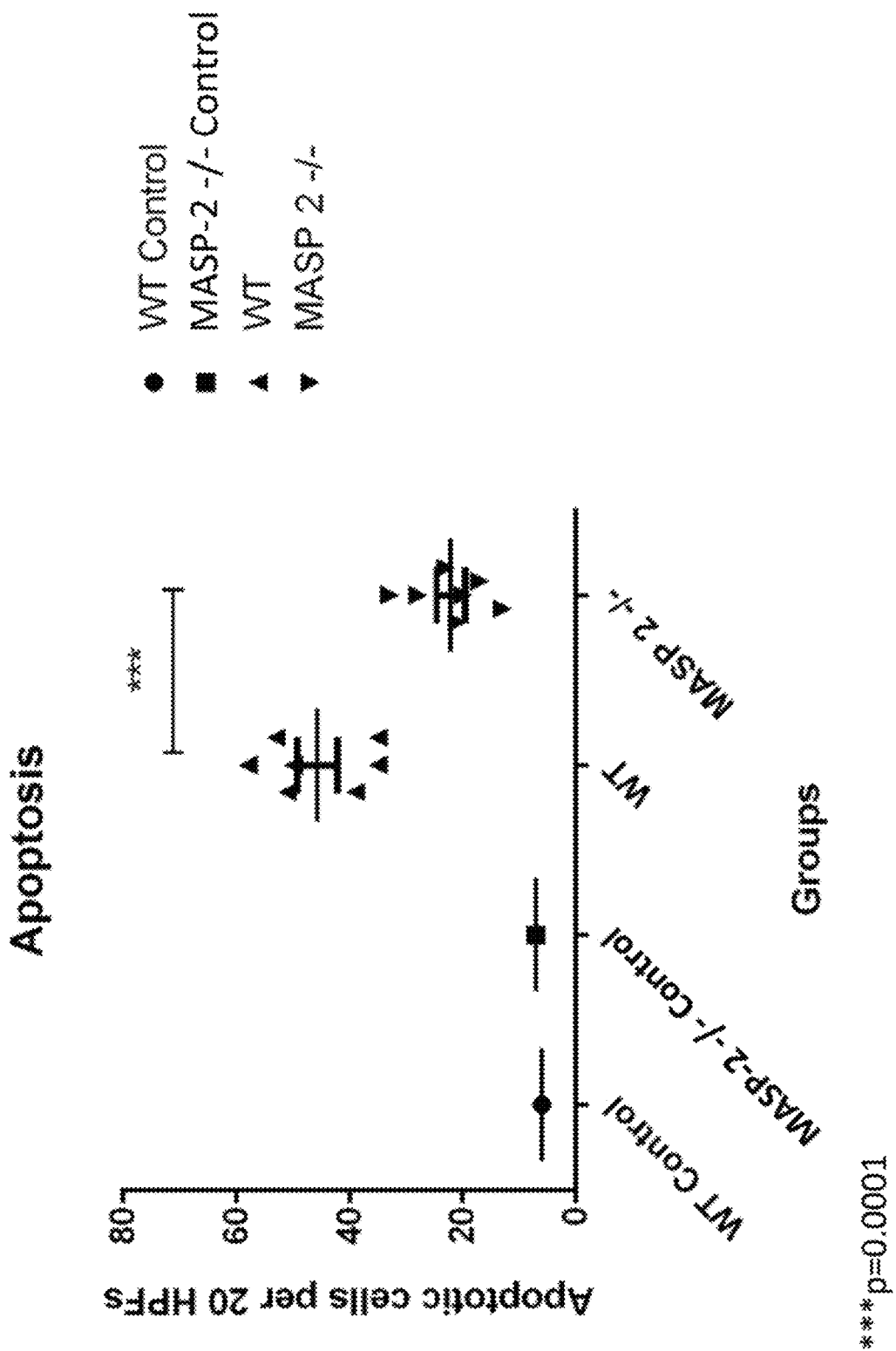
FIG. 31 graphically illustrates the frequency of TUNEL apoptotic cells counted in serially selected 20 high power fields (HPFs) from tissue sections from the renal cortex in wild-type control mice (n=1), MASP-2−/− control mice (n=1), wild-type mice treated with BSA (n=6) and MASP-2−/− mice treated with BSA (n=7), as described in Example 16.

FIG. 31 graphically illustrates the frequency of TUNEL apoptotic cells counted in serially selected 20 high power fields (HPFs) from tissue sections from the renal cortex in wild-type control mice (n=1), MASP-2−/− control mice (n=1), wild-type mice treated with BSA (n=6) and MASP-2−/− mice treated with BSA (n=7). As shown in FIG. 31, a significantly higher rate of apoptosis in the cortex was observed in kidneys obtained from wild-type mice treated with BSA as compared to kidneys obtained from the MASP-2−/− mice treated with BSA (p=0.0001).

OVERALL SUMMARY OF RESULTS AND CONCLUSIONS

The results in this Example demonstrate that MASP-2−/− mice have reduced renal injury in a protein overload model. Therefore, MASP-2 inhibitory agents, such as MASP-2 inhibitory antibodies would be expected to inhibit or prevent the detrimental cycle of inflammation and proteinuria and improve outcomes in chronic kidney disease.

Example 17

This Example describes analysis of a monoclonal MASP-2 inhibitory antibody for efficacy in reducing and/or preventing renal inflammation and tubulointerstitial injury in a mouse protein overload proteinurea model in wild-type mice.

Background/Rationale:

As described in Example 16, in a protein overload model of proteinuria it was determined that MASP-2−/− mice exhibited significantly better outcomes (e.g., less tubulointerstitial injury and less renal inflammation) than wild-type mice, implicating a pathogenic role for the lectin pathway in proteinuric kidney disease.

As described in Example 13, a monoclonal MASP-2 inhibitory antibody (OMS646-SGMI-2) was generated that specifically blocks the function of the human lectin pathway and has also been shown to block the lectin pathway in mice. In this example, the MASP-2 inhibitory antibody OMS646-SGMI-2 was analyzed in a mouse protein overload protein-urea model for efficacy in reducing and/or preventing renal inflammation and tubulointerstitial injury in wild-type mice.

Methods:

This study evaluated the effect of MASP-2 inhibitory antibody (10 mg/kg OMS646-SGMI-2), compared to a human IgG4 isotype control antibody, ET904 (10 mg/kg), and a saline control.

Similar to the study described in Example 16, this study employed protein overload to induce proteinuric kidney disease (Ishola et al., *European Renal Association* 21:591-597, 2006). Proteinuria was induced in unilaterally nephrectomized Balb/c mice by daily i.p. injections with escalating doses (2 g/kg to 15 g/kg) of low endotoxin bovine serum albumin (BSA) for a total of 15 days, as described in Example 16.

Antibody treatments were administered by biweekly i.p. injection starting 7 days before proteinuria induction and continued throughout the study. This dosing scheme was selected based on previous PK/PD and pharmacoclogy studies demonstrating sustained lectin pathway suppression (data not shown). Mice were sacrificed on day 15 and kidneys were harvested and processed for H&E and immunostaining. Stained tissue sections from the renal cortex were analyzed by digital image capture followed by quantification using automated image analysis software.

Immunohistochemistry staining and apoptosis assessment were carried out as described in Example 16.

Results:

Assessment of Proteinuria

To confirm the presence of proteinuria in the mice, the total excreted proteins in urine was measured in urine samples collected over a 24 hour period at day 15 (the end of the experiment). It was determined that the urine samples showed a mean of almost a six-fold increase in total protein levels in the groups that were treated with BSA as compared to the control groups not treated with BSA (data not shown), confirming the presence of proteinuria 10 in the mice treated with BSA. No significant difference was observed in the protein levels between the BSA-treated groups.

Assessment of Histological Changes

Figure 32:
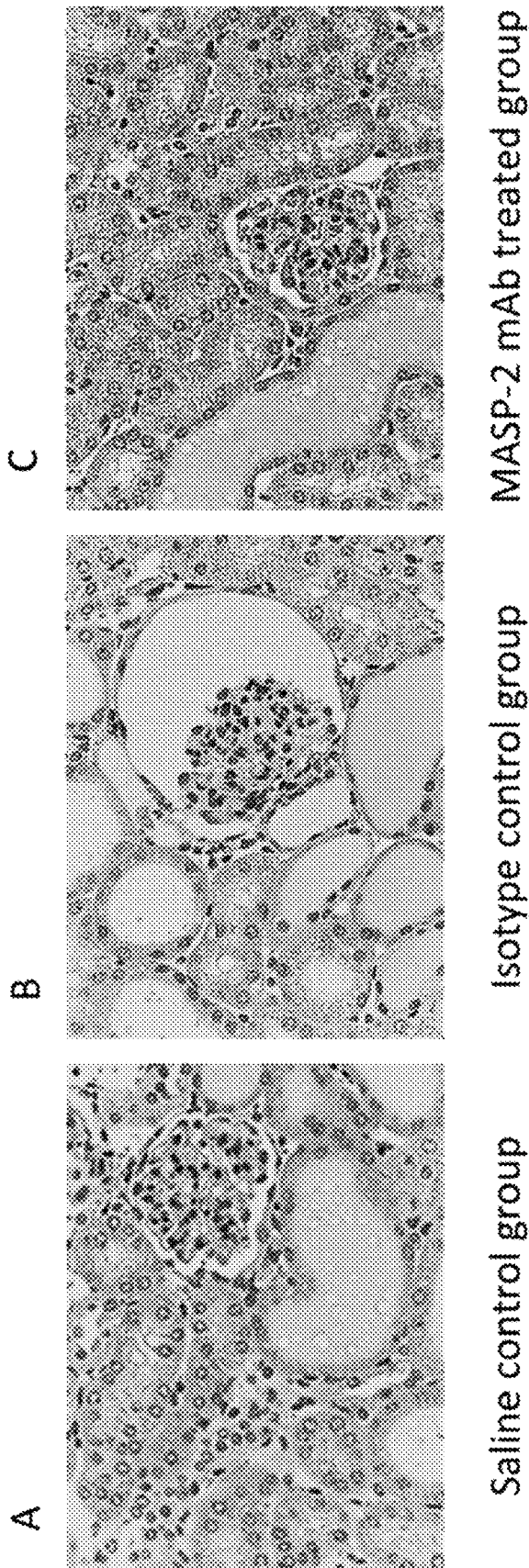
FIG. 32 shows representative H&E stained tissue sections from the following groups of mice at day 15 after treatment with BSA: (panel A) wild-type control mice treated with saline, (panel B) isotype antibody treated control mice and (panel C) wild-type mice treated with a MASP-2 inhibitory antibody, as described in Example 17.

FIG. 32 shows representative H&E stained tissue sections from the following groups of mice at day 15 after treatment with BSA: (panel A) wild-type control mice treated with saline; (panel B) isotype antibody treated control mice; and (panel C) wild-type mice treated with MASP-2 inhibitory antibody.

As shown in FIG. 32, there is a much higher degree of tissue preservation in the MASP-2 inhibitory antibody-treated group (panel C) as compared to the wild-type group treated with saline (panel A) or isotype control (panel B) at the same level of protein overload challenge.

Assessment of Apoptosis

Figure 33:
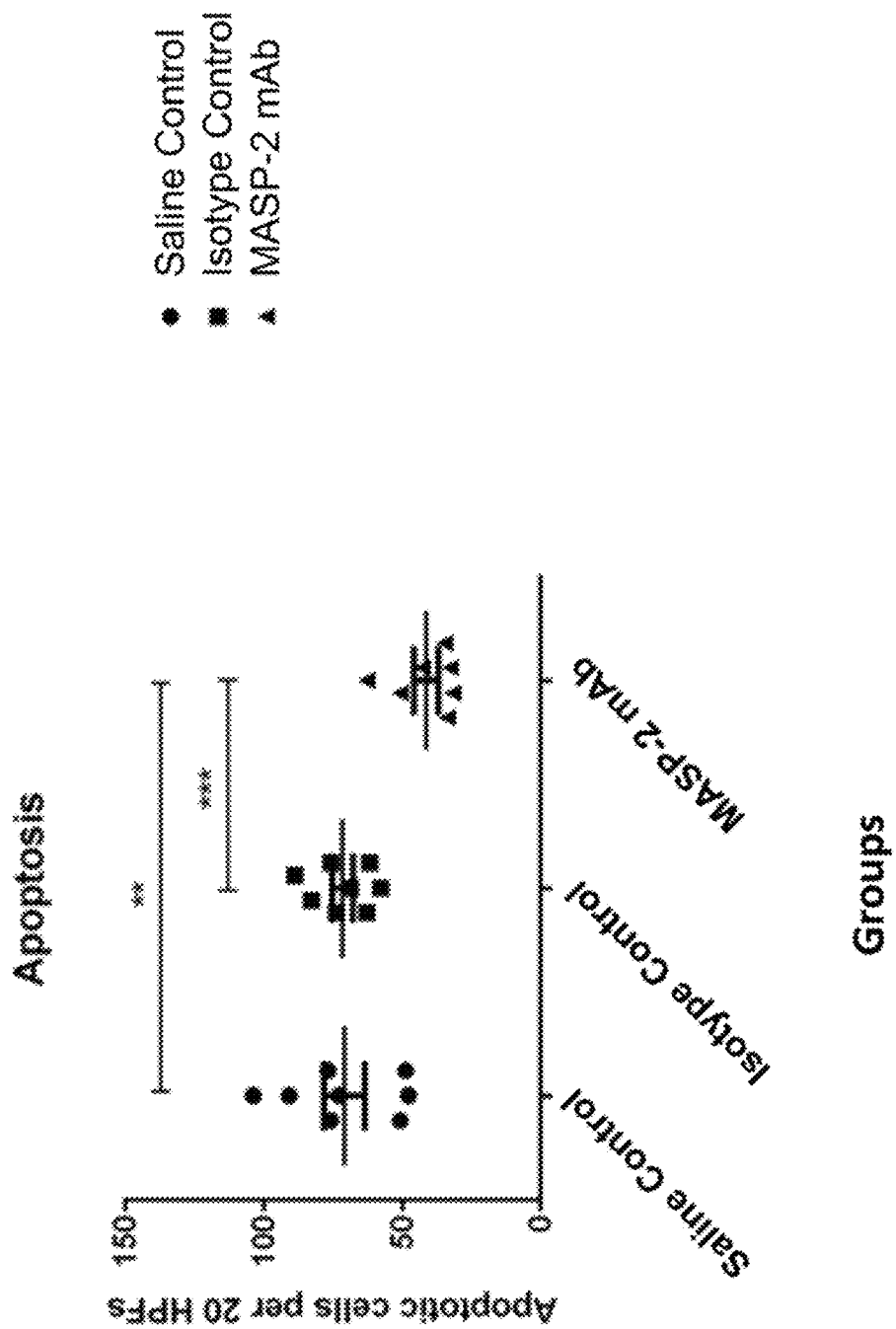
FIG. 33 graphically illustrates the frequency of TUNEL apoptotic cells counted in serially selected 20 high power fields (HPFs) from tissue sections from the renal cortex in wild-type mice treated with saline control and BSA (n=8), wild-type mice treated with the isotype control antibody and BSA (n=8) and wild-type mice treated with a MASP-2 inhibitory antibody and BSA (n=7), as described in Example 17.

Apoptosis was assessed in the tissue sections by staining with terminal deoxynucleotidyl transferase dUTP nick end labeling (TUNEL) and the frequency of TUNEL stained apoptotic cells were counted in serially selected 20 high power fields (HPFs) from the cortex. FIG. 33 graphically illustrates the frequency of TUNEL apoptotic cells counted in serially selected 20 high power fields (HPFs) from tissue sections from the renal cortex in wild-type mice treated with saline control and BSA (n=8), wild-type mice treated with the isotype control antibody and BSA (n=8) and wild-type mice treated with the MASP-2 inhibitory antibody and BSA (n=7). As shown in FIG. 33, a highly significantly decrease in the rate of apoptosis in the cortex was observed in kidneys obtained from the MASP-2 inhibitory antibody treated group as compared to the saline and isotype control treated group (p=0.0002 for saline control v MASP-2 inhibitory antibody; p=0.0052 for isotype control v. MASP-2 inhibitory antibody).

Assessment of Cytokine Infiltration

Interleukin 6 (IL-6), Transforming Growth Factor Beta (TGFβ) and Tumor Necrosis Factor Alpha (TNFα), which are pro-inflammatory cytokines known to be up-regulated in proximal tubules of wild-type mice in a model of proteinuria, were assessed in the kidney tissue sections obtained in this study.

Figure 34:
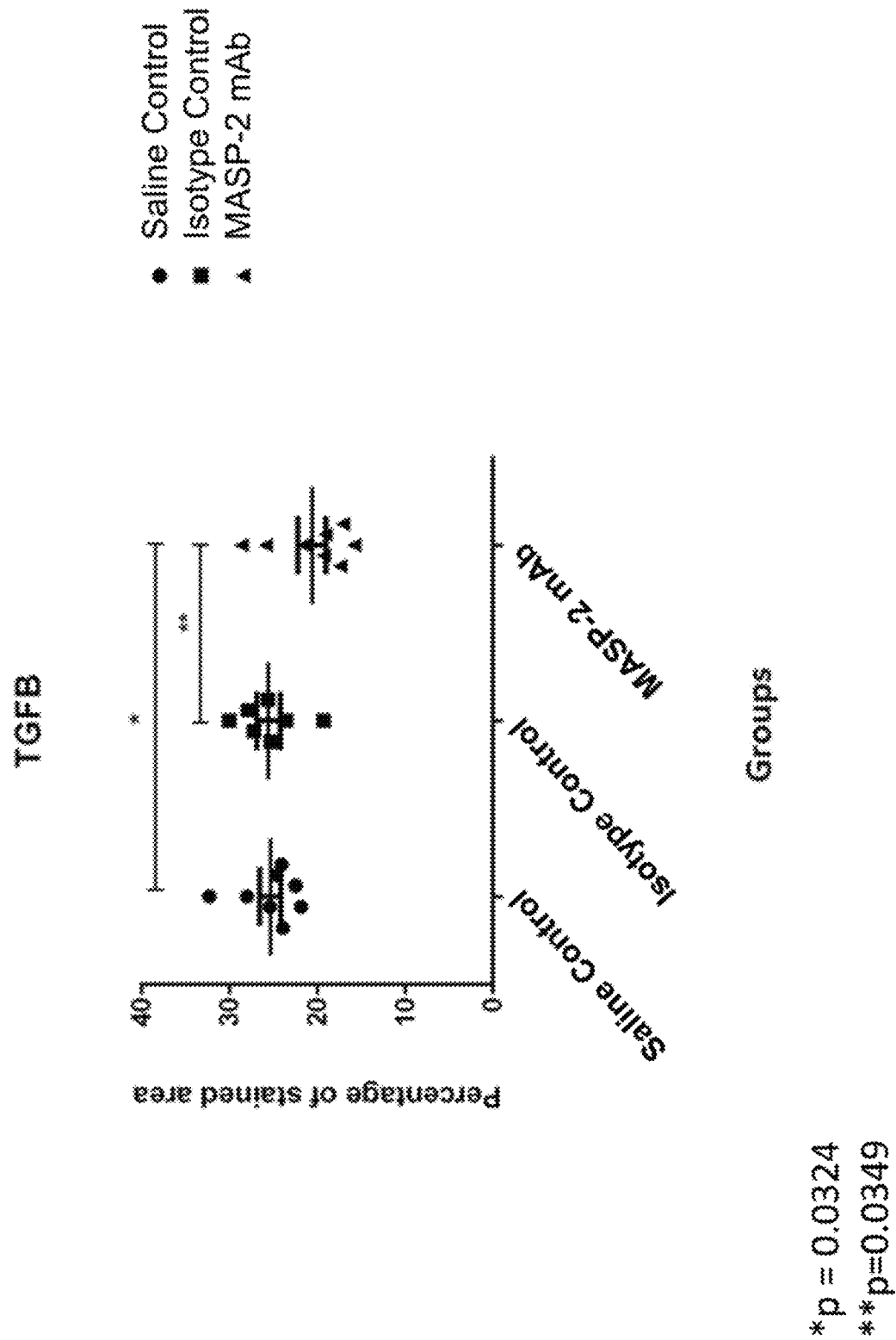
FIG. 34 graphically illustrates the results of computer-based image analysis of stained tissue sections with anti-TGFβ antibody (measured as % TGFβ antibody-stained area) in wild-type mice treated with BSA and saline (n=8), wild-type mice treated with BSA and isotype control antibody (n=7) and wild-type mice treated with BSA and MASP-2 inhibitory antibody (n=8), as described in Example 17.

FIG. 34 graphically illustrates the results of computer-based image analysis of stained tissue sections with anti-TGFβ antibody (measured as % TGFβ antibody-stained area) in wild-type mice treated with BSA and saline (n=8), wild-type mice treated with BSA and isotype control antibody (n=7) and wild-type mice treated with BSA and MASP-2 inhibitory antibody (n=8). As shown in FIG. 34, quantification of the TGFβ stained areas showed a significant reduction in the levels of TGFβ in the MASP-2 inhibitory antibody-treated mice as compared to the saline and isotype control antibody-treated control groups (p values=0.0324 and 0.0349, respectively).

Figure 35:
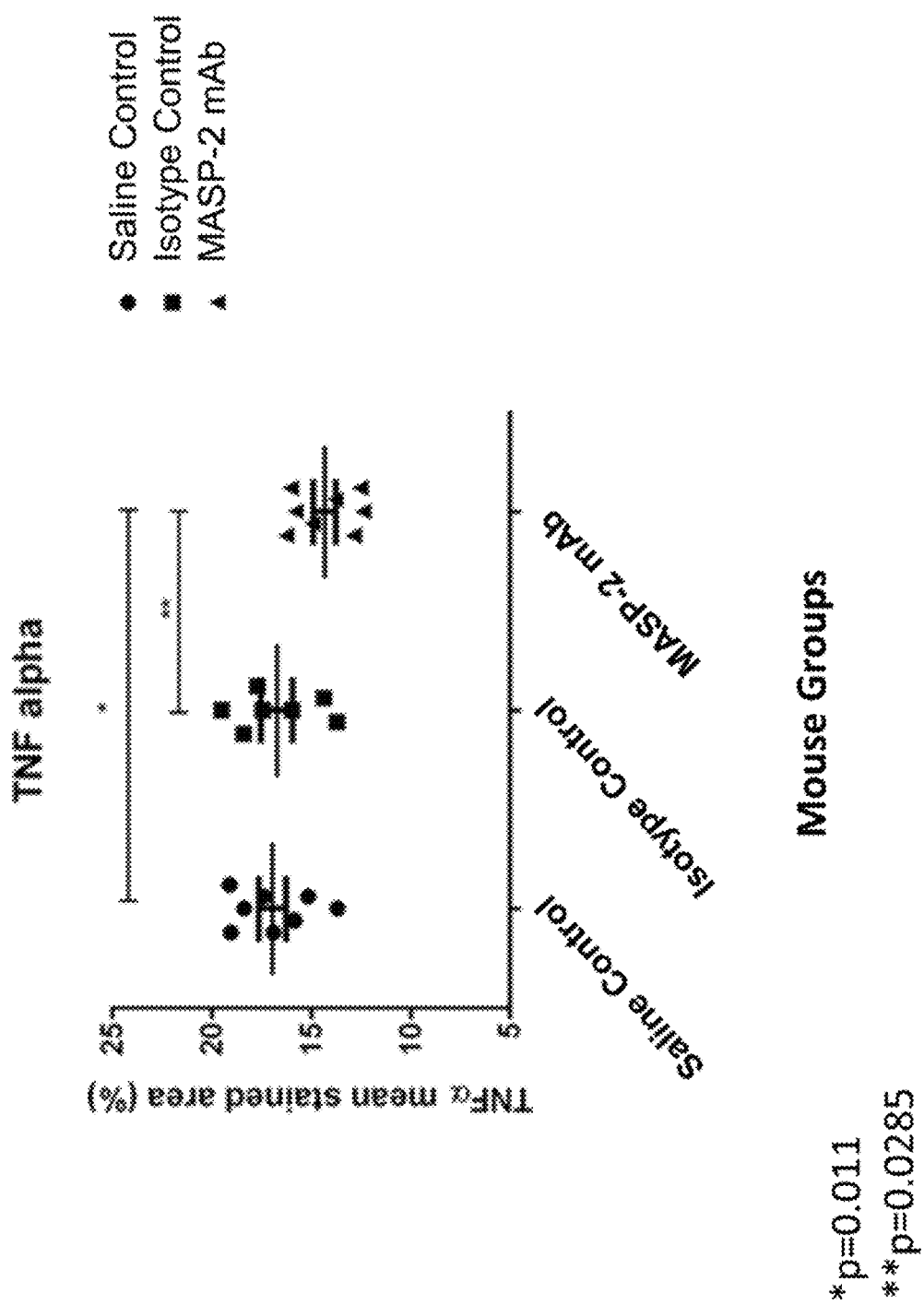
FIG. 35 graphically illustrates the results of computer-based image analysis of stained tissue sections with anti-TNFα antibody (measured as % TNFα antibody-stained area) in wild-type mice treated with BSA and saline (n=8), BSA and isotype control antibody (n=7) and wild-type mice treated with BSA and MASP-2 inhibitory antibody (n=8), as described in Example 17.

FIG. 35 graphically illustrates the results of computer-based image analysis of stained tissue sections with anti-TNFα antibody (measured as % TNFα antibody-stained area) in wild-type mice treated with BSA and saline (n=8), BSA and isotype control antibody (n=7) and wild-type mice treated with BSA and MASP-2 inhibitory antibody (n=8). As shown in FIG. 35, analysis of stained sections showed a significant reduction in the level of TNFα in the MASP-2 inhibitory antibody-treated group as compared to the saline control group (p=0.011) as well as the isotype control group (p=0.0285).

Figure 36:
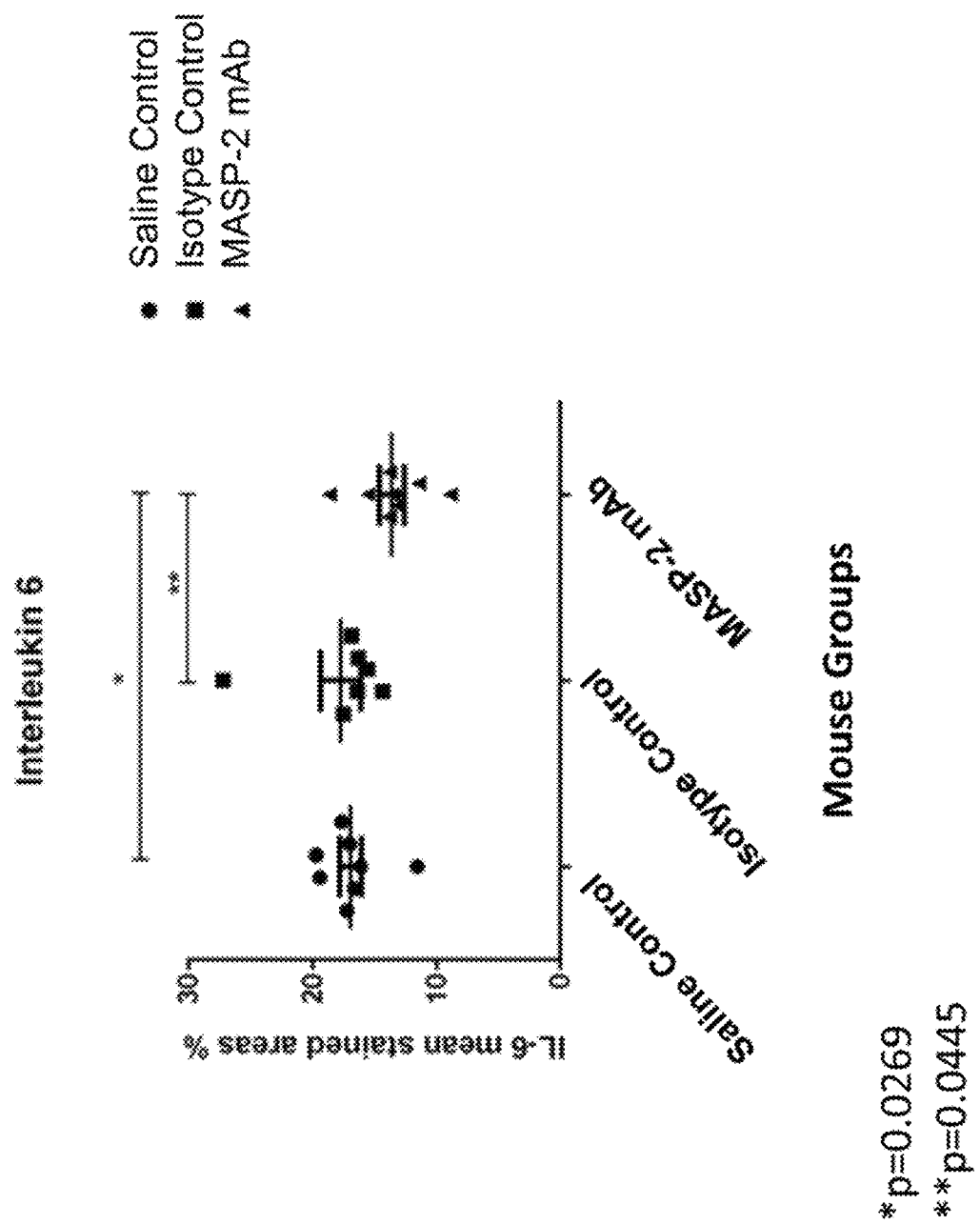
FIG. 36 graphically illustrates the results of computer-based image analysis of stained tissue sections with anti-IL-6 antibody (measured as % IL-6 antibody-stained area) in in wild-type mice treated with BSA and saline (n=8), BSA and isotype control antibody (n=7) and wild-type mice treated with BSA and MASP-2 inhibitory antibody (n=8), as described in Example 17.

FIG. 36 graphically illustrates the results of computer-based image analysis of stained tissue sections with anti-IL-6 antibody (measured as % IL-6 antibody-stained area) in in wild-type mice treated with BSA and saline (n=8), BSA and isotype control antibody (n=7) and wild-type mice treated with BSA and MASP-2 inhibitory antibody (n=8). As shown in FIG. 36, analysis of stained sections showed a significant reduction in the level of IL-6 in the MASP-2 inhibitory antibody-treated group as compared to the saline control group (p=0.0269) as well as to the isotype control group (p=0.0445).

OVERALL SUMMARY OF RESULTS AND CONCLUSIONS

The results in this Example demonstrate that the use of a MASP-2 inhibitory antibody provides protection against renal injury in a protein overload model, which is consistent with the results described in Example 16 demonstrating that MASP-2-/- mice have reduced renal injury in the proteinuria model.

Example 18

This Example provides results generated using an Adriamycin-induced nephrology model of renal fibrosis, inflammation and tubulointerstitial injury in MASP-2-/- and wild-type mice to evaluate the role of the lectin pathway in Adriamycin-induced nephropathy.

Background/Rationale:

Adriamycin is an anthracycline antitumor antibiotic used in the treatment of a wide range of cancers, including hematological malignancies, soft tissue sarcomas and many types of carcinomas. Adriamycin-induced nephropathy is well established rodent model of chronic kidney disease that has enabled a better understanding of the progression of chronic proteinuria (Lee and Harris, *Nephrology*, 16:30-38, 2011). The type of structural and functional injury in Adriamycin-induced nephropathy is very similar to that of chronic proteinuric renal disease in humans (Pippin et al., *American Journal of Renal Physiology* 296:F213-29, 2009).

Adriamycin-induced nephropathy is characterized by an injury to the podocytes followed by glomerulosclerosis, tubulointerstitial inflammation and fibrosis. It has been shown in many studies that Adriamycin-induced nephropathy is modulated by both immune and non-immune derived mechanisms (Lee and Harris, *Nephrology,* 16:30-38, 2011). Adriamycin-induced nephropathy has several strengths as a model of kidney disease. First, it is a highly reproducible and predicable model of renal injury. This is because it is characterized by the induction of renal injury within a few days of drug administration, which allows for ease of experimental design as the timing of injury is consistent. It is also a model in which the degree of tissue injury is severe while associated with acceptable mortality (<5%) and morbidity (weight loss). Therefore, due to the severity and timing of renal injury in Adriamycin-induced nephropathy, it is a model suitable for testing interventions that protect against renal injury.

As described in Examples 16 and 17, in a protein overload model of proteinuria it was determined that MASP-2-/- mice and mice treated with a MASP-2 inhibitory antibody exhibited significantly better outcomes (e.g., less tubulointerstitial injury, and less renal inflammation) than wild-type mice, implicating a pathogenic role for the lectin pathway in proteinuric kidney disease.

In this example, MASP-2-/- mice were analyzed in comparison with wild-type mice in the Adriamycin-induced nephrology model (AN) to determine if MASP-2 deficiency reduces and/or prevents renal inflammation and tubulointerstitial injury induced by Adriamycin.

Methods:
1. Dosage and Time Point Optimization

An initial experiment was carried out to determine the dose of Adriamycin and time point at which BALB/c mice develop a level of renal inflammation suitable for testing therapeutic intervention.

Three groups of wild-type BALB/c mice (n=8) were injected with a single dose of Adriamycin (10.5 mg/kg) administered IV. Mice were culled at three time points: one week, two weeks and four weeks after Adriamycin administration. Control mice were injected with saline only.

Results:

All mice in the three groups showed signs of glomerulosclerosis and proteinuria, as determined by H&E staining, with incrementally increasing degree of tissue inflammation as measured by macrophage infiltration in the kidney (data not shown). The degree of tissue injury was mild in the one week group, moderate in the two week group and severe in the four week group (data not shown). The two week time point was selected for the rest of the study.

2. Analysis of Adriamycin-Induced Nephrology in Wild-Type and MASP-2-/- Mice

In order to elucidate the role of the lectin pathway of complement in the Adriamycin-induced nephrology, a group of MASP-2-/- mice (BALB/c) were compared to wild-type mice (BALB/c) at the same dose of Adriamycin. The MASP-2-/- mice were backcrossed with BALB/c mice for 10 generations.

Wild-type (n=8) and MASP-2-/- (n=8) were injected IV with Adriamycin (10.5 mg/kg) and three mice of each strain were give saline only as a control. All mice were culled two weeks after the treatment and tissues were collected. The degree of histopatholigical injury was assessed by H&E staining.

Figure 37:
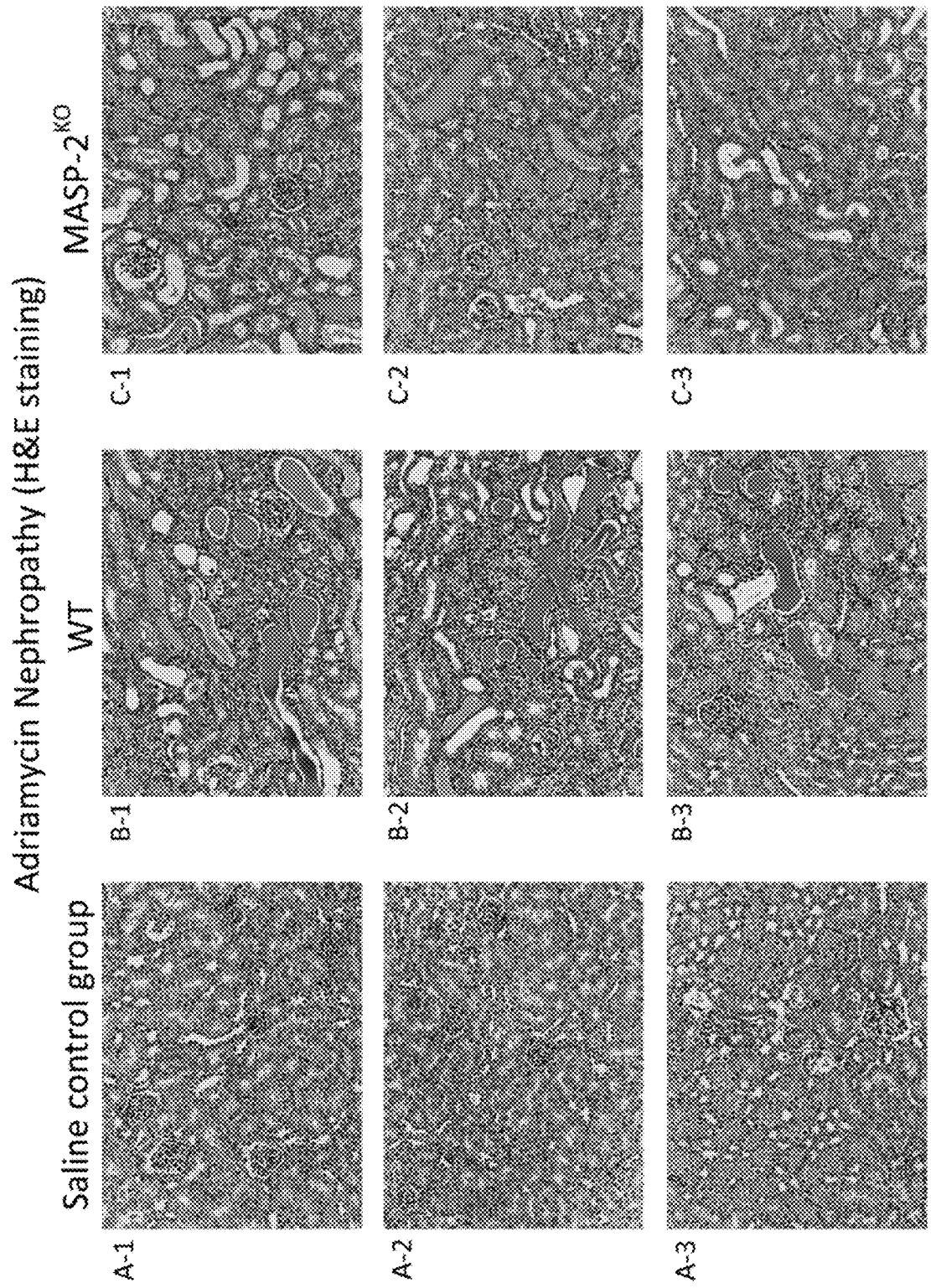
FIG. 37 shows representative H&E stained tissue sections from the following groups of mice at day 14 after treatment with Adriamycin or saline only (control): (panels A-1, A-2, A-3) wild-type control mice treated with only saline; (panels B-1, B-2, B-3) wild-type mice treated with Adriamycin; and (panels C-1, C-2, C-3) MASP-2−/− mice treated with Adriamycin, as described in Example 18.

Results:

FIG. 37 shows representative H&E stained tissue sections from the following groups of mice at day 14 after treatment with Adriamycin or saline only (control): (panels A-1, A-2, A-3) wild-type control mice treated with only saline; (panels B-1, B-2, B-3) wild-type mice treated with Adriamycin; and (panels C-1, C-2, C-3) MASP-2-/- mice treated with Adriamycin. Each photo (e.g., panel A-1, A-2, A-3) represents a different mouse.

As shown in FIG. 37, there is a much higher degree of tissue preservation in the MASP-2-/- group treated with Adriamycin as compared to the wild-type group treated with the same dose of Adriamycin.

Figure 38:
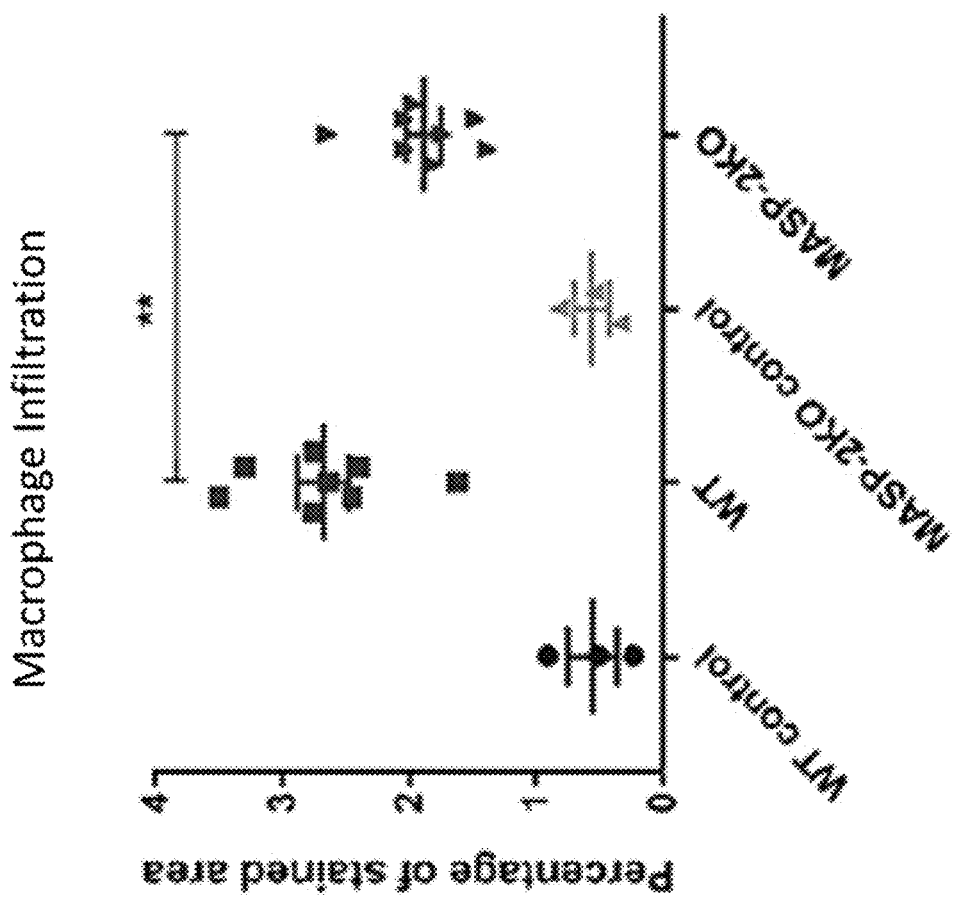
FIG. 38 graphically illustrates the results of computer-based image analysis of kidney tissue sections stained with macrophage-specific antibody F4/80 showing the macrophage mean stained area (%) from the following groups of mice at day 14 after treatment with Adriamycin or saline only (wild-type control): wild-type control mice treated with only saline; wild-type mice treated with Adriamycin; MASP-2−/− mice treated with saline only, and MASP-2−/− mice treated with Adriamycin, wherein **p=0.007, as described in Example 18.

FIG. 38 graphically illustrates the results of computer-based image analysis of kidney tissue sections stained with macrophage-specific antibody F4/80 showing the macrophage mean stained area (%) from the following groups of mice at day 14 after treatment with Adriamycin or saline only (wild-type control): wild-type control mice treated with only saline; wild-type mice treated with Adriamycin; MASP-2-/- mice treated with saline only, and MASP-2-/- mice treated with Adriamycin. As shown in FIG. 38, MASP-2-/- mice treated with Adriamycin have reduced macrophage infiltration (**$p=0.00^7$) compared to wild-type mice treated with Adriamycin.

Figure 39:
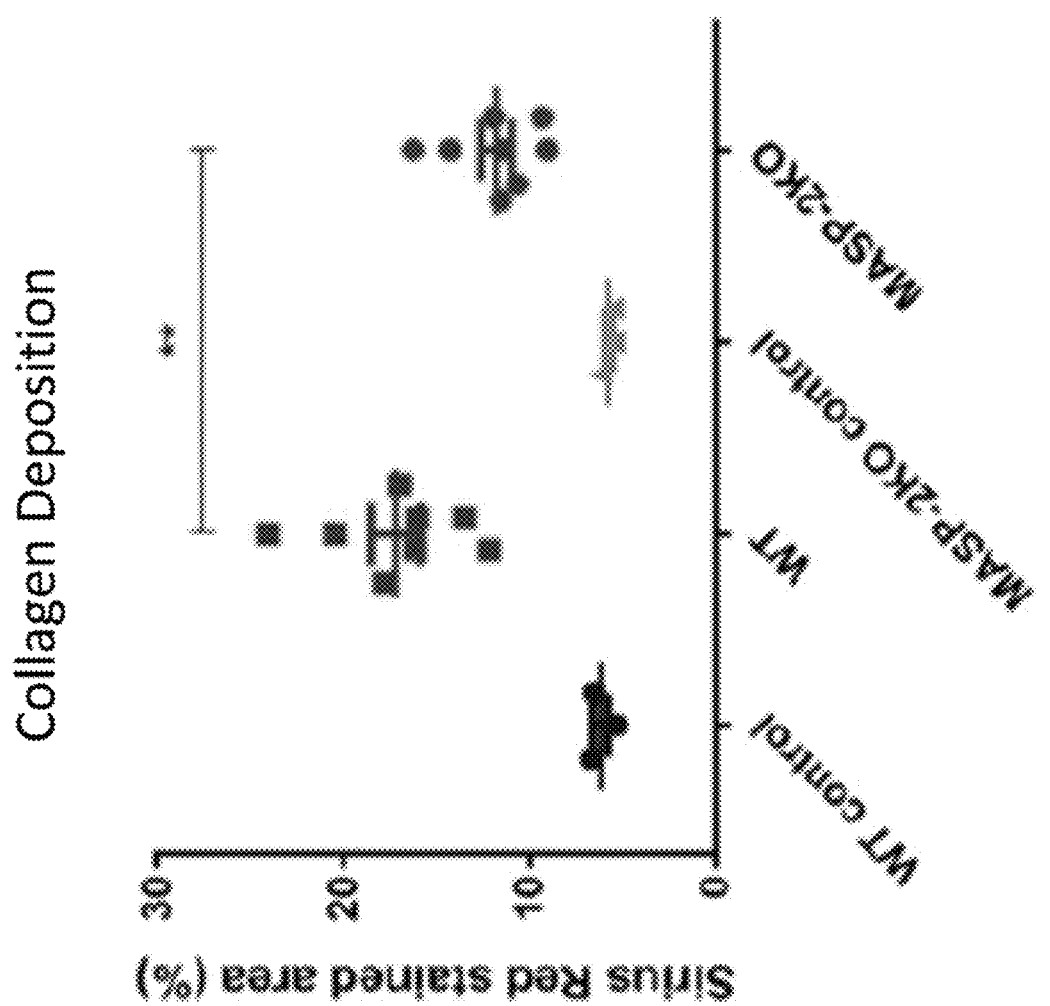
FIG. 39 graphically illustrates the results of computer-based image analysis of kidney tissue sections stained with Sirius Red, showing the collagen deposition stained area (%) from the following groups of mice at day 14 after treatment with Adriamycin or saline only (wild-type control): wild-type control mice treated with only saline; wild-type mice treated with Adriamycin; MASP-2−/− mice treated with saline only, and MASP-2−/− mice treated with Adriamycin, wherein **p=0.005, as described in Example 18.

FIG. 39 graphically illustrates the results of computer-based image analysis of kidney tissue sections stained with Sirius Red, showing the collagen deposition stained area (%) from the following groups of mice at day 14 after treatment with Adriamycin or saline only (wild-type control): wild-type control mice treated with only saline; wild-type mice treated with Adriamycin; MASP-2-/- mice treated with saline only, and MASP-2-/- mice treated with Adriamycin. As shown in FIG. 39, MASP-2-/- mice treated with Adriamycin have reduced collagen deposition (**$p=0.005$) compared to wild-type mice treated with Adriamycin.

OVERALL SUMMARY AND CONCLUSIONS

The amelioration of renal tubulointerstitial inflammation is a key target for the treatment of kidney disease. The results presented herein indicate that the lectin pathway of complement activation contributes significantly to the development of renal tubulointerstitial inflammation. As further demonstrated herein, a MASP-2 inhibitory agent, such as a MASP-2 inhibitory antibody, may be used as a novel therapeutic approach in the treatment of proteinuric nephropathy, Adriamycin nephropathy and amelioration of renal tubulointerstitial inflammation.

Example 19

This Example describes the initial results of an ongoing Phase 2 clinical trial to evaluate the safety and clinical efficacy of a fully human monoclonal MASP-2 inhibitory antibody in adults with steroid-dependent immunoglobulin A nephropathy (IgAN) and in adults with steroid-dependent membranous nephropathy (MN).

BACKGROUND

Chronic kidney diseases affect more than 20 million people in the United States (Drawz P. et al., *Anm Intern Med* 162(11); ITC 1-16, 2015). Glomerulonephropathies (GNs), including IgAN and MN are kidney diseases in which the glomeruli are damaged and frequently lead to end-stage renal disease and dialysis. Several types of primary GNs exist, the most common being IgAN. Many of these patients have persistent renal inflammation and progressive deterioration. Often these patients are treated with corticosteroids or immunosuppressive agents, which have many serious long-term adverse consequences. Many patients continue to deteriorate even on these treatments. No treatments are approved for the treatment of IgAN or MN.

IgA Nephropathy

Immunoglobulin A nephropathy (IgAN) is an autoimmune kidney disease resulting in intrarenal inflammation and kidney injury. IgAN is the most common primary glomerular disease globally. With an annual incidence of approximately 2.5 per 100,000, it is estimated that 1 in 1400 persons in the U.S. will develop IgAN. As many as 40% of patients with IgAN will develop end-stage renal disease (ESRD). Patients typically present with microscopic hematuria with mild to moderate proteinuria and variable levels of renal insufficiency (Wyatt R. J., et al., *N Engl J Med* 368(25):2402-14, 2013). Clinical markers such as impaired kidney function, sustained hypertension, and heavy proteinuria (over 1 g per day) are associated with poor prognosis (Goto M et al., *Nephrol Dial Transplant* 24(10):3068-74, 2009; Berthoux F. et al., *J Am Soc Nephrol* 22(4):752-61, 2011). Proteinuria is the strongest prognostic factor independent of other risk factors in multiple large observational studies and prospective trials (Coppo R. et al., *J Nephrol* 18(5):503-12, 2005; Reich H. N., et al., *J Am Soc Nephrol* 18(12):3177-83, 2007). It is estimated that 15-20% of patients reach ESRD within 10 years of disease onset if left untreated (D'Amico G., *Am J Kidney Dis* 36(2):227-37, 2000).

The diagnostic hallmark of IgAN is the predominance of IgA deposits, alone or with IgG, IgM, or both, in the glomerular mesangium. In IgAN, renal biopsies reveal glomerular deposition of mannan-binding lectin (MBL), a key recognition molecule for activation of MASP-2, the effector enzyme of the complement system's lectin pathway. Glomerular MBL deposits, usually co-localized with IgA and indicating complement activation, and high levels of urinary MBL are associated with an unfavorable prognosis in IgAN, with these patients demonstrating more severe histological changes and mesangial proliferation than patients without MBL deposition or high levels of urinary MBL (Matsuda M. et al., *Nephron* 80(4):408-13, 1998; Liu L L et al., *Clin Exp Immunol* 169(2): 148-155, 2012; Roos A. et al., *J Am Soc Nephrol* 17(6): 1724-34, 2006; Liu L L et al., *Clin Exp Immunol* 174(1):152-60, 2013). Remission rates also are substantially lower for patients with MBL deposition (Liu L L et al., *Clin Erp Immunol* 174(1):152-60, 2013).

Current therapy for IgAN includes blood pressure control and, frequently, corticosteroids and/or other immunosuppressive agents, such as cyclophosphamide, azathioprine, or mycofenolate mofetil, for severe disease (e.g., crescentic IgAN). The Kidney Disease Improving Global Outcomes (KDIGO) Guidelines for Glomerulonephritis (Int. Soc ofNephrol 2(2):139-274, 2012) recommend that corticosteroids should be administered to patients with proteinuria of greater than or equal to 1 g/day, with a usual treatment duration of 6 months. However, even with aggressive immunosuppressive treatment, which is associated with serious long-term sequelae, some patients have progressive deterioration of renal function. There is no approved treatment for IgAN, and even with the use of angiotensin-converting enzyme (ACE) inhibitors or angiotensin receptor blockers (ARBs) to control blood pressure, increased proteinuria persists in some patients. None of these treatments have been shown to stop or even slow the progression of IgAN in patients who are at risk for rapid progression of the disease.

Membranous Nephropathy

The annual incidence of membranous nephropathy (MN) is approximately 10-12 per 1,000,000. Patients with MN can have a variable clinical course, but approximately 25% will develop end-stage renal disease.

Membranous nephropathy is an immune-mediated glomerular disease and one of the most common causes of the nephrotic syndrome in adults. The disease is characterized by the formation of immune deposits, primarily IgG4, on the outer aspect of the glomerular basement membrane, which contain podocyte antigens and antibodies specific to those antigens, resulting in complement activation. Initial manifestations of MN are related to the nephrotic syndrome: proteinuria, hypoalbuminemia, hyperlipidemia, and edema.

Although MN may spontaneously remit without treatment, as many as one third of patients demonstrate progressive loss of kidney function and progress to ESRD at a median of 5 years after diagnosis. Often, corticosteroids are used to treat MN and there is a need to develop alternative therapies. Additionally, patients determined to be at moderate risk for progression, based on severity of proteinuria, are treated with prednisone in conjunction with cyclophosphamide or a calcinuerin inhibitor, and these two treatments together are often associated with severe systemic adverse effects.

Methods:

Two Phase 1 clinicial trials carried out in healthy volunteers have demonstrated that both intravenous and subcutaneous dosing of a MASP-2 inhibitory antibody, OMS646, resulted in sustained lectin pathway inhibition.

This Example describes interim results from an ongoing Phase 2, uncontrolled, multicenter study of a MASP-2 inhibitory antibody, OMS646, in subjects with IgAN and MN. Inclusion criteria require that all patients in this study, regardless of renal disease subtype, have been maintained on a stable dose of corticosteroids for at least 12 weeks prior to study enrollment (i.e., the patients are steroid-dependent). The study is a single-arm pilot study with 12 weeks of treatment and a 6-week follow-up period.

Approximately four subjects are planned to be enrolled per disease. The study is designed to evaluate whether OMS646 may improve renal function (e.g., improve proteinuria) and decrease corticosteroid needs in subjects with IgAN and MN. To date, 2 patients with IgA nephropathy and 2 patients with membranous nephropathy have completed treatment in the study.

At study entry each subject must have high levels of protein in the urine despite ongoing treatment with a stable corticosteroid dose. These criteria select for patients who are unlikely to spontaneously improve during the study period.

The subjects were age ≥18 at screening and were only included in the study if they had a diagnosis of one of the following: IgAN diagnosed on kidney biopsy or primary MN diagnosed on kidney biopsy. The enrolled patients also had to meet all of the following inclusion criteria:

(1) have average urine albumin/creatinine ratio >0.6 from three samples collected consecutively and daily prior to each of 2 visits during the screening period;

(2) have been on >10 mg of prednisone or equivalent dose for at least 12 weeks prior to screening visit 1;

(3) if on immunosuppressive treatment (e.g., cyclophosphamide, mycophenolate mofetil), have been on a stable dose for at least 2 months prior to Screening Visit 1 with no expected change in the dose for the study duration;

(4) have an estimated glomerular filtration rate (eGFR) ≥30 mL/min/1.73 m$^2$ calculated by the MDRD equation[1];

[1] MDRD Equation: eGFR (mL/min/1.73 m$^2$)=175×(SCr)$^{-1.154}$×(Age)$^{-0.203}$× (0.742 if female)×(1.212 if African American). Note: SCr=Serum Creatinine measurement should be mg/dL.

(5) are on a physician-directed, stable, optimized treatment with angiotensin converting enzyme inhibitors (ACEI) and/or angiotensin receptor blockers (ARB) and have a systolic blood pressure of <150 mmHg and a diastolic blood pressure of <90 mmHg at rest:

(6) have not used belimumab, eculizumab or rituzimab within 6 months of screening visit 1; and (7) do not have a history of renal transplant.

The monoclonal antibody used in this study, OMS646, is a fully human IgG4 monoclonal antibody that binds to and inhibits human MASP-2. MASP-2 is the effector enzyme of the lectin pathway. As demonstrated in Example 12, OMS646 avidly binds to recombinant MASP-2 (apparent equilibrium dissociation constant in the range of 100 μM) and exhibits greater than 5,000-fold selectivity over the homologous proteins C1s, C1r, and MASP-1. In functional assays, OMS646 inhibits the human lectin pathway with nanomolar potency (concentration leading to 50% inhibition [$IC_{50}$] of approximately 3 nM) but has no significant effect on the classical pathway. OMS646 administered either by intravenous (IV) or subcutaneous (SC) injection to mice, non-human primates, and humans resulted in high plasma concentrations that were associated with suppression of lectin pathway activation in an ex vivo assay.

In this study, the OMS646 drug substance was provided at a concentration of 100 mg/mL, which was further diluted for IV administration. The appropriate calculated volume of OMS646 100 mg/mL injection solution was withdrawn from the vial using a syringe for dose preparation. The infusion bag was administered within four hours of preparation.

The study consists of screening (28 days), treatment (12 weeks) and follow-up (6 weeks) periods, as shown in the Study Design Schematic below.

tigator. Subjects were treated with OMS646 through the corticosteroid taper and through the full 12 weeks of treatment. The patients were then followed for an additional 6 weeks after their last treatment. The taper of corticosteroids and OMS646 treatment permitted assessment of whether OMS646 allowed for a decrease in the dose of corticosteroid required to maintain stable renal function.

The key efficacy measures in this study are the change in urine albumin-to-creatinine ratio (uACR) and 24-hour protein levels from baseline to 12 weeks. Measurement of urinary protein or albumin is routinely used to assess kidney involvement and persistent high levels of urinary protein correlates with renal disease progression. The uACR is used clinically to assess proteinuria.

Efficacy Analyses

The analysis value for uACR is defined as the average of all the values obtained for a time point. The planned number of uACRs is three at each scheduled time point. The baseline value of the uACR is defined as the average of the analysis values at the two screening visits.

Figure 40:
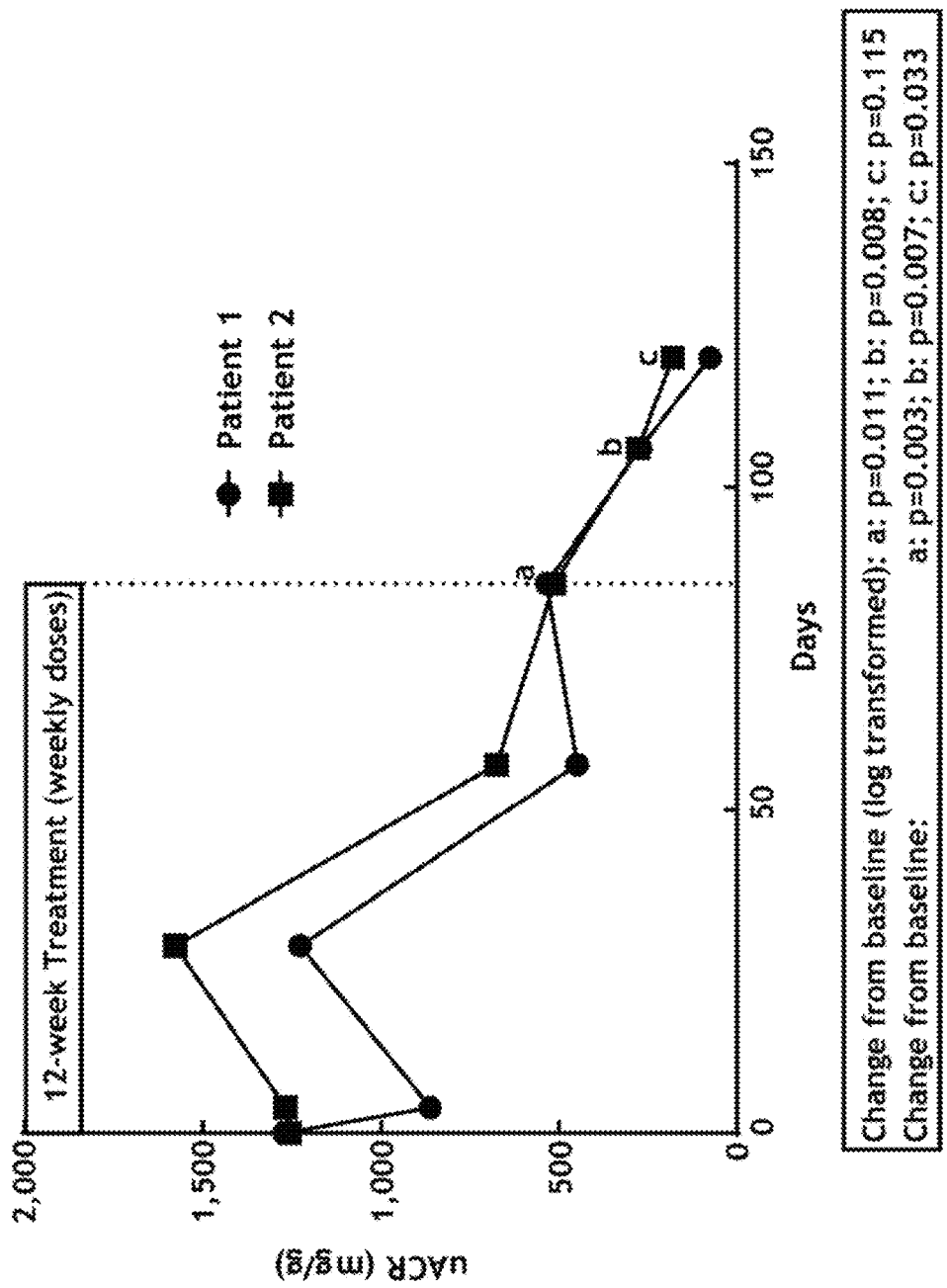
FIG. 40 graphically illustrates the urine albumin/creatinine ratio (uACR) in two IgA patients during the course of a twelve week study with weekly treatment with a MASP-2 inhibitory antibody (OMS646), as described in Example 19.

Results:

FIG. 40 graphically illustrates the uACRin two IgAN patients during the course of a twelve week study with weekly treatment with 4 mg/kg MASP-2 inhibitory antibody (OMS646). As shown in FIG. 40, the change from baseline is statistically significant at time point "a" (p=0.003); time point "b" (p=0.007) and a time point "c" (p=0.033) by the untransformed analysis. TABLE 12 provides the 24-hour urine-protein data for the two IgAN patients treated with OMS646.

Study Design Schematic

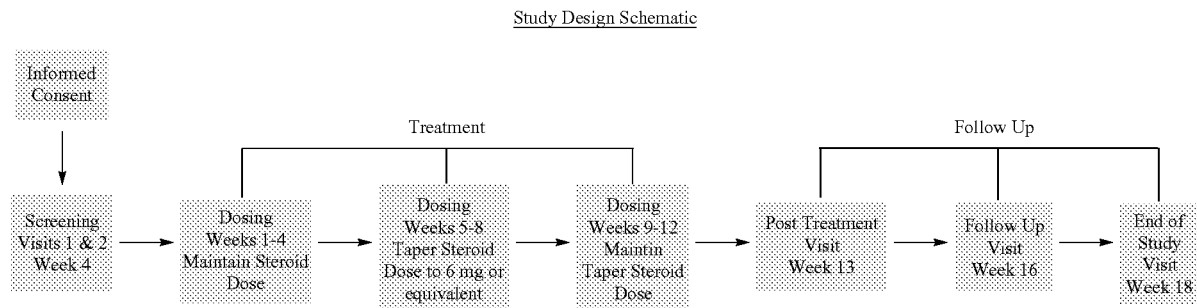

Within the screening period and before the first OMS646 dose, consented subjects provided three urine samples (collected once daily) on each of two three-consecutive-day periods to establish baseline values of the urine albumin-to-creatinine ratio. Following the screening period, eligible subjects received OMS646 4 mg/kg IV once weekly for 12 weeks (treatment period). There was a 6-week follow-up period after the last dose of OMS646.

During the initial 4 weeks of treatment with OMS646, subjects were maintained on their stable pre-study dose of corticosteroids. At the end of the initial 4-weeks of the 12-week treatment period, subjects underwent corticosteroid taper (i.e., the corticosteroid dose was reduced), if tolerated, over 4 weeks, followed by 4 weeks during which the resultant corticosteroid dose was maintained. The target was a taper ≤6 mg prednisone (or equivalent dose) daily. Over this period, the taper was discontinued in subjects who had deterioration of renal function, as determined by the inves-

TABLE 12

24-hour Urine Protein (mg/day) in OMS646-treated IgAN Patients

| Time of Sample | Patient #1 (mg/24 hours) | Patient #2 (mg/24 hours) | Mean |
|---|---|---|---|
| Baseline | 3876 | 2437 | 3156 |
| Day 85 | 1783 | 455 | 1119 | p = 0.017

As shown in FIG. 40 and TABLE 12, the patients with IgAN demonstrated a clinically and statistically significant improvement in kidney function over the course of the study. There were statistically significant decreases in both uACR (see FIG. 40) and 24-hour urine protein concentration (see TABLE 12). As shown in the uACR data in FIG. 40, the mean baseline uACR was 1264 mg/g and reached 525 mg/g at the end of treatment (p=0.011) decreasing to 128 mg/g at the end of the follow-up period. As further shown in FIG. 40, the treatment effect was maintained throughout the follow-up period. Measures of 24-hour urine protein excretion tracked uACRs, with a mean reduction from 3156 mg/24 hours to 1119 mg/24 hours (p=0.017). Treatment effects across the two patients were highly consistent. Both patients experienced reductions of approximately 2000 mg/day and both achieved a partial remission (defined as greater than 50 percent reduction in 24-hour urine protein excretion and/or resultant protein exertion less than 1000 mg/day; complete remission defined as protein excretion less than 300 mg/day). The magnitude of the 24-hour proteinuria reductions in both IgA nephropathy patients is associated with a significant improvement in renal survival. Both IgA nephropathy patients were also able to taper their steroids substantially, each reducing the daily dose to ≤5 mg (60 mg to 0 mg; 30 mg to 5 mg).

The two MN patients also demonstrated reductions in uACR during treatment with OMS646. One MN patient had a decrease in uACR from 1003 mg/g to 69 mg/g and maintained this low level throughout the follow-up period. The other MN patient had a decrease in uACR from 1323 mg/g to 673 mg/g, with a variable course after treatment. The first MN patient showed a marked reduction in 24-hour urine protein level (10,771 mg/24 hours at baseline to 325 mg/24 hours on Day 85), achieving partial and nearly complete remission, while the other remained essentially unchanged (4272 mg/24 hours at baseline to 4502 mg/24 on Day 85). Steroids were tapered in the two MN patients from 30 mg to 15 mg and from 10 mg to 5 mg.

In summary, consistent improvements in renal function were observed in IgAN and MN subjects treated with the MASP-2 inhibitory antibody OMS646. The effects of OMS646 treatment in the patients with IgAN are robust and consistent, suggesting a strong efficacy signal. These effects are supported by the results in MN patients. The time course and magnitude of the uACR changes during treatment were consistent between all four patients with IgAN and MN. No significant safety concerns have been observed. Patients in this study represent a difficult-to-treat group and a therapeutic effect in these patients is believed to be predictive of efficacy with a MASP-2 inhibitory antibody, such as OMS646, in IgAN and MN patients, such as patients suffering from steroid-dependent IgAN and MN (i.e., patients undergoing treatment with a stable corticosteroid dose prior to treatment with a MASP-2 inhibitory antibody), including those at risk for rapid progression to end-stage renal disease.

In accordance with the foregoing, in one embodiment, the invention provides a method of treating a human subject suffering from IgAN or MN comprising administering to the subject a composition comprising an amount of a MASP-2 inhibitory antibody effective to inhibit MASP-2-dependent complement activation. In one embodiment, the method comprises administering to the human subject suffering from IgAN or MN an amount of a MASP-2 inhibitory antibody sufficient to improve renal function (e.g., improve proteinuria). In one embodiment, the subject is suffering from steroid-dependent IgAN. In one embodiment, the subject is suffering from steroid-dependent MN. In one embodiment, the MASP-2 inhibitory antibody is administered to the subject suffering from steroid-dependent IgAN or steroid-dependent MN in an amount sufficient to improve renal function and/or decrease corticosteroid dosage in said subject.

In one embodiment, the method further comprises identifying a human subject suffering from steroid-dependent IgAN prior to the step of administering to the subject a composition comprising an amount of a MASP-2 inhibitory antibody effective to inhibit MASP-2-dependent complement activation.

In one embodiment, the method further comprises identifying a human subject suffering from steroid-dependent MN prior to the step of administering to the subject a composition comprising an amount of a MASP-2 inhibitory antibody effective to inhibit MASP-2-dependent complement activation.

In accordance with any of the disclosed embodiments herein, the MASP-2 inhibitory antibody exhibits at least one or more of the following characteristics: said antibody binds human MASP-2 with a $K_D$ of 10 nM or less, said antibody binds an epitope in the CCP1 domain of MASP-2, said antibody inhibits C3b deposition in an in vitro assay in 1% human serum at an IC50 of 10 nM or less, said antibody inhibits C3b deposition in 90% human serum with an $IC_{50}$ of 30 nM or less, wherein the antibody is an antibody fragment selected from the group consisting of Fv, Fab, Fab', $F(ab)_2$ and $F(ab')_2$, wherein the antibody is a single-chain molecule, wherein said antibody is an IgG2 molecule, wherein said antibody is an IgG1 molecule, wherein said antibody is an IgG4 molecule, wherein the IgG4 molecule comprises a S228P mutation. In one embodiment, the antibody binds to MASP-2 and selectively inhibits the lectin pathway and does not substantially inhibit the classical pathway (i.e., inhibits the lectin pathway while leaving the classical complement pathway intact).

In one embodiment, the MASP-2 inhibitory antibody is administered in an amount effective to improve at least one or more clinical parameters associated renal function, such as an improvement in proteinuria (e.g., a decrease in uACR and/or a decrease in 24-hour urine protein concentration, such as greater than 20 percent reduction in 24-hour urine protein excretion, or such as greater than 30 percent reduction in 24-hour urine protein excretion, or such as greater than 40 percent reduction in 24-hour urine protein excretion, or such as greater than 50 percent reduction in 24-hour urine protein excretion).

In some embodiments, the method comprises administering a MASP-2 inhibitory antibody to a subject suffering from IgAN (such as steroid-dependent IgAN), via a catheter (e.g., intravenously) for a first time period (e.g., at least one day to a week or two weeks or three weeks or four weeks or longer) followed by administering a MASP-2 inhibitory antibody to the subject subcutaneously for a second time period (e.g., a chronic phase of at least two weeks or longer).

In some embodiments, the method comprises administering a MASP-2 inhibitory agent to a subject suffering from MN (such as steroid-dependent MN), via a catheter (e.g., intravenously) for a first time period (e.g., at least one day to a week or two weeks or three weeks or four weeks or longer) followed by administering a MASP-2 inhibitory antibody to the subject subcutaneously for a second time period (e.g., a chronic phase of at least two weeks or longer).

In some embodiments, the method comprises administering a MASP-2 inhibitory antibody to a subject suffering from IgAN (such as steroid-dependent IgAN) or MN (such as steroid-dependent MN) either intravenously, intramuscularly, or subcutaneously. Treatment may be chronic and administered daily to monthly, but preferably at least every two weeks, or at least once a week, such as twice a week or three times a week.

In one embodiment, the method comprises treating a subject suffering from IgAN (such as steroid-dependent IgAN) or MN (such as steroid-dependent MN) comprising administering to the subject a composition comprising an amount of a MASP-2 inhibitory antibody, or antigen binding fragment thereof, comprising a heavy chain variable region comprising CDR-H1, CDR-H2 and CDR-H3 of the amino acid sequence set forth as SEQ ID NO:67 and a light-chain variable region comprising CDR-L1, CDR-L2 and CDR-L3 of the amino acid sequence set forth as SEQ ID NQ:69. In some embodiments, the composition comprises a MASP-2 inhibitory antibody comprising (a) a heavy-chain variable region comprising: i) a heavy-chain CDR-H1 comprising the amino acid sequence from 31-35 of SEQ ID NO:67; and ii) a heavy-chain CDR-H2 comprising the amino acid sequence from 50-65 of SEQ ID NO:67; and iii) a heavy-chain CDR-H3 comprising the amino acid sequence from 95-107 of SEQ ID NO:67 and b) a light-chain variable region comprising: i) a light-chain CDR-L1 comprising the amino acid sequence from 24-34 of SEQ ID NO:69; and ii) a light-chain CDR-L2 comprising the amino acid sequence from 50-56 of SEQ ID NO:69; and iii) a light-chain CDR-L3 comprising the amino acid sequence from 89-97 of SEQ ID NO:69, or (II) a variant thereof comprising a heavy-chain variable region with at least 90% identity to SEQ ID NO:67 (e.g., at least 91%, at least 92%, at least 93%, at least 94%, at least 95%, at least 96%, at least 97%, at least 98%, at least 99% identity to SEQ ID NO:67) and a light-chain variable region with at least 90% identity (e.g., at least 91%, at least 92%, at least 93%, at least 94%, at least 95%, at least 96%, at least 97%, at least 98%, at least 99% identity to SEQ ID NO:69.

In some embodiments, the method comprises administering to the subject a composition comprising an amount of a MASP-2 inhibitory antibody, or antigen binding fragment thereof, comprising a heavy-chain variable region comprising the amino acid sequence set forth as SEQ ID NO:67 and a light-chain variable region comprising the amino acid sequence set forth as SEQ ID NO:69.

In some embodiments, the method comprises administering to the subject a composition comprising a MASP-2 inhibitory antibody, or antigen binding fragment thereof, that specifically recognizes at least part of an epitope on human MASP-2 recognized by reference antibody OMS646 comprising a heavy-chain variable region as set forth in SEQ ID NO:67 and a light-chain variable region as set forth in SEQ ID NO:69.

In some embodiments, the method comprises administering to a subject suffering from, or at risk for developing IgAN (such as steroid-dependent IgAN) or MN (such as steroid-dependent MN), a composition comprising a MASP-2 inhibitory antibody, or antigen binding fragment thereof comprising a heavy-chain variable region comprising the amino acid sequence set forth as SEQ ID NO:67 and a light-chain variable region comprising the amino acid sequence set forth as SEQ ID NO:69 in a dosage from 1 mg/kg to 10 mg/kg (i.e., 1 mg/kg, 2 mg/kg, 3 mg/kg, 4 mg/kg, 5 mg/kg, 6 mg/kg, 7 mg/kg, 8 mg/kg, 9 mg/kg or 10 mg/kg) at least once weekly (such as at least twice weekly or at least three times weekly) for a period of at least 3 weeks, or for at least 4 weeks, or for at least 5 weeks, or for at least 6 weeks, or for at least 7 weeks, or for at least 8 weeks, or for at least 9 weeks, or for at least 10 weeks, or for at least 11 weeks, or for at least 12 weeks.

OTHER EMBODIMENTS

All publications, patent applications, and patents mentioned in this specification are herein incorporated by reference.

Various modifications and variations of the described methods and compositions of the invention will be apparent to those skilled in the art without departing from the scope and spirit of the invention. Although the invention has been described in connection with specific desired embodiments, it should be understood that the invention as claimed should not be unduly limited to such specific embodiments.

In accordance with the foregoing, the invention features the following embodiments.

1. A method for treating, inhibiting, alleviating or preventing fibrosis in a mammalian subject suffering, or at risk of developing a disease or disorder caused or exacerbated by fibrosis and/or inflammation, comprising administering to the subject an amount of a MASP-2 inhibitory agent effective to inhibit fibrosis.

2. The method according to paragraph 1, wherein the MASP-2 inhibitory agent is a MASP-2 antibody or fragment thereof.

3. The method according to paragraph 2, wherein the MASP-2 inhibitory agent is a MASP-2 monoclonal antibody, or fragment thereof that specifically binds to a portion of SEQ ID NO:6.

4. The method according to paragraph 2, wherein the MASP-2 antibody or fragment thereof specifically binds to a polypeptide comprising SEQ ID NO:6 with an affinity of at least 10 times greater than it binds to a different antigen in the complement system.

5. The method according to paragraph 2, wherein the antibody or fragment thereof is selected from the group consisting of a recombinant antibody, an antibody having reduced effector function, a chimeric antibody, a humanized antibody and a human antibody.

6. The method according to paragraph 1, wherein the MASP-2 inhibitory agent selectively inhibits lectin pathway complement activation without substantially inhibiting C1q-dependent complement activation.

7. The method according to paragraph 1, wherein the MASP-2 inhibitory agent is administered subcutaneously, intraperitoneally, intra-muscularly, intra-arterially, intravenously, or as an inhalant.

8. The method according to any of paragraphs 1 to 7, wherein the disease or disorder caused or exacerbated by fibrosis and/or inflammation is associated with an ischemia reperfusion injury.

9. The method according to any of paragraphs 1 to 7, wherein the disease or disorder caused or exacerbated by fibrosis and/or inflammation is not associated with an ischemia reperfusion injury.

10. The method according to any of paragraphs 1 to 7, wherein the subject exhibits proteinuria prior to administration of the MASP-2 inhibitory agent and administration of the MASP-2 inhibitory agent decreases proteinuria in the subject.

11. The method according to any of paragraphs 1 to 7, wherein the subject is suffering from a disease or disorder caused or exacerbated by renal fibrosis and/or inflammation.

12. The method according to paragraph 11, wherein the MASP-2 inhibitory agent is administered in an amount effective to inhibit tubulointerstitial fibrosis.

13. The method according to paragraph 11, wherein the MASP-2 inhibitory agent is administered in an amount effective to reduce, delay or eliminate the need for dialysis in the subject.

14. The method according to paragraph 11, wherein the disease or disorder is selected from the group consisting of chronic kidney disease, chronic renal failure, glomerular disease (e.g., focal segmental glomerulosclerosis), an immune complex disorder (e.g., IgA nephropathy, membranous nephropathy), lupus nephritis, nephrotic syndrome, diabetic nephropathy, tubulointerstitial damage and glomerulonepthritis (e.g., C3 glomerulopathy).

15. The method according to any of paragraphs 1 to 7, wherein the subject is suffering from a disease or disorder caused or exacerbated by pulmonary fibrosis and/or inflammation.

16. The method according to paragraph 15, wherein the disease or disorder is selected from the group consisting of chronic obstructive pulmonary disease, cystic fibrosis, pulmonary fibrosis associated with scleroderma, bronchiectasis and pulmonary hypertension.

17. The method according to any of paragraphs 1 to 7, wherein the subject is suffering from a disease or disorder caused or exacerbated by hepatic fibrosis and/or inflammation.

18. The method according to paragraph 17, wherein the disease or disorder is selected from the group consisting of cirrhosis, nonalcoholic fatty liver disease (steatohepatitis), liver fibrosis secondary to alcohol abuse, liver fibrosis secondary to acute or chronic hepatitis, biliary disease and toxic liver injury (e.g., hepatotoxicity due to drug-induced liver damage induced by acetaminophen or other drug, such as a nephrotoxin).

19. The method according to any of paragraphs 1 to 7, wherein the subject is suffering from a disease or disorder caused or exacerbated by cardiac fibrosis and/or inflammation.

20. The method according to paragraph 19, wherein the disease or condition is selected from the group consisting of cardiac fibrosis, myocardial infarction, valvular fibrosis, atrial fibrosis, endomyocardial fibrosis arrhythmogenic right ventricular cardiomyopathy (ARVC).

21. The method according to any of paragraphs 1 to 7, wherein the subject is suffering from a disease or disorder caused or exacerbated by vascular fibrosis.

22. The method according to paragraph 21, wherein the disease or disorder is selected from the group consisting of a vascular disease, an atherosclerotic vascular disease, vascular stenosis, restenosis, vasculitis, phlebitis, deep vein thrombosis and abdominal aortic aneurysm.

23. The method according to any of paragraphs 1 to 7, wherein the subject is suffering from a disease or disorder caused or exacerbated by fibrosis of the skin.

24. The method according to paragraph 23, wherein the disease or disorder is selected from the group consisting of excessive wound healing, scleroderma, systemic sclerosis, keloids, connective tissue diseases, scarring, and hypertrophic scars.

25. The method according to any of paragraphs 1 to 7, wherein the subject is suffering from a disease or disorder caused or exacerbated by fibrosis of the joints.

26. The method according to paragraph 25, wherein the disease or disorder is arthrofibrosis.

27. The method according to any of paragraphs 1 to 7, wherein the subject is suffering from a disease or disorder caused or exacerbated by fibrosis of the central nervous system.

28. The method according to paragraph 27, wherein the disease or disorder is selected from the group consisting of stroke, traumatic brain injury and spinal cord injury.

29. The method according to any of paragraphs 1 to 7, wherein the subject is suffering from a disease or disorder caused or exacerbated by fibrosis of the digestive system.

30. The method according to paragraph 29, wherein the disease or disorder is selected from the group consisting of Crohn's disease, pancreatic fibrosis and ulcerative colitis.

31. The method according to any of paragraphs 1 to 7, wherein the subject is suffering from a disease or disorder caused or exacerbated by ocular fibrosis.

32. The method according to paragraph 31, wherein the disease or disorder is selected from the group consisting of anterior subcapsular cataract, posterior capsule opacification, macular degeneration, and retinal and vitreal retinopathy.

33. The method according to any of paragraphs 1 to 7, wherein the subject is suffering from a disease or disorder caused or exacerbated by fibrosis of the musculoskeletal bone or soft-tissue structure.

34. The method according to paragraph 33, wherein the disease or disorder is selected from the group consisting of osteoporosis and/or osteopenia associated with cystic fibrosis, myelodysplastic conditions with increased bone fibrosis, adhesive capsulitis, Dupuytren's contracture and myelofibrosis.

35. The method according to any of paragraphs 1 to 7, wherein the subject is suffering from a disease or disorder caused or exacerbated by fibrosis of the reproductive organs.

36. The method according to paragraph 35, wherein the disease or disorder is selected from the group consisting of endometriosis and Peyronie's disease.

37. The method according to any of paragraphs 1 to 7, wherein the subject is suffering from a chronic infectious disease that causes fibrosis and/or inflammation.

38. The method according to paragraph 37, wherein the infectious disease is selected from the group consisting of alpha virus, Hepatitis A, Hepatitis B, Hepatitis C, tuberculosis, HIV and influenza.

39. The method according to any of paragraphs 1 to 7, wherein the subject is suffering from an autoimmune disease that causes fibrosis and/or inflammation.

40. The method according to paragraph 39, wherein the autoimmune disease is selected from the group consisting of scleroderma and systemic lupus erythematosus (SLE).

41. The method according to any of paragraphs 1 to 7, wherein the subject is suffering from scarring associated with trauma.

42. The method according to paragraph 41, wherein the scarring associated with trauma is selected from the group consisting of surgical complications (e.g., surgical adhesions wherein scar tissue can form between internal organs causing contracture, pain and can cause infertility), chemotherapeutic drug-induced fibrosis, radiation-induced fibrosis and scarring associated with burns.

43. The method according to any of paragraphs 1 to 7, wherein the disease or disorder caused or exacerbated by fibrosis and/or inflammation is selected from the group consisting of organ transplant, breast fibrosis, muscle fibrosis, retroperitoneal fibrosis, thyroid fibrosis, lymph node fibrosis, bladder fibrosis and pleural fibrosis.

44. A method of preventing or reducing renal damage in a subject suffering from a disease or condition associated with proteinuria comprising administering an amount of a MASP-2 inhibitory agent effective to reduce or prevent proteinurea in the subject.

45. The method according to paragraph 44, wherein the MASP-2 inhibitory agent is a MASP-2 inhibitory antibody or fragment thereof.

46. The method according to paragraph 44 or 45, wherein the MASP-2 inhibitory agent is administered in an amount and for a time effective to achieve at least a 20 percent reduction in 24-hour urine protein excretion as compared to baseline 24-hour urine protein excretion prior to treatment.

47. The method according to any of paragraphs 44 to 46, wherein the disease or condition associated with proteinuria is selected from the group consisting of nephrotic syndrome, pre-eclampsia, eclampsia, toxic lesions of kidneys, amyloidosis, collagen vascular diseases (e.g., systemic lupus erythematosus), dehydration, glomerular diseases (e.g. membranous glomerulonephritis, focal segmental glomerulonephritis, C3 glomerulopathy, minimal change disease, lipoid nephrosis), strenuous exercise, stress, benign orthostatis (postural) proteinuria, focal segmental glomerulosclerosis, IgA nephropathy (i.e., Berger's disease), IgM nephropathy, membranoproliferative glomerulonephritis, membranous nephropathy, minimal change disease, sarcoidosis, Alport's syndrome, diabetes mellitus (diabetic nephropathy), drug-induced toxicity (e.g., NSAIDS, nicotine, penicillamine, lithium carbonate, gold and other heavy metals, ACE inhibitors, antibiotics (e.g., adriamycin) or opiates (e.g. heroin) or other nephrotoxins); Fabry's disease, infections (e.g., HIV, syphilis, hepatitis A, B or C, poststreptococcal infection, urinary schistosomiasis); aminoaciduria, Fanconi syndrome, hypertensive nephrosclerosis, interstitial nephritis, sickle cell disease, hemoglobinuria, multiple myeloma, myoglobinuria, organ rejection (e.g., kidney transplant rejection), ebola hemorrhagic fever, Nail patella syndrome, familial mediterranean fever, HELLP syndrome, systemic lupus erythematosus, Wegener's granulomatosis, Rheumatoid arthritis, Glycogen storage disease type 1, Goodpasture's syndrome, Henoch-Schonlein purpura, urinary tract infection which has spread to the kidneys, Sjögren's syndrome and post-infections glomerulonepthritis.

48. The method according to any of paragraphs 44 to 46, wherein the disease or condition associated with proteinuria is IgA nephropathy (i.e., Berger's disease).

49. The method according to any of paragraphs 44 to 46, wherein the disease or condition associated with proteinuria is membranous nephropathy.

50. A method of inhibiting the progression of chronic kidney disease, comprising administering an amount of a MASP-2 inhibitory agent effective to reduce or prevent tubulointerstitial fibrosis in a subject in need thereof.

51. The method according to paragraph 50, wherein the MASP-2 inhibitory agent is a MASP-2 inhibitory antibody, or fragment thereof.

52. The method according to paragraph 50, wherein the subject in need thereof exhibits proteinuria prior to administration of the MASP-2 inhibitory agent and administration of the MASP-2 inhibitory agent decreases proteinuria in the subject, such that the subject has at least a 20 percent reduction in 24-hour urine protein excretion as compared to baseline 24-hour urine protein excretion in the subject prior to treatment.

53. The method according to paragraph 50, wherein the MASP-2 inhibitory agent is administered in an amount effective to reduce, delay or eliminate the need for dialysis in the subject.

54. A method of protecting a kidney from renal injury in a subject that has undergone, is undergoing, or will undergo treatment with one or more nephrotoxic agents, comprising administering an amount of a MASP-2 inhibitory agent effective to prevent or ameliorate the incidence of drug-induced nephropathy.

55. The method according to paragraph 54, wherein the MASP-2 inhibitory agent is a MASP-2 inhibitory antibody, or fragment thereof.

56. The method according to paragraph 54, wherein the MASP-2 inhibitory agent is administered prior to said nephrotoxic agent.

57. The method according to paragraph 54, wherein the MASP-2 inhibitory agent is co-administered simultaneously with said nephrotoxic agent.

58. The method according to paragraph 54, wherein the MASP-2 inhibitory agent is administered after said nephrotoxic agent to treat nephrotoxicity.

59. A method of treating a human subject suffering from Immunoglobulin A Nephropathy (IgAN) comprising administering to the subject a composition comprising an amount of a MASP-2 inhibitory antibody, or antigen-binding fragment thereof, effective to inhibit MASP-2-dependent complement activation.

60. The method according to paragraph 59, wherein the subject is suffering from steroid-dependent IgAN.

61. The method according to paragraph 59 or 60, wherein the MASP-2 inhibitory antibody is a monoclonal antibody, or fragment thereof that specifically binds to human MASP-2.

62. The method according to any of paragraphs 59 to 61, wherein the antibody or fragment thereof is selected from the group consisting of a recombinant antibody, an antibody having reduced effector function, a chimeric antibody, a humanized antibody, and a human antibody.

63. The method according to any of paragraphs 59 to 62, wherein the MASP-2 inhibitory antibody does not substantially inhibit the classical pathway.

64. The method according to any of paragraphs 59 to 63, wherein the MASP-2 inhibitory antibody inhibits C3b deposition in 90% human serum with an $IC_{50}$ of 30 nM or less.

65. The method according to paragraph 59, wherein the method further comprises identifying a human subject having steroid-dependent IgAN prior to the step of administering to the subject a composition comprising an amount of a MASP-2 inhibitory antibody, or antigen-binding fragment thereof, effective to improve renal function.

66. The method according to any of paragraphs 59 to 65, wherein the MASP-2 inhibitory antibody or antigen-binding fragment thereof is administered in an amount effective to improve renal function.

67. The method according to paragraph 66, wherein the MASP-2 inhibitory antibody or antigen-binding fragment thereof is administered in an amount effective and for a time sufficient to achieve at least a 20 percent reduction in 24-hour urine protein excretion as compared to baseline 24-hour urine protein excretion in the subject prior to treatment.

68. The method according to paragraph 59, wherein the composition is administered in an amount sufficient to improve renal function and decrease the corticosteroid dosage in said subject.

69. The method according to any of paragraphs 59 to 68, wherein the MASP-2 inhibitory antibody or antigen-binding fragment thereof comprises a heavy chain variable region comprising CDR-H1, CDR-H2 and CDR-H3 of the amino acid sequence set forth as SEQ ID NO:67 and a light chain variable region comprising CDR-L1, CDR-L2 and CDR-L3 of the amino acid sequence set forth as SEQ ID NO:70.

70. A method of treating a human subject suffering from membranous nephropathy (MN) comprising administering to the subject a composition comprising an amount of a MASP-2 inhibitory antibody, or antigen-binding fragment thereof, effective to inhibit MASP-2-dependent complement activation.

71. The method according to paragraph 70, wherein the subject is suffering from steroid-dependent MN.

72. The method according to paragraph 70 or 71, wherein the MASP-2 inhibitory antibody is a monoclonal antibody, or fragment thereof that specifically binds to human MASP-2.

73. The method according to any of paragraphs 70 to 72, wherein the antibody or fragment thereof is selected from the group consisting of a recombinant antibody, an antibody having reduced effector function, a chimeric antibody, a humanized antibody, and a human antibody.

74. The method according to any of paragraphs 70 to 73, wherein the MASP-2 inhibitory antibody does not substantially inhibit the classical pathway.

75. The method according to any of paragraphs 70 to 74, wherein the MASP-2 inhibitory antibody inhibits C3b deposition in 90% human serum with an $IC_{50}$ of 30 nM or less.

76. The method according to paragraph 70, wherein the method further comprises identifying a human subject having steroid-dependent MN prior to the step of administering to the subject a composition comprising an amount of a MASP-2 inhibitory antibody, or antigen-binding fragment thereof, effective to improve renal function.

77. The method according to any of paragraphs 70 to 76, wherein the MASP-2 inhibitory antibody or antigen-binding fragment thereof is administered in an amount effective to improve renal function.

78. The method according to paragraph 77, wherein the MASP-2 inhibitory antibody or antigen-binding fragment thereof is administered in an amount effective and for a time sufficient to achieve at least a 20 percent reduction in 24-hour urine protein excretion as compared to baseline 24-hour urine protein excretion in the subject prior to treatment.

79. The method according to paragraph 70 or 71, wherein the composition is administered in an amount sufficient to improve renal function and decrease the corticosteroid dosage in said subject.

80. The method according to any of paragraphs 70 to 79, wherein the MASP-2 inhibitory antibody or antigen-binding fragment thereof comprises a heavy chain variable region comprising CDR-H1, CDR-H2 and CDR-H3 of the amino acid sequence set forth as SEQ ID NO:67 and a light chain variable region comprising CDR-L1, CDR-L2 and CDR-L3 of the amino acid sequence set forth as SEQ ID NO:70.

While illustrative embodiments have been illustrated and described, it will be appreciated that various changes can be made therein without departing from the spirit and scope of the invention.

---

The embodiments of the invention in which an exclusive property or privilege is claimed are defined as follows:

1. A method of treating a human subject suffering from steroid-dependent Immunoglobulin A Nephropathy (IgAN) comprising:
   (a) identifying a human subject having steroid-dependent IgAN, wherein the human subject having steroid-dependent IgAN has been maintained on a stable dose of corticosteroids for at least 12 weeks; and
   (b) administering to the subject a composition comprising a MASP-2 inhibitory monoclonal antibody, or antigen-binding fragment thereof that specifically binds to human MASP-2, in an amount effective and for a time sufficient to achieve at least a 30% reduction in 24-hour urine protein excretion as compared to baseline 24-hour urine protein excretion in the subject prior to MASP-2 inhibitory antibody treatment.

2. The method of claim 1, wherein the antibody or fragment thereof is selected from the group consisting of a recombinant antibody, an antibody having reduced effector function, a chimeric antibody, a humanized antibody, and a human antibody.

3. The method of claim 1, wherein the MASP-2 inhibitory antibody does not substantially inhibit the classical pathway.

4. The method of claim 1, wherein the MASP-2 inhibitory antibody inhibits C3b deposition in 90% human serum with an $IC_{50}$ of 30 nM or less.

5. The method of claim 1, wherein the MASP-2 inhibitory antibody or antigen-binding fragment thereof is administered in an amount effective and for a time sufficient to achieve at least a 40% reduction in 24-hour urine protein excretion as compared to baseline 24-hour urine protein excretion in the subject prior to treatment.

6. The method of claim 1, wherein the MASP-2 inhibitory antibody or antigen-binding fragment thereof comprises a heavy chain variable region comprising CDR-H1, CDR-H2 and CDR-H3 of the amino acid sequence set forth as SEQ ID NO:67 and a light chain variable region comprising CDR-L1, CDR-L2 and CDR-L3 of the amino acid sequence set forth as SEQ ID NO: 69.

7. The method of claim 1, wherein the MASP-2 inhibitory antibody or antigen-binding fragment thereof comprises a heavy chain variable region set forth as SEQ ID NO:67 and a light chain variable region set forth as SEQ ID NO:69.

8. The method of claim 1, wherein the MASP-2 inhibitory monoclonal antibody, or antigen-binding fragment thereof that specifically binds to human MASP-2, is administered in an amount effective and for a time sufficient to decrease the corticosteroid dosage in said subject as compared to the corticosteroid dosage required to maintain stable renal function in said subject prior to treatment with the composition.

* * * * *